US009527856B2

(12) United States Patent
Braje et al.

(10) Patent No.: US 9,527,856 B2
(45) Date of Patent: Dec. 27, 2016

(54) OXINDOLE COMPOUNDS CARRYING A CO-BOUND SPIRO SUBSTITUENT AND USE THEREOF FOR TREATING VASOPRESSIN-RELATED DISEASES

(71) Applicant: AbbVie Deutschland GmbH & Co. KG, Wiesbaden (DE)

(72) Inventors: Wilfried Braje, Ludwigshafen (DE); Hervé Geneste, Ludwigshafen (DE); Wilfried Hornberger, Ludwigshafen (DE); Katja Jantos, Ludwigshafen (DE); Andreas Kling, Ludwigshafen (DE); Claudia Krack, Ludwigshafen (DE); Marcel Van Gaalen, Göttingen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 14/713,824

(22) Filed: May 15, 2015

(65) Prior Publication Data

US 2015/0344489 A1 Dec. 3, 2015

Related U.S. Application Data

(60) Provisional application No. 61/993,874, filed on May 15, 2014.

(51) Int. Cl.
C07D 471/10 (2006.01)
C07D 295/135 (2006.01)
C07D 305/08 (2006.01)
C07D 401/14 (2006.01)
C07D 487/10 (2006.01)
C07D 209/40 (2006.01)
C07D 213/64 (2006.01)

(52) U.S. Cl.
CPC ......... *C07D 487/10* (2013.01); *C07D 209/40* (2013.01); *C07D 213/64* (2013.01); *C07D 295/135* (2013.01); *C07D 305/08* (2013.01); *C07D 401/14* (2013.01); *C07D 471/10* (2013.01)

(58) Field of Classification Search
CPC . C07D 471/10; C07D 295/135; C07D 305/08; C07D 401/14; C07D 487/10; C07D 209/40; C07D 213/64
See application file for complete search history.

(56) References Cited

U.S. PATENT DOCUMENTS

2014/0194440 A1 7/2014 Braje et al.
2015/0158845 A1 6/2015 Braje et al.

FOREIGN PATENT DOCUMENTS

WO 2009/071689 6/2009
WO 2009/071690 6/2009

OTHER PUBLICATIONS

International Search Report for Application No. PCT/EP2015/060761 dated Aug. 3, 2015 (4 pages).

*Primary Examiner* — Rebecca Anderson
(74) *Attorney, Agent, or Firm* — Neal Gerber & Eisenberg LLP

(57) ABSTRACT

The present invention relates to novel substituted oxindole derivatives of formula I

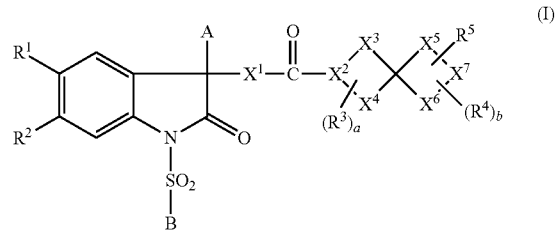

wherein the variables are as defined in the claims and the description. The invention further relates to pharmaceutical compositions comprising compounds I and their use for the treatment of vasopressin-related disorders.

38 Claims, No Drawings

OXINDOLE COMPOUNDS CARRYING A CO-BOUND SPIRO SUBSTITUENT AND USE THEREOF FOR TREATING VASOPRESSIN-RELATED DISEASES

CROSS-REFERENCE TO RELATED APPLICATION(S)

This claims priority to U.S. Provisional Patent Application No. 61/993,874, filed on May 15, 2014, the entire contents of which is fully incorporated herein by reference.

The present invention relates to novel substituted oxindole derivatives, pharmaceutical compositions comprising them, and their use for the treatment of vasopressin-related disorders.

Vasopressin is an endogenous hormone which exerts various effects on organs and tissues. It is suspected that the vasopressin system is involved in various pathological states such as, for example, heart failure and high blood pressure. At present, three receptors (V1a, V1b or V3, and V2) via which vasopressin mediates its numerous effects are known. Antagonists of these receptors are therefore being investigated as possible new therapeutic approaches for the treatment of diseases (M. Thibonnier, Exp. Opin. Invest. Drugs 1998, 7(5), 729-740; T. Ryckmans, Current Opinion in Drug Discovery & Development 13 (2010), 538-547; G. Decaux et al., Lancet 371 (2008), 1624-1632; R. Lemmens-Gruber, M. Kamyar, Cell. Mol. Life Sci. 63 (2006), 1766-1779).

1-(Het)Arylsulfonyl-1,3-dihydro-2H-indol-2-ones have previously been described as ligands of vasopressin receptors, for example in WO 2005/030755, WO 2006/005609, WO 2006/080574, WO 2008/080970, WO 2008/080971, WO 2008/080972, WO 2008/080973, WO 2009/071687, WO 2009/071689, WO 2009/071690, WO2009/071691, WO 2009/083559, WO 2010/009775 or WO 2010/142739.

Besides the binding affinity for the vasopressin V1b receptor, further properties may be advantageous for the treatment and/or prophylaxis of vasopressin-related disorders, such as, for example:

1.) a selectivity for the vasopressin V1b receptor compared with the vasopressin V1a receptor, i.e. the quotient of the binding affinity for the V1a receptor (Ki(V1a) (determined in the unit "nanomolar (nM)") and the binding affinity for the V1b receptor (Ki(V1b)) (determined in the unit "nanomolar (nM)". A larger quotient Ki(V1a)/Ki(V1b) means a greater V1b selectivity;

2.) a selectivity for the vasopressin V1b receptor compared with the vasopressin V2 receptor, i.e. the quotient of the binding affinity for the V2 receptor (Ki(V2) (determined in the unit "nanomolar (nM)") and the binding affinity for the V1b receptor (Ki(V1b)) (determined in the unit "nanomolar (nM)". A larger quotient Ki(V2)/Ki(V1b) means a greater V1b selectivity;

3.) a selectivity for the vasopressin V1b receptor compared with the oxytocin OT receptor, i.e. the quotient of the binding affinity for the OT receptor (Ki(OT) (determined in the unit "nanomolar (nM)") and the binding affinity for the V1b receptor (Ki(V1b)) (determined in the unit "nanomolar (nM)". A larger quotient Ki(OT)/Ki(V1b) means a greater V1b selectivity;

4.) the metabolic stability, for example determined from the half-lives, measured in vitro, in liver microsomes from various species (e.g. rat or human);

5.) no or only low inhibition of cytochrome P450 (CYP) enzymes: cytochrome P450 (CYP) is the name for a superfamily of heme proteins having enzymatic activity (oxidase). They are also particularly important for the degradation (metabolism) of foreign substances such as drugs or xenobiotics in mammalian organisms. The principal representatives of the types and subtypes of CYP in the human body are: CYP 1A2, CYP 2C9, CYP 2D6 and CYP 3A4. If CYP 3A4 inhibitors (e.g. grapefruit juice, cimetidine, erythromycin) are used at the same time as medicinal substances which are degraded by this enzyme system and thus compete for the same binding site on the enzyme, the degradation thereof may be slowed down and thus effects and side effects of the administered medicinal substance may be undesirably enhanced;

6.) a suitable solubility in water (in mg/ml);

7.) suitable pharmacokinetics (time course of the concentration of the compound of the invention in plasma or in tissue, for example brain). The pharmacokinetics can be described by the following parameters: half-life (in h), volume of distribution (in 1·kg-1), plasma clearance (in 1·h-1·kg-1), AUC (area under the curve, area under the concentration-time curve, in ng·h·1-1), oral bioavailability (the dose-normalized ratio of AUC after oral administration and AUC after intravenous administration), the so-called brain-plasma ratio (the ratio of AUC in brain tissue and AUC in plasma);

8.) no or only low blockade of the hERG channel: compounds which block the hERG channel may cause a prolongation of the QT interval and thus lead to serious disturbances of cardiac rhythm (for example so-called "torsade de pointes"). The potential of compounds to block the hERG channel can be determined by means of the displacement assay with radiolabelled dofetilide which is described in the literature (G. J. Diaz et al., Journal of Pharmacological and Toxicological Methods, 50 (2004), 187 199). A smaller IC50 in this dofetilide assay means a greater probability of potent hERG blockade. In addition, the blockade of the hERG channel can be measured by electrophysiological experiments on cells which have been transfected with the hERG channel, by so-called whole-cell patch clamping (G. J. Diaz et al., Journal of Pharmacological and Toxicological Methods, 50 (2004), 187-199).

It was therefore an object of the present invention to provide compounds for the treatment or prophylaxis of various vasopressin-related diseases. The compounds were intended to have a high activity and selectivity, especially a high affinity and selectivity vis-á-vis the vasopressin V1b receptor. In addition, the substance of the invention was intended to have one or more of the aforementioned advantages 1.) to 8.).

The object is achieved by compounds of the formula I

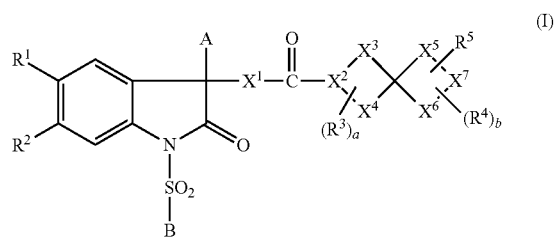

wherein
A is a ring selected from phenyl and 6-membered hetaryl containing 1 or 2 nitrogen atoms as ring members, where ring A carries one substituent $R^6$ and optionally one substituent $R^7$;

B is a ring selected from phenyl, pyridyl and quinolinyl, where ring B may carry 1, 2 or 3 substituents $R^8$;

$X^1$ is NH, $CH_2$ or O;

$X^2$ is N or CH;

$X^3$, $X^4$, $X^5$ and $X^6$, independently of each other, are selected from $-CH_2-$, $-O-$, $-S(O)_c-$, $-NH-$, $-C(O)-$, $-CH_2CH_2-$, $-CH_2O-$, $-OCH_2-$, $-S(O)_cCH_2-$, $-CH_2S(O)_c-$, $CH_2NH-$, $-NHCH_2-$, $-CH_2C(O)-$ and $-C(O)CH_2-$;

$X^7$ is NH, $CH_2$ or O;

$R^1$ is selected from cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^2$ is selected from hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^3$ and $R^4$, independently of each other and independently of each occurrence, are selected from hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy and $NR^9R^{10}$, and in case that $R^3$ or $R^4$ are bound to a carbon ring atom, are additionally selected from halogen; or two non-geminal radicals $R^3$ form together a group $-(CH_2)_k-$, where k is 1, 2, 3 or 4, where 1 or 2 hydrogen atoms in this group may be replaced by a methyl group; or two non-geminal radicals $R^4$ form together a group $-(CH_2)_k-$, where k is 1, 2, 3 or 4, where 1 or 2 hydrogen atoms in this group may be replaced by a methyl group; or two geminal radicals $R^3$ form together a group $-(CH_2)_j-$, where j is 2, 3, 4 or 5, where 1 or 2 hydrogen atoms in this group may be replaced by a methyl group; or two geminal radicals $R^4$ form together a group $-(CH_2)_j-$, where j is 2, 3, 4 or 5, where 1 or 2 hydrogen atoms in this group may be replaced by a methyl group; with the proviso that $R^3$ and $R^4$ are not halogen, hydroxyl, $C_1$-$C_4$-alkoxy or $C_1$-$C_4$-haloalkoxy if they are bound to a carbon atom in α-position to a nitrogen ring atom;

$R^5$ is selected from hydrogen, cyano, $C_1$-$C_6$-alkyl, $C_2$-$C_6$-alkenyl, $C_2$-$C_6$-alkynyl, $C_3$-$C_7$-cycloalkyl, where the four last-mentioned radicals may be partially or fully halogenated and/or may carry one or more substituents $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; $-OR^{13}$; $-S(O)_lR^{13}$; $NR^{14}R^{15}$; and $-C(=O)R^{16}$;

$R^6$ and $R^7$, independently of each other, are selected from halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

each $R^8$ is independently selected from halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^9$ and $R^{10}$, independently of each other, are selected from hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl;

each $R^{11}$ is independently selected from cyano, $-OR^{13}$, $-S(O)_lR^{13}$, $NR^{14}R^{15}$, $-C(=O)R^{16}$, $C_3$-$C_6$-cycloalkyl, $C_3$-$C_6$-halocycloalkyl, phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members, and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally selected from $C_1$-$C_4$-alkyl and $C_1$-$C_4$-haloalkyl;

each $R^{12}$ is independently selected from halogen, hydroxyl, cyano, nitro, $C_1$-$C_4$-alkyl, $C_1$-$C_4$-haloalkyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, phenyl, phenoxy, benzyloxy, where the phenyl moiety in the three last-mentioned radicals may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members, where the heteromonocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{13}$ is independently selected from hydrogen, $C_1$-$C_4$-alkyl, $C_1$-$C_4$-haloalkyl, $C_1$-$C_4$-alkyl which carries one substituent $R^{17}$, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, phenyl which may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

$R^{14}$ and $R^{15}$, independently of each other and independently of each occurrence, are selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl which may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; a 3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members, where the heterocyclic ring may carry 1, 2 or 3 substituents selected from halogen, hydroxyl, cyano, $C_1$-$C_4$-alkyl, $C_1$-$C_4$-haloalkyl, $C_1$-$C_4$-alkoxy and $C_1$-$C_4$-haloalkoxy; $C_1$-$C_4$-alkylcarbonyl and $C_1$-$C_4$-haloalkylcarbonyl;

each $R^{16}$ is independently selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl, —$OR^{13}$ and $NR^{14}R^{15}$;

each $R^{17}$ is independently selected from cyano, hydroxyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $NR^{14}R^{15}$; $C_1$-$C_4$-alkylcarbonyl, $C_1$-$C_4$-haloalkylcarbonyl, $C_3$-$C_6$-cycloalkyl, $C_3$-$C_6$-halocycloalkyl, phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members, and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$;

a is 0, 1 or 2;
b is 0, 1 or 2;
c is 0, 1 or 2; and
l is 0, 1 or 2;

and the N-oxides, stereoisomers and pharmaceutically acceptable salts thereof, and the compound of the formula I, wherein at least one of the atoms has been replaced by its stable, non-radioactive isotope.

Accordingly, the present invention relates to compounds of the formula I (also "compounds I" hereinafter) and the N-oxides, stereoisomers and the pharmaceutically acceptable salts of the compounds I.

In another aspect, the invention relates to a pharmaceutical composition comprising a therapeutically effective amount of at least one compound of formula I or an N-oxide, a stereoisomer or a pharmaceutically acceptable salt thereof, or comprising at least one compound as defined above or below wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance.

In yet another aspect, the invention relates to a compound of formula I or an N-oxide, a stereoisomer or a pharmaceutically acceptable salt thereof for use as a medicament.

In yet another aspect, the invention relates to a compound of formula I or an N-oxide, a stereoisomer or a pharmaceutically acceptable salt thereof for the treatment and/or prophylaxis of vasopressin-related diseases, especially of disorders which respond to the modulation of the vasopressin receptor, in particular of the V1b receptor.

In yet another aspect, the invention relates to the use of a compound of formula I or of an N-oxide, a stereoisomer or a pharmaceutically acceptable salt thereof for the manufacture of a medicament for the treatment and/or prophylaxis of vasopressin-related diseases; especially of disorders which respond to the modulation of the vasopressin receptor, in particular of the V1b receptor.

The pharmaceutically acceptable salts of compounds of the formula I, which are also referred to as physiologically tolerated salts, are ordinarily obtainable by reacting the free base of the compounds I of the invention (i.e. of the compounds I according to structural formula I) with suitable acids. Examples of suitable acids are listed in "Fortschritte der Arzneimittelforschung", 1966, Birkhäuser Verlag, vol. 10, pp. 224-285. These include for example hydrochloric acid, citric acid, tartaric acid, lactic acid, phosphoric acid, methanesulfonic acid, acetic acid, trifluoroacetic acid, formic acid, maleic acid and fumaric acid.

The term "stereoisomers" encompasses both optical isomers, such as enantiomers or diastereomers, the latter existing due to more than one center of chirality in the molecule, as well as geometrical isomers (cis/trans isomers; correctly speaking, these are also diastereomers). The term "stereoisomers" also encompasses conformers (to be more precise configuration isomers) which are caused by the hindered or decelerated inversion at one or more nitrogen atoms, especially ring nitrogen atoms, such as $X^7$ (if this is N, of course); like the isomers described by Y. Naruse et al. in Tetrahedron Asymmetry 2013, 24, 169-171.

Depending on the substitution pattern, the compounds of the formula I may have one or more centers of chirality, in which case they are present as mixtures of enantiomers or diastereomers. One center of chirality is the carbon ring atom in the 3-position of the oxindole scaffold (the carbon atom which carries the group $X^1$—C(O)-spiro rings and ring A). The compounds of the formula I may further have axial chirality due to the spiro system. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

Halogen in the terms of the present invention is fluorine, chlorine, bromine or iodine, preferably fluorine, chlorine or bromine and especially fluorine or chlorine.

$C_1$-$C_3$-Alkyl is a linear or branched alkyl radical having 1 to 3 carbon atoms, such as methyl, ethyl, n-propyl or isopropyl. $C_1$-$C_4$-Alkyl is a linear or branched alkyl radical having 1 to 4 carbon atoms, such as methyl, ethyl, n-propyl, isopropyl, n-butyl, sec-butyl, isobutyl or tert-butyl. $C_1$-$C_6$-Alkyl is a linear or branched alkyl radical having 1 to 6 carbon atoms, such as methyl, ethyl, n-propyl, isopropyl, n-butyl, sec-butyl, isobutyl, tert-butyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-tri-methylpropyl, 1-ethyl-1-methylpropyl, or 1-ethyl-2-methylpropyl.

Fluorinated alkyl is a straight-chain or branched alkyl group having from 1 to 4 (=fluorinated $C_1$-$C_4$-alkyl), in particular 1 to 3 carbon atoms (=fluorinated $C_1$-$C_3$-alkyl), more preferably 1 or 2 carbon atoms (=fluorinated $C_1$-$C_2$-alkyl), wherein at least one, e.g. 1, 2, 3, 4 or all of the hydrogen atoms are replaced by fluorine atoms. Examples for fluorinated $C_1$-$C_2$-alkyl are fluoromethyl, difluoromethyl, trifluoromethyl, 1-fluoroethyl, (R)-1-fluoroethyl, (S)-1-fluoroethyl, 2-fluoroethyl, 1,1-difluoroethyl, 2,2-difluoroethyl, 2,2,2-trifluoroethyl, pentafluoroethyl and the like. Examples for fluorinated $C_1$-$C_3$-alkyl are, apart those mentioned above for fluorinated $C_1$-$C_2$-alkyl, 1-fluoropropyl, (R)-1-fluoropropyl, (S)-1-fluoropropyl, 2-fluoropropyl, 3-fluoropropyl, 1,1-difluoropropyl, 2,2-difluoropropyl, 3,3-difluoropropyl, 3,3,3-trifluoropropyl, 2-fluoropropyl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1- methylethyl, 2-fluoro-1-(fluoromethyl)ethyl, 1-(difluoromethyl)-2,2-difluoroethyl and the like. Examples for fluorinated $C_1$-$C_4$-alkyl are, apart those mentioned above for fluorinated $C_1$-$C_3$-alkyl, 1-fluorobutyl, (R)-1-fluorobutyl, (S)-1-fluorobutyl, 2-fluorobutyl, 3-fluorobutyl, 4-fluorobutyl, 1,1-difluorobutyl, 2,2-difluorobutyl, 3,3-difluorobutyl, 4,4-difluorobutyl, 4,4,4-trifluorobutyl, and the like.

Haloalkyl, which is also expressed as "alkyl which is partially or fully halogenated", is a straight-chain or branched alkyl group having from 1 to 6 (=$C_1$-$C_6$-haloalkyl), in particular 1 to 4 carbon atoms (=$C_1$-$C_4$-haloalkyl), wherein at least one, e.g. 1, 2, 3, 4 or all of the hydrogen atoms are replaced by a halogen atom. Examples for $C_1$-$C_4$-haloalkyl are, apart those mentioned above for fluorinated $C_1$-$C_4$-alkyl, chloromethyl, bromomethyl, dichloromethyl, trichloromethyl, chlorofluoromethyl, dichlorofluoromethyl, chlorodifluoromethyl, 1-chloroethyl, 1-bromoethyl, 2-chloro-2-fluoroethyl, 2-chloro-2,2-difluoroethyl, 2,2-dichloro-2-fluoroethyl, 2,2,2-trichloroethyl, 3-chloropropyl, 4-chlorobutyl and the like. Examples for $C_1$-$C_6$-haloalkyl are, apart from those listed for $C_1$-$C_4$-haloalkyl, 1-fluoropentyl, 1-chloropenthyl, 1-bromopentyl, 1-fluorohexyl, 1-chlorohexy, 1-bromohexyl and the like.

$C_1$-$C_3$-Hydroxyalkyl is $C_1$-$C_3$-alkyl as defined above wherein one of the hydrogen atoms is replaced by a hydroxyl group. Examples are hydroxymethyl, 1- and 2-hydroxyethyl, 1-, 2- and 3-hydroxy-n-propyl, 1-(hydroxymethyl)-ethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl") carbon atoms and a double bond in any position. Examples for $C_2$-$C_3$-alkenyl are ethenyl, 1-propenyl, 2-propenyl or 1-methylethenyl. Examples for $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl. Examples for $C_2$-$C_6$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl") or 2 to 6 ("$C_2$-$C_6$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position. Examples for $C_2$-$C_3$-alkynyl are ethynyl, 1-propynyl or 2-propynyl. Examples for $C_2$-$C_4$-alkynyl are ethynyl, 1-propynyl, 2-propynyl, 1-butynyl, 2-butynyl, 3-butynyl, 1-methyl-2-propynyl and the like. Examples for $C_2$-$C_6$-alkynyl are ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like.

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl") or 2 to 6 ("$C_2$-$C_6$-haloalkynyl") carbon atoms and one or two triple bonds in any position (as mentioned above), where some or all of the hydrogen atoms in these groups are replaced by halogen atoms as mentioned above, in particular fluorine, chlorine and bromine.

$C_3$-$C_7$-Cycloalkyl is a monocyclic saturated hydrocarbon radical having 3 to 7, in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of $C_3$-$C_4$-cycloalkyl comprise cyclopropyl and cyclobutyl. Examples of $C_3$-$C_5$-cycloalkyl comprise cyclopropyl, cyclobutyl and cyclopentyl. Examples of $C_3$-$C_6$-cycloalkyl comprise cyclopropyl, cyclobutyl, cyclopentyl and cyclohexyl. Examples of $C_3$-$C_7$-cycloalkyl comprise cyclopropyl, cyclobutyl, cyclopentyl, cyclohexyl and cycloheptyl.

Fluorinated $C_3$-$C_7$-cycloalkyl is a monocyclic saturated hydrocarbon radical having 3 to 7, in particular 3 to 6 ("fluorinated $C_3$-$C_6$-cycloalkyl") or 3 to 5 ("fluorinated $C_3$-$C_5$-cycloalkyl") or 3 to 4 ("fluorinated $C_3$-$C_4$-cycloalkyl") carbon ring members (as mentioned above) in which some or all of the hydrogen atoms are replaced by fluorine atoms. Examples for fluorinated $C_3$-$C_4$-cycloalkyl are 1-fluorocyclopropyl, 2-fluorocyclopropyl, 2,2-difluorocyclopropyl, 1-fluorocyclobutyl, 2-fluorocyclobutyl, 3-fluorocyclobutyl, 2,2-difluorocyclobutyl, 3,3-difluorocyclobutyl and the like. Examples for fluorinated $C_3$-$C_5$-cycloalkyl are additionally 1-fluorocyclopentyl, 2-fluorocyclopentyl, 3-fluorocyclopentyl, 2,2-difluorocyclopentyl, 3,3-difluorocyclopentyl, and the like. Examples for fluorinated $C_3$-$C_6$-cycloalkyl are additionally 1-fluorocyclohexyl, 2-fluorocyclohexyl, 3-fluorocyclohexyl, 4-fluorocyclohexyl, 2,2-difluorocyclohexyl, 3,3-difluorocyclohexyl, 4,4-difluorocyclohexyl, and the like. Examples for fluorinated $C_3$-$C_7$-cycloalkyl are additionally 1-fluorocycloheptyl, 2-fluorocycloheptyl, 3-fluorocycloheptyl, 4-fluorocycloheptyl, 2,2-difluorocycloheptyl, 3,3-difluorocycloheptyl, 4,4-difluorocycloheptyl, and the like.

$C_3$-$C_7$-Halocycloalkyl is a monocyclic saturated hydrocarbon radical having 3 to 7, in particular 3 to 6 ("$C_3$-$C_6$-halocycloalkyl") or 3 to 5 ("$C_3$-$C_5$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "$C_3$-$C_6$-cycloalkyl-$C_1$-$C_4$-alkyl" which is bound to the remainder of the molecule via a $C_1$-$C_4$-alkyl group, as defined above. Examples for $C_3$-$C_6$-cycloalkyl-$C_1$-$C_4$-alkyl are cyclopropylmethyl, 1-cyclopropyl-1-ethyl, 1-cyclopropyl-2-ethyl, 1-cyclopropyl-1-propyl, 1-cyclopropyl-2-propyl, 2-cyclopropyl-1-propyl, 2-cyclopropyl-2-propyl, 1-cyclopropyl-3-propyl, cyclobutylmethyl, 1-cyclobutyl-1-ethyl, 1-cyclobutyl-2-ethyl, 1-cyclobutyl-1-propyl, 1-cyclobutyl-2-propyl, 2-cyclobutyl-1-propyl, 2-cyclobutyl-2-propyl, 1-cyclobutyl-3-propyl, cyclopentylmethyl, 1-cyclopentyl-1-ethyl, 1-cyclopentyl-2-ethyl, 1-cyclopentyl-1-propyl, 1-cyclopentyl-2-propyl, 2-cyclopentyl-1-propyl, 2-cyclopentyl-2-propyl, 1-cyclopentyl-3-propyl, cyclohexylmethyl, 1-cyclohexyl-1-ethyl, 1-cyclohexyl-2-ethyl, 1-cyclohexyl-1-propyl, 1-cyclohexyl-2-propyl, 2-cyclohexyl-1-propyl, 2-cyclohexyl-2-propyl and 1-cyclohexyl-3-propyl.

$C_3$-$C_6$-Cycloalkylmethyl is for example cyclopropylmethyl, cyclobutylmethyl, cyclopentylmethyl and cyclohexylmethyl.

$C_1$-$C_3$-Alkoxy is a linear or branched alkyl radical linked via an oxygen atom and having 1 to 3 carbon atoms. Examples are methoxy, ethoxy, n-propoxy and isopropoxy. $C_1$-$C_4$-Alkoxy is a linear or branched alkyl radical linked via an oxygen atom and having 1 to 4 carbon atoms. Examples are methoxy, ethoxy, n-propoxy, isopropoxy, n-butoxy, sec-butoxy, isobutoxy and tert-butoxy.

$C_1$-$C_4$-Haloalkoxy is $C_1$-$C_4$-alkoxy as defined above wherein at least one, e.g. 1, 2, 3, 4 or all of the hydrogen atoms are replaced by a halogen atom. Preferably, $C_1$-$C_4$-haloalkoxy is fluorinated $C_1$-$C_4$-alkoxy. This is a straight-chain or branched alkoxy group having from 1 to 4, in particular 1 to 3 carbon atoms (=fluorinated $C_1$-$C_3$-alkoxy), more preferably 1 or 2 carbon atoms (=fluorinated $C_1$-$C_2$-alkoxy), wherein at least one, e.g. 1, 2, 3, 4 or all of the hydrogen atoms are replaced by fluorine atoms, such as in fluoromethoxy, difluoromethoxy, trifluoromethoxy, 1-fluoroethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1-fluoropropoxy, (R)-1-fluoropropoxy, (S)-1-fluoropropoxy, 2-fluoropropoxy, 3-fluoropropoxy, 1,1-difluoropropoxy, 2,2-difluoropropoxy, 3,3-difluoropropoxy, 3,3,3-trifluoropropoxy, 2-fluoro-1-methylethoxy, (R)-2-fluoro-1-methylethoxy, (S)-2-fluoro-1-methylethoxy, 2,2-difluoro-1-methylethoxy, (R)-2,2-difluoro-1-methylethoxy, (S)-2,2-difluoro-1-methylethoxy, 1,2-difluoro-1-methylethoxy, (R)-1,2-difluoro-1-methylethoxy, (S)-1,2-difluoro-1-methylethoxy, 2,2,2-trifluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, etc.

$C_1$-$C_4$-Alkylthio is a $C_1$-$C_4$-alkyl group, as defined above, attached via a sulfur atom. Examples are methylthio, ethylthio, n-propylthio, 1-methylethylthio (isopropylthio), butylthio, 1-methylpropylthio (sec-butylthio), 2-methylpropylthio (isobutylthio) or 1,1-dimethylethylthio (tert-butylthio).

$C_1$-$C_4$-Haloalkylthio is a $C_1$-$C_4$-haloalkyl group, as defined above, attached via a sulfur atom. Examples are $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, $SC_2F_5$, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio.

$C_1$-$C_4$-Alkylsulfinyl is a $C_1$-$C_4$-alkyl group, as defined above, attached via a sulfinyl [S(O)]group. Examples are methylsulfinyl, ethylsulfinyl, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl).

$C_1$-$C_4$-Haloalkylsulfinyl is a $C_1$-$C_4$-haloalkyl group, as defined above, attached via a sulfinyl [S(O)]group. Examples are $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl, $S(O)C_2F_5$, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl.

$C_1$-$C_4$-Alkylsulfonyl is a $C_1$-$C_4$-alkyl group, as defined above, attached via a sulfonyl [$S(O)_2$]group. Examples are methylsulfonyl, ethylsulfonyl, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl).

$C_1$-$C_4$-Haloalkylsulfonyl is a $C_1$-$C_4$-haloalkyl group, as defined above, attached via a sulfonyl [$S(O)_2$]group. Examples are $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, $S(O)_2C_2F_5$, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-(CH₂F)-2-fluoroethylsulfonyl, 1-(CH₂Cl)-2-chloroethylsulfonyl, 1-(CH₂Br)-2-bromoethylsulfonyl, 4-fluorobutylsulfonyl, 4-chlorobutylsulfonyl, 4-bromobutylsulfonyl or nonafluorobutylsulfonyl.

$C_1$-$C_4$-Alkylcarbonyl is a $C_1$-$C_4$-alkyl group, as defined above, attached via a carbonyl [C(=O)]group. Examples are acetyl (methylcarbonyl), propionyl (ethylcarbonyl), propylcarbonyl, isopropylcarbonyl, n-butylcarbonyl and the like.

$C_1$-$C_4$-Haloalkylcarbonyl is a $C_1$-$C_4$-haloalkyl group, as defined above, attached via a carbonyl [C(=O)]group. Examples are trifluoromethylcarbonyl, 2,2,2-trifluoroethylcarbonyl and the like.

Examples for "6-membered hetaryl containing 1 or 2 nitrogen atoms as ring members" are pyridyl, such as pyridin-2-yl, pyridin-3-yl or pyridin-4-yl, pyridazinyl, such as pyridazin-3-yl or pyridazin-4-yl, pyrimidinyl, such as pyrimidin-2-yl, pyrimidin-4-yl or pyrimidin-5-yl, and pyrazinyl.

The term "3-, 4-, 5-, 6- or 7-membered saturated, partially unsaturated or maximally unsaturated heterocyclic ring containing 1, 2 or 3 heteroatoms or heteroatom groups selected from O, N, S, NO, SO and $SO_2$ as ring members" denotes a 3-, 4-, 5-, 6- or 7-membered saturated, partially unsaturated or maximum unsaturated heteromonocyclic ring containing 1, 2 or 3 heteroatoms or heteroatom groups selected from O, N, S, NO, SO and $SO_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. Partially unsaturated rings contain less C—C and/or C—N and/or N—N double bonds than allowed by the ring size. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5-, 6- or 7-membered saturated, partially unsaturated or maximum unsaturated heterocyclic ring containing 1, 2 or 3 heteroatoms or heteroatom groups selected from O, N, S, NO, SO and $SO_2$, as ring members" [wherein "maximum unsaturated" includes also "aromatic"] as used herein denotes monocyclic radicals, the monocyclic radicals being saturated, partially unsaturated or maximum unsaturated (including aromatic). 7-membered rings cannot be aromatic; they are homoaromatic if maximally unsaturated (3 double bonds).

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan 2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine.

In the present invention, the "heterobicyclic rings" contain two rings which have at least one ring atom in common.

At least one of the two rings contains a heteroatom or heteroatom group selected from N, O, S, NO, SO and SO$_2$ as ring member. The term comprises condensed (fused) ring systems, in which the two rings have two neighboring ring atoms in common, as well as spiro systems, in which the rings have only one ring atom in common, and bridged systems with at least three ring atoms in common.

Examples for Fused Systems:

Examples for a 7-, 8-, 9- or 10-membered saturated heterobicyclic ring containing 1, 2 or 3 (or 4) heteroatoms or heteroatom groups selected from N, O, S, NO, SO and SO$_2$, as ring members are:

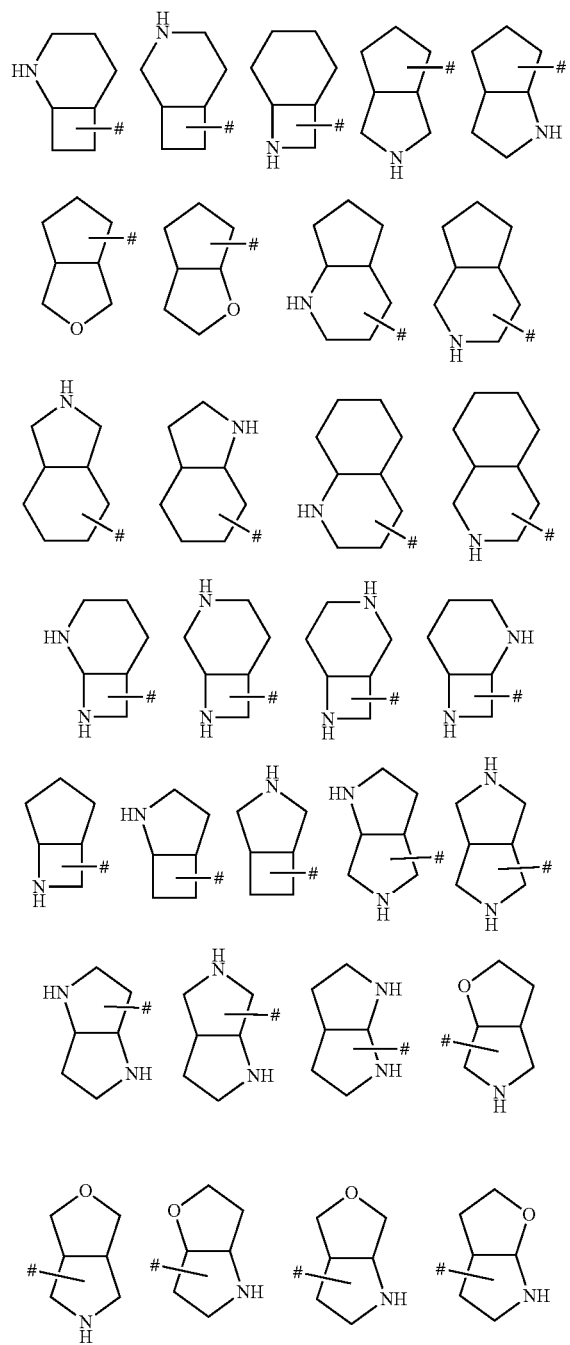
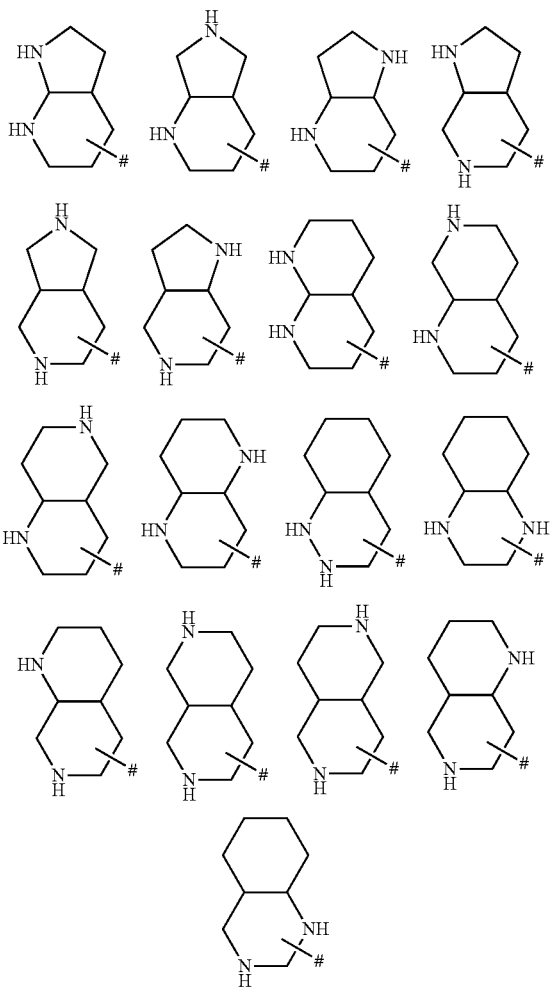

Examples for a 8-, 9- or 10-membered partially unsaturated heterobicyclic ring containing 1, 2 or 3 (or 4) heteroatoms or heteroatom groups selected from N, O, S, NO, SO and SO$_2$, as ring members are:

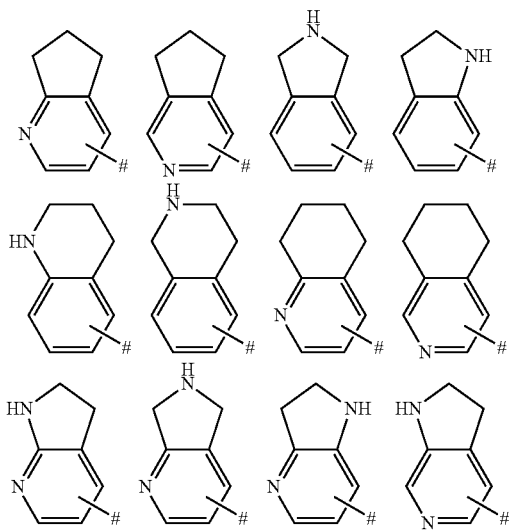

-continued

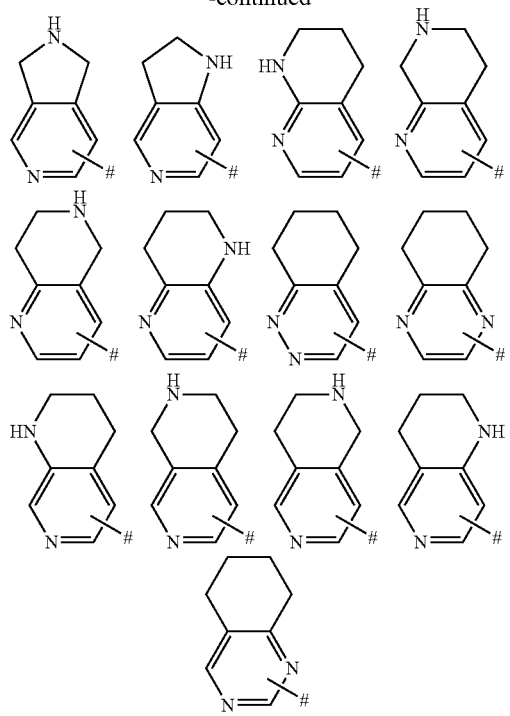

Examples for a 8-, 9- or 10-membered maximally unsaturated heterobicyclic ring containing 1, 2 or 3 (or 4) heteroatoms or heteroatom groups selected from N, O, S, NO, SO and SO$_2$, as ring members are:

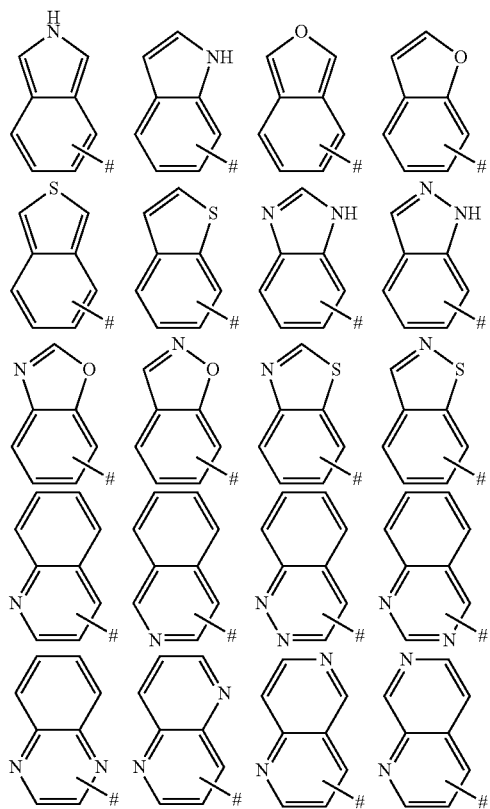

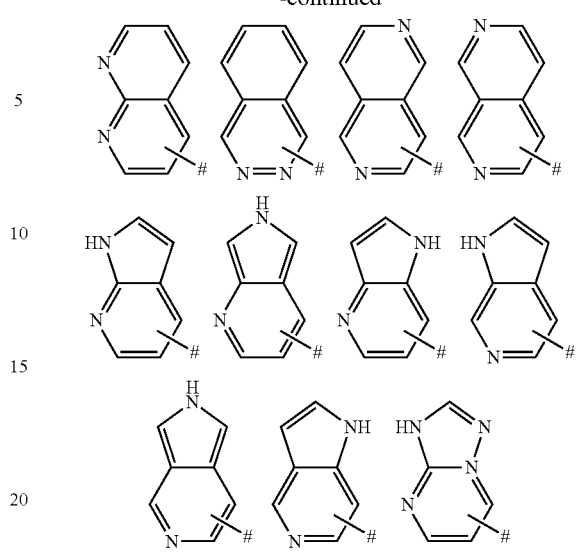

Examples for spiro-bound 7-, 8-, 9- or 10-membered heterobicyclic rings containing 1, 2 or 3 (or 4) heteroatoms or heteroatom groups selected from N, O, S, NO, SO and SO$_2$, as ring members are

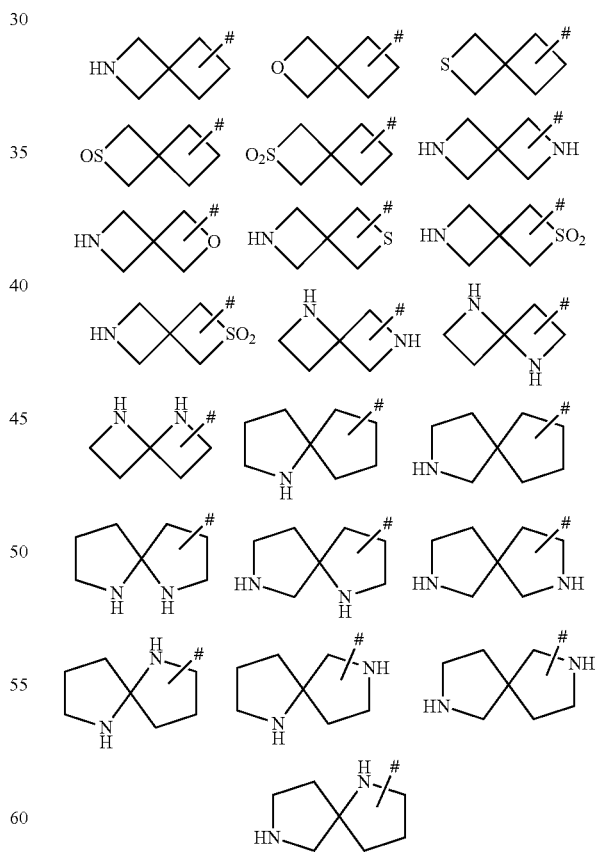

Examples for bridged 7-, 8-, 9- or 10-membered heterobicyclic rings containing 1, 2 or 3 (or 4) heteroatoms or heteroatom groups selected from N, O, S, NO, SO and SO$_2$, as ring members are

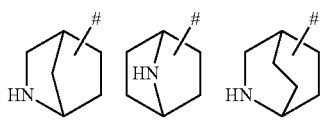

and the like.

In the above structures # denotes the attachment point to the remainder of the molecule. The attachment point is not restricted to the ring on which is shown, but can be on either of the fused rings, and may be on a carbon or on a nitrogen ring atom. If the rings carry one or more substituents, these may be bound to carbon and/or to nitrogen ring atoms.

The compounds of the invention of the formula I and their N-oxides, stereoisomers and pharmacologically acceptable salts may also be present in the form of solvates or hydrates. Solvates mean in the context of the present invention crystalline forms of the compounds I or of their pharmaceutically acceptable salts which comprise solvent molecules incorporated in the crystal lattice. The solvent molecules are preferably incorporated in stoichiometric ratios. Hydrates are a specific form of solvates; the solvent in this case being water.

The statements made hereinafter concerning suitable and preferred features of the invention, especially concerning the radicals A, B, $X^1$, $X^2$, $X^3$, $X^4$, $X^5$, $X^6$, $X^7$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, a, b, c, k, l, m, n, o and p in the compound I, but also concerning the features of the process of the invention and of the use according to the invention apply both taken on their own as well as preferably in any possible combination with one another.

The compounds I are preferably provided in the form of the free base (i.e. according to structural formula I) or in the form of their acid addition salts.

As a matter of course, each radical $R^3$, if present, replaces a hydrogen atom of the ring members $X^2$, $X^3$ and/or $X^4$, e.g. the hydrogen atom in $X^2$ if this is CH or the hydrogen atom(s) in the $CH_2$ or NH moieties of $X^3$ and/or $X^4$.

Alike, each radical $R^4$, if present, as well as the mandatory radical $R^5$ replace a hydrogen atom of the ring members $X^5$, $X^6$ and/or $X^7$, e.g. the hydrogen atom(s) in the $CH_2$ or NH moieties of $X^5$, $X^6$ and/or $X^7$.

$R^5$ can be bound to any of the ring members $X^5$, $X^6$ and/or $X^7$, but if $X^7$ is NH or $CH_2$, $R^5$ is preferably bound to $X^7$, where it replaces a hydrogen atom of this NH or $CH_2$ group $X^7$ (so that $X^7$ is $NR^5$ or $CHR^5$ or $C(R^4)R^5$).

If $X^3$, $X^4$, $X^5$, $X^6$ or $X^7$ are NH, preferably they do not carry an N-bound radical $R^3$, $R^4$ or $R^5$.

In a preferred embodiment, $X^1$ is NH or $CH_2$, and in particular NH.

In a preferred embodiment, $X^3$, $X^4$, $X^5$ and $X^6$, independently of each other, are selected from —$CH_2$— and —$CH_2CH_2$—.

In a preferred embodiment, $X^7$ is NH or $CH_2$, and in particular NH.

In a particular embodiment, if $X^2$ is CH, $X^1$ is simultaneously NH or O, especially NH.

A is preferably phenyl or pyridyl, in particular phenyl or 3-pyridyl, where A carries one substituent $R^6$ and optionally one substituent $R^7$.

In a preferred embodiment, A is phenyl or 3-pyridyl, and carries the radical $R^6$ in the 2-position and the radical $R^7$, if present, in the 4- or 5-position, relative to the 1-position of the attachment point of A to the remainder of the molecule.

In particular, A is phenyl or 3-pyridyl, and carries the radical $R^6$ in the 2-position, relative to the 1-position of the attachment point of A to the remainder of the molecule, and carries no radical $R^7$.

B is preferably phenyl or 2-pyridyl, where B may carry 1, 2 or 3 substituents $R^8$.

In case that B is 2-pyridyl and carries one substituent $R^8$, this is preferably bound in the 4-position, relative to the 1-position of the attachment point of B to the remainder of the molecule (i.e. to the sulfonyl group).

In case that B is phenyl and carries one substituent $R^8$, this is preferably bound in the 2- or 4-position, relative to the 1-position of the attachment point of B to the remainder of the molecule (i.e. to the sulfonyl group).

In case that B is 2-pyridyl and carries two substituents $R^8$, these are preferably bound in the 4- and 5- or 4- and 6-positions, relative to the 1-position of the attachment point of B to the remainder of the molecule (i.e. to the sulfonyl group).

In case that B is phenyl and carries two substituents $R^8$, these are preferably bound in the 2- and 4-positions, relative to the 1-position of the attachment point of B to the remainder of the molecule (i.e. to the sulfonyl group).

In case that B is phenyl and carries three substituents $R^8$, these are preferably bound in the 2-, 4- and 6-positions, relative to the 1-position of the attachment point of B to the remainder of the molecule (i.e. to the sulfonyl group).

$R^1$ is preferably selected from halogen and cyano, and in particular from cyano, fluorine and chlorine. Specifically, $R^1$ is cyano.

$R^2$ is preferably selected from hydrogen and halogen, and in particular from hydrogen and fluorine.

$R^3$ and $R^4$, independently of each other and independently of each occurrence, are preferably selected from halogen and $C_1$-$C_4$-alkyl, and in particular from F, Cl and $CH_3$, with the proviso that $R^3$ and $R^4$ are not halogen if they are bound to a carbon atom in α-position to a nitrogen ring atom; and are in particular $CH_3$.

$R^5$ is preferably selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkyl which carries one substituent $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and in case that $R^5$ is bound to a carbon ring atom, it is additionally selected from —$OR^{13}$; where $R^{11}$, $R^{12}$ and $R^{13}$ have one of the above general or, in particular, one of the below preferred meanings.

More preferably, $R^5$ is selected from hydrogen, $C_1$-$C_6$-alkyl, fluorinated $C_1$-$C_6$-alkyl, $C_1$-$C_6$-alkyl which carries one substituent $R^{11}$; a 3-, 4-, 5- or 6-membered saturated heteromonocyclic ring containing 1 or 2 heteroatoms or heteroatom groups selected from O, N, S, NO, SO and $SO_2$ as ring members; and a 7-, 8-, 9-, 10- or 11-membered saturated heterobicyclic ring containing 1 or 2 heteroatoms or heteroatom groups selected from O, N, S, NO, SO and $SO_2$ as ring members, where the heteromonocyclic or heterobicyclic ring may carry 1, 2 or 3 substituents $R^{12}$; and in case that $R^5$ is bound to a carbon ring atom, it is additionally selected from —OR$^{13}$; where R$^{11}$, R$^{12}$ and R$^{13}$ have one of the above general or, in particular, one of the below preferred meanings.

In particular, R$^5$ is selected from hydrogen, C$_1$-C$_4$-alkyl, C$_1$-C$_4$-alkyl which carries one substituent R$^{11}$; a 4-, 5- or 6-membered saturated heteromonocyclic ring containing 1 or 2 heteroatoms selected from O, N and S as ring members; and a 7-, 8-, 9-, 10- or 11-membered saturated heterobicyclic spiro ring containing 1 or 2 heteroatoms selected from O, N and S as ring members, where the heteromonocyclic or heterobicyclic ring may carry 1 or 2 substituents R$^{12}$; and in case that R$^5$ is bound to a carbon ring atom, it is additionally selected from —OR$^{13}$; where R$^{11}$, R$^{12}$ and R$^{13}$ have one of the above general or, in particular, one of the below preferred meanings.

The 4-, 5- or 6-membered saturated heteromonocyclic ring R$^5$ containing 1 or 2 heteroatoms selected from O, N and S as ring members is in particular selected from oxetan-3-yl, azetidin-3-yl, pyrrolidin-3-yl, piperidin-4-yl, piperazin-1-yl and morpholin-4-yl, and specifically from oxetan-3-yl, azetidin-3-yl, piperidin-4-yl, piperazin-1-yl and morpholin-4-yl.

The 7-, 8-, 9-, 10- or 11-membered saturated heterobicyclic spiro ring R$^5$ containing 1 or 2 heteroatoms selected from O, N and S as ring members is in particular selected from the following bicyclic radicals:

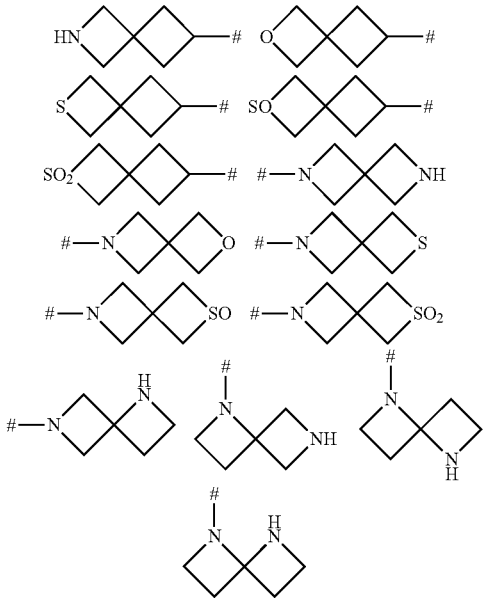

and is specifically

R$^{11}$ is preferably selected from cyano, —OR$^{13}$; NR$^{14}$R$^{15}$; a 3-, 4-, 5-, 6- or 7-membered saturated heteromonocyclic ring containing 1, 2 or 3 heteroatoms or heteroatom groups selected from O, N, S, NO, SO and SO$_2$ as ring members, and a 5-, 6-, 7-, 8-, 9-, 10- or 11-membered saturated heterobicyclic ring containing 1, 2 or 3 heteroatoms or heteroatom groups selected from O, N, S, NO, SO and SO$_2$ as ring members, where the heteromoncyclic or heterobicyclic ring may carry 1, 2 or 3 substituents R$^{12}$; and as a substituent on a cycloalkyl ring, R$^{11}$ is additionally selected from C$_1$-C$_4$-alkyl and C$_1$-C$_4$-haloalkyl; where R$^{12}$, R$^{13}$, R$^{14}$ and R$^{15}$ have one of the above general or, in particular, one of the below preferred meanings.

In particular, R$^{11}$ is selected from NR$^{14}$R$^{15}$, where R$^{14}$ and R$^{15}$ are independently selected from hydrogen and C$_1$-C$_4$-alkyl; and a 4-, 5- or 6-membered saturated heteromonocyclic ring containing 1 or 2 heteroatoms or heteroatom groups selected from O, N, S, NO, SO and SO$_2$ as ring members, where the heteromonocyclic ring may carry 1 or 2 or 3 substituents R$^{12}$, where R$^{12}$ has one of the above general or, in particular, one of the below preferred meanings.

The 4-, 5- or 6-membered saturated heteromonocyclic ring R$^{11}$ containing 1 or 2 heteroatoms selected from O, N, S, NO, SO and SO$_2$ as ring members is in particular selected from oxetan-3-yl, azetidin-1-yl, azetidin-3-yl, pyrrolidin-1-yl, pyrrolidin-3-yl, piperidin-1-yl, piperidin-4-yl, piperazin-1-yl, and morpholin-4-yl, and specifically from piperidin-1-yl, piperazin-1-yl and morpholin-4-yl.

R$^{12}$ is preferably selected from halogen, cyano, C$_1$-C$_4$-alkyl, fluorinated C$_1$-C$_4$-alkyl, C$_1$-C$_4$-alkoxy, fluorinated C$_1$-C$_4$-alkoxy, phenyl which may carry 1, 2 or 3 substituents selected from halogen, hydroxyl, cyano, C$_1$-C$_4$-alkyl, fluorinated C$_1$-C$_4$-alkyl, C$_1$-C$_4$-alkoxy and fluorinated C$_1$-C$_4$-alkoxy; and a 3-, 4-, 5- or 6-membered saturated heteromonocyclic ring containing 1, 2 or 3 heteroatoms or heteroatom groups selected from O, N, S, NO, SO and SO$_2$ as ring members, where the heteromonocyclic ring may carry 1, 2 or 3 substituents selected from halogen, hydroxyl, cyano, C$_1$-C$_4$-alkyl, fluorinated C$_1$-C$_4$-alkyl, C$_1$-C$_4$-alkoxy and fluorinated C$_1$-C$_4$-alkoxy, and in particular from C$_1$-C$_4$-alkyl, fluorinated C$_1$-C$_4$-alkyl, and a 3-, 4-, 5- or 6-membered saturated heteromonocyclic ring containing 1 or 2 heteroatoms selected from O, N and S as ring members.

The 3-, 4-, 5- or 6-membered saturated heteromonocyclic ring R$^{12}$ is in particular selected from oxetan-3-yl, azetidin-3-yl, pyrrolidin-3-yl, piperidin-4-yl, piperazin-1-yl, and morpholin-4-yl, and is specifically from oxetan-3-yl.

R$^{13}$ is preferably selected from hydrogen, C$_1$-C$_4$-alkyl, C$_1$-C$_4$-haloalkyl and C$_1$-C$_4$-alkyl which carries one substituent R$^{17}$; and is in particular C$_1$-C$_4$-alkyl which carries one substituent R$^{17}$; where R$^{17}$ has one of the above general or, in particular, one of the below preferred meanings.

R$^{17}$ is preferably selected from NR$^{14}$R$^{15}$; phenyl which may carry 1, 2 or 3 substituents R$^{12}$; and a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and SO$_2$ as ring members; where R$^{14}$ and R$^{15}$ have one of the above general or, in particular, one of the below preferred meanings. More preferably R$^{17}$ is a 3-, 4-, 5- or 6-membered saturated heteromonocyclic ring containing 1, 2 or 3 heteroatoms or heteroatom groups selected from O, N, S, NO, SO and SO$_2$ as ring members, and in particular a 6-membered saturated heteromonocyclic ring containing 1 or 2 heteroatoms or heteroatom groups selected from O, N and S, such as piperidin-1-yl, piperazin-1-yl or, especially, morpholin-4-yl.

R$^6$ is preferably C$_1$-C$_3$-alkoxy, preferably methoxy, ethoxy or isopropoxy; and in particular methoxy or ethoxy.

R$^7$ is preferably halogen or C$_1$-C$_3$-alkoxy, in particular fluorine or methoxy.

Preferably each R$^8$ is independently selected from halogen, cyano, C$_1$-C$_3$-alkyl, fluorinated C$_1$-C$_3$-alkyl, C$_1$-C$_3$-alkoxy and fluorinated C$_1$-C$_3$-alkoxy, more preferably from fluorine, cyano, methyl, methoxy and trifluoromethoxy, and in particular from fluorine, cyano, methyl and methoxy.

Preferably, a is 0 or 1, and in particular 0.
Preferably, b is 0 or 1, and in particular 0.

In a particular embodiment, the compound of formula I is a compound of formula IA

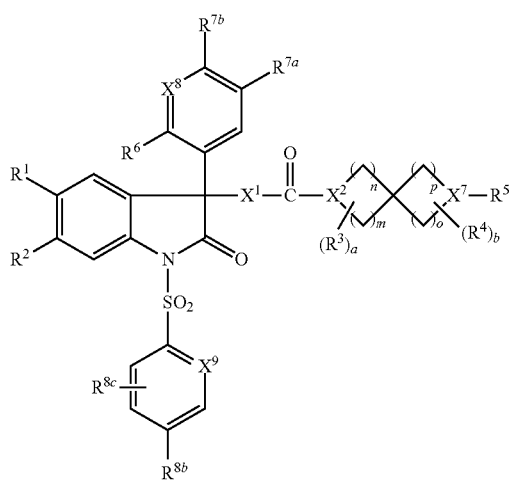

(IA)

where
$X^1$, $X^2$, $X^7$, $R^1$, $R^2$, $R^3$, $R^4$, $R^5$, $R^6$, a and b have one of the above general or, in particular, one of the above preferred definitions (to be however more precise, $X^7$ is CH or N);
$X^8$ is N or CH;
$X^9$ is N or C—$R^{8a}$;
$R^{7a}$ and $R^{7b}$, independently of each other, are hydrogen or have one of the general or, in particular, one of the preferred definitions given above for $R^7$; and are in particular hydrogen;
$R^{8a}$, $R^{8b}$ and $R^{8c}$, independently of each other, are hydrogen or have one of the general or, in particular, one of the preferred definitions given above for $R^8$; and
m, n, o and p are independently of each other 1 or 2.

Preferably, m and n are both 1 or are both 2.
Preferably, o and p are both 1 or are both 2.

The invention preferably relates to compounds of the formula 1A in which
$X^1$ is NH or $CH_2$;
$X^2$ is N or CH;
$X^7$ is N or CH;
$X^8$ is N or CH;
$X^9$ is N or $CR^{8a}$;
$R^1$ is halogen or cyano;
$R^2$ is hydrogen or halogen;
$R^3$ and $R^4$, independently of each other and independently of each occurrence, are selected from halogen and $C_1$-$C_4$-alkyl, with the proviso that $R^3$ and $R^4$ are not halogen if they are bound to a carbon atom in α-position to a nitrogen ring atom; and are in particular $CH_3$;
$R^5$ is selected from hydrogen, $C_1$-$C_6$-alkyl, fluorinated $C_1$-$C_6$-alkyl, $C_3$-$C_6$-cycloalkyl, fluorinated $C_3$-$C_6$-cycloalkyl, $C_1$-$C_6$-alkyl which carries one substituent $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and in case that $X^7$ is CH, $R^5$ is additionally selected from —$OR^{13}$;
$R^6$ is $C_1$-$C_3$-alkoxy;
$R^{7a}$ and $R^{7b}$, independently of each other, are hydrogen, halogen or $C_1$-$C_3$-alkoxy;
$R^{8a}$ (if present), $R^{8b}$ and $R^{8c}$, independently of each other, are selected from hydrogen, halogen, cyano, $C_1$-$C_3$-alkyl, fluorinated $C_1$-$C_3$-alkyl, $C_1$-$C_3$-alkoxy and fluorinated $C_1$-$C_3$-alkoxy;
$R^{11}$ is selected from cyano, —$OR^{13}$; $NR^{14}R^{15}$; a 3-, 4-, 5-, 6- or 7-membered saturated heteromonocyclic ring containing 1, 2 or 3 heteroatoms or heteroatom groups selected from O, N, S, NO, SO and $SO_2$ as ring members, and a 5-, 6-, 7-, 8-, 9-, 10- or 11-membered saturated heterobicyclic ring containing 1, 2 or 3 heteroatoms or heteroatom groups selected from O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally selected from $C_1$-$C_4$-alkyl and $C_1$-$C_4$-haloalkyl;
$R^{12}$ is selected from halogen, cyano, $C_1$-$C_4$-alkyl, fluorinated $C_1$-$C_4$-alkyl, $C_1$-$C_4$-alkoxy, fluorinated $C_1$-$C_4$-alkoxy, phenyl which may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy; and a 3-, 4-, 5- or 6-membered saturated heteromonocyclic ring containing 1, 2 or 3 heteroatoms or heteroatom groups selected from O, N, S, NO, SO and $SO_2$ as ring members, where the heteromonocyclic ring may carry 1, 2 or 3 substituents selected from halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy;
$R^{13}$ is selected from hydrogen, $C_1$-$C_4$-alkyl, $C_1$-$C_4$-haloalkyl and $C_1$-$C_4$-alkyl which carries one substituent $R^{17}$;
$R^{14}$ and $R^{15}$, independently of each other, are selected from hydrogen and $C_1$-$C_4$-alkyl;
$R^{17}$ is selected from $NR^{14}R^{15}$; phenyl which may carry 1, 2 or 3 substituents $R^{12}$; and a 3-, 4-, 5-, 6- or 7-membered saturated, partially unsaturated or maximally unsaturated heteromonocyclic ring containing 1, 2 or 3 heteroatoms or heteroatom groups selected from O, N, S, NO, SO and $SO_2$ as ring members;
a is 0 or 1;
b is 0 or 1;
m and n are both 1 or are both 2; and
o and p are both 1 or are both 2.

The invention more preferably relates to compounds of the formula IA in which
$X^1$ is NH or $CH_2$;
$X^2$ is N or CH;
$X^7$ is N or CH;
$X^8$ is N or CH;
$X^9$ is N or $CR^{8a}$;
$R^1$ is cyano, fluorine or chlorine;
$R^2$ is hydrogen or fluorine;
$R^5$ is selected from hydrogen, $C_1$-$C_6$-alkyl, fluorinated $C_1$-$C_6$-alkyl, $C_1$-$C_6$-alkyl which carries one substituent $R^{11}$; a 3-, 4-, 5- or 6-membered saturated heteromonocyclic ring containing 1 or 2 heteroatoms or heteroatom groups selected from O, N, S, NO, SO and $SO_2$ as ring members; and a 7-, 8-, 9-, 10- or 11-membered saturated heterobicyclic ring containing 1 or 2 heteroatoms or heteroatom groups selected from O, N, S, NO, SO and SO$_2$ as ring members, where the heteromonocyclic or heterobicyclic ring may carry 1, 2 or 3 substituents R$^{12}$; and in case that X$^7$ is CH, R$^5$ is additionally selected from —OR$^{13}$;

R$^6$ is methoxy, ethoxy or isopropoxy;

R$^{7a}$ and R$^{7b}$, independently of each other, are hydrogen, fluorine or methoxy;

R$^{8a}$ (if present), R$^{8b}$ and R$^{8c}$, independently of each other, are selected from hydrogen, fluorine, cyano, methyl, methoxy and trifluoromethoxy;

R$^{11}$ is selected from NR$^{14}$R$^{15}$ and a 4-, 5- or 6-membered saturated heteromonocyclic ring containing 1 or 2 heteroatoms or heteroatom groups selected from O, N, S, NO, SO and SO$_2$ as ring members, where the heteromonocyclic ring may carry 1 or 2 or 3 substituents R$^{12}$;

R$^{12}$ is selected from C$_1$-C$_4$-alkyl, fluorinated C$_1$-C$_4$-alkyl, and a 3-, 4-, 5- or 6-membered saturated heteromonocyclic ring containing 1 or 2 heteroatoms selected from O, N and S as ring members;

R$^{13}$ is selected C$_1$-C$_4$-alkyl which carries one substituent R$^{17}$;

R$^{14}$ and R$^{15}$ are independently selected from hydrogen and C$_1$-C$_4$-alkyl;

R$^{17}$ is a 3-, 4-, 5- or 6-membered saturated heteromonocyclic ring containing 1, 2 or 3 heteroatoms or heteroatom groups selected from O, N, S, NO, SO and SO$_2$ as ring members;

a is 0;
b is 0;
m and n are both 1 or are both 2; and
o and p are both 1 or are both 2.

In particular, the invention relates to compounds of the formula IA in which
X$^1$ is NH or CH$_2$;
X$^2$ is N or CH;
X$^7$ is N or CH;
X$^8$ is N or CH;
X$^9$ is N or CR$^{8a}$;
R$^1$ is cyano;
R$^2$ is hydrogen or fluorine;
R$^5$ is selected from hydrogen, C$_1$-C$_4$-alkyl, C$_1$-C$_4$-alkyl which carries one substituent R$^{11}$; a 4-, 5- or 6-membered saturated heteromonocyclic ring containing 1 or 2 heteroatoms selected from O, N and S as ring members; and a 7-, 8-, 9-, 10- or 11-membered saturated heterobicyclic spiro ring containing 1 or 2 heteroatoms selected from O, N and S as ring members, where the heteromonocyclic or heterobicyclic ring may carry 1 or 2 substituents R$^{12}$; and in case that X$^7$ is CH, R$^5$ is additionally selected from —OR$^{13}$;

R$^6$ is methoxy or ethoxy;
R$^{7a}$ and R$^{7b}$ are hydrogen;
R$^{8a}$ (if present) and R$^{8b}$, independently of each other, are selected from hydrogen, fluorine, cyano, methyl and methoxy;
R$^{8c}$ is hydrogen;
R$^{11}$ is selected from NR$^{14}$R$^{15}$ and a 4-, 5- or 6-membered saturated heteromonocyclic ring containing 1 or 2 heteroatoms or heteroatom groups selected from O, N, S, NO, SO and SO$_2$ as ring members, where the heteromonocyclic ring may carry 1 or 2 or 3 substituents R$^{12}$;
R$^{12}$ is selected from C$_1$-C$_4$-alkyl, fluorinated C$_1$-C$_4$-alkyl, and a 3-, 4-, 5- or 6-membered saturated heteromonocyclic ring containing 1 or 2 heteroatoms selected from O, N and S as ring members;

R$^{13}$ is selected C$_1$-C$_4$-alkyl which carries one substituent R$^{17}$;

R$^{14}$ and R$^{15}$ are independently selected from hydrogen and C$_1$-C$_4$-alkyl;

R$^{17}$ is a 6-membered saturated heteromonocyclic ring containing 1 or 2 heteroatoms or heteroatom groups selected from O, N and S;

a is 0;
b is 0;
m and n are both 1 or are both 2; and
o and p are both 1 or are both 2.

Examples of preferred embodiments of the present invention are compounds of the formulae I.1 to I.128 and the N-oxides, stereoisomers (inclusively the conformers) and the pharmaceutically acceptable salts thereof, in which the radicals X$^1$, R$^1$, R$^2$, R$^5$, R$^{8a}$, R$^{8b}$ and R$^{8c}$ have one of the above general or preferred meanings. In particular, preferred compounds are the individual compounds compiled in the tables 1 to 53760 below.

Moreover, the meanings mentioned below for the individual variables in the tables are per se, independently of the combination in which they are mentioned, a particularly preferred embodiment of the substituents in question.

I.1

I.2

-continued
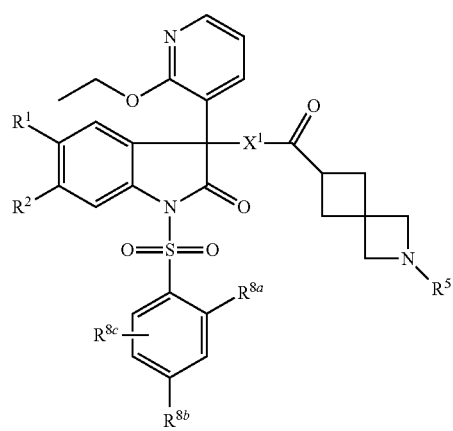
I.3
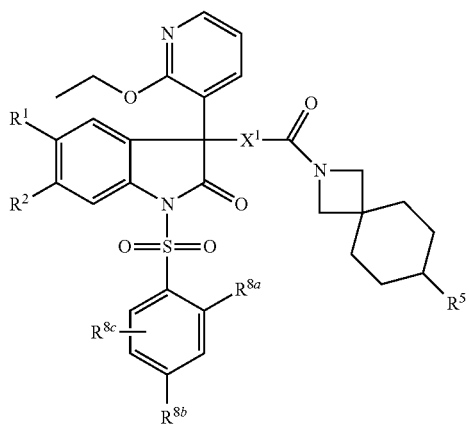
I.6
I.4
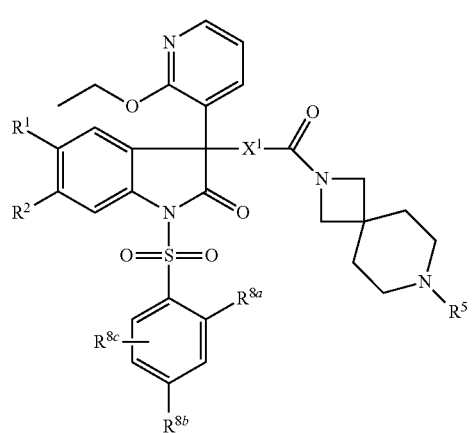
I.7
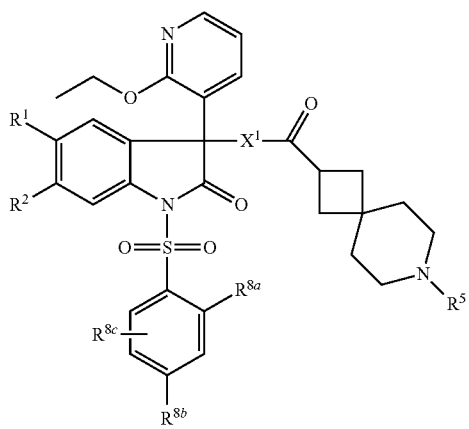
I.5
I.8

I.9
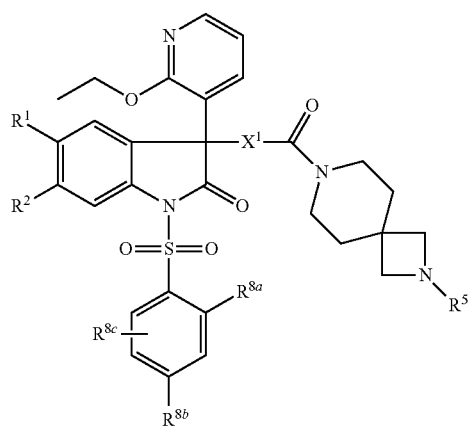
I.10
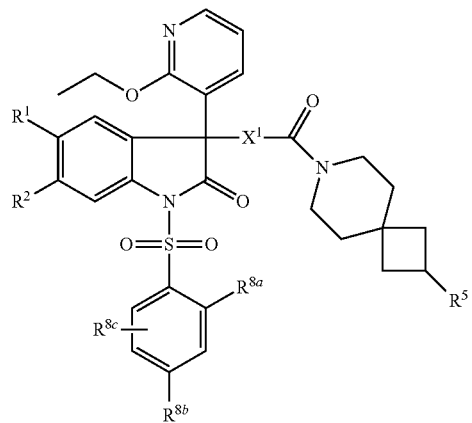
I.11
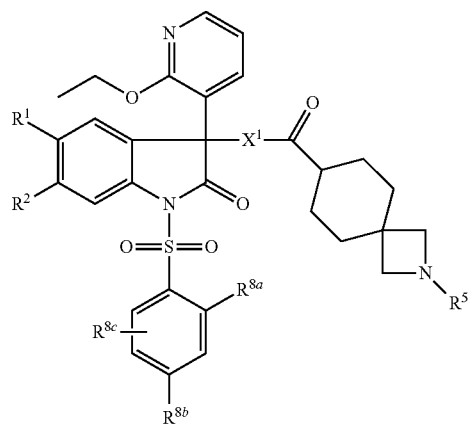
I.12
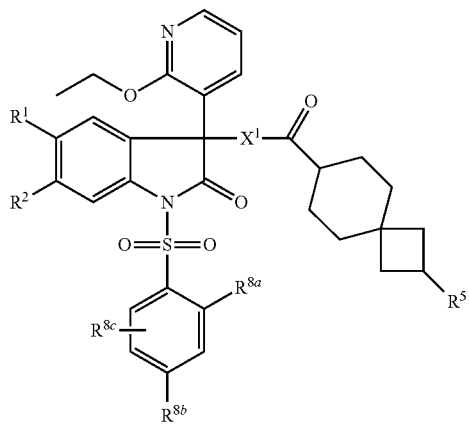
I.13
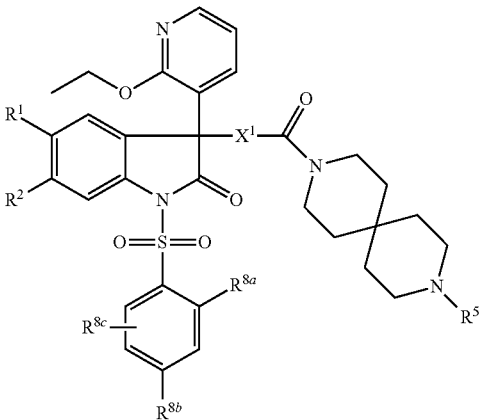
I.14
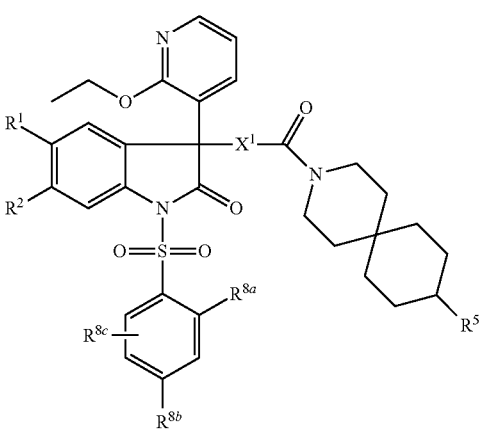

I.15
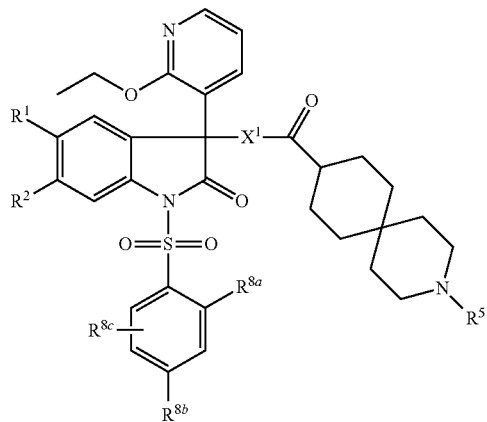
I.16
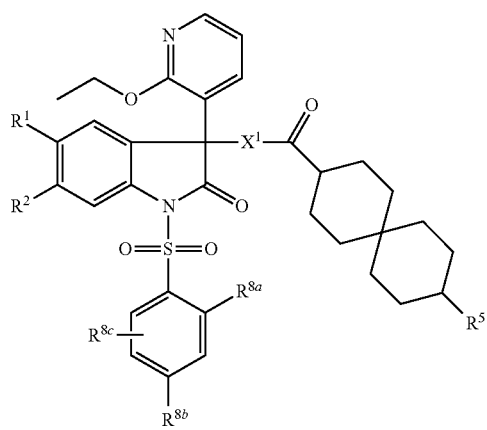
I.17
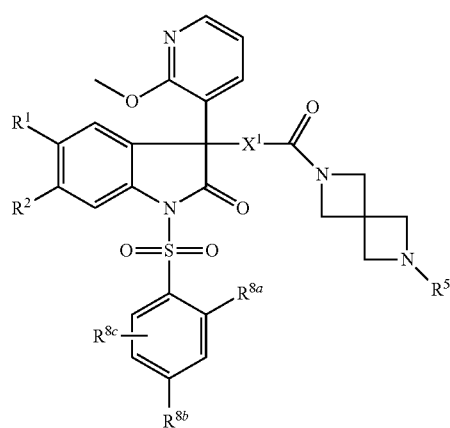
I.18
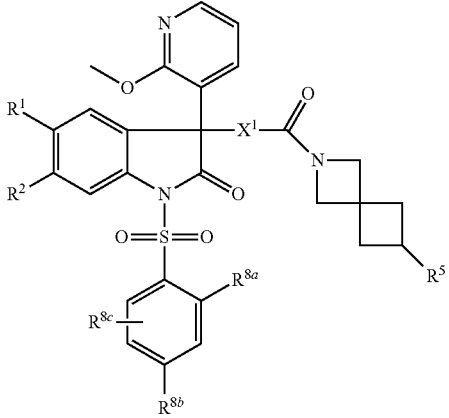
I.19
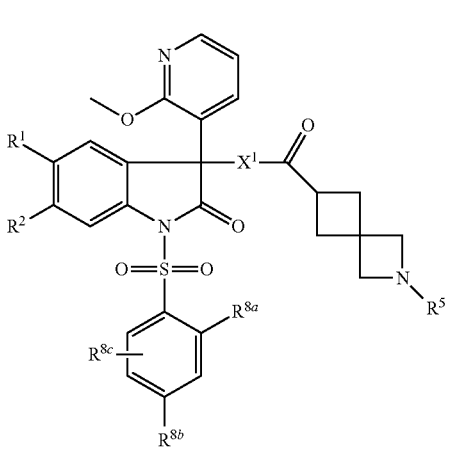
I.20
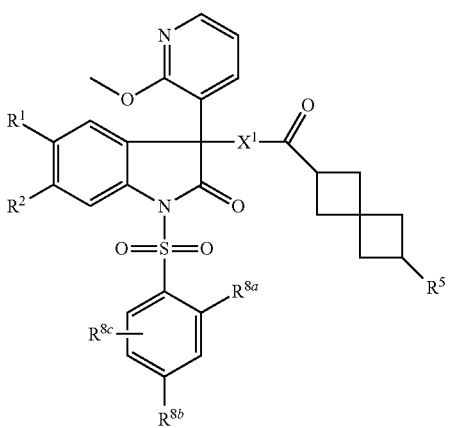

-continued
I.21
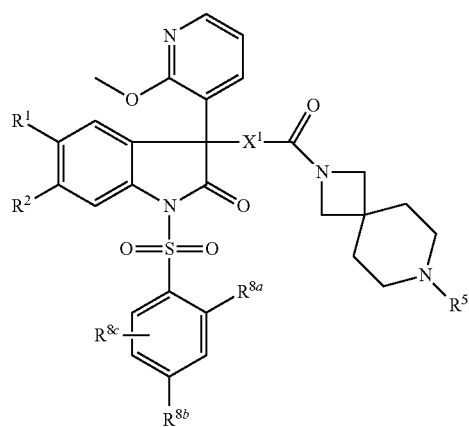
I.24
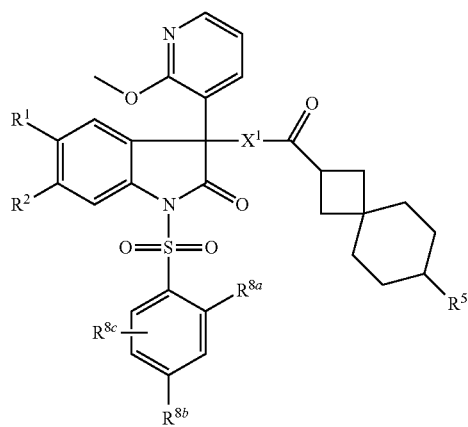
I.22
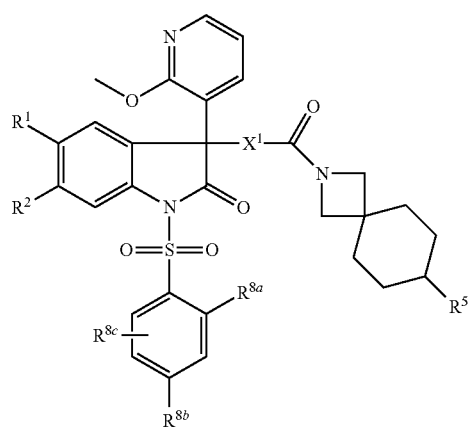
I.25
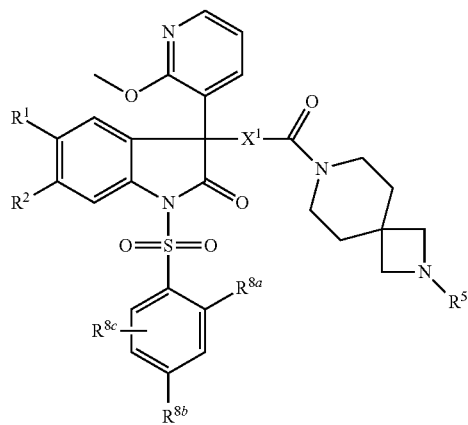
I.23
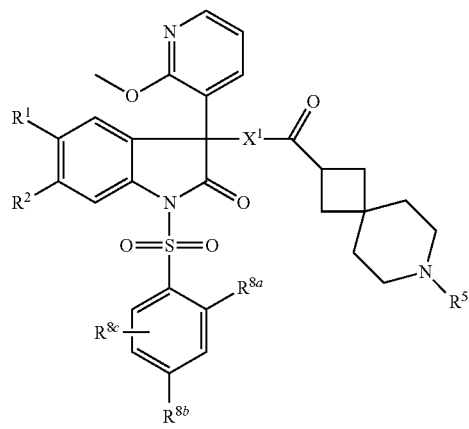
I.26
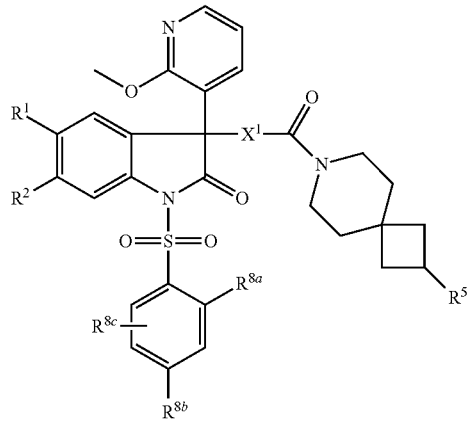

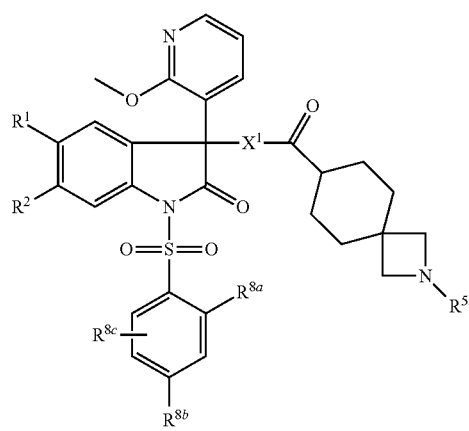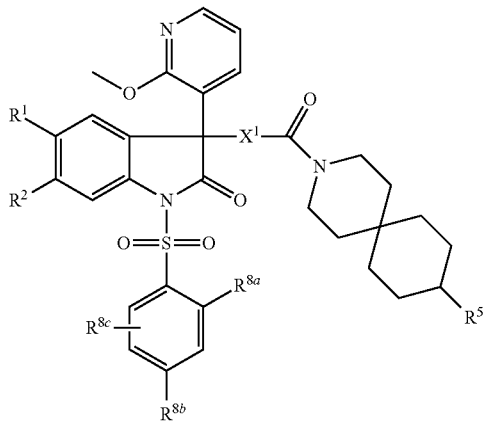

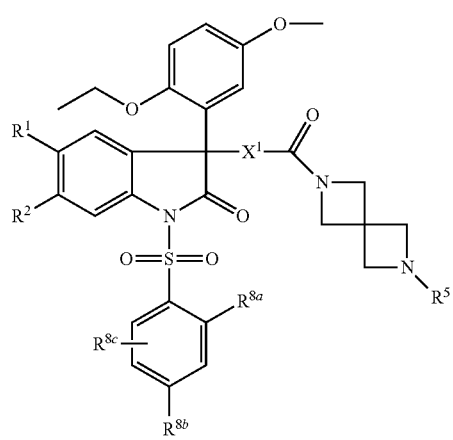
I.33
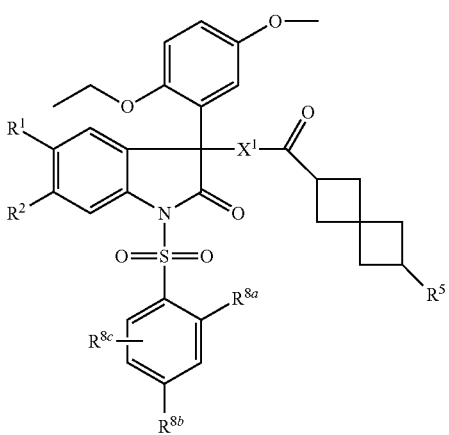
I.36
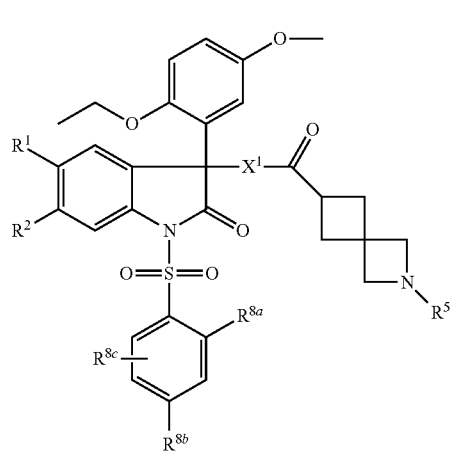
I.34
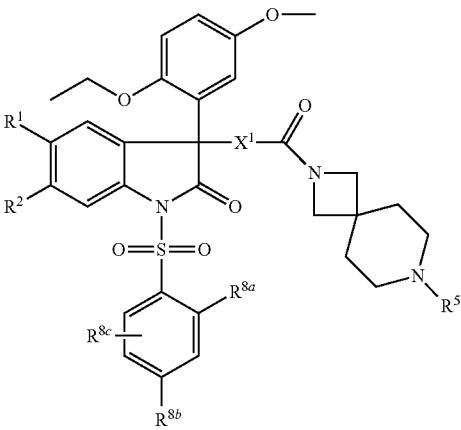
I.37
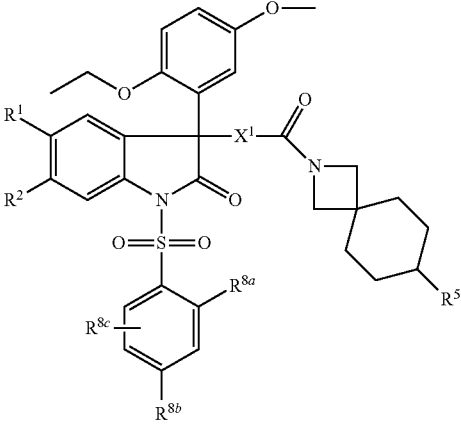
I.35
I.38

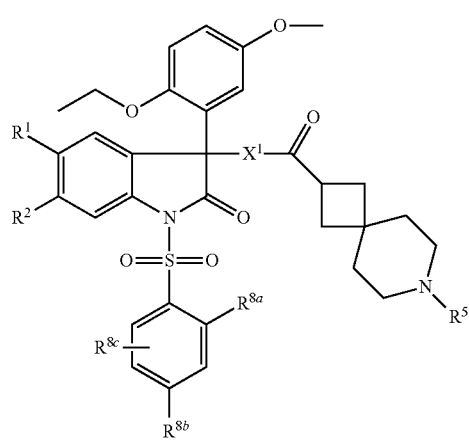
I.39
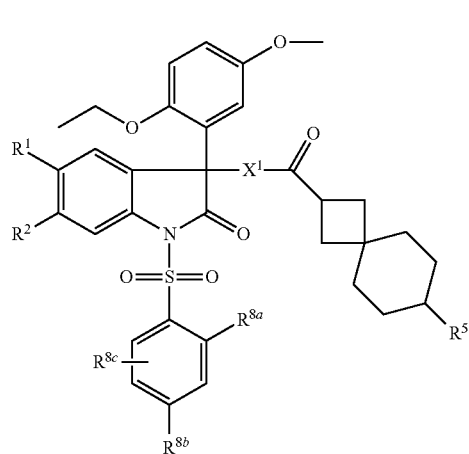
I.40
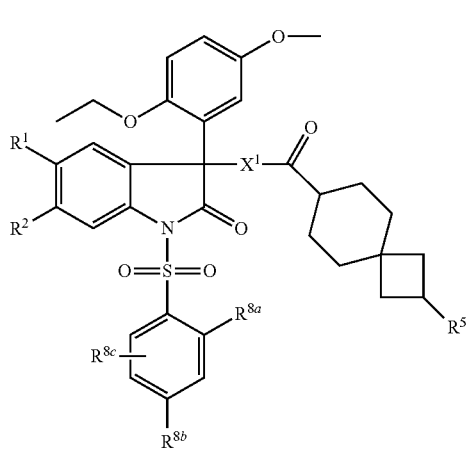
I.41
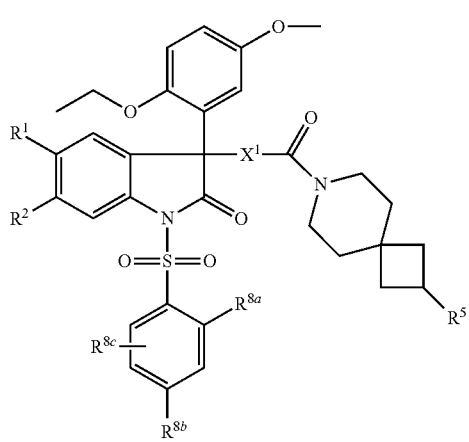
I.42
I.43
I.44

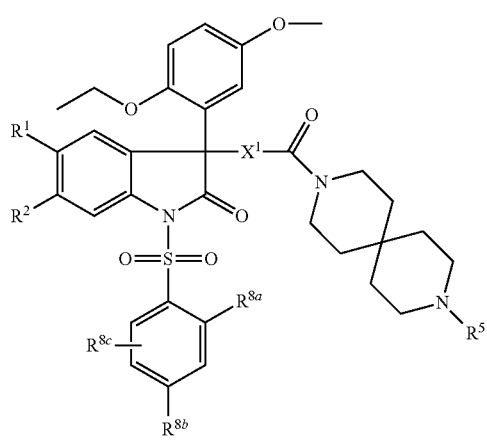
I.45
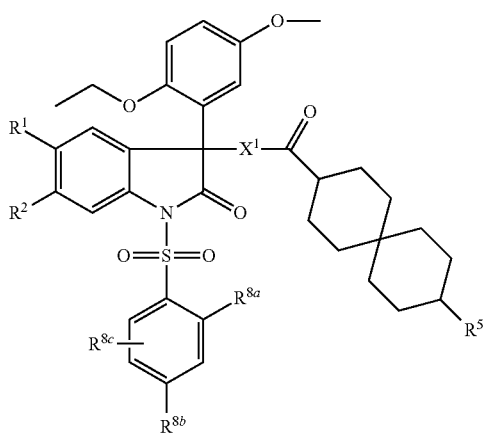
I.48
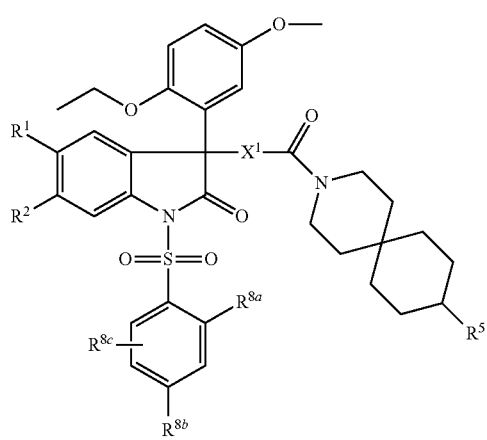
I.46
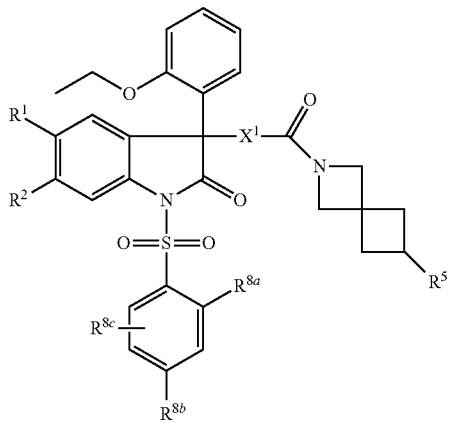
I.49
I.47
I.50

I.51
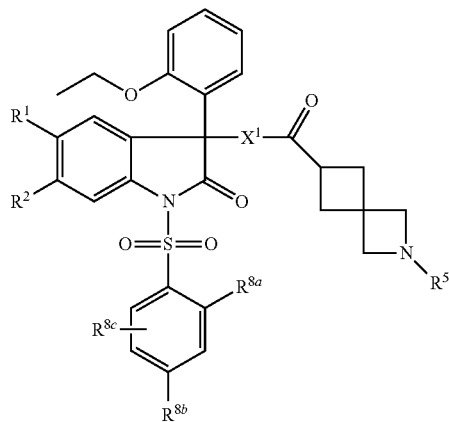
I.52
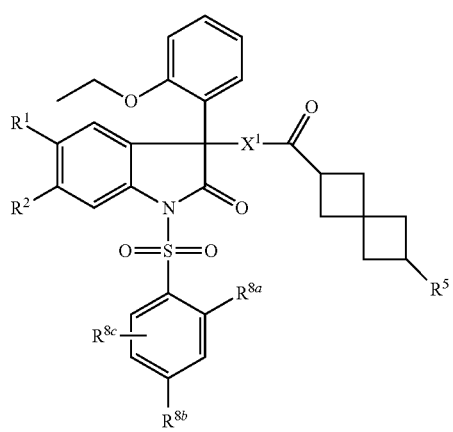
I.53
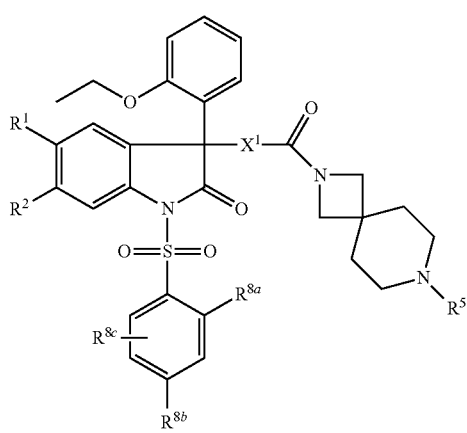
I.54
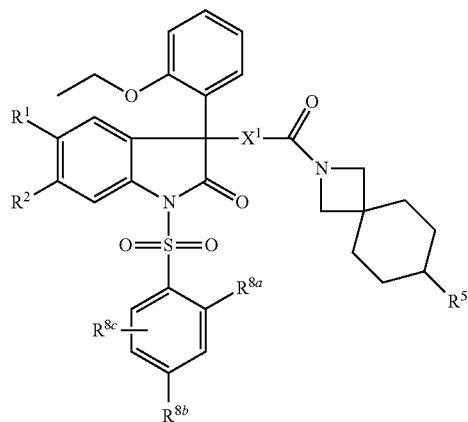
I.55
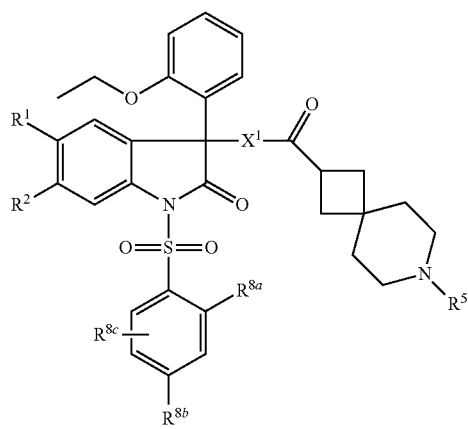
I.56
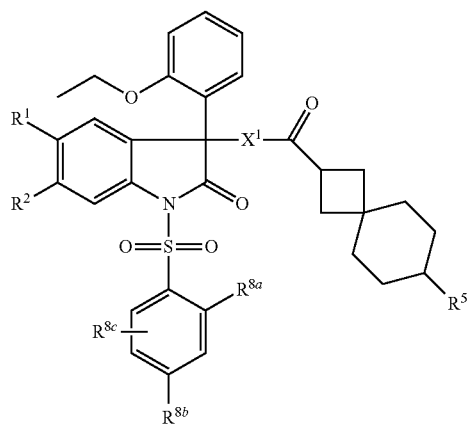

I.57
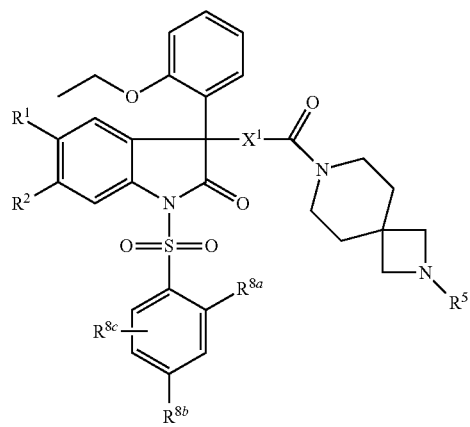
I.58
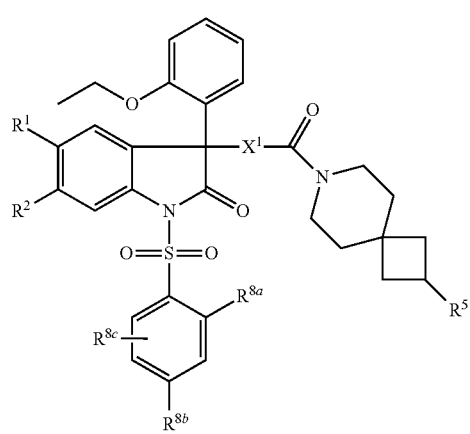
I.59
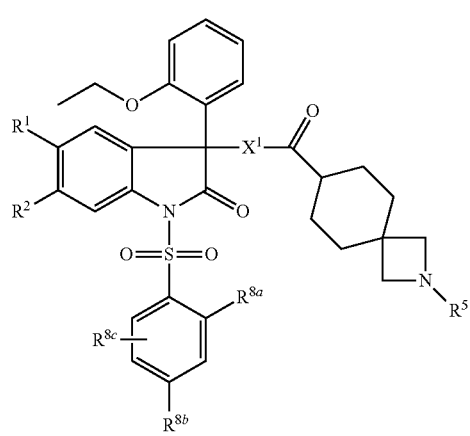
I.60
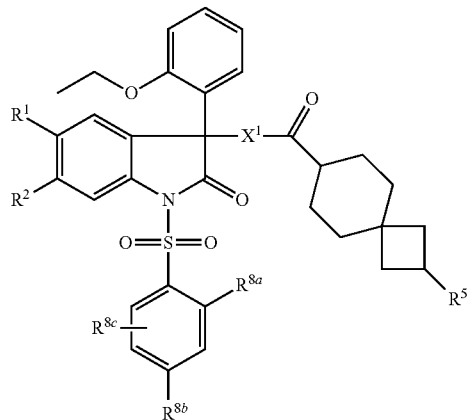
I.61
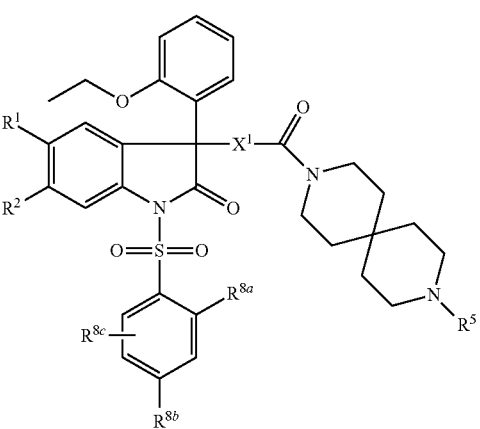
I.62
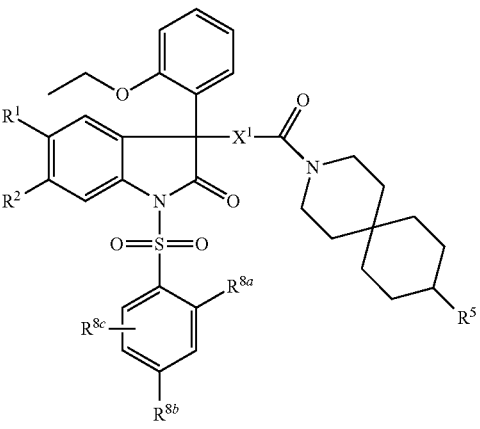

-continued
I.63
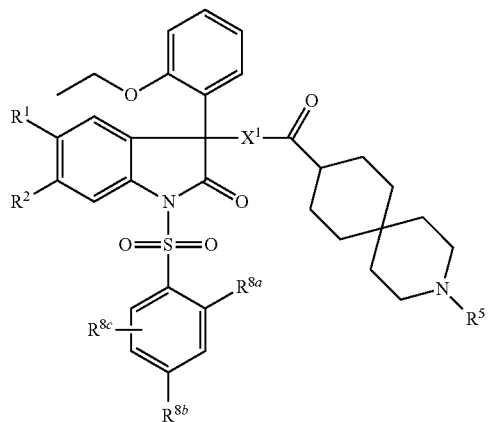
I.64
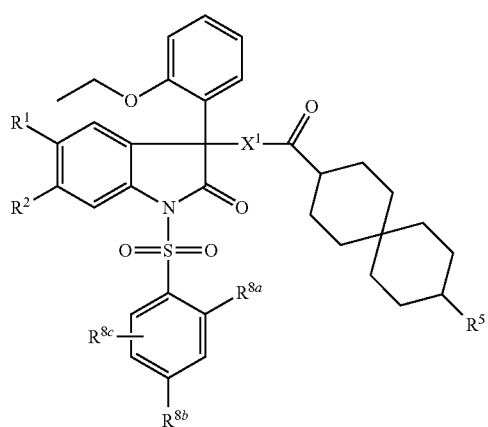
I.65
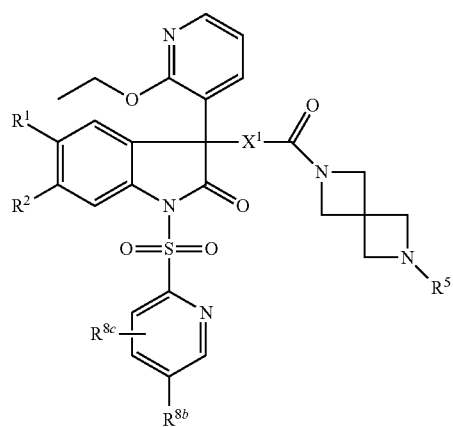
-continued
I.66
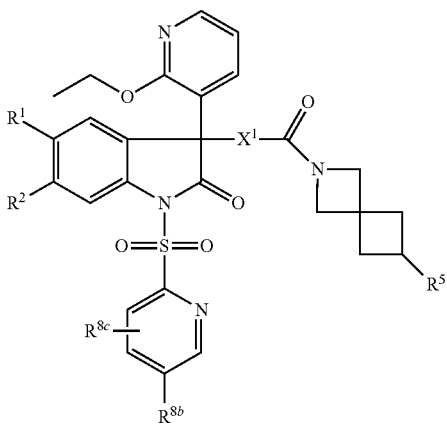
I.67
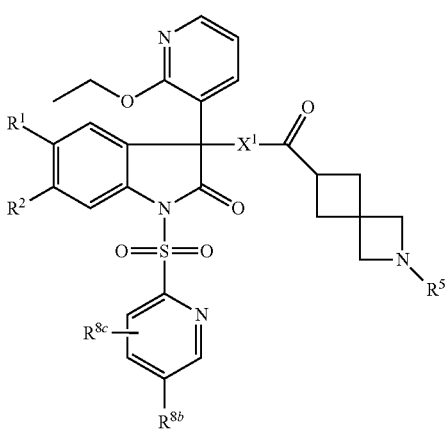
I.68
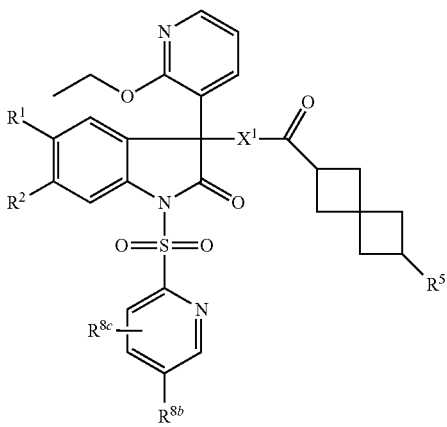

I.69
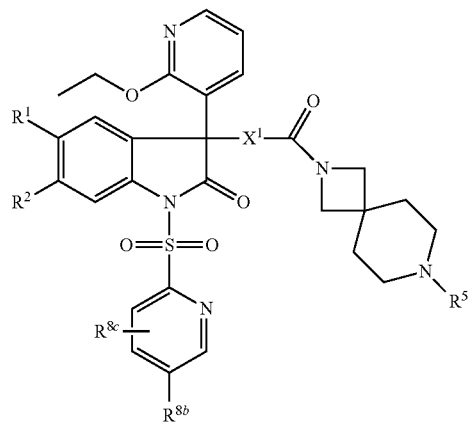
I.72
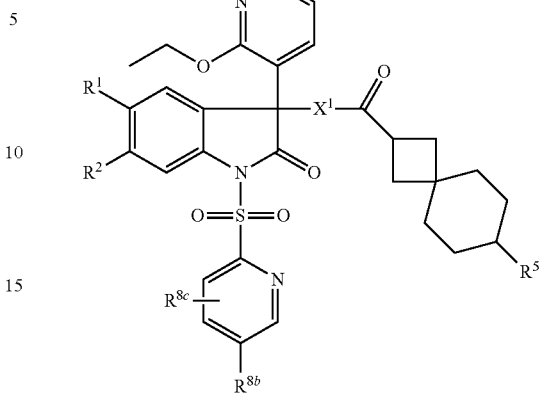
I.70
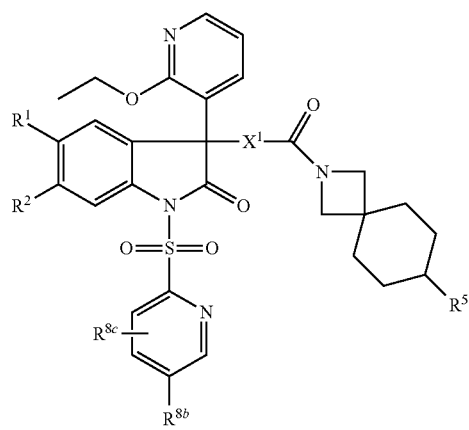
I.73
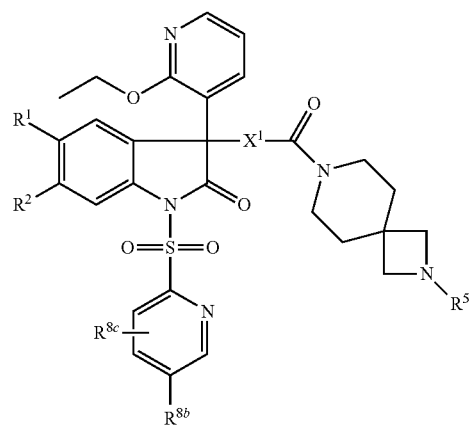
I.71
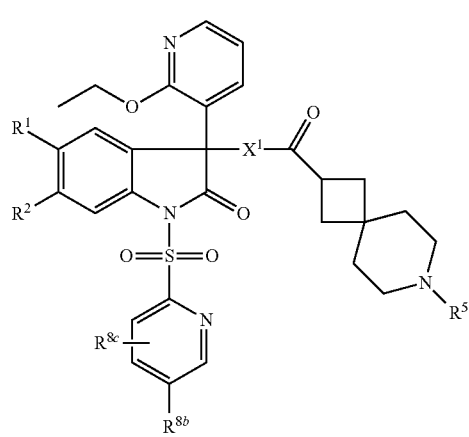
I.74
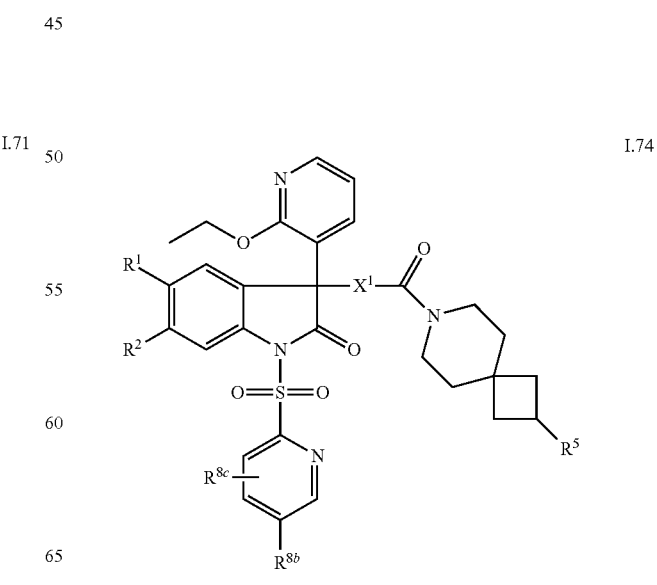

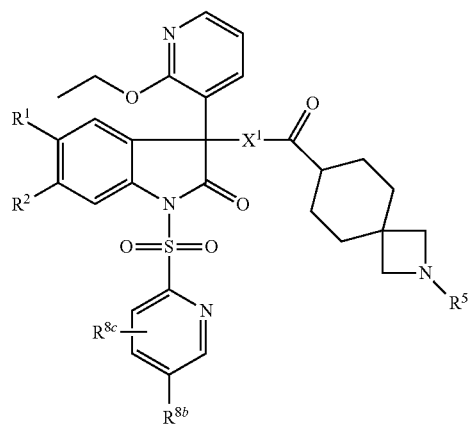
I.75
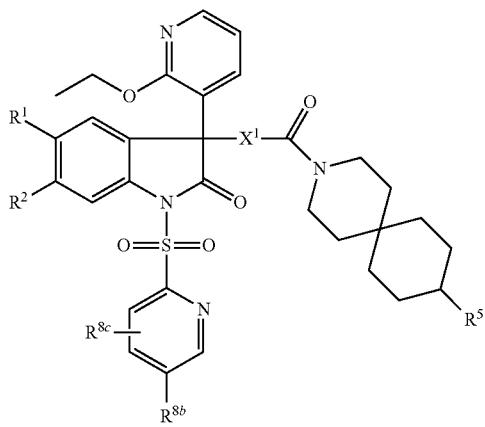
I.78
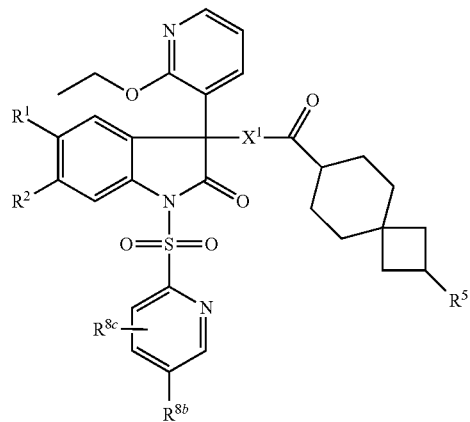
I.76
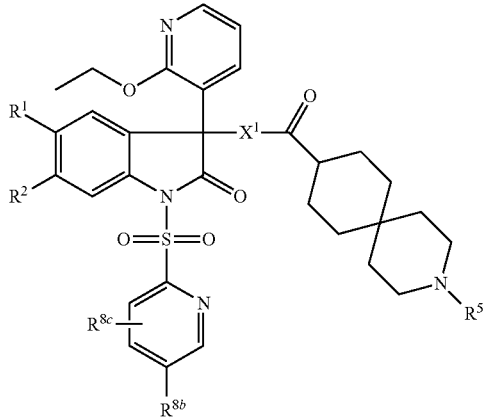
I.79
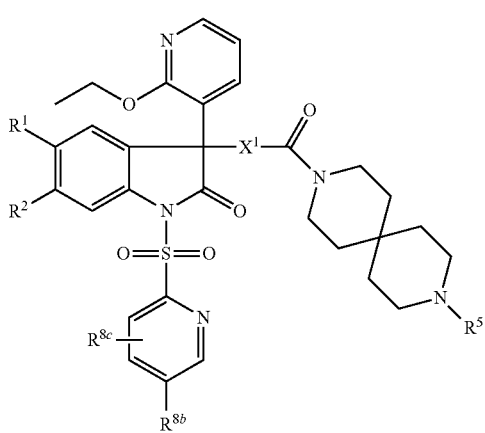
I.77
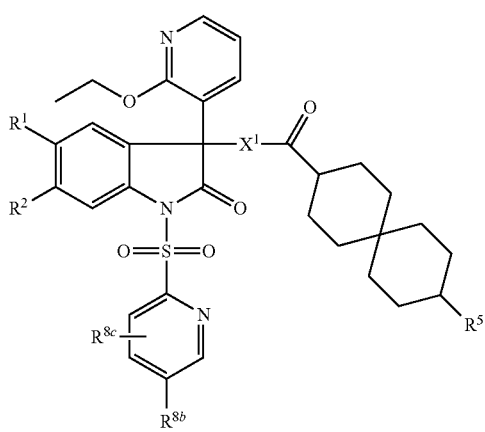
I.80

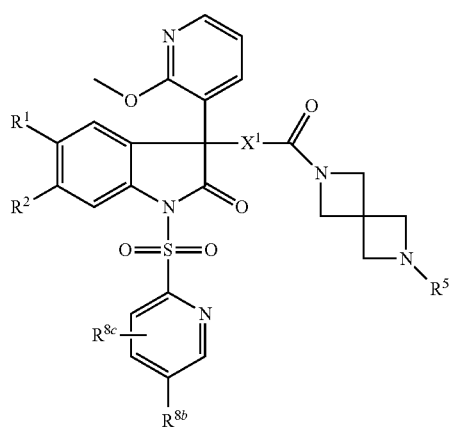
I.81
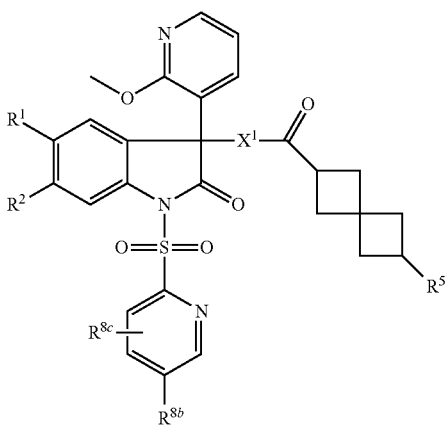
I.84
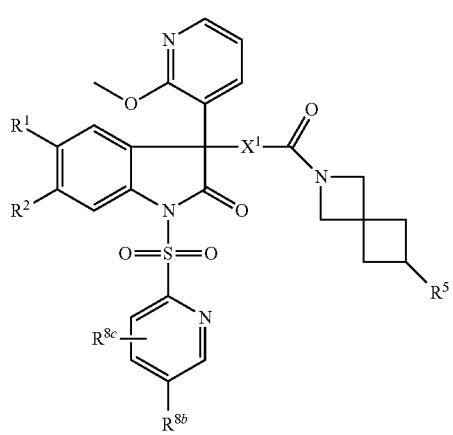
I.82
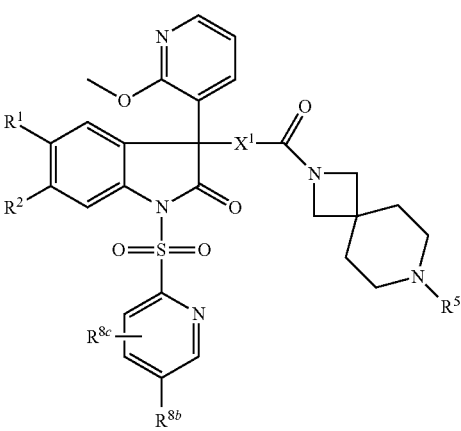
I.85
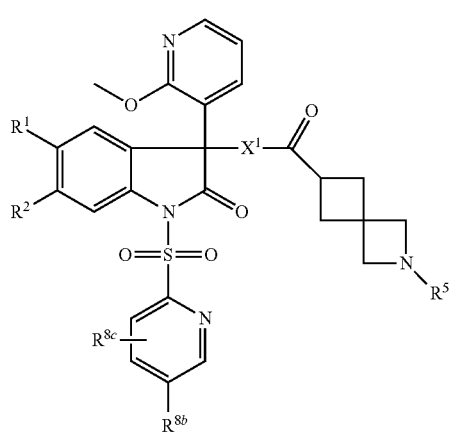
I.83
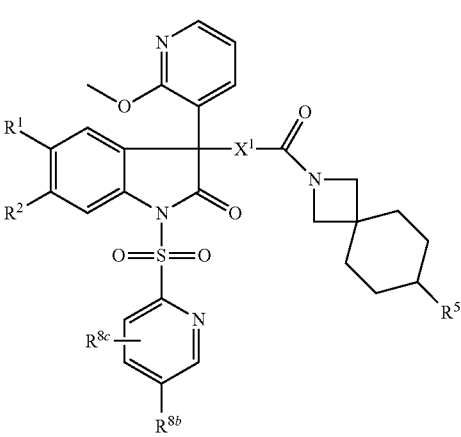
I.86

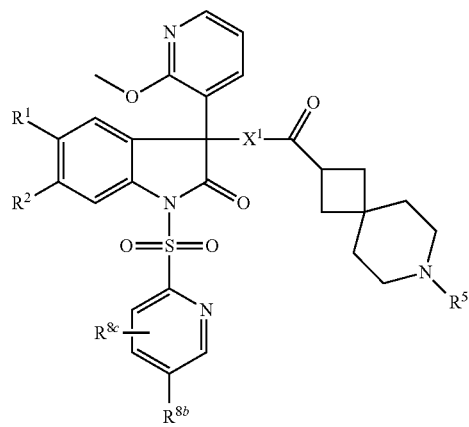
I.87
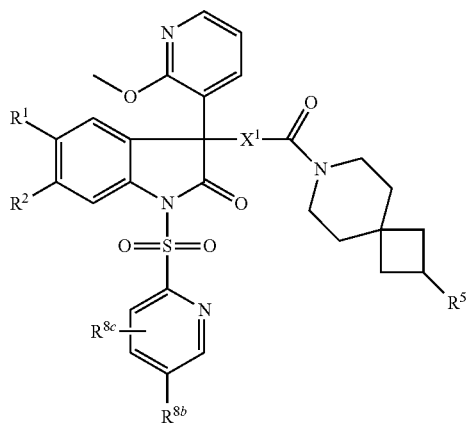
I.90
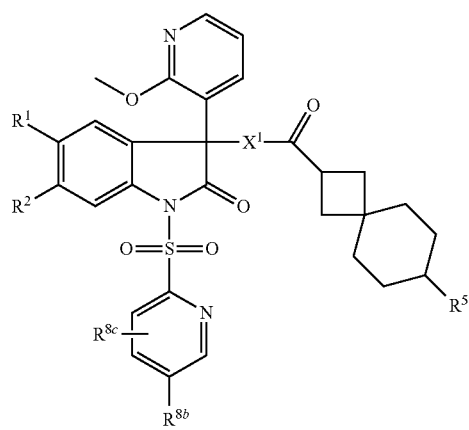
I.88
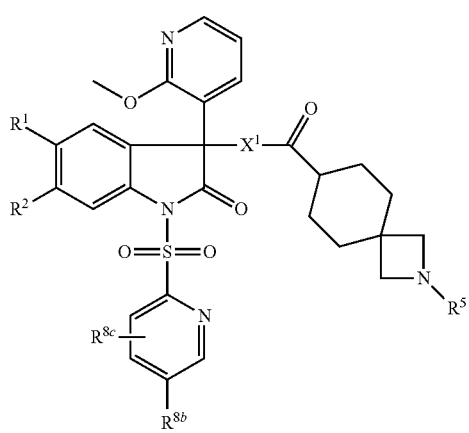
I.91
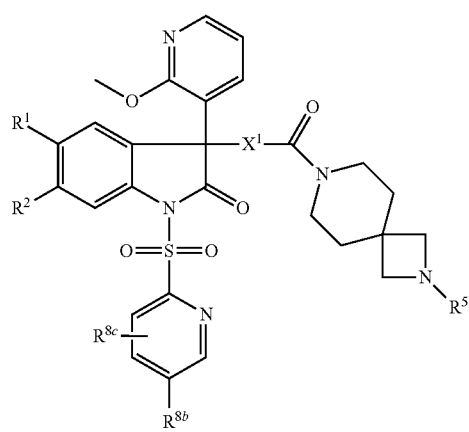
I.89
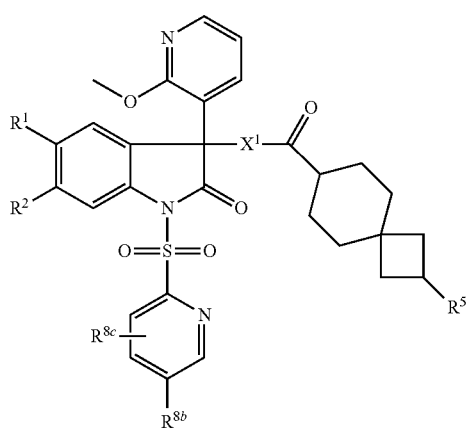
I.92

I.93
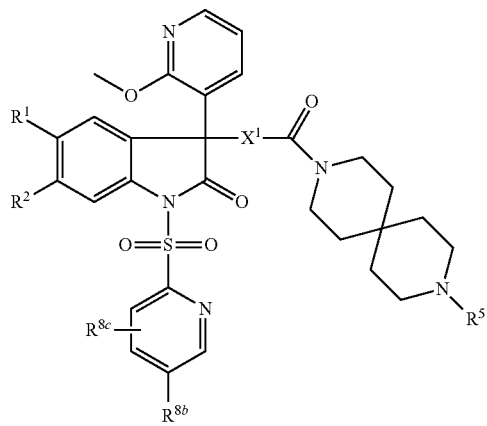
I.94
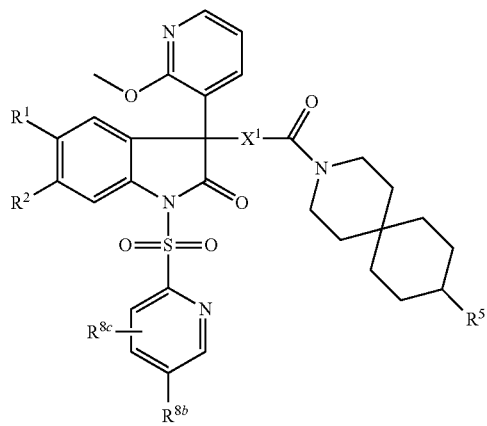
I.95
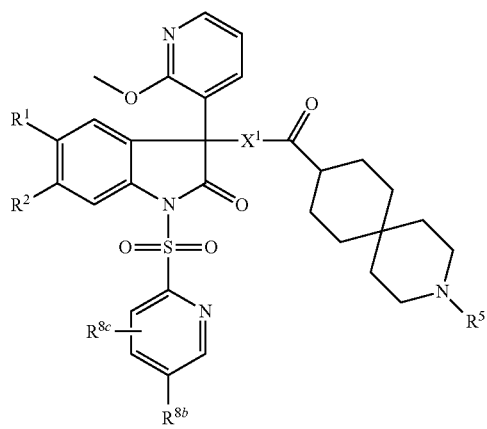
I.96
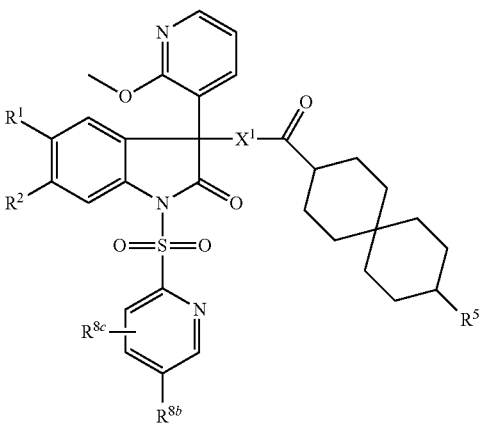
I.97
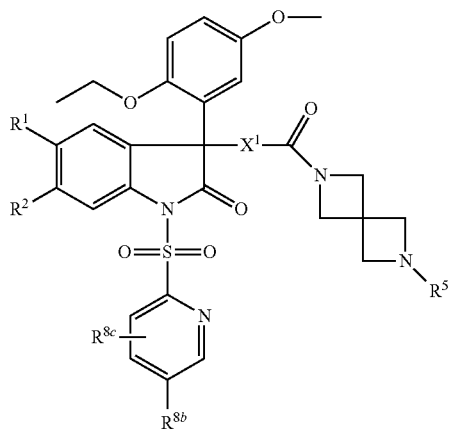
I.98

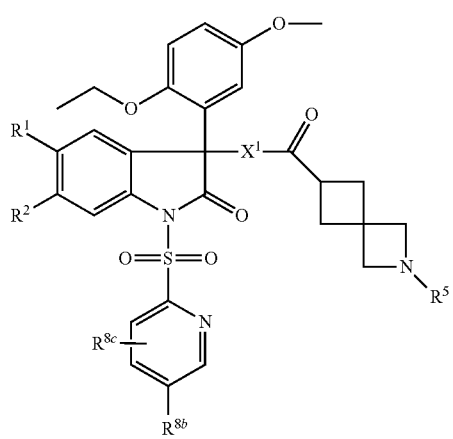
I.99
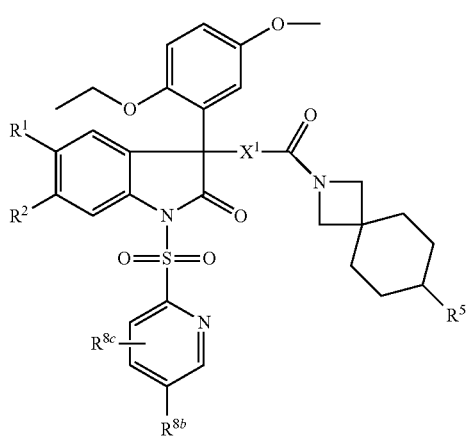
I.102
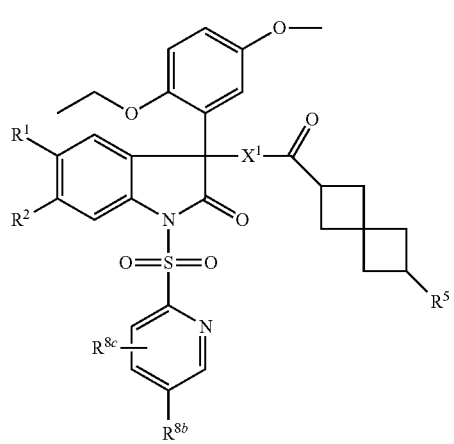
I.100
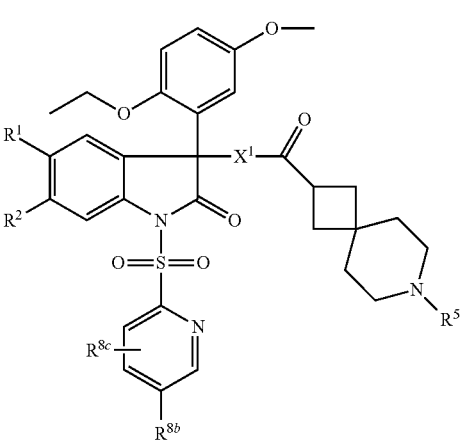
I.103
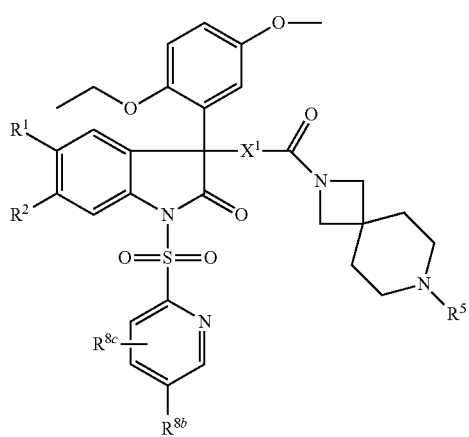
I.101
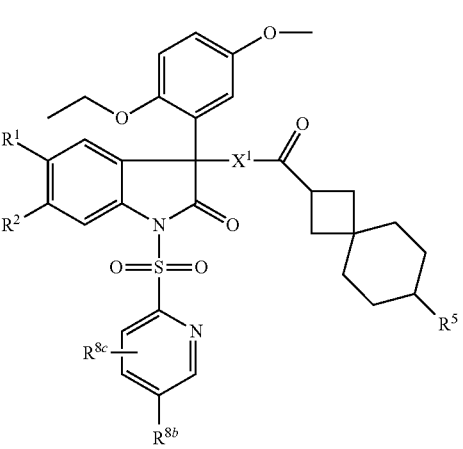
I.104

-continued
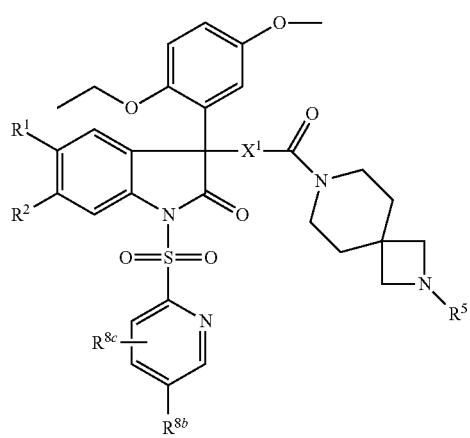
I.105
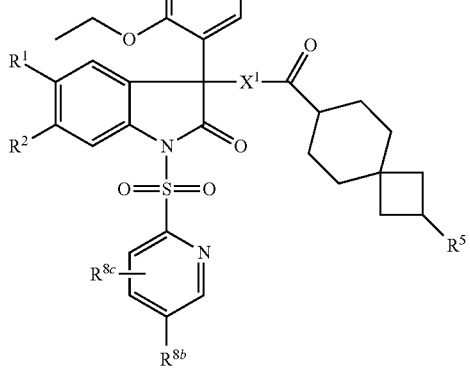
I.108
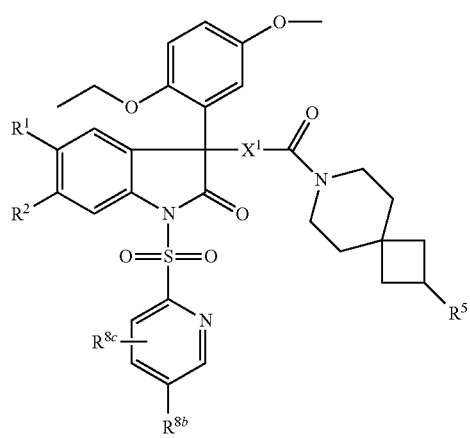
I.106
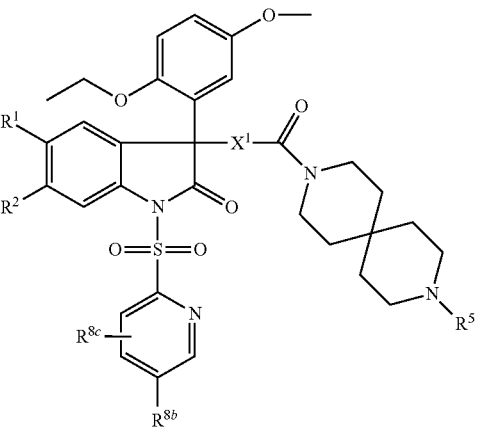
I.109
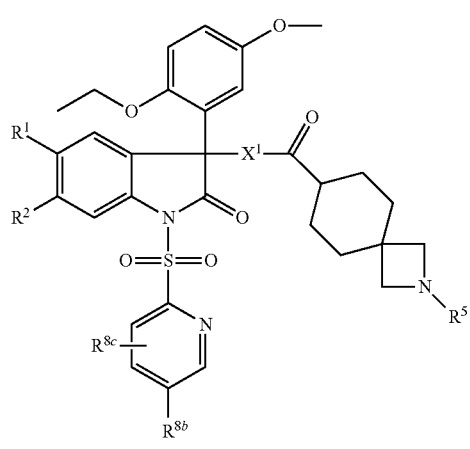
I.107
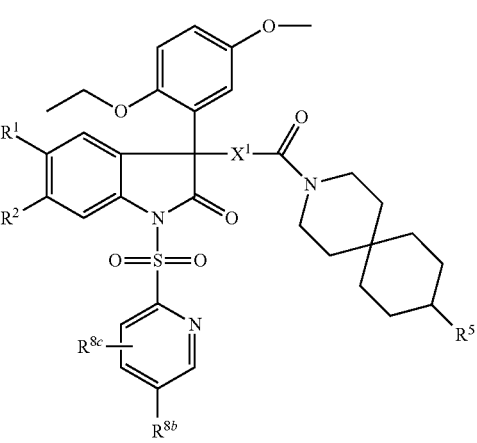
I.110

-continued
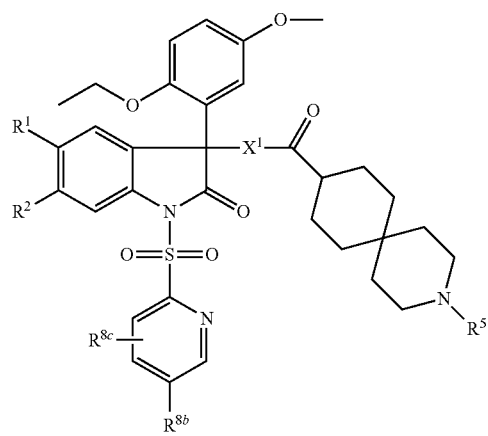
I.111
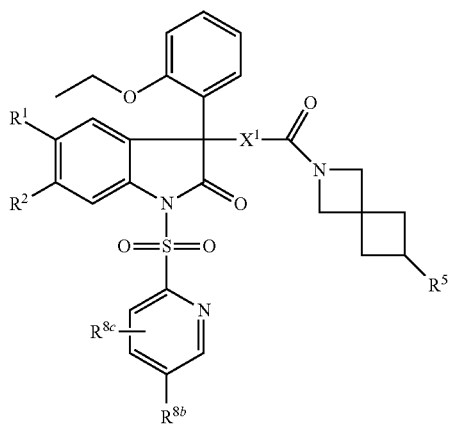
I.114
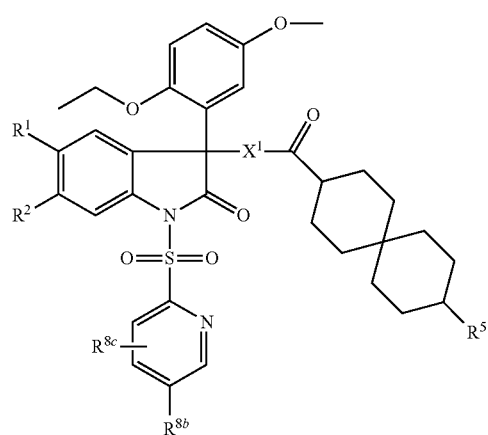
I.112
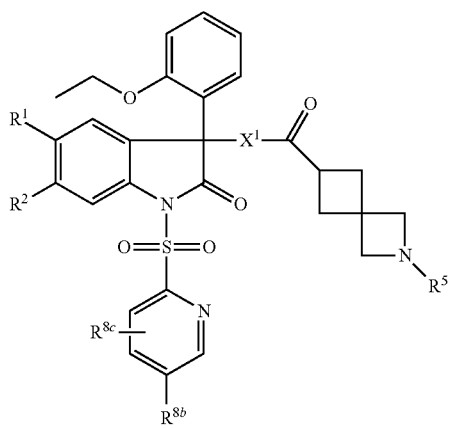
I.115
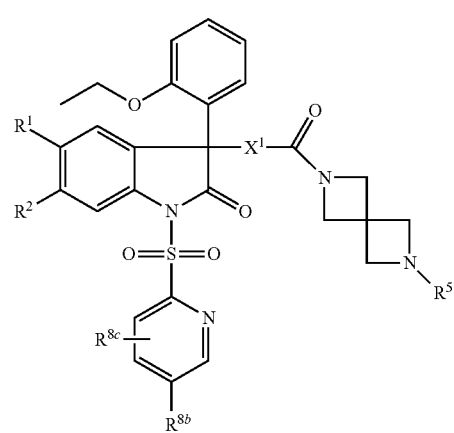
I.113
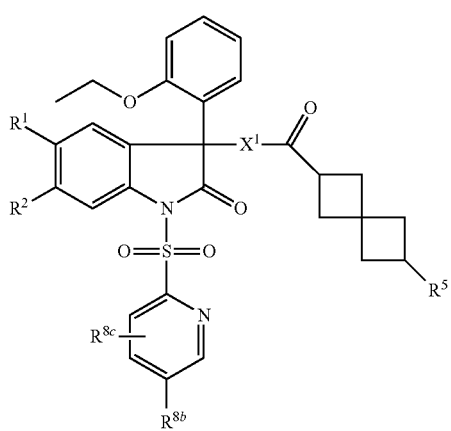
I.116

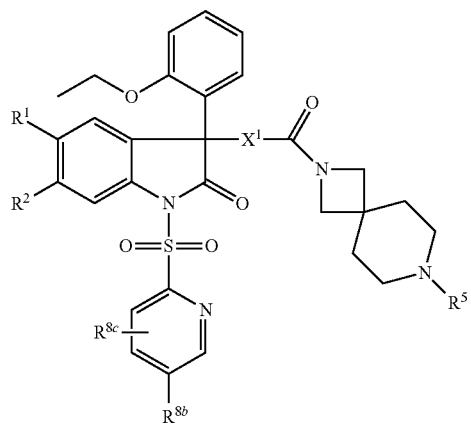
I.117
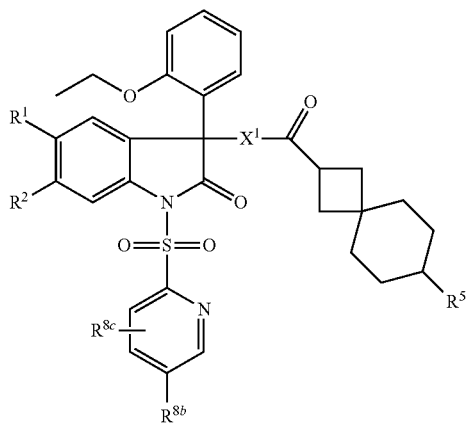
I.120
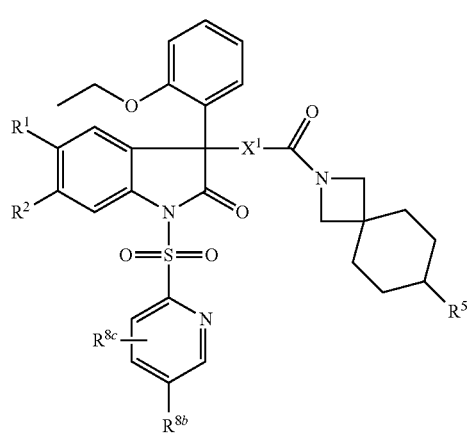
I.118
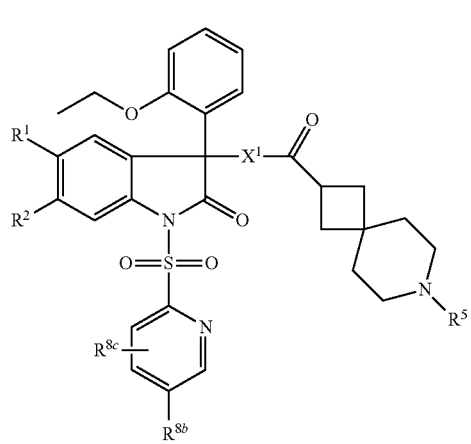
I.119
I.121
I.122

I.123 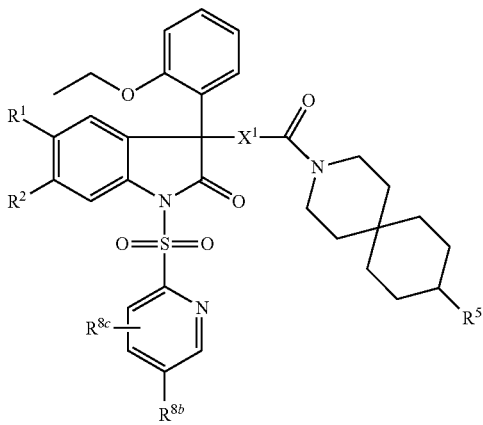

I.124 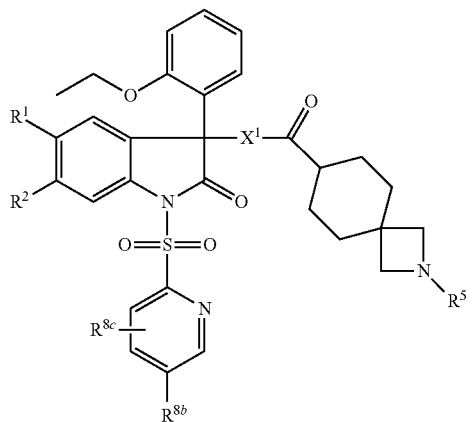

I.125 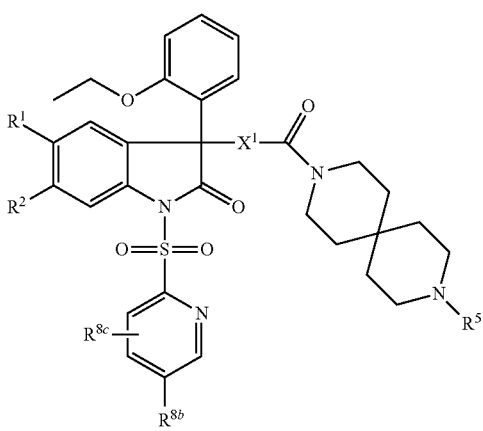

I.126 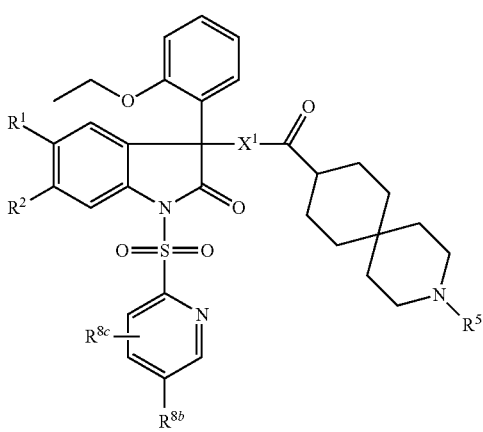

I.127 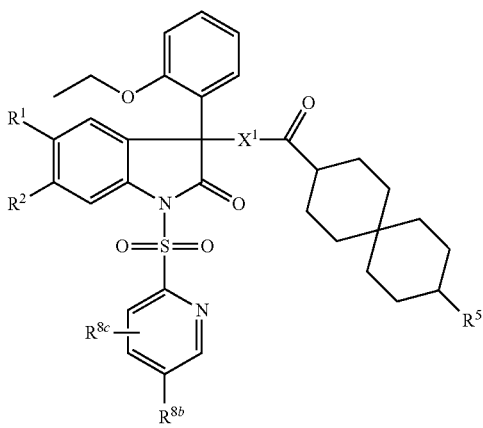

I.128 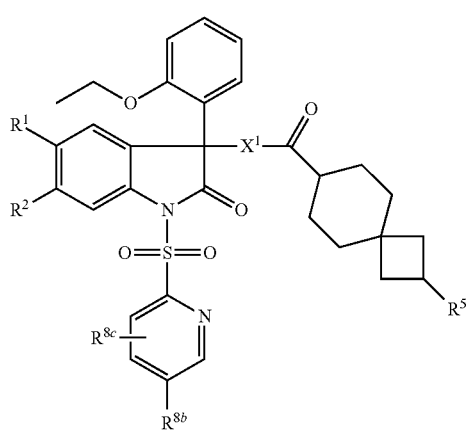

Table 1

Compounds of the formula I.1 in which $X^1$ is NH, $R^5$ is hydrogen, and $R^1$, $R^2$, $R^{8a}$, $R^{8b}$ and $R^{8c}$ for a compound corresponds in each case to one row of Table A Table 2

Compounds of the formula I.1 in which $X^1$ is NH, $R^5$ is methyl, and $R^1$, $R^2$, $R^{8a}$, $R^{8b}$ and $R^{8c}$ for a compound corresponds in each case to one row of Table A Table 3

Compounds of the formula I.1 in which $X^1$ is NH, $R^5$ is ethyl, and $R^1$, $R^2$, $R^{8a}$, $R^{8b}$ and $R^{8c}$ for a compound corresponds in each case to one row of Table A Table 4
Compounds of the formula I.1 in which $X^1$ is NH, $R^5$ is n-propyl, and $R^1$, $R^2$, $R^{8a}$, $R^{8b}$ and $R^{8c}$ for a compound corresponds in each case to one row of Table A Table 5
Compounds of the formula I.1 in which $X^1$ is NH, $R^5$ is isopropyl, and $R^1$, $R^2$, $R^{8a}$, $R^{8b}$ and $R^{8c}$ for a compound corresponds in each case to one row of Table A Table 6
Compounds of the formula I.1 in which $X^1$ is NH, $R^5$ is n-butyl, and $R^1$, $R^2$, $R^{8a}$, $R^{8b}$ and $R^{8c}$ for a compound corresponds in each case to one row of Table A Table 7
Compounds of the formula I.1 in which $X^1$ is NH, $R^5$ is sec-butyl, and $R^1$, $R^2$, $R^{8a}$, $R^{8b}$ and $R^{8c}$ for a compound corresponds in each case to one row of Table A Table 8
Compounds of the formula I.1 in which $X^1$ is NH, $R^5$ is isobutyl, and $R^1$, $R^2$, $R^{8a}$, $R^{8b}$ and $R^{8c}$ for a compound corresponds in each case to one row of Table A Table 9
Compounds of the formula I.1 in which $X^1$ is NH, $R^5$ is tert-butyl, and $R^1$, $R^2$, $R^{8a}$, $R^{8b}$ and $R^{8c}$ for a compound corresponds in each case to one row of Table A Table 10
Compounds of the formula I.1 in which $X^1$ is NH, $R^5$ is $CH_2CHF_2$, and $R^1$, $R^2$, $R^{8a}$, $R^{8b}$ and $R^{8c}$ for a compound corresponds in each case to one row of Table A Table 11
Compounds of the formula I.1 in which $X^1$ is NH, $R^5$ is $CH_2CF_3$, and $R^1$, $R^2$, $R^{8a}$, $R^{8b}$ and $R^{8c}$ for a compound corresponds in each case to one row of Table A Table 12
Compounds of the formula I.1 in which $X^1$ is NH, $R^5$ is cyclopropyl, and $R^1$, $R^2$, $R^{8a}$, $R^{8b}$ and $R^{8c}$ for a compound corresponds in each case to one row of Table A Table 13
Compounds of the formula I.1 in which $X^1$ is NH, $R^5$ is cyclobutyl, and $R^1$, $R^2$, $R^{8a}$, $R^{8b}$ and $R^{8c}$ for a compound corresponds in each case to one row of Table A Table 14
Compounds of the formula I.1 in which $X^1$ is NH, $R^5$ is cyclopentyl, and $R^1$, $R^2$, $R^{8a}$, $R^{8b}$ and $R^{8c}$ for a compound corresponds in each case to one row of Table A Table 15
Compounds of the formula I.1 in which $X^1$ is NH, $R^5$ is cyclohexyl, and $R^1$, $R^2$, $R^{8a}$, $R^{8b}$ and $R^{8c}$ for a compound corresponds in each case to one row of Table A Table 16
Compounds of the formula I.1 in which $X^1$ is NH, $R^5$ is oxetan-3-yl, and $R^1$, $R^2$, $R^{8a}$, $R^{8b}$ and $R^{8c}$ for a compound corresponds in each case to one row of Table A Table 17
Compounds of the formula I.1 in which $X^1$ is NH, $R^5$ is azetidin-3-yl, and $R^1$, $R^2$, $R^{8a}$, $R^{8b}$ and $R^{8c}$ for a compound corresponds in each case to one row of Table A Table 18
Compounds of the formula I.1 in which $X^1$ is NH, $R^5$ is 1-methylazetidin-3-yl, and $R^1$, $R^2$, $R^{8a}$, $R^{8b}$ and $R^{8c}$ for a compound corresponds in each case to one row of Table A Table 19
Compounds of the formula I.1 in which $X^1$ is NH, $R^5$ is 1-ethylazetidin-3-yl, and $R^1$, $R^2$, $R^{8a}$, $R^{8b}$ and $R^{8c}$ for a compound corresponds in each case to one row of Table A Table 20
Compounds of the formula I.1 in which $X^1$ is NH, $R^5$ is 1-propylazetidin-3-yl, and $R^1$, $R^2$, $R^{8a}$, $R^{8b}$ and $R^{8c}$ for a compound corresponds in each case to one row of Table A Table 21
Compounds of the formula I.1 in which $X^1$ is NH, $R^5$ is 1-isopropylazetidin-3-yl, and $R^1$, $R^2$, $R^{8a}$, $R^{8b}$ and $R^{8c}$ for a compound corresponds in each case to one row of Table A Table 22
Compounds of the formula I.1 in which $X^1$ is NH, $R^5$ is 1-(oxetan-3-yl)-azetidin-3-yl, and $R^1$, $R^2$, $R^{8a}$, $R^{8b}$ and $R^{8c}$ for a compound corresponds in each case to one row of Table A Table 23
Compounds of the formula I.1 in which $X^1$ is NH, $R^5$ is pyrrolidin-3-yl, and $R^1$, $R^2$, $R^{8a}$, $R^{8b}$ and $R^{8c}$ for a compound corresponds in each case to one row of Table A Table 24
Compounds of the formula I.1 in which $X^1$ is NH, $R^5$ is 1-methylpyrrolidin-3-yl, and $R^1$, $R^2$, $R^{8a}$, $R^{8b}$ and $R^{8c}$ for a compound corresponds in each case to one row of Table A Table 25
Compounds of the formula I.1 in which $X^1$ is NH, $R^5$ is 1-ethylpyrrolidin-3-yl, and $R^1$, $R^2$, $R^{8a}$, $R^{8b}$ and $R^{8c}$ for a compound corresponds in each case to one row of Table A Table 26
Compounds of the formula I.1 in which $X^1$ is NH, $R^5$ is 1-propylpyrrolidin-3-yl, and $R^1$, $R^2$, $R^{8a}$, $R^{8b}$ and $R^{8c}$ for a compound corresponds in each case to one row of Table A Table 27
Compounds of the formula I.1 in which $X^1$ is NH, $R^5$ is 1-isopropylpyrrolidin-3-yl, and $R^1$, $R^2$, $R^{8a}$, $R^{8b}$ and $R^{8c}$ for a compound corresponds in each case to one row of Table A Table 28
Compounds of the formula I.1 in which $X^1$ is NH, $R^5$ is 1-(oxetan-3-yl)-pyrrolidin-3-yl, and $R^1$, $R^2$, $R^{8a}$, $R^{8b}$ and $R^{8c}$ for a compound corresponds in each case to one row of Table A Table 29
Compounds of the formula I.1 in which $X^1$ is NH, $R^5$ is piperidin-4-yl, and $R^1$, $R^2$, $R^{8a}$, $R^{8b}$ and $R^{8c}$ for a compound corresponds in each case to one row of Table A Table 30
Compounds of the formula I.1 in which $X^1$ is NH, $R^5$ is 1-methylpiperidin-4-yl, and $R^1$, $R^2$, $R^{8a}$, $R^{8b}$ and $R^{8c}$ for a compound corresponds in each case to one row of Table A Table 31
Compounds of the formula I.1 in which $X^1$ is NH, $R^5$ is 1-ethylpiperidin-4-yl, and $R^1$, $R^2$, $R^{8a}$, $R^{8b}$ and $R^{8c}$ for a compound corresponds in each case to one row of Table A Table 32
Compounds of the formula I.1 in which $X^1$ is NH, $R^5$ is 1-propylpiperidin-4-yl, and $R^1$, $R^2$, $R^{8a}$, $R^{8b}$ and $R^{8c}$ for a compound corresponds in each case to one row of Table A Table 33
Compounds of the formula I.1 in which $X^1$ is NH, $R^5$ is 1-isopropylpiperidin-4-yl, and $R^1$, $R^2$, $R^{8a}$, $R^{8b}$ and $R^{8c}$ for a compound corresponds in each case to one row of Table A Table 34
Compounds of the formula I.1 in which $X^1$ is NH, $R^5$ is 1-(oxetan-3-yl)-piperidin-4-yl, and $R^1$, $R^2$, $R^{8a}$, $R^{8b}$ and $R^{8c}$ for a compound corresponds in each case to one row of Table A Table 35
Table 36
Compounds of the formula I.1 in which $X^1$ is NH, $R^5$ is 2-aza-spiro[3.3]heptan-6-yl, and $R^1$, $R^2$, $R^{8a}$, $R^{8b}$ and $R^{8c}$ for a compound corresponds in each case to one row of Table A Table 37
Compounds of the formula I.1 in which $X^1$ is NH, $R^5$ is 2-methyl-2-aza-spiro[3.3]heptan-6-yl, and $R^1$, $R^2$, $R^{8a}$, $R^{8b}$ and $R^{8c}$ for a compound corresponds in each case to one row of Table A Table 38
Compounds of the formula I.1 in which $X^1$ is NH, $R^5$ is 2-ethyl-2-aza-spiro[3.3]heptan-6-yl, and $R^1$, $R^2$, $R^{8a}$, $R^{8b}$ and $R^{8c}$ for a compound corresponds in each case to one row of Table A Table 39
Compounds of the formula I.1 in which $X^1$ is NH, $R^5$ is 2-propyl-2-aza-spiro[3.3]heptan-6-yl, and $R^1$, $R^2$, $R^{8a}$, $R^{8b}$ and $R^{8c}$ for a compound corresponds in each case to one row of Table A Table 40
Compounds of the formula I.1 in which $X^1$ is NH, $R^5$ is 2-isopropyl-2-aza-spiro[3.3]heptan-6-yl, and $R^1$, $R^2$, $R^{8a}$, $R^{8b}$ and $R^{8c}$ for a compound corresponds in each case to one row of Table A Table 41
Compounds of the formula I.1 in which $X^1$ is NH, $R^5$ is 2-(oxetan-3-yl)-2-aza-spiro[3.3]heptan-6-yl, and $R^1$, $R^2$, $R^{8a}$, $R^{8b}$ and $R^{8c}$ for a compound corresponds in each case to one row of Table A Table 42
Compounds of the formula I.1 in which $X^1$ is NH, $R^5$ is 2-(azetidin-3-yl)-2-aza-spiro[3.3]heptan-6-yl, and $R^1$, $R^2$, $R^{8a}$, $R^{8b}$ and $R^{8c}$ for a compound corresponds in each case to one row of Table A Table 43
Compounds of the formula I.1 in which $X^1$ is NH, $R^5$ is —$CH_2CH_2$—$NH_2$, and $R^1$, $R^2$, $R^{8a}$, $R^{8b}$ and $R^{8c}$ for a compound corresponds in each case to one row of Table A Table 44
Compounds of the formula I.1 in which $X^1$ is NH, $R^5$ is —$(CH_2)_3$—$NH_2$, and $R^1$, $R^2$, $R^{8a}$, $R^{8b}$ and $R^{8c}$ for a compound corresponds in each case to one row of Table A Table 45
Compounds of the formula I.1 in which $X^1$ is NH, $R^5$ is —$CH_2CH_2$—$N(H)CH_3$, and $R^1$, $R^2$, $R^{8a}$, $R^{8b}$ and $R^{8c}$ for a compound corresponds in each case to one row of Table A Table 46
Compounds of the formula I.1 in which $X^1$ is NH, $R^5$ is —$(CH_2)_3$—$N(H)CH_3$, and $R^1$, $R^2$, $R^{8a}$, $R^{8b}$ and $R^{8c}$ for a compound corresponds in each case to one row of Table A Table 47
Compounds of the formula I.1 in which $X^1$ is NH, $R^5$ is —$CH_2CH_2$—$N(CH_3)_2$, and $R^1$, $R^2$, $R^{8a}$, $R^{8b}$ and $R^{8c}$ for a compound corresponds in each case to one row of Table A Table 48
Compounds of the formula I.1 in which $X^1$ is NH, $R^5$ is —$(CH_2)_3$—$N(CH_3)_2$, and $R^1$, $R^2$, $R^{8a}$, $R^{8b}$ and $R^{8c}$ for a compound corresponds in each case to one row of Table A Table 49
Compounds of the formula I.1 in which $X^1$ is NH, $R^5$ is —$CH_2CH_2$—$N(H)CH_2CH_3$, and $R^1$, $R^2$, $R^{8a}$, $R^{8b}$ and $R^{8c}$ for a compound corresponds in each case to one row of Table A Table 50
Compounds of the formula I.1 in which $X^1$ is NH, $R^5$ is —$(CH_2)_3$—$N(H)CH_2CH_3$, and $R^1$, $R^2$, $R^{8a}$, $R^{8b}$ and $R^{8c}$ for a compound corresponds in each case to one row of Table A Table 51
Compounds of the formula I.1 in which $X^1$ is NH, $R^5$ is —$CH_2CH_2$—$N(CH_2CH_3)_2$, and $R^1$, $R^2$, $R^{8a}$, $R^{8b}$ and $R^{8c}$ for a compound corresponds in each case to one row of Table A Table 52
Compounds of the formula I.1 in which $X^1$ is NH, $R^5$ is —$(CH_2)_3$—$N(CH_2CH_3)_2$, and $R^1$, $R^2$, $R^{8a}$, $R^{8b}$ and $R^{8c}$ for a compound corresponds in each case to one row of Table A Table 53
Compounds of the formula I.1 in which $X^1$ is NH, $R^5$ is —$CH_2CH_2$—$N(H)CH_2CH_2CH_3$, and $R^1$, $R^2$, $R^{8a}$, $R^{8b}$ and $R^{8c}$ for a compound corresponds in each case to one row of Table A Table 54
Compounds of the formula I.1 in which $X^1$ is NH, $R^5$ is —$(CH_2)_3$—$N(H)CH_2CH_2CH_3$, and $R^1$, $R^2$, $R^{8a}$, $R^{8b}$ and $R^{8c}$ for a compound corresponds in each case to one row of Table A Table 55
Compounds of the formula I.1 in which $X^1$ is NH, $R^5$ is —$CH_2CH_2$—$N(CH_2CH_2CH_3)_2$, and $R^1$, $R^2$, $R^{8a}$, $R^{8b}$ and $R^{8c}$ for a compound corresponds in each case to one row of Table A Table 56
Compounds of the formula I.1 in which $X^1$ is NH, $R^5$ is —$(CH_2)_3$—$N(CH_2CH_2CH_3)_2$, and $R^1$, $R^2$, $R^{8a}$, $R^{8b}$ and $R^{8c}$ for a compound corresponds in each case to one row of Table A Table 57
Compounds of the formula I.1 in which $X^1$ is NH, $R^5$ is —$CH_2CH_2$-aziridin-1-yl, and $R^1$, $R^2$, $R^{8a}$, $R^{8b}$ and $R^{8c}$ for a compound corresponds in each case to one row of Table A Table 58
Compounds of the formula I.1 in which $X^1$ is NH, $R^5$ is —$CH_2CH_2$-azetidin-1-yl, and $R^1$, $R^2$, $R^{8a}$, $R^{8b}$ and $R^{8c}$ for a compound corresponds in each case to one row of Table A Table 59
Compounds of the formula I.1 in which $X^1$ is NH, $R^5$ is —$CH_2CH_2$-pyrrolidin-1-yl, and $R^1$, $R^2$, $R^{8a}$, $R^{8b}$ and $R^{8c}$ for a compound corresponds in each case to one row of Table A Table 60
Compounds of the formula I.1 in which $X^1$ is NH, $R^5$ is —$CH_2CH_2$-piperidin-1-yl, and $R^1$, $R^2$, $R^{8a}$, $R^{8b}$ and $R^{8c}$ for a compound corresponds in each case to one row of Table A Table 61
Compounds of the formula I.1 in which $X^1$ is NH, $R^5$ is —$CH_2CH_2$-piperazin-1-yl, and $R^1$, $R^2$, $R^{8a}$, $R^{8b}$ and $R^{8c}$ for a compound corresponds in each case to one row of Table A Table 62
Compounds of the formula I.1 in which $X^1$ is NH, $R^5$ is —$CH_2CH_2$-(1-methylpiperazin-4-yl), and $R^1$, $R^2$, $R^{8a}$, $R^{8b}$ and $R^{8c}$ for a compound corresponds in each case to one row of Table A Table 63
Compounds of the formula I.1 in which $X^1$ is NH, $R^5$ is —$CH_2CH_2$-(1-ethylpiperazin-4-yl), and $R^1$, $R^2$, $R^{8a}$, $R^{8b}$ and $R^{8c}$ for a compound corresponds in each case to one row of Table A Table 64
Compounds of the formula I.1 in which $X^1$ is NH, $R^5$ is —$CH_2CH_2$-(1-propylpiperazin-4-yl), and $R^1$, $R^2$, $R^{8a}$, $R^{8b}$ and $R^{8c}$ for a compound corresponds in each case to one row of Table A Table 65
Compounds of the formula I.1 in which $X^1$ is NH, $R^5$ is —$CH_2CH_2$-(1-isopropylpiperazin-4-yl), and $R^1$, $R^2$, $R^{8a}$, $R^{8b}$ and $R^{8c}$ for a compound corresponds in each case to one row of Table A Table 66
Compounds of the formula I.1 in which $X^1$ is NH, $R^5$ is —$CH_2CH_2$-(1-(oxetan-3-yl)-piperazin-4-yl), and $R^1$, $R^2$, $R^{8a}$, $R^{8b}$ and $R^{8c}$ for a compound corresponds in each case to one row of Table A Table 67
Compounds of the formula I.1 in which $X^1$ is NH, $R^5$ is —$CH_2CH_2$-morpholin-4-yl, and $R^1$, $R^2$, $R^{8a}$, $R^{8b}$ and $R^{8c}$ for a compound corresponds in each case to one row of Table A Table 68
Compounds of the formula I.1 in which $X^1$ is NH, $R^5$ is —$CH_2CH_2$-(2-oxa-6-aza-spiro[3.3]heptan-6-yl, and $R^1$, $R^2$, $R^{8a}$, $R^{8b}$ and $R^{8c}$ for a compound corresponds in each case to one row of Table A Table 69
Compounds of the formula I.1 in which $X^1$ is NH, $R^5$ is —$CH_2CH_2$-(2-aza-spiro[3.3]heptan-2-yl), and $R^1$, $R^2$, $R^{8a}$, $R^{8b}$ and $R^{8c}$ for a compound corresponds in each case to one row of Table A Table 70
Compounds of the formula I.1 in which $X^1$ is NH, $R^5$ is —$CH_2CH_2$-(2,6-di-aza-spiro[3.3]heptan-2-yl), and $R^1$, $R^2$, $R^{8a}$, $R^{8b}$ and $R^{8c}$ for a compound corresponds in each case to one row of Table A Table 71
Compounds of the formula I.1 in which $X^1$ is NH, $R^5$ is —$CH_2CH_2$-(2-methyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 72
Compounds of the formula I.1 in which $X^1$ is NH, $R^5$ is —$CH_2CH_2$-(2-ethyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 73
Compounds of the formula I.1 in which $X^1$ is NH, $R^5$ is —$CH_2CH_2$-(2-propyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 74
Compounds of the formula I.1 in which $X^1$ is NH, $R^5$ is —$CH_2CH_2$-(2-isopropyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 75
Compounds of the formula I.1 in which $X^1$ is NH, $R^5$ is —$CH_2CH_2$-(2-(oxetan-3-yl)-2,6-di-aza-spiro[3.3]heptan-6-yl), and $R^1$, $R^2$, $R^{8a}$, $R^{8b}$ and $R^{8c}$ for a compound corresponds in each case to one row of Table A Table 76
Compounds of the formula I.1 in which $X^1$ is NH, $R^5$ is —$(CH_2)_3$-aziridin-1-yl, and $R^1$, $R^2$, $R^{8a}$, $R^{8b}$ and $R^{8c}$ for a compound corresponds in each case to one row of Table A Table 77
Compounds of the formula I.1 in which $X^1$ is NH, $R^5$ is —$(CH_2)_3$-azetidin-1-yl, and $R^1$, $R^2$, $R^{8a}$, $R^{8b}$ and $R^{8c}$ for a compound corresponds in each case to one row of Table A Table 78
Compounds of the formula I.1 in which $X^1$ is NH, $R^5$ is —$(CH_2)_3$-pyrrolidin-1-yl, and $R^1$, $R^2$, $R^{8a}$, $R^{8b}$ and $R^{8c}$ for a compound corresponds in each case to one row of Table A Table 79
Compounds of the formula I.1 in which $X^1$ is NH, $R^5$ is —$(CH_2)_3$-piperidin-1-yl, and $R^1$, $R^2$, $R^{8a}$, $R^{8b}$ and $R^{8c}$ for a compound corresponds in each case to one row of Table A Table 80
Compounds of the formula I.1 in which $X^1$ is NH, $R^5$ is —$(CH_2)_3$-piperazin-1-yl, and $R^1$, $R^2$, $R^{8a}$, $R^{8b}$ and $R^{8c}$ for a compound corresponds in each case to one row of Table A Table 81
Compounds of the formula I.1 in which $X^1$ is NH, $R^5$ is —$(CH_2)_3$-(1-methylpiperazin-4-yl), and $R^1$, $R^2$, $R^{8a}$, $R^{8b}$ and $R^{8c}$ for a compound corresponds in each case to one row of Table A Table 82
Compounds of the formula I.1 in which $X^1$ is NH, $R^5$ is —$(CH_2)_3$-(1-ethylpiperazin-4-yl), and $R^1$, $R^2$, $R^{8a}$, $R^{8b}$ and $R^{8c}$ for a compound corresponds in each case to one row of Table A Table 83
Compounds of the formula I.1 in which $X^1$ is NH, $R^5$ is —$(CH_2)_3$-(1-propylpiperazin-4-yl), and $R^1$, $R^2$, $R^{8a}$, $R^{8b}$ and $R^{8c}$ for a compound corresponds in each case to one row of Table A Table 84
Compounds of the formula I.1 in which $X^1$ is NH, $R^5$ is —$(CH_2)_3$-(1-isopropylpiperazin-4-yl), and $R^1$, $R^2$, $R^{8a}$, $R^{8b}$ and $R^{8c}$ for a compound corresponds in each case to one row of Table A Table 85
Compounds of the formula I.1 in which $X^1$ is NH, $R^5$ is —$(CH_2)_3$-(1-(oxetan-3-yl)-piperazin-4-yl), and $R^1$, $R^2$, $R^{8a}$, $R^{8b}$ and $R^{8c}$ for a compound corresponds in each case to one row of Table A Table 86
Compounds of the formula I.1 in which $X^1$ is NH, $R^5$ is —$(CH_2)_3$-morpholin-4-yl, and $R^1$, $R^2$, $R^{8a}$, $R^{8b}$ and $R^{8c}$ for a compound corresponds in each case to one row of Table A Table 87
Compounds of the formula I.1 in which $X^1$ is NH, $R^5$ is —$(CH_2)_3$-(2-oxa-6-aza-spiro[3.3]heptan-6-yl, and $R^1$, $R^2$, $R^{8a}$, $R^{8b}$ and $R^{8c}$ for a compound corresponds in each case to one row of Table A Table 88
Compounds of the formula I.1 in which $X^1$ is NH, $R^5$ is —$(CH_2)_3$-(2-aza-spiro[3.3]heptan-2-yl), and $R^1$, $R^2$, $R^{8a}$, $R^{8b}$ and $R^{8c}$ for a compound corresponds in each case to one row of Table A Table 89
Compounds of the formula I.1 in which $X^1$ is NH, $R^5$ is —$(CH_2)_3$-(2,6-di-aza-spiro[3.3]heptan-2-yl), and $R^1$, $R^2$, $R^{8a}$, $R^{8b}$ and $R^{8c}$ for a compound corresponds in each case to one row of Table A Table 90
Compounds of the formula I.1 in which $X^1$ is NH, $R^5$ is —$(CH_2)_3$-(2-methyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 91
Compounds of the formula I.1 in which $X^1$ is NH, $R^5$ is —$(CH_2)_3$-(2-ethyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 92
Compounds of the formula I.1 in which $X^1$ is NH, $R^5$ is —$(CH_2)_3$-(2-propyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 93
Compounds of the formula I.1 in which $X^1$ is NH, $R^5$ is —$(CH_2)_3$-(2-isopropyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 94
Compounds of the formula I.1 in which $X^1$ is NH, $R^5$ is —(CH$_2$)$_3$-(2-(oxetan-3-yl)-2,6-di-aza-spiro[3.3]heptan-6-yl), and $R^1$, $R^2$, $R^{8a}$, $R^{8b}$ and $R^{8c}$ for a compound corresponds in each case to one row of Table A Table 95
Compounds of the formula I.1 in which $X^1$ is NH, $R^5$ is —CH$_2$CH$_2$—OCH$_3$, and $R^1$, $R^2$, $R^{8a}$, $R^{8b}$ and $R^{8c}$ for a compound corresponds in each case to one row of Table A Table 96
Compounds of the formula I.1 in which $X^1$ is NH, $R^5$ is —CH$_2$CH$_2$—OCH$_2$CH$_3$, and $R^1$, $R^2$, $R^{8a}$, $R^{8b}$ and $R^{8c}$ for a compound corresponds in each case to one row of Table A Table 97
Compounds of the formula I.1 in which $X^1$ is NH, $R^5$ is —CH$_2$CH$_2$—OCH(CH$_3$)$_2$, and $R^1$, $R^2$, $R^{8a}$, $R^{8b}$ and $R^{8c}$ for a compound corresponds in each case to one row of Table A Table 98
Compounds of the formula I.1 in which $X^1$ is NH, $R^5$ is —(CH$_2$)$_3$—OCH$_3$, and $R^1$, $R^2$, $R^{8a}$, $R^{8b}$ and $R^{8c}$ for a compound corresponds in each case to one row of Table A Table 99
Compounds of the formula I.1 in which $X^1$ is NH, $R^5$ is —(CH$_2$)$_3$—OCH$_2$CH$_3$, and $R^1$, $R^2$, $R^{8a}$, $R^{8b}$ and $R^{8c}$ for a compound corresponds in each case to one row of Table A Table 100
Compounds of the formula I.1 in which $X^1$ is NH, $R^5$ is —(CH$_2$)$_3$—OCH(CH$_3$)$_2$, and $R^1$, $R^2$, $R^{8a}$, $R^{8b}$ and $R^{8c}$ for a compound corresponds in each case to one row of Table A Tables 101 to 200
Compounds of the formula I.1 in which $X^1$ is CH$_2$, $R^5$ is as defined in tables 1 to 100 and $R^1$, $R^2$, $R^{8a}$, $R^{8b}$ and $R^{8c}$ for a compound corresponds in each case to one row of Table A Tables 201 to 300
Compounds of the formula I.1 in which $X^1$ is O, $R^5$ is as defined in tables 1 to 100 and $R^1$, $R^2$, $R^{8a}$, $R^{8b}$ and $R^{8c}$ for a compound corresponds in each case to one row of Table A Tables 301 to 600
Compounds of the formula I.2 in which the combination of $X^1$ and $R^5$ is as defined in tables 1 to 300 and $R^1$, $R^2$, $R^{8a}$, $R^{8b}$ and $R^{8c}$ for a compound corresponds in each case to one row of Table A Table 601
Compounds of the formula I.2 in which $X^1$ is NH, $R^5$ is CH$_2$F, and $R^1$, $R^2$, $R^{8a}$, $R^{8b}$ and $R^{8c}$ for a compound corresponds in each case to one row of Table A Table 602
Compounds of the formula I.2 in which $X^1$ is NH, $R^5$ is CHF$_2$, and $R^1$, $R^2$, $R^{8a}$, $R^{8b}$ and $R^{8c}$ for a compound corresponds in each case to one row of Table A Table 603 Compounds of the formula I.2 in which $X^1$ is NH, $R^5$ is CF$_3$, and $R^1$, $R^2$, $R^{8a}$, $R^{8b}$ and $R^{8c}$ for a compound corresponds in each case to one row of Table A Table 604
Compounds of the formula I.2 in which $X^1$ is NH, $R^5$ is CF$_2$CF$_3$, and $R^1$, $R^2$, $R^{8a}$, $R^{8b}$ and $R^{8c}$ for a compound corresponds in each case to one row of Table A Table 605
Compounds of the formula I.2 in which $X^1$ is NH, $R^5$ is oxiran-2-yl, and $R^1$, and $R^{8c}$ for a compound corresponds in each case to one row of Table A Table 606
Compounds of the formula I.2 in which $X^1$ is NH, $R^5$ is aziridin-1-yl, and $R^1$, $R^2$, $R^{8a}$, $R^{8b}$ and $R^{8c}$ for a compound corresponds in each case to one row of Table A Table 607
Compounds of the formula I.2 in which $X^1$ is NH, $R^5$ is aziridin-2-yl, and $R^1$, $R^2$, $R^{8a}$, $R^{8b}$ and $R^{8c}$ for a compound corresponds in each case to one row of Table A Table 608
Compounds of the formula I.2 in which $X^1$ is NH, $R^5$ is 1-methylaziridin-2-yl, and $R^1$, $R^2$, $R^{8a}$, $R^{8b}$ and $R^{8c}$ for a compound corresponds in each case to one row of Table A Table 609
Compounds of the formula I.2 in which $X^1$ is NH, $R^5$ is 1-ethylaziridin-2-yl, and $R^1$, $R^2$, $R^{8a}$, $R^{8b}$ and $R^{8c}$ for a compound corresponds in each case to one row of Table A Table 610
Compounds of the formula I.2 in which $X^1$ is NH, $R^5$ is 1-propylaziridin-2-yl, and $R^1$, $R^2$, $R^{8a}$, $R^{8b}$ and $R^{8c}$ for a compound corresponds in each case to one row of Table A Table 611
Compounds of the formula I.2 in which $X^1$ is NH, $R^5$ is 1-isopropylaziridin-2-yl, and $R^1$, $R^2$, $R^{8a}$, $R^{8b}$ and $R^{8c}$ for a compound corresponds in each case to one row of Table A Table 612
Compounds of the formula I.2 in which $X^1$ is NH, $R^5$ is 1-(oxetan-3-yl)-aziridin-2-yl, and $R^1$, $R^2$, $R^{8a}$, $R^{8b}$ and $R^{8c}$ for a compound corresponds in each case to one row of Table A Table 613
Compounds of the formula I.2 in which $X^1$ is NH, $R^5$ is azetidin-1-yl, and $R^1$, $R^2$, $R^{8a}$, $R^{8b}$ and $R^{8c}$ for a compound corresponds in each case to one row of Table A Table 614
Compounds of the formula I.2 in which $X^1$ is NH, $R^5$ is piperdin-1-yl, and $R^1$, $R^2$, $R^{8a}$, $R^{8b}$ and $R^{8c}$ for a compound corresponds in each case to one row of Table A Table 615
Compounds of the formula I.2 in which $X^1$ is NH, $R^5$ is piperdin-1-yl, and $R^1$, $R^2$, $R^{8a}$, $R^{8b}$ and $R^{8c}$ for a compound corresponds in each case to one row of Table A Table 616
Compounds of the formula I.2 in which $X^1$ is NH, $R^5$ is piperazin-1-yl, and $R^1$, $R^2$, $R^{8a}$, $R^{8b}$ and $R^{8c}$ for a compound corresponds in each case to one row of Table A Table 617
Compounds of the formula I.2 in which $X^1$ is NH, $R^5$ is 1-methylpiperazin-4-yl, and $R^1$, $R^2$, $R^{8a}$, $R^{8b}$ and $R^{8c}$ for a compound corresponds in each case to one row of Table A Table 618
Compounds of the formula I.2 in which $X^1$ is NH, $R^5$ is 1-ethylpiperazin-4-yl, and $R^1$, $R^2$, $R^{8a}$, $R^{8b}$ and $R^{8c}$ for a compound corresponds in each case to one row of Table A Table 619
Compounds of the formula I.2 in which $X^1$ is NH, $R^5$ is 1-propylpiperazin-4-yl, and $R^1$, $R^2$, $R^{8a}$, $R^{8b}$ and $R^{8c}$ for a compound corresponds in each case to one row of Table A Table 620
Compounds of the formula I.2 in which $X^1$ is NH, $R^5$ is 1-isopropylpiperazin-4-yl, and $R^1$, $R^2$, $R^{8a}$, $R^{8b}$ and $R^{8c}$ for a compound corresponds in each case to one row of Table A Table 621
Compounds of the formula I.2 in which $X^1$ is NH, $R^5$ is 1-(oxetan-3-yl)-piperazin-4-yl, and $R^1$, $R^2$, $R^{8a}$, $R^{8b}$ and $R^{8c}$ for a compound corresponds in each case to one row of Table A Table 622
Compounds of the formula I.2 in which $X^1$ is NH, $R^5$ is morpholin-4-yl, and $R^1$, $R^2$, $R^{8a}$, $R^{8b}$ and $R^{8c}$ for a compound corresponds in each case to one row of Table A Table 623
Compounds of the formula I.2 in which $X^1$ is NH, $R^5$ is 2-oxa-6-aza-spiro[3.3]heptan-6-yl, and $R^1$, $R^2$, $R^{8a}$, $R^{8b}$ and $R^{8c}$ for a compound corresponds in each case to one row of Table A Table 624
Compounds of the formula I.2 in which $X^1$ is NH, $R^5$ is 2-aza-spiro[3.3]heptan-2-yl, and $R^1$, $R^2$, $R^{8a}$, $R^{8b}$ and $R^{8c}$ for a compound corresponds in each case to one row of Table A Table 625
Compounds of the formula I.2 in which $X^1$ is NH, $R^5$ is 2,6-di-aza-spiro[3.3]heptan-2-yl, and $R^1$, $R^2$, $R^{8a}$, $R^{8b}$ and $R^{8c}$ for a compound corresponds in each case to one row of Table A Table 626
Compounds of the formula I.2 in which $X^1$ is NH, $R^5$ is 2-methyl-2,6-di-aza-spiro[3.3]heptan-6-yl, and $R^1$, $R^2$, $R^{8a}$, $R^{8b}$ and $R^{8c}$ for a compound corresponds in each case to one row of Table A Table 627
Compounds of the formula I.2 in which $X^1$ is NH, $R^5$ is 2-ethyl-2,6-di-aza-spiro[3.3]heptan-6-yl, and $R^1$, $R^2$, $R^{8a}$, $R^{8b}$ and $R^{8c}$ for a compound corresponds in each case to one row of Table A Table 628
Compounds of the formula I.2 in which $X^1$ is NH, $R^5$ is 2-propyl-2,6-di-aza-spiro[3.3]heptan-6-yl, and $R^1$, $R^2$, $R^{8a}$, $R^{8b}$ and $R^{8c}$ for a compound corresponds in each case to one row of Table A Table 629
Compounds of the formula I.2 in which $X^1$ is NH, $R^5$ is 2-isopropyl-2,6-di-aza-spiro[3.3]heptan-6-yl, and $R^1$, $R^2$, $R^{8a}$, $R^{8b}$ and $R^{8c}$ for a compound corresponds in each case to one row of Table A Table 630
Compounds of the formula I.2 in which $X^1$ is NH, $R^5$ is 2-(oxetan-3-yl)-2,6-di-aza-spiro[3.3]heptan-6-yl, and $R^1$, $R^2$, $R^{8a}$, $R^{8b}$ and $R^{8c}$ for a compound corresponds in each case to one row of Table A Table 631
Compounds of the formula I.2 in which $X^1$ is NH, $R^5$ is —$CH_2$—$NH_2$, and $R^1$, $R^2$, $R^{8a}$, $R^{8b}$ and $R^{8c}$ for a compound corresponds in each case to one row of Table A Table 632
Compounds of the formula I.2 in which $X^1$ is NH, $R^5$ is —$CH_2$—$N(H)CH_3$, and $R^1$, $R^2$, $R^{8a}$, $R^{8b}$ and $R^{8c}$ for a compound corresponds in each case to one row of Table A Table 633 Compounds of the formula I.2 in which $X^1$ is NH, $R^5$ is —$CH_2$—$N(CH_3)_2$, and $R^1$, $R^2$, $R^{8a}$, $R^{8b}$ and $R^{8c}$ for a compound corresponds in each case to one row of Table A Table 634
Compounds of the formula I.2 in which $X^1$ is NH, $R^5$ is —$CH_2$—$N(H)CH_2CH_3$, and $R^1$, $R^2$, $R^{8a}$, $R^{8b}$ and $R^{8c}$ for a compound corresponds in each case to one row of Table A Table 635
Compounds of the formula I.2 in which $X^1$ is NH, $R^5$ is —$CH_2$—$N(CH_2CH_3)_2$, and $R^1$, $R^2$, $R^{8a}$, $R^{8b}$ and $R^{8c}$ for a compound corresponds in each case to one row of Table A Table 636
Compounds of the formula I.2 in which $X^1$ is NH, $R^5$ is —$CH_2$—$N(H)CH_2CH_2CH_3$, and $R^1$, $R^2$, $R^{8a}$, $R^{8b}$ and $R^{8c}$ for a compound corresponds in each case to one row of Table A Table 637
Compounds of the formula I.2 in which $X^1$ is NH, $R^5$ is —$CH_2$—$N(CH_2CH_2CH_3)_2$, and $R^1$, $R^2$, $R^{8a}$, $R^{8b}$ and $R^{8c}$ for a compound corresponds in each case to one row of Table A Table 638
Compounds of the formula I.2 in which $X^1$ is NH, $R^5$ is —$CH_2$-aziridin-1-yl, and $R^1$, $R^2$, $R^{8a}$, $R^{8b}$ and $R^{8c}$ for a compound corresponds in each case to one row of Table A Table 639
Compounds of the formula I.2 in which $X^1$ is NH, $R^5$ is —$CH_2$-azetidin-1-yl, and $R^1$, $R^2$, $R^{8a}$, $R^{8b}$ and $R^{8c}$ for a compound corresponds in each case to one row of Table A Table 640
Compounds of the formula I.2 in which $X^1$ is NH, $R^5$ is —$CH_2$-pyrrolidin-1-yl, and $R^1$, $R^2$, $R^{8a}$, $R^{8b}$ and $R^{8c}$ for a compound corresponds in each case to one row of Table A Table 641
Compounds of the formula I.2 in which $X^1$ is NH, $R^5$ is —$CH_2$-piperidin-1-yl, and $R^1$, $R^2$, $R^{8a}$, $R^{8b}$ and $R^{8c}$ for a compound corresponds in each case to one row of Table A Table 642
Compounds of the formula I.2 in which $X^1$ is NH, $R^5$ is —$CH_2$-piperazin-1-yl, and $R^1$, $R^2$, $R^{8a}$, $R^{8b}$ and $R^{8c}$ for a compound corresponds in each case to one row of Table A Table 643
Compounds of the formula I.2 in which $X^1$ is NH, $R^5$ is —$CH_2$-(1-methylpiperazin-4-yl), and $R^1$, $R^2$, $R^{8a}$, $R^{8b}$ and $R^{8c}$ for a compound corresponds in each case to one row of Table A Table 644
Compounds of the formula I.2 in which $X^1$ is NH, $R^5$ is —$CH_2$-(1-ethylpiperazin-4-yl), and $R^1$, $R^2$, $R^{8a}$, $R^{8b}$ and $R^{8c}$ for a compound corresponds in each case to one row of Table A Table 645
Compounds of the formula I.2 in which $X^1$ is NH, $R^5$ is —$CH_2$-(1-propylpiperazin-4-yl), and $R^1$, $R^2$, $R^{8a}$, $R^{8b}$ and $R^{8c}$ for a compound corresponds in each case to one row of Table A Table 646
Compounds of the formula I.2 in which $X^1$ is NH, $R^5$ is —$CH_2$-(1-isopropylpiperazin-4-yl), and $R^1$, $R^2$, $R^{8a}$, $R^{8b}$ and $R^{8c}$ for a compound corresponds in each case to one row of Table A Table 647
Compounds of the formula I.2 in which $X^1$ is NH, $R^5$ is —$CH_2$-(1-(oxetan-3-yl)-piperazin-4-yl), and $R^1$, $R^2$, $R^{8a}$, $R^{8b}$ and $R^{8c}$ for a compound corresponds in each case to one row of Table A Table 648
Compounds of the formula I.2 in which $X^1$ is NH, $R^5$ is —$CH_2$-azetidin-1-yl, and $R^1$, $R^2$, $R^{8a}$, $R^{8b}$ and $R^{8c}$ for a compound corresponds in each case to one row of Table A Table 649
Compounds of the formula I.2 in which $X^1$ is NH, $R^5$ is —$CH_2$-pyrrolidin-1-yl, and $R^1$, $R^2$, $R^{8a}$, $R^{8b}$ and $R^{8c}$ for a compound corresponds in each case to one row of Table A Table 650
Compounds of the formula I.2 in which $X^1$ is NH, $R^5$ is —$CH_2$-piperidin-1-yl, and $R^1$, $R^2$, $R^{8a}$, $R^{8b}$ and $R^{8c}$ for a compound corresponds in each case to one row of Table A Table 651
Compounds of the formula I.2 in which $X^1$ is NH, $R^5$ is —$CH_2$-piperazin-1-yl, and $R^1$, $R^2$, $R^{8a}$, $R^{8b}$ and $R^{8c}$ for a compound corresponds in each case to one row of Table A Table 652
Compounds of the formula I.2 in which $X^1$ is NH, $R^5$ is —$CH_2$-(1-methylpiperazin-4-yl), and $R^1$, $R^2$, $R^{8a}$, $R^{8b}$ and $R^{8c}$ for a compound corresponds in each case to one row of Table A Table 653
Compounds of the formula I.2 in which $X^1$ is NH, $R^5$ is —$CH_2$-(1-ethylpiperazin-4-yl), and $R^1$, $R^2$, $R^{8a}$, $R^{8b}$ and $R^{8c}$ for a compound corresponds in each case to one row of Table A Table 654
Compounds of the formula I.2 in which $X^1$ is NH, $R^5$ is —$CH_2$-(1-propylpiperazin-4-yl), and $R^1$, $R^2$, $R^{8a}$, $R^{8b}$ and $R^{8c}$ for a compound corresponds in each case to one row of Table A Table 655
Compounds of the formula I.2 in which $X^1$ is NH, $R^5$ is —$CH_2$-(1-isopropylpiperazin-4-yl), and $R^1$, $R^2$, $R^{8a}$, $R^{8b}$ and $R^{8c}$ for a compound corresponds in each case to one row of Table A Table 656
Compounds of the formula I.2 in which $X^1$ is NH, $R^5$ is —$CH_2$-(1-(oxetan-3-yl)-piperazin-4-yl), and $R^1$, $R^2$, $R^{8a}$, $R^{8b}$ and $R^{8c}$ for a compound corresponds in each case to one row of Table A Table 657
Compounds of the formula I.2 in which $X^1$ is NH, $R^5$ is —$CH_2$-morpholin-4-yl, and $R^1$, $R^2$, $R^{8a}$, $R^{8b}$ and $R^{8c}$ for a compound corresponds in each case to one row of Table A Table 658
Compounds of the formula I.2 in which $X^1$ is NH, $R^5$ is —$CH_2$-(2-oxa-6-aza-spiro[3.3]heptan-6-yl), and $R^1$, $R^2$, $R^{8a}$, $R^{8b}$ and $R^{8c}$ for a compound corresponds in each case to one row of Table A Table 659
Compounds of the formula I.2 in which $X^1$ is NH, $R^5$ is —$CH_2$-(2-aza-spiro[3.3]heptan-2-yl), and $R^1$, $R^2$, $R^{8a}$, $R^{8b}$ and $R^{8c}$ for a compound corresponds in each case to one row of Table A Table 660
Compounds of the formula I.2 in which $X^1$ is NH, $R^5$ is —$CH_2$-(2,6-di-aza-spiro[3.3]heptan-2-yl), and $R^1$, $R^2$, $R^{8a}$, $R^{8b}$ and $R^{8c}$ for a compound corresponds in each case to one row of Table A Table 661
Compounds of the formula I.2 in which $X^1$ is NH, $R^5$ is —$CH_2$-(2-methyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 662
Compounds of the formula I.2 in which $X^1$ is NH, $R^5$ is —$CH_2$-(2-ethyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 663
Compounds of the formula I.2 in which $X^1$ is NH, $R^5$ is —$CH_2$-(2-propyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 664
Compounds of the formula I.2 in which $X^1$ is NH, $R^5$ is —$CH_2$-(2-isopropyl-2,6-di-aza-spiro[3.3]heptan-6-yl), and $R^1$, $R^2$, $R^{8a}$, $R^{8b}$ and $R^{8c}$ for a compound corresponds in each case to one row of Table A Table 665
Compounds of the formula I.2 in which $X^1$ is NH, $R^5$ is —$CH_2$-(2-(oxetan-3-yl)-2,6-di-aza-spiro[3.3]heptan-6-yl), and $R^1$, $R^2$, $R^{8a}$, $R^{8b}$ and $R^{8c}$ for a compound corresponds in each case to one row of Table A Table 666
Compounds of the formula I.2 in which $X^1$ is NH, $R^5$ is —O—$CH_2CH_2$—$NH_2$, and $R^1$, $R^2$, $R^{8a}$, $R^{8b}$ and $R^{8c}$ for a compound corresponds in each case to one row of Table A Table 667
Compounds of the formula I.2 in which $X^1$ is NH, $R^5$ is —O—$CH_2CH_2$—$NHCH_3$, and $R^1$, $R^2$, $R^{8a}$, $R^{8b}$ and $R^{8c}$ for a compound corresponds in each case to one row of Table A Table 668
Compounds of the formula I.2 in which $X^1$ is NH, $R^5$ is —O—$CH_2CH_2$—$N(CH_3)_2$, and $R^1$, $R^2$, $R^{8a}$, $R^{8b}$ and $R^{8c}$ for a compound corresponds in each case to one row of Table A Table 669
Compounds of the formula I.2 in which $X^1$ is NH, $R^5$ is —O—$CH_2CH_2$—$N(H)CH_2CH_3$, and $R^1$, $R^2$, $R^{8a}$, $R^{8b}$ and $R^{8c}$ for a compound corresponds in each case to one row of Table A Table 670
Compounds of the formula I.2 in which $X^1$ is NH, $R^5$ is —O—$CH_2CH_2$—$N(CH_2CH_3)_2$, and $R^1$, $R^2$, $R^{8a}$, $R^{8b}$ and $R^{8c}$ for a compound corresponds in each case to one row of Table A Table 671
Compounds of the formula I.2 in which $X^1$ is NH, $R^5$ is —O—$CH_2CH_2$-aziridin-1-yl, and $R^1$, $R^2$, $R^{8a}$, $R^{8b}$ and $R^{8c}$ for a compound corresponds in each case to one row of Table A Table 672
Compounds of the formula I.2 in which $X^1$ is NH, $R^5$ is —O—$CH_2CH_2$-azetidin-1-yl, and $R^1$, $R^2$, $R^{8a}$, $R^{8b}$ and $R^{8c}$ for a compound corresponds in each case to one row of Table A Table 673
Compounds of the formula I.2 in which $X^1$ is NH, $R^5$ is —O—$CH_2CH_2$-pyrrolidin-1-yl, and $R^1$, $R^2$, $R^{8a}$, $R^{8b}$ and $R^{8c}$ for a compound corresponds in each case to one row of Table A Table 674
Compounds of the formula I.2 in which $X^1$ is NH, $R^5$ is —O—$CH_2CH_2$-piperidin-1-yl, and $R^1$, $R^2$, $R^{8a}$, $R^{8b}$ and $R^{8c}$ for a compound corresponds in each case to one row of Table A Table 675
Compounds of the formula I.2 in which $X^1$ is NH, $R^5$ is —O—$CH_2CH_2$-piperazin-1-yl, and $R^1$, $R^2$, $R^{8a}$, $R^{8b}$ and $R^{8c}$ for a compound corresponds in each case to one row of Table A Table 676
Compounds of the formula I.2 in which $X^1$ is NH, $R^5$ is —O—$CH_2CH_2$-(1-methylpiperazin-4-yl, and $R^1$, $R^2$, $R^{8a}$, $R^{8b}$ and $R^{8c}$ for a compound corresponds in each case to one row of Table A Table 677
Compounds of the formula I.2 in which $X^1$ is NH, $R^5$ is —O—$CH_2CH_2$-(1-ethylpiperazin-4-yl, and $R^1$, $R^2$, $R^{8a}$, $R^{8b}$ and $R^{8c}$ for a compound corresponds in each case to one row of Table A Table 678
Compounds of the formula I.2 in which $X^1$ is NH, $R^5$ is —O—$CH_2CH_2$-(1-propylpiperazin-4-yl, and $R^1$, $R^2$, $R^{8a}$, $R^{8b}$ and $R^{8c}$ for a compound corresponds in each case to one row of Table A Table 679
Compounds of the formula I.2 in which $X^1$ is NH, $R^5$ is —O—$CH_2CH_2$-(1-isopropylpiperazin-4-yl, and $R^1$, $R^2$, $R^{8a}$, $R^{8b}$ and $R^{8c}$ for a compound corresponds in each case to one row of Table A Table 680
Compounds of the formula I.2 in which $X^1$ is NH, $R^5$ is —O—CH$_2$CH$_2$-morpholin-4-yl, and $R^1$, $R^2$, $R^{8a}$, $R^{8b}$ and $R^{8c}$ for a compound corresponds in each case to one row of Table A Tables 681 to 760
Compounds of the formula I.2 in which $X^1$ is CH$_2$, $R^5$ is as defined in tables 601 to 680, and $R^1$, $R^2$, $R^{8a}$, $R^{8b}$ and $R^{8c}$ for a compound corresponds in each case to one row of Table A Tables 761 to 840
Compounds of the formula I.2 in which $X^1$ is O, $R^5$ is as defined in tables 601 to 680, and $R^1$, $R^2$, $R^{8a}$, $R^{8b}$ and $R^{8c}$ for a compound corresponds in each case to one row of Table A Tables 841 to 1140
Compounds of the formula I.3 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 1141 to 1680
Compounds of the formula I.4 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 1681 to 1980
Compounds of the formula I.5 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 1981 to 2520
Compounds of the formula I.6 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 2521 to 2820
Compounds of the formula I.7 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 2821 to 3360
Compounds of the formula I.8 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 3361 to 3660
Compounds of the formula I.9 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 3661 to 4200
Compounds of the formula I.10 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 4201 to 4500
Compounds of the formula I.11 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 4501 to 5040
Compounds of the formula I.12 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 5041 to 5340
Compounds of the formula I.13 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 5341 to 5880
Compounds of the formula I.14 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 5881 to 6180
Compounds of the formula I.15 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 6181 to 6720
Compounds of the formula I.16 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 6721 to 7020
Compounds of the formula I.17 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 7021 to 7560
Compounds of the formula I.18 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 7561 to 7860
Compounds of the formula I.19 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 7861 to 8400
Compounds of the formula I.20 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 8401 to 8700
Compounds of the formula I.21 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 8701 to 9240
Compounds of the formula I.22 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 9241 to 9540
Compounds of the formula I.23 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 9541 to 10080
Compounds of the formula I.24 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 10081 to 10380
Compounds of the formula I.25 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 10381 to 10920
Compounds of the formula I.26 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 10921 to 11220
Compounds of the formula I.27 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 11221 to 11760
Compounds of the formula I.28 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 11761 to 12060
Compounds of the formula I.29 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 12061 to 12600
Compounds of the formula I.30 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 12601 to 12900
Compounds of the formula I.31 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 12901 to 13440
Compounds of the formula I.32 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 13441 to 13740
Compounds of the formula I.33 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 13741 to 14280
Compounds of the formula I.34 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 14281 to 14580
Compounds of the formula I.35 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 14581 to 15120
Compounds of the formula I.36 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 15121 to 15420
Compounds of the formula I.37 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 15421 to 15960
Compounds of the formula I.38 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 15961 to 16260
Compounds of the formula I.39 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 16261 to 16800
Compounds of the formula I.40 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 16801 to 17100
Compounds of the formula I.41 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 17101 to 17640
Compounds of the formula I.42 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 17641 to 17940
Compounds of the formula I.43 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 17941 to 18480
Compounds of the formula I.44 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 18481 to 18780
Compounds of the formula I.45 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 18781 to 19320
Compounds of the formula I.46 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 19321 to 19620
Compounds of the formula I.47 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 19621 to 20160
Compounds of the formula I.48 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 20161 to 20460
Compounds of the formula I.49 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 20461 to 21000
Compounds of the formula I.50 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 21001 to 21300
Compounds of the formula I.51 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 21301 to 21840
Compounds of the formula I.52 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 21841 to 22140
Compounds of the formula I.53 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 22141 to 22680
Compounds of the formula I.54 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 22681 to 22980
Compounds of the formula I.55 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 22981 to 23520
Compounds of the formula I.56 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 23521 to 23820
Compounds of the formula I.57 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 23821 to 24360

Compounds of the formula I.58 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 24361 to 24660

Compounds of the formula I.59 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 24661 to 25200

Compounds of the formula I.60 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 25201 to 25500

Compounds of the formula I.61 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 25501 to 26040

Compounds of the formula I.62 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 26041 to 26340

Compounds of the formula I.63 in which $X^1$ and $R^5$ are as defined in tables 1 to 300, and $R^1$, $R^2$, $R^{8a}$, $R^{8b}$ and $R^{8c}$ for a compound corresponds in each case to one row of Table A Tables 26341 to 26880

Compounds of the formula I.64 in which $X^1$ and $R^5$ are as defined in tables 301 to 840, and $R^1$, $R^2$, $R^{8a}$, $R^{8b}$ and $R^{8c}$ for a compound corresponds in each case to one row of Table A Tables 26881 to 27180

Compounds of the formula I.65 in which $X^1$ and $R^5$ are as defined in tables 1 to 300, and $R^1$, $R^2$, $R^{8b}$ and $R^{8c}$ for a compound corresponds in each case to one row of Table B Tables 27181 to 27720

Compounds of the formula I.66 in which $X^1$ and $R^5$ are as defined in tables 301 to 840, and $R^1$, $R^2$, $R^{8b}$ and $R^{8c}$ for a compound corresponds in each case to one row of Table B Tables 27721 to 28020

Compounds of the formula I.67 in which $X^1$ and $R^5$ are as defined in tables 1 to 300, and $R^1$, $R^2$, $R^{8b}$ and $R^{8c}$ for a compound corresponds in each case to one row of Table B Tables 28021 to 28560

Compounds of the formula I.68 in which $X^1$ and $R^5$ are as defined in tables 301 to 840, and $R^1$, $R^2$, $R^{8b}$ and $R^{8c}$ for a compound corresponds in each case to one row of Table B Tables 28561 to 28860

Compounds of the formula I.69 in which $X^1$ and $R^5$ are as defined in tables 1 to 300, and $R^1$, $R^2$, $R^{8b}$ and $R^{8c}$ for a compound corresponds in each case to one row of Table B Tables 28861 to 29400

Compounds of the formula I.70 in which $X^1$ and $R^5$ are as defined in tables 301 to 840, and $R^1$, $R^2$, $R^{8b}$ and $R^{8c}$ for a compound corresponds in each case to one row of Table B Tables 29401 to 29700

Compounds of the formula I.71 in which $X^1$ and $R^5$ are as defined in tables 1 to 300, and $R^1$, $R^2$, $R^{8b}$ and $R^{8c}$ for a compound corresponds in each case to one row of Table B Tables 29701 to 30240

Compounds of the formula I.72 in which $X^1$ and $R^5$ are as defined in tables 301 to 840, and $R^1$, $R^2$, $R^{8b}$ and $R^{8c}$ for a compound corresponds in each case to one row of Table B Tables 30241 to 30540

Compounds of the formula I.73 in which $X^1$ and $R^5$ are as defined in tables 1 to 300, and $R^1$, $R^2$, $R^{8b}$ and $R^{8c}$ for a compound corresponds in each case to one row of Table B Tables 30541 to 31080

Compounds of the formula I.74 in which $X^1$ and $R^5$ are as defined in tables 301 to 840, and $R^1$, $R^2$, $R^{8b}$ and $R^{8c}$ for a compound corresponds in each case to one row of Table B Tables 31081 to 31380

Compounds of the formula I.75 in which $X^1$ and $R^5$ are as defined in tables 1 to 300, and $R^1$, $R^2$, $R^{8b}$ and $R^{8c}$ for a compound corresponds in each case to one row of Table B Tables 31381 to 31920

Compounds of the formula I.76 in which $X^1$ and $R^5$ are as defined in tables 301 to 840, and $R^1$, $R^2$, $R^{8b}$ and $R^{8c}$ for a compound corresponds in each case to one row of Table B Tables 31921 to 32220

Compounds of the formula I.77 in which $X^1$ and $R^5$ are as defined in tables 1 to 300, and $R^1$, $R^2$, $R^{8b}$ and $R^{8c}$ for a compound corresponds in each case to one row of Table B Tables 32221 to 32760

Compounds of the formula I.78 in which $X^1$ and $R^5$ are as defined in tables 301 to 840, and $R^1$, $R^2$, $R^{8b}$ and $R^{8c}$ for a compound corresponds in each case to one row of Table B Tables 32761 to 33060

Compounds of the formula I.79 in which $X^1$ and $R^5$ are as defined in tables 1 to 300, and $R^1$, $R^2$, $R^{8b}$ and $R^{8c}$ for a compound corresponds in each case to one row of Table B Tables 33061 to 33600

Compounds of the formula I.80 in which $X^1$ and $R^5$ are as defined in tables 301 to 840, and $R^1$, $R^2$, $R^{8b}$ and $R^{8c}$ for a compound corresponds in each case to one row of Table B Tables 33601 to 33900

Compounds of the formula I.81 in which $X^1$ and $R^5$ are as defined in tables 1 to 300, and $R^1$, $R^2$, $R^{8b}$ and $R^{8c}$ for a compound corresponds in each case to one row of Table B Tables 33901 to 34440

Compounds of the formula I.82 in which $X^1$ and $R^5$ are as defined in tables 301 to 840, and $R^1$, $R^2$, $R^{8b}$ and $R^{8c}$ for a compound corresponds in each case to one row of Table B Tables 34441 to 34740

Compounds of the formula I.83 in which $X^1$ and $R^5$ are as defined in tables 1 to 300, and $R^1$, $R^2$, $R^{8b}$ and $R^{8c}$ for a compound corresponds in each case to one row of Table B Tables 34741 to 35280

Compounds of the formula I.84 in which $X^1$ and $R^5$ are as defined in tables 301 to 840, and $R^1$, $R^2$, $R^{8b}$ and $R^{8c}$ for a compound corresponds in each case to one row of Table B Tables 35281 to 35580

Compounds of the formula I.85 in which $X^1$ and $R^5$ are as defined in tables 1 to 300, and $R^1$, $R^2$, $R^{8b}$ and $R^{8c}$ for a compound corresponds in each case to one row of Table B Tables 35581 to 36120

Compounds of the formula I.86 in which $X^1$ and $R^5$ are as defined in tables 301 to 840, and $R^1$, $R^2$, $R^{8b}$ and $R^{8c}$ for a compound corresponds in each case to one row of Table B Tables 36121 to 36420

Compounds of the formula I.87 in which $X^1$ and $R^5$ are as defined in tables 1 to 300, and $R^1$, $R^2$, $R^{8b}$ and $R^{8c}$ for a compound corresponds in each case to one row of Table B Tables 36421 to 36960

Compounds of the formula I.88 in which $X^1$ and $R^5$ are as defined in tables 301 to 840, and $R^1$, $R^2$, $R^{8b}$ and $R^{8c}$ for a compound corresponds in each case to one row of Table B Tables 36961 to 37260

Compounds of the formula I.89 in which $X^1$ and $R^5$ are as defined in tables 1 to 300, and $R^1$, $R^2$, $R^{8b}$ and $R^{8c}$ for a compound corresponds in each case to one row of Table B Tables 37261 to 37800
Compounds of the formula I.90 in which $X^1$ and $R^5$ are as defined in tables 301 to 840, and $R^1$, $R^2$, $R^{8b}$ and $R^{8c}$ for a compound corresponds in each case to one row of Table B Tables 37801 to 38100
Compounds of the formula I.91 in which $X^1$ and $R^5$ are as defined in tables 1 to 300, and $R^1$, $R^2$, $R^{8b}$ and $R^{8c}$ for a compound corresponds in each case to one row of Table B Tables 38101 to 38640
Compounds of the formula I.92 in which $X^1$ and $R^5$ are as defined in tables 301 to 840, and $R^1$, $R^2$, $R^{8b}$ and $R^{8c}$ for a compound corresponds in each case to one row of Table B Tables 38641 to 38940
Compounds of the formula I.93 in which $X^1$ and $R^5$ are as defined in tables 1 to 300, and $R^1$, $R^2$, $R^{8b}$ and $R^{8c}$ for a compound corresponds in each case to one row of Table B Tables 38941 to 39480
Compounds of the formula I.94 in which $X^1$ and $R^5$ are as defined in tables 301 to 840, and $R^1$, $R^2$, $R^{8b}$ and $R^{8c}$ for a compound corresponds in each case to one row of Table B Tables 39481 to 39780
Compounds of the formula I.95 in which $X^1$ and $R^5$ are as defined in tables 1 to 300, and $R^1$, $R^2$, $R^{8b}$ and $R^{8c}$ for a compound corresponds in each case to one row of Table B Tables 39781 to 40320
Compounds of the formula I.96 in which $X^1$ and $R^5$ are as defined in tables 301 to 840, and $R^1$, $R^2$, $R^{8b}$ and $R^{8c}$ for a compound corresponds in each case to one row of Table B Tables 40321 to 40620
Compounds of the formula I.97 in which $X^1$ and $R^5$ are as defined in tables 1 to 300, and $R^1$, $R^2$, $R^{8b}$ and $R^{8c}$ for a compound corresponds in each case to one row of Table B Tables 40621 to 41160
Compounds of the formula I.98 in which $X^1$ and $R^5$ are as defined in tables 301 to 840, and $R^1$, $R^2$, $R^{8b}$ and $R^{8c}$ for a compound corresponds in each case to one row of Table B Tables 41161 to 41460
Compounds of the formula I.99 in which $X^1$ and $R^5$ are as defined in tables 1 to 300, and $R^1$, $R^2$, $R^{8b}$ and $R^{8c}$ for a compound corresponds in each case to one row of Table B Tables 41461 to 42000
Compounds of the formula I.100 in which $X^1$ and $R^5$ are as defined in tables 301 to 840, and $R^1$, $R^2$, $R^{8b}$ and $R^{8c}$ for a compound corresponds in each case to one row of Table B Tables 42001 to 42300
Compounds of the formula I.101 in which $X^1$ and $R^5$ are as defined in tables 1 to 300, and $R^1$, $R^2$, $R^{8b}$ and $R^{8c}$ for a compound corresponds in each case to one row of Table B Tables 42301 to 42840
Compounds of the formula I.102 in which $X^1$ and $R^5$ are as defined in tables 301 to 840, and $R^1$, $R^2$, $R^{8b}$ and $R^{8c}$ for a compound corresponds in each case to one row of Table B Tables 42841 to 43140
Compounds of the formula I.103 in which $X^1$ and $R^5$ are as defined in tables 1 to 300, and $R^1$, $R^2$, $R^{8b}$ and $R^{8c}$ for a compound corresponds in each case to one row of Table B Tables 43141 to 43680
Compounds of the formula I.104 in which $X^1$ and $R^5$ are as defined in tables 301 to 840, and $R^1$, $R^2$, $R^{8b}$ and $R^{8c}$ for a compound corresponds in each case to one row of Table B Tables 43681 to 43980
Compounds of the formula I.105 in which $X^1$ and $R^5$ are as defined in tables 1 to 300, and $R^1$, $R^2$, $R^{8b}$ and $R^{8c}$ for a compound corresponds in each case to one row of Table B Tables 43981 to 44520
Compounds of the formula I.106 in which $X^1$ and $R^5$ are as defined in tables 301 to 840, and $R^1$, $R^2$, $R^{8b}$ and $R^{8c}$ for a compound corresponds in each case to one row of Table B Tables 44521 to 44820
Compounds of the formula I.107 in which $X^1$ and $R^5$ are as defined in tables 1 to 300, and $R^1$, $R^2$, $R^{8b}$ and $R^{8c}$ for a compound corresponds in each case to one row of Table B Tables 44821 to 45360
Compounds of the formula I.108 in which $X^1$ and $R^5$ are as defined in tables 301 to 840, and $R^1$, $R^2$, $R^{8b}$ and $R^{8c}$ for a compound corresponds in each case to one row of Table B Tables 45361 to 45660
Compounds of the formula I.109 in which $X^1$ and $R^5$ are as defined in tables 1 to 300, and $R^1$, $R^2$, $R^{8b}$ and $R^{8c}$ for a compound corresponds in each case to one row of Table B Tables 45661 to 46200
Compounds of the formula I.110 in which $X^1$ and $R^5$ are as defined in tables 301 to 840, and $R^1$, $R^2$, $R^{8b}$ and $R^{8c}$ for a compound corresponds in each case to one row of Table B Tables 46201 to 46500
Compounds of the formula I.111 in which $X^1$ and $R^5$ are as defined in tables 1 to 300, and $R^1$, $R^2$, $R^{8b}$ and $R^{8c}$ for a compound corresponds in each case to one row of Table B Tables 46501 to 47040
Compounds of the formula I.112 in which $X^1$ and $R^5$ are as defined in tables 301 to 840, and $R^1$, $R^2$, $R^{8b}$ and $R^{8c}$ for a compound corresponds in each case to one row of Table B Tables 47041 to 47340
Compounds of the formula I.113 in which $X^1$ and $R^5$ are as defined in tables 1 to 300, and $R^1$, $R^2$, $R^{8b}$ and $R^{8c}$ for a compound corresponds in each case to one row of Table B Tables 47341 to 47880
Compounds of the formula I.114 in which $X^1$ and $R^5$ are as defined in tables 301 to 840, and $R^1$, $R^2$, $R^{8b}$ and $R^{8c}$ for a compound corresponds in each case to one row of Table B Tables 47881 to 48180
Compounds of the formula I.115 in which $X^1$ and $R^5$ are as defined in tables 1 to 300, and $R^1$, $R^2$, $R^{8b}$ and $R^{8c}$ for a compound corresponds in each case to one row of Table B Tables 48181 to 48720
Compounds of the formula I.116 in which $X^1$ and $R^5$ are as defined in tables 301 to 840, and $R^1$, $R^2$, $R^{8b}$ and $R^{8c}$ for a compound corresponds in each case to one row of Table B Tables 48721 to 49020
Compounds of the formula I.117 in which $X^1$ and $R^5$ are as defined in tables 1 to 300, and $R^1$, $R^2$, $R^{8b}$ and $R^{8c}$ for a compound corresponds in each case to one row of Table B Tables 49021 to 49560
Compounds of the formula I.118 in which $X^1$ and $R^5$ are as defined in tables 301 to 840, and $R^1$, $R^2$, $R^{8b}$ and $R^{8c}$ for a compound corresponds in each case to one row of Table B Tables 49561 to 49860
Compounds of the formula I.119 in which $X^1$ and $R^5$ are as defined in tables 1 to 300, and $R^1$, $R^2$, $R^{8b}$ and $R^{8c}$ for a compound corresponds in each case to one row of Table B Tables 49861 to 50400
Compounds of the formula I.120 in which $X^1$ and $R^5$ are as defined in tables 301 to 840, and $R^1$, $R^2$, $R^{8b}$ and $R^{8c}$ for a compound corresponds in each case to one row of Table B Tables 50401 to 50700
Compounds of the formula I.121 in which $X^1$ and $R^5$ are as defined in tables 1 to 300, and $R^1$, $R^2$, $R^{8b}$ and $R^{8c}$ for a compound corresponds in each case to one row of Table B Tables 50701 to 51240
Compounds of the formula I.122 in which $X^1$ and $R^5$ are as defined in tables 301 to 840, and $R^1$, $R^2$, $R^{8b}$ and $R^{8c}$ for a compound corresponds in each case to one row of Table B Tables 51241 to 51540

Compounds of the formula I.123 in which $X^1$ and $R^5$ are as defined in tables 1 to 300, and $R^1$, $R^2$, $R^{8b}$ and $R^{8c}$ for a compound corresponds in each case to one row of Table B Tables 51541 to 52080

Compounds of the formula I.124 in which $X^1$ and $R^5$ are as defined in tables 301 to 840, and $R^1$, $R^2$, $R^{8b}$ and $R^{8c}$ for a compound corresponds in each case to one row of Table B Tables 52081 to 52380

Compounds of the formula I.125 in which $X^1$ and $R^5$ are as defined in tables 1 to 300, and $R^1$, $R^2$, $R^{8b}$ and $R^{8c}$ for a compound corresponds in each case to one row of Table B Tables 52381 to 52920

Compounds of the formula I.126 in which $X^1$ and $R^5$ are as defined in tables 301 to 840, and $R^1$, $R^2$, $R^{8b}$ and $R^{8c}$ for a compound corresponds in each case to one row of Table B Tables 52921 to 53220

Compounds of the formula I.127 in which $X^1$ and $R^5$ are as defined in tables 1 to 300, and $R^1$, $R^2$, $R^{8b}$ and $R^{8c}$ for a compound corresponds in each case to one row of Table B Tables 53221 to 53760

Compounds of the formula I.128 in which $X^1$ and $R^5$ are as defined in tables 301 to 840, and $R^1$, $R^2$, $R^{8b}$ and $R^{8c}$ for a compound corresponds in each case to one row of Table B

TABLE A

| Example No. | $R^{8a}$ | $R^{8b}$ | $R^{8c}$ | $R^1$ | $R^2$ |
|---|---|---|---|---|---|
| A-1. | H | H | H | CN | H |
| A-2. | F | H | H | CN | H |
| A-3. | $CH_3$ | H | H | CN | H |
| A-4. | $OCH_3$ | H | H | CN | H |
| A-5. | $CH_2F$ | H | H | CN | H |
| A-6. | $CHF_2$ | H | H | CN | H |
| A-7. | $CF_3$ | H | H | CN | H |
| A-8. | $OCH_2F$ | H | H | CN | H |
| A-9. | $OCHF_2$ | H | H | CN | H |
| A-10. | $OCF_3$ | H | H | CN | H |
| A-11. | H | F | H | CN | H |
| A-12. | H | $CH_3$ | H | CN | H |
| A-13. | H | $OCH_3$ | H | CN | H |
| A-14. | H | CN | H | CN | H |
| A-15. | H | $CH_2F$ | H | CN | H |
| A-16. | H | $CHF_2$ | H | CN | H |
| A-17. | H | $CF_3$ | H | CN | H |
| A-18. | H | $OCH_2F$ | H | CN | H |
| A-19. | H | $OCHF_2$ | H | CN | H |
| A-20. | H | $OCF_3$ | H | CN | H |
| A-21. | H | H | 3-F | CN | H |
| A-22. | H | H | 3-$CH_3$ | CN | H |
| A-23. | H | H | 3-$OCH_3$ | CN | H |
| A-24. | H | H | 5-F | CN | H |
| A-25. | H | H | 5-$CH_3$ | CN | H |
| A-26. | H | H | 5-$OCH_3$ | CN | H |
| A-27. | F | F | H | CN | H |
| A-28. | F | $CH_3$ | H | CN | H |
| A-29. | F | $OCH_3$ | H | CN | H |
| A-30. | F | CN | H | CN | H |
| A-31. | F | $CH_2F$ | H | CN | H |
| A-32. | F | $CHF_2$ | H | CN | H |
| A-33. | F | $CF_3$ | H | CN | H |
| A-34. | F | $OCH_2F$ | H | CN | H |
| A-35. | F | $OCHF_2$ | H | CN | H |
| A-36. | F | $OCF_3$ | H | CN | H |
| A-37. | F | H | 3-F | CN | H |
| A-38. | F | H | 3-$CH_3$ | CN | H |
| A-39. | F | H | 3-$OCH_3$ | CN | H |
| A-40. | F | H | 5-F | CN | H |
| A-41. | F | H | 5-$CH_3$ | CN | H |
| A-42. | F | H | 5-$OCH_3$ | CN | H |
| A-43. | $CH_3$ | F | H | CN | H |
| A-44. | $CH_3$ | $CH_3$ | H | CN | H |
| A-45. | $CH_3$ | $OCH_3$ | H | CN | H |
| A-46. | $CH_3$ | CN | H | CN | H |
| A-47. | $CH_3$ | $CH_2F$ | H | CN | H |

TABLE A-continued

| Example No. | $R^{8a}$ | $R^{8b}$ | $R^{8c}$ | $R^1$ | $R^2$ |
|---|---|---|---|---|---|
| A-48. | $CH_3$ | $CHF_2$ | H | CN | H |
| A-49. | $CH_3$ | $CF_3$ | H | CN | H |
| A-50. | $CH_3$ | $OCH_2F$ | H | CN | H |
| A-51. | $CH_3$ | $OCHF_2$ | H | CN | H |
| A-52. | $CH_3$ | $OCF_3$ | H | CN | H |
| A-53. | $CH_3$ | H | 3-F | CN | H |
| A-54. | $CH_3$ | H | 3-$CH_3$ | CN | H |
| A-55. | $CH_3$ | H | 3-$OCH_3$ | CN | H |
| A-56. | $CH_3$ | H | 5-F | CN | H |
| A-57. | $CH_3$ | H | 5-$CH_3$ | CN | H |
| A-58. | $CH_3$ | H | 5-$OCH_3$ | CN | H |
| A-59. | $OCH_3$ | F | H | CN | H |
| A-60. | $OCH_3$ | $CH_3$ | H | CN | H |
| A-61. | $OCH_3$ | $OCH_3$ | H | CN | H |
| A-62. | $OCH_3$ | CN | H | CN | H |
| A-63. | $OCH_3$ | $CH_2F$ | H | CN | H |
| A-64. | $OCH_3$ | $CHF_2$ | H | CN | H |
| A-65. | $OCH_3$ | $CF_3$ | H | CN | H |
| A-66. | $OCH_3$ | $OCH_2F$ | H | CN | H |
| A-67. | $OCH_3$ | $OCHF_2$ | H | CN | H |
| A-68. | $OCH_3$ | $OCF_3$ | H | CN | H |
| A-69. | $OCH_3$ | H | 3-F | CN | H |
| A-70. | $OCH_3$ | H | 3-$CH_3$ | CN | H |
| A-71. | $OCH_3$ | H | 3-$OCH_3$ | CN | H |
| A-72. | $OCH_3$ | H | 5-F | CN | H |
| A-73. | $OCH_3$ | H | 5-$CH_3$ | CN | H |
| A-74. | $OCH_3$ | H | 5-$OCH_3$ | CN | H |
| A-75. | H | F | 3-F | CN | H |
| A-76. | H | F | 3-$CH_3$ | CN | H |
| A-77. | H | F | 3-$OCH_3$ | CN | H |
| A-78. | H | F | 5-F | CN | H |
| A-79. | H | F | 5-$CH_3$ | CN | H |
| A-80. | H | F | 5-$OCH_3$ | CN | H |
| A-81. | H | $CH_3$ | 3-F | CN | H |
| A-82. | H | $CH_3$ | 3-$CH_3$ | CN | H |
| A-83. | H | $CH_3$ | 3-$OCH_3$ | CN | H |
| A-84. | H | $CH_3$ | 5-F | CN | H |
| A-85. | H | $CH_3$ | 5-$CH_3$ | CN | H |
| A-86. | H | $CH_3$ | 5-$OCH_3$ | CN | H |
| A-87. | H | $OCH_3$ | 3-F | CN | H |
| A-88. | H | $OCH_3$ | 3-$CH_3$ | CN | H |
| A-89. | H | $OCH_3$ | 3-$OCH_3$ | CN | H |
| A-90. | H | $OCH_3$ | 5-F | CN | H |
| A-91. | H | $OCH_3$ | 5-$CH_3$ | CN | H |
| A-92. | H | $OCH_3$ | 5-$OCH_3$ | CN | H |
| A-93. | H | CN | 3-F | CN | H |
| A-94. | H | CN | 3-$CH_3$ | CN | H |
| A-95. | H | CN | 3-$OCH_3$ | CN | H |
| A-96. | H | CN | 5-F | CN | H |
| A-97. | H | CN | 5-$CH_3$ | CN | H |
| A-98. | H | CN | 5-$OCH_3$ | CN | H |
| A-99. | H | $CH_2F$ | 3-F | CN | H |
| A-100. | H | $CH_2F$ | 3-$CH_3$ | CN | H |
| A-101. | H | $CH_2F$ | 3-$OCH_3$ | CN | H |
| A-102. | H | $CH_2F$ | 5-F | CN | H |
| A-103. | H | $CH_2F$ | 5-$CH_3$ | CN | H |
| A-104. | H | $CH_2F$ | 5-$OCH_3$ | CN | H |
| A-105. | H | $CHF_2$ | 3-F | CN | H |
| A-106. | H | $CHF_2$ | 3-$CH_3$ | CN | H |
| A-107. | H | $CHF_2$ | 3-$OCH_3$ | CN | H |
| A-108. | H | $CHF_2$ | 5-F | CN | H |
| A-109. | H | $CHF_2$ | 5-$CH_3$ | CN | H |
| A-110. | H | $CHF_2$ | 5-$OCH_3$ | CN | H |
| A-111. | H | $CF_3$ | 3-F | CN | H |
| A-112. | H | $CF_3$ | 3-$CH_3$ | CN | H |
| A-113. | H | $CF_3$ | 3-$OCH_3$ | CN | H |
| A-114. | H | $CF_3$ | 5-F | CN | H |
| A-115. | H | $CF_3$ | 5-$CH_3$ | CN | H |
| A-116. | H | $CF_3$ | 5-$OCH_3$ | CN | H |
| A-117. | H | $OCH_2F$ | 3-F | CN | H |
| A-118. | H | $OCH_2F$ | 3-$CH_3$ | CN | H |
| A-119. | H | $OCH_2F$ | 3-$OCH_3$ | CN | H |
| A-120. | H | $OCH_2F$ | 5-F | CN | H |
| A-121. | H | $OCH_2F$ | 5-$CH_3$ | CN | H |
| A-122. | H | $OCH_2F$ | 5-$OCH_3$ | CN | H |
| A-123. | H | $OCHF_2$ | 3-F | CN | H |
| A-124. | H | $OCHF_2$ | 3-$CH_3$ | CN | H |
| A-125. | H | $OCHF_2$ | 3-$OCH_3$ | CN | H |

TABLE A-continued

| Example No. | $R^{8a}$ | $R^{8b}$ | $R^{8c}$ | $R^1$ | $R^2$ |
|---|---|---|---|---|---|
| A-126. | H | OCHF$_2$ | 5-F | CN | H |
| A-127. | H | OCHF$_2$ | 5-CH$_3$ | CN | H |
| A-128. | H | OCHF$_2$ | 5-OCH$_3$ | CN | H |
| A-129. | H | OCF$_3$ | 3-F | CN | H |
| A-130. | H | OCF$_3$ | 3-CH$_3$ | CN | H |
| A-131. | H | OCF$_3$ | 3-OCH$_3$ | CN | H |
| A-132. | H | OCF$_3$ | 5-F | CN | H |
| A-133. | H | OCF$_3$ | 5-CH$_3$ | CN | H |
| A-134. | H | OCF$_3$ | 5-OCH$_3$ | CN | H |
| A-135. | F | F | 3-F | CN | H |
| A-136. | F | F | 3-CH$_3$ | CN | H |
| A-137. | F | F | 3-OCH$_3$ | CN | H |
| A-138. | F | F | 5-F | CN | H |
| A-139. | F | F | 5-CH$_3$ | CN | H |
| A-140. | F | F | 5-OCH$_3$ | CN | H |
| A-141. | F | CH$_3$ | 3-F | CN | H |
| A-142. | F | CH$_3$ | 3-CH$_3$ | CN | H |
| A-143. | F | CH$_3$ | 3-OCH$_3$ | CN | H |
| A-144. | F | CH$_3$ | 5-F | CN | H |
| A-145. | F | CH$_3$ | 5-CH$_3$ | CN | H |
| A-146. | F | CH$_3$ | 5-OCH$_3$ | CN | H |
| A-147. | F | OCH$_3$ | 3-F | CN | H |
| A-148. | F | OCH$_3$ | 3-CH$_3$ | CN | H |
| A-149. | F | OCH$_3$ | 3-OCH$_3$ | CN | H |
| A-150. | F | OCH$_3$ | 5-F | CN | H |
| A-151. | F | OCH$_3$ | 5-CH$_3$ | CN | H |
| A-152. | F | OCH$_3$ | 5-OCH$_3$ | CN | H |
| A-153. | F | CN | 3-F | CN | H |
| A-154. | F | CN | 3-CH$_3$ | CN | H |
| A-155. | F | CN | 3-OCH$_3$ | CN | H |
| A-156. | F | CN | 5-F | CN | H |
| A-157. | F | CN | 5-CH$_3$ | CN | H |
| A-158. | F | CN | 5-OCH$_3$ | CN | H |
| A-159. | F | CH$_2$F | 3-F | CN | H |
| A-160. | F | CH$_2$F | 3-CH$_3$ | CN | H |
| A-161. | F | CH$_2$F | 3-OCH$_3$ | CN | H |
| A-162. | F | CH$_2$F | 5-F | CN | H |
| A-163. | F | CH$_2$F | 5-CH$_3$ | CN | H |
| A-164. | F | CH$_2$F | 5-OCH$_3$ | CN | H |
| A-165. | F | CHF$_2$ | 3-F | CN | H |
| A-166. | F | CHF$_2$ | 3-CH$_3$ | CN | H |
| A-167. | F | CHF$_2$ | 3-OCH$_3$ | CN | H |
| A-168. | F | CHF$_2$ | 5-F | CN | H |
| A-169. | F | CHF$_2$ | 5-CH$_3$ | CN | H |
| A-170. | F | CHF$_2$ | 5-OCH$_3$ | CN | H |
| A-171. | F | CF$_3$ | 3-F | CN | H |
| A-172. | F | CF$_3$ | 3-CH$_3$ | CN | H |
| A-173. | F | CF$_3$ | 3-OCH$_3$ | CN | H |
| A-174. | F | CF$_3$ | 5-F | CN | H |
| A-175. | F | CF$_3$ | 5-CH$_3$ | CN | H |
| A-176. | F | CF$_3$ | 5-OCH$_3$ | CN | H |
| A-177. | F | OCH$_2$F | 3-F | CN | H |
| A-178. | F | OCH$_2$F | 3-CH$_3$ | CN | H |
| A-179. | F | OCH$_2$F | 3-OCH$_3$ | CN | H |
| A-180. | F | OCH$_2$F | 5-F | CN | H |
| A-181. | F | OCH$_2$F | 5-CH$_3$ | CN | H |
| A-182. | F | OCH$_2$F | 5-OCH$_3$ | CN | H |
| A-183. | F | OCHF$_2$ | 3-F | CN | H |
| A-184. | F | OCHF$_2$ | 3-CH$_3$ | CN | H |
| A-185. | F | OCHF$_2$ | 3-OCH$_3$ | CN | H |
| A-186. | F | OCHF$_2$ | 5-F | CN | H |
| A-187. | F | OCHF$_2$ | 5-CH$_3$ | CN | H |
| A-188. | F | OCHF$_2$ | 5-OCH$_3$ | CN | H |
| A-189. | F | OCF$_3$ | 3-F | CN | H |
| A-190. | F | OCF$_3$ | 3-CH$_3$ | CN | H |
| A-191. | F | OCF$_3$ | 3-OCH$_3$ | CN | H |
| A-192. | F | OCF$_3$ | 5-F | CN | H |
| A-193. | F | OCF$_3$ | 5-CH$_3$ | CN | H |
| A-194. | F | OCF$_3$ | 5-OCH$_3$ | CN | H |
| A-195. | CH$_3$ | F | 3-F | CN | H |
| A-196. | CH$_3$ | F | 3-CH$_3$ | CN | H |
| A-197. | CH$_3$ | F | 3-OCH$_3$ | CN | H |
| A-198. | CH$_3$ | F | 5-F | CN | H |
| A-199. | CH$_3$ | F | 5-CH$_3$ | CN | H |
| A-200. | CH$_3$ | F | 5-OCH$_3$ | CN | H |
| A-201. | CH$_3$ | CH$_3$ | 3-F | CN | H |
| A-202. | CH$_3$ | CH$_3$ | 3-CH$_3$ | CN | H |
| A-203. | CH$_3$ | CH$_3$ | 3-OCH$_3$ | CN | H |
| A-204. | CH$_3$ | CH$_3$ | 5-F | CN | H |
| A-205. | CH$_3$ | CH$_3$ | 5-CH$_3$ | CN | H |
| A-206. | CH$_3$ | CH$_3$ | 5-OCH$_3$ | CN | H |
| A-207. | CH$_3$ | OCH$_3$ | 3-F | CN | H |
| A-208. | CH$_3$ | OCH$_3$ | 3-CH$_3$ | CN | H |
| A-209. | CH$_3$ | OCH$_3$ | 3-OCH$_3$ | CN | H |
| A-210. | CH$_3$ | OCH$_3$ | 5-F | CN | H |
| A-211. | CH$_3$ | OCH$_3$ | 5-CH$_3$ | CN | H |
| A-212. | CH$_3$ | OCH$_3$ | 5-OCH$_3$ | CN | H |
| A-213. | CH$_3$ | CN | 3-F | CN | H |
| A-214. | CH$_3$ | CN | 3-CH$_3$ | CN | H |
| A-215. | CH$_3$ | CN | 3-OCH$_3$ | CN | H |
| A-216. | CH$_3$ | CN | 5-F | CN | H |
| A-217. | CH$_3$ | CN | 5-CH$_3$ | CN | H |
| A-218. | CH$_3$ | CN | 5-OCH$_3$ | CN | H |
| A-219. | CH$_3$ | CH$_2$F | 3-F | CN | H |
| A-220. | CH$_3$ | CH$_2$F | 3-CH$_3$ | CN | H |
| A-221. | CH$_3$ | CH$_2$F | 3-OCH$_3$ | CN | H |
| A-222. | CH$_3$ | CH$_2$F | 5-F | CN | H |
| A-223. | CH$_3$ | CH$_2$F | 5-CH$_3$ | CN | H |
| A-224. | CH$_3$ | CH$_2$F | 5-OCH$_3$ | CN | H |
| A-225. | CH$_3$ | CHF$_2$ | 3-F | CN | H |
| A-226. | CH$_3$ | CHF$_2$ | 3-CH$_3$ | CN | H |
| A-227. | CH$_3$ | CHF$_2$ | 3-OCH$_3$ | CN | H |
| A-228. | CH$_3$ | CHF$_2$ | 5-F | CN | H |
| A-229. | CH$_3$ | CHF$_2$ | 5-CH$_3$ | CN | H |
| A-230. | CH$_3$ | CHF$_2$ | 5-OCH$_3$ | CN | H |
| A-231. | CH$_3$ | CF$_3$ | 3-F | CN | H |
| A-232. | CH$_3$ | CF$_3$ | 3-CH$_3$ | CN | H |
| A-233. | CH$_3$ | CF$_3$ | 3-OCH$_3$ | CN | H |
| A-234. | CH$_3$ | CF$_3$ | 5-F | CN | H |
| A-235. | CH$_3$ | CF$_3$ | 5-CH$_3$ | CN | H |
| A-236. | CH$_3$ | CF$_3$ | 5-OCH$_3$ | CN | H |
| A-237. | CH$_3$ | OCH$_2$F | 3-F | CN | H |
| A-238. | CH$_3$ | OCH$_2$F | 3-CH$_3$ | CN | H |
| A-239. | CH$_3$ | OCH$_2$F | 3-OCH$_3$ | CN | H |
| A-240. | CH$_3$ | OCH$_2$F | 5-F | CN | H |
| A-241. | CH$_3$ | OCH$_2$F | 5-CH$_3$ | CN | H |
| A-242. | CH$_3$ | OCH$_2$F | 5-OCH$_3$ | CN | H |
| A-243. | CH$_3$ | OCHF$_2$ | 3-F | CN | H |
| A-244. | CH$_3$ | OCHF$_2$ | 3-CH$_3$ | CN | H |
| A-245. | CH$_3$ | OCHF$_2$ | 3-OCH$_3$ | CN | H |
| A-246. | CH$_3$ | OCHF$_2$ | 5-F | CN | H |
| A-247. | CH$_3$ | OCHF$_2$ | 5-CH$_3$ | CN | H |
| A-248. | CH$_3$ | OCHF$_2$ | 5-OCH$_3$ | CN | H |
| A-249. | CH$_3$ | OCF$_3$ | 3-F | CN | H |
| A-250. | CH$_3$ | OCF$_3$ | 3-CH$_3$ | CN | H |
| A-251. | CH$_3$ | OCF$_3$ | 3-OCH$_3$ | CN | H |
| A-252. | CH$_3$ | OCF$_3$ | 5-F | CN | H |
| A-253. | CH$_3$ | OCF$_3$ | 5-CH$_3$ | CN | H |
| A-254. | CH$_3$ | OCF$_3$ | 5-OCH$_3$ | CN | H |
| A-255. | OCH$_3$ | F | 3-F | CN | H |
| A-256. | OCH$_3$ | F | 3-CH$_3$ | CN | H |
| A-257. | OCH$_3$ | F | 3-OCH$_3$ | CN | H |
| A-258. | OCH$_3$ | F | 5-F | CN | H |
| A-259. | OCH$_3$ | F | 5-CH$_3$ | CN | H |
| A-260. | OCH$_3$ | F | 5-OCH$_3$ | CN | H |
| A-261. | OCH$_3$ | CH$_3$ | 3-F | CN | H |
| A-262. | OCH$_3$ | CH$_3$ | 3-CH$_3$ | CN | H |
| A-263. | OCH$_3$ | CH$_3$ | 3-OCH$_3$ | CN | H |
| A-264. | OCH$_3$ | CH$_3$ | 5-F | CN | H |
| A-265. | OCH$_3$ | CH$_3$ | 5-CH$_3$ | CN | H |
| A-266. | OCH$_3$ | CH$_3$ | 5-OCH$_3$ | CN | H |
| A-267. | OCH$_3$ | OCH$_3$ | 3-F | CN | H |
| A-268. | OCH$_3$ | OCH$_3$ | 3-CH$_3$ | CN | H |
| A-269. | OCH$_3$ | OCH$_3$ | 3-OCH$_3$ | CN | H |
| A-270. | OCH$_3$ | OCH$_3$ | 5-F | CN | H |
| A-271. | OCH$_3$ | OCH$_3$ | 5-CH$_3$ | CN | H |
| A-272. | OCH$_3$ | OCH$_3$ | 5-OCH$_3$ | CN | H |
| A-273. | OCH$_3$ | CN | 3-F | CN | H |
| A-274. | OCH$_3$ | CN | 3-CH$_3$ | CN | H |
| A-275. | OCH$_3$ | CN | 3-OCH$_3$ | CN | H |
| A-276. | OCH$_3$ | CN | 5-F | CN | H |
| A-277. | OCH$_3$ | CN | 5-CH$_3$ | CN | H |
| A-278. | OCH$_3$ | CN | 5-OCH$_3$ | CN | H |
| A-279. | OCH$_3$ | CH$_2$F | 3-F | CN | H |
| A-280. | OCH$_3$ | CH$_2$F | 3-CH$_3$ | CN | H |
| A-281. | OCH$_3$ | CH$_2$F | 3-OCH$_3$ | CN | H |

TABLE A-continued

| Example No. | R$^{8a}$ | R$^{8b}$ | R$^{8c}$ | R$^1$ | R$^2$ |
|---|---|---|---|---|---|
| A-282. | OCH$_3$ | CH$_2$F | 5-F | CN | H |
| A-283. | OCH$_3$ | CH$_2$F | 5-CH$_3$ | CN | H |
| A-284. | OCH$_3$ | CH$_2$F | 5-OCH$_3$ | CN | H |
| A-285. | OCH$_3$ | CHF$_2$ | 3-F | CN | H |
| A-286. | OCH$_3$ | CHF$_2$ | 3-CH$_3$ | CN | H |
| A-287. | OCH$_3$ | CHF$_2$ | 3-OCH$_3$ | CN | H |
| A-288. | OCH$_3$ | CHF$_2$ | 5-F | CN | H |
| A-289. | OCH$_3$ | CHF$_2$ | 5-CH$_3$ | CN | H |
| A-290. | OCH$_3$ | CHF$_2$ | 5-OCH$_3$ | CN | H |
| A-291. | OCH$_3$ | CF$_3$ | 3-F | CN | H |
| A-292. | OCH$_3$ | CF$_3$ | 3-CH$_3$ | CN | H |
| A-293. | OCH$_3$ | CF$_3$ | 3-OCH$_3$ | CN | H |
| A-294. | OCH$_3$ | CF$_3$ | 5-F | CN | H |
| A-295. | OCH$_3$ | CF$_3$ | 5-CH$_3$ | CN | H |
| A-296. | OCH$_3$ | CF$_3$ | 5-OCH$_3$ | CN | H |
| A-297. | OCH$_3$ | OCH$_2$F | 3-F | CN | H |
| A-298. | OCH$_3$ | OCH$_2$F | 3-CH$_3$ | CN | H |
| A-299. | OCH$_3$ | OCH$_2$F | 3-OCH$_3$ | CN | H |
| A-300. | OCH$_3$ | OCH$_2$F | 5-F | CN | H |
| A-301. | OCH$_3$ | OCH$_2$F | 5-CH$_3$ | CN | H |
| A-302. | OCH$_3$ | OCH$_2$F | 5-OCH$_3$ | CN | H |
| A-303. | OCH$_3$ | OCHF$_2$ | 3-F | CN | H |
| A-304. | OCH$_3$ | OCHF$_2$ | 3-CH$_3$ | CN | H |
| A-305. | OCH$_3$ | OCHF$_2$ | 3-OCH$_3$ | CN | H |
| A-306. | OCH$_3$ | OCHF$_2$ | 5-F | CN | H |
| A-307. | OCH$_3$ | OCHF$_2$ | 5-CH$_3$ | CN | H |
| A-308. | OCH$_3$ | OCHF$_2$ | 5-OCH$_3$ | CN | H |
| A-309. | OCH$_3$ | OCF$_3$ | 3-F | CN | H |
| A-310. | OCH$_3$ | OCF$_3$ | 3-CH$_3$ | CN | H |
| A-311. | OCH$_3$ | OCF$_3$ | 3-OCH$_3$ | CN | H |
| A-312. | OCH$_3$ | OCF$_3$ | 5-F | CN | H |
| A-313. | OCH$_3$ | OCF$_3$ | 5-CH$_3$ | CN | H |
| A-314. | OCH$_3$ | OCF$_3$ | 5-OCH$_3$ | CN | H |
| A-315. | CH$_2$F | F | 3-F | CN | H |
| A-316. | CH$_2$F | F | 3-CH$_3$ | CN | H |
| A-317. | CH$_2$F | F | 3-OCH$_3$ | CN | H |
| A-318. | CH$_2$F | F | 5-F | CN | H |
| A-319. | CH$_2$F | F | 5-CH$_3$ | CN | H |
| A-320. | CH$_2$F | F | 5-OCH$_3$ | CN | H |
| A-321. | CH$_2$F | CH$_3$ | 3-F | CN | H |
| A-322. | CH$_2$F | CH$_3$ | 3-CH$_3$ | CN | H |
| A-323. | CH$_2$F | CH$_3$ | 3-OCH$_3$ | CN | H |
| A-324. | CH$_2$F | CH$_3$ | 5-F | CN | H |
| A-325. | CH$_2$F | CH$_3$ | 5-CH$_3$ | CN | H |
| A-326. | CH$_2$F | CH$_3$ | 5-OCH$_3$ | CN | H |
| A-327. | CH$_2$F | OCH$_3$ | 3-F | CN | H |
| A-328. | CH$_2$F | OCH$_3$ | 3-CH$_3$ | CN | H |
| A-329. | CH$_2$F | OCH$_3$ | 3-OCH$_3$ | CN | H |
| A-330. | CH$_2$F | OCH$_3$ | 5-F | CN | H |
| A-331. | CH$_2$F | OCH$_3$ | 5-CH$_3$ | CN | H |
| A-332. | CH$_2$F | OCH$_3$ | 5-OCH$_3$ | CN | H |
| A-333. | CH$_2$F | CN | 3-F | CN | H |
| A-334. | CH$_2$F | CN | 3-CH$_3$ | CN | H |
| A-335. | CH$_2$F | CN | 3-OCH$_3$ | CN | H |
| A-336. | CH$_2$F | CN | 5-F | CN | H |
| A-337. | CH$_2$F | CN | 5-CH$_3$ | CN | H |
| A-338. | CH$_2$F | CN | 5-OCH$_3$ | CN | H |
| A-339. | CH$_2$F | CH$_2$F | 3-F | CN | H |
| A-340. | CH$_2$F | CH$_2$F | 3-CH$_3$ | CN | H |
| A-341. | CH$_2$F | CH$_2$F | 3-OCH$_3$ | CN | H |
| A-342. | CH$_2$F | CH$_2$F | 5-F | CN | H |
| A-343. | CH$_2$F | CH$_2$F | 5-CH$_3$ | CN | H |
| A-344. | CH$_2$F | CH$_2$F | 5-OCH$_3$ | CN | H |
| A-345. | CH$_2$F | CHF$_2$ | 3-F | CN | H |
| A-346. | CH$_2$F | CHF$_2$ | 3-CH$_3$ | CN | H |
| A-347. | CH$_2$F | CHF$_2$ | 3-OCH$_3$ | CN | H |
| A-348. | CH$_2$F | CHF$_2$ | 5-F | CN | H |
| A-349. | CH$_2$F | CHF$_2$ | 5-CH$_3$ | CN | H |
| A-350. | CH$_2$F | CHF$_2$ | 5-OCH$_3$ | CN | H |
| A-351. | CH$_2$F | CF$_3$ | 3-F | CN | H |
| A-352. | CH$_2$F | CF$_3$ | 3-CH$_3$ | CN | H |
| A-353. | CH$_2$F | CF$_3$ | 3-OCH$_3$ | CN | H |
| A-354. | CH$_2$F | CF$_3$ | 5-F | CN | H |
| A-355. | CH$_2$F | CF$_3$ | 5-CH$_3$ | CN | H |
| A-356. | CH$_2$F | CF$_3$ | 5-OCH$_3$ | CN | H |
| A-357. | CH$_2$F | OCH$_2$F | 3-F | CN | H |
| A-358. | CH$_2$F | OCH$_2$F | 3-CH$_3$ | CN | H |
| A-359. | CH$_2$F | OCH$_2$F | 3-OCH$_3$ | CN | H |
| A-360. | CH$_2$F | OCH$_2$F | 5-F | CN | H |
| A-361. | CH$_2$F | OCH$_2$F | 5-CH$_3$ | CN | H |
| A-362. | CH$_2$F | OCH$_2$F | 5-OCH$_3$ | CN | H |
| A-363. | CH$_2$F | OCHF$_2$ | 3-F | CN | H |
| A-364. | CH$_2$F | OCHF$_2$ | 3-CH$_3$ | CN | H |
| A-365. | CH$_2$F | OCHF$_2$ | 3-OCH$_3$ | CN | H |
| A-366. | CH$_2$F | OCHF$_2$ | 5-F | CN | H |
| A-367. | CH$_2$F | OCHF$_2$ | 5-CH$_3$ | CN | H |
| A-368. | CH$_2$F | OCHF$_2$ | 5-OCH$_3$ | CN | H |
| A-369. | CH$_2$F | OCF$_3$ | 3-F | CN | H |
| A-370. | CH$_2$F | OCF$_3$ | 3-CH$_3$ | CN | H |
| A-371. | CH$_2$F | OCF$_3$ | 3-OCH$_3$ | CN | H |
| A-372. | CH$_2$F | OCF$_3$ | 5-F | CN | H |
| A-373. | CH$_2$F | OCF$_3$ | 5-CH$_3$ | CN | H |
| A-374. | CH$_2$F | OCF$_3$ | 5-OCH$_3$ | CN | H |
| A-375. | CHF$_2$ | F | 3-F | CN | H |
| A-376. | CHF$_2$ | F | 3-CH$_3$ | CN | H |
| A-377. | CHF$_2$ | F | 3-OCH$_3$ | CN | H |
| A-378. | CHF$_2$ | F | 5-F | CN | H |
| A-379. | CHF$_2$ | F | 5-CH$_3$ | CN | H |
| A-380. | CHF$_2$ | F | 5-OCH$_3$ | CN | H |
| A-381. | CHF$_2$ | CH$_3$ | 3-F | CN | H |
| A-382. | CHF$_2$ | CH$_3$ | 3-CH$_3$ | CN | H |
| A-383. | CHF$_2$ | CH$_3$ | 3-OCH$_3$ | CN | H |
| A-384. | CHF$_2$ | CH$_3$ | 5-F | CN | H |
| A-385. | CHF$_2$ | CH$_3$ | 5-CH$_3$ | CN | H |
| A-386. | CHF$_2$ | CH$_3$ | 5-OCH$_3$ | CN | H |
| A-387. | CHF$_2$ | OCH$_3$ | 3-F | CN | H |
| A-388. | CHF$_2$ | OCH$_3$ | 3-CH$_3$ | CN | H |
| A-389. | CHF$_2$ | OCH$_3$ | 3-OCH$_3$ | CN | H |
| A-390. | CHF$_2$ | OCH$_3$ | 5-F | CN | H |
| A-391. | CHF$_2$ | OCH$_3$ | 5-CH$_3$ | CN | H |
| A-392. | CHF$_2$ | OCH$_3$ | 5-OCH$_3$ | CN | H |
| A-393. | CHF$_2$ | CN | 3-F | CN | H |
| A-394. | CHF$_2$ | CN | 3-CH$_3$ | CN | H |
| A-395. | CHF$_2$ | CN | 3-OCH$_3$ | CN | H |
| A-396. | CHF$_2$ | CN | 5-F | CN | H |
| A-397. | CHF$_2$ | CN | 5-CH$_3$ | CN | H |
| A-398. | CHF$_2$ | CN | 5-OCH$_3$ | CN | H |
| A-399. | CHF$_2$ | CH$_2$F | 3-F | CN | H |
| A-400. | CHF$_2$ | CH$_2$F | 3-CH$_3$ | CN | H |
| A-401. | CHF$_2$ | CH$_2$F | 3-OCH$_3$ | CN | H |
| A-402. | CHF$_2$ | CH$_2$F | 5-F | CN | H |
| A-403. | CHF$_2$ | CH$_2$F | 5-CH$_3$ | CN | H |
| A-404. | CHF$_2$ | CH$_2$F | 5-OCH$_3$ | CN | H |
| A-405. | CHF$_2$ | CHF$_2$ | 3-F | CN | H |
| A-406. | CHF$_2$ | CHF$_2$ | 3-CH$_3$ | CN | H |
| A-407. | CHF$_2$ | CHF$_2$ | 3-OCH$_3$ | CN | H |
| A-408. | CHF$_2$ | CHF$_2$ | 5-F | CN | H |
| A-409. | CHF$_2$ | CHF$_2$ | 5-CH$_3$ | CN | H |
| A-410. | CHF$_2$ | CHF$_2$ | 5-OCH$_3$ | CN | H |
| A-411. | CHF$_2$ | CF$_3$ | 3-F | CN | H |
| A-412. | CHF$_2$ | CF$_3$ | 3-CH$_3$ | CN | H |
| A-413. | CHF$_2$ | CF$_3$ | 3-OCH$_3$ | CN | H |
| A-414. | CHF$_2$ | CF$_3$ | 5-F | CN | H |
| A-415. | CHF$_2$ | CF$_3$ | 5-CH$_3$ | CN | H |
| A-416. | CHF$_2$ | CF$_3$ | 5-OCH$_3$ | CN | H |
| A-417. | CHF$_2$ | OCH$_2$F | 3-F | CN | H |
| A-418. | CHF$_2$ | OCH$_2$F | 3-CH$_3$ | CN | H |
| A-419. | CHF$_2$ | OCH$_2$F | 3-OCH$_3$ | CN | H |
| A-420. | CHF$_2$ | OCH$_2$F | 5-F | CN | H |
| A-421. | CHF$_2$ | OCH$_2$F | 5-CH$_3$ | CN | H |
| A-422. | CHF$_2$ | OCH$_2$F | 5-OCH$_3$ | CN | H |
| A-423. | CHF$_2$ | OCHF$_2$ | 3-F | CN | H |
| A-424. | CHF$_2$ | OCHF$_2$ | 3-CH$_3$ | CN | H |
| A-425. | CHF$_2$ | OCHF$_2$ | 3-OCH$_3$ | CN | H |
| A-426. | CHF$_2$ | OCHF$_2$ | 5-F | CN | H |
| A-427. | CHF$_2$ | OCHF$_2$ | 5-CH$_3$ | CN | H |
| A-428. | CHF$_2$ | OCHF$_2$ | 5-OCH$_3$ | CN | H |
| A-429. | CHF$_2$ | OCF$_3$ | 3-F | CN | H |
| A-430. | CHF$_2$ | OCF$_3$ | 3-CH$_3$ | CN | H |
| A-431. | CHF$_2$ | OCF$_3$ | 3-OCH$_3$ | CN | H |
| A-432. | CHF$_2$ | OCF$_3$ | 5-F | CN | H |
| A-433. | CHF$_2$ | OCF$_3$ | 5-CH$_3$ | CN | H |
| A-434. | CHF$_2$ | OCF$_3$ | 5-OCH$_3$ | CN | H |
| A-435. | CF$_3$ | F | 3-F | CN | H |
| A-436. | CF$_3$ | F | 3-CH$_3$ | CN | H |
| A-437. | CF$_3$ | F | 3-OCH$_3$ | CN | H |

TABLE A-continued

| Example No. | $R^{8a}$ | $R^{8b}$ | $R^{8c}$ | $R^1$ | $R^2$ |
|---|---|---|---|---|---|
| A-438. | $CF_3$ | F | 5-F | CN | H |
| A-439. | $CF_3$ | F | 5-$CH_3$ | CN | H |
| A-440. | $CF_3$ | F | 5-$OCH_3$ | CN | H |
| A-441. | $CF_3$ | $CH_3$ | 3-F | CN | H |
| A-442. | $CF_3$ | $CH_3$ | 3-$CH_3$ | CN | H |
| A-443. | $CF_3$ | $CH_3$ | 3-$OCH_3$ | CN | H |
| A-444. | $CF_3$ | $CH_3$ | 5-F | CN | H |
| A-445. | $CF_3$ | $CH_3$ | 5-$CH_3$ | CN | H |
| A-446. | $CF_3$ | $CH_3$ | 5-$OCH_3$ | CN | H |
| A-447. | $CF_3$ | $OCH_3$ | 3-F | CN | H |
| A-448. | $CF_3$ | $OCH_3$ | 3-$CH_3$ | CN | H |
| A-449. | $CF_3$ | $OCH_3$ | 3-$OCH_3$ | CN | H |
| A-450. | $CF_3$ | $OCH_3$ | 5-F | CN | H |
| A-451. | $CF_3$ | $OCH_3$ | 5-$CH_3$ | CN | H |
| A-452. | $CF_3$ | $OCH_3$ | 5-$OCH_3$ | CN | H |
| A-453. | $CF_3$ | CN | 3-F | CN | H |
| A-454. | $CF_3$ | CN | 3-$CH_3$ | CN | H |
| A-455. | $CF_3$ | CN | 3-$OCH_3$ | CN | H |
| A-456. | $CF_3$ | CN | 5-F | CN | H |
| A-457. | $CF_3$ | CN | 5-$CH_3$ | CN | H |
| A-458. | $CF_3$ | CN | 5-$OCH_3$ | CN | H |
| A-459. | $CF_3$ | $CH_2F$ | 3-F | CN | H |
| A-460. | $CF_3$ | $CH_2F$ | 3-$CH_3$ | CN | H |
| A-461. | $CF_3$ | $CH_2F$ | 3-$OCH_3$ | CN | H |
| A-462. | $CF_3$ | $CH_2F$ | 5-F | CN | H |
| A-463. | $CF_3$ | $CH_2F$ | 5-$CH_3$ | CN | H |
| A-464. | $CF_3$ | $CH_2F$ | 5-$OCH_3$ | CN | H |
| A-465. | $CF_3$ | $CHF_2$ | 3-F | CN | H |
| A-466. | $CF_3$ | $CHF_2$ | 3-$CH_3$ | CN | H |
| A-467. | $CF_3$ | $CHF_2$ | 3-$OCH_3$ | CN | H |
| A-468. | $CF_3$ | $CHF_2$ | 5-F | CN | H |
| A-469. | $CF_3$ | $CHF_2$ | 5-$CH_3$ | CN | H |
| A-470. | $CF_3$ | $CHF_2$ | 5-$OCH_3$ | CN | H |
| A-471. | $CF_3$ | $CF_3$ | 3-F | CN | H |
| A-472. | $CF_3$ | $CF_3$ | 3-$CH_3$ | CN | H |
| A-473. | $CF_3$ | $CF_3$ | 3-$OCH_3$ | CN | H |
| A-474. | $CF_3$ | $CF_3$ | 5-F | CN | H |
| A-475. | $CF_3$ | $CF_3$ | 5-$CH_3$ | CN | H |
| A-476. | $CF_3$ | $CF_3$ | 5-$OCH_3$ | CN | H |
| A-477. | $CF_3$ | $OCH_2F$ | 3-F | CN | H |
| A-478. | $CF_3$ | $OCH_2F$ | 3-$CH_3$ | CN | H |
| A-479. | $CF_3$ | $OCH_2F$ | 3-$OCH_3$ | CN | H |
| A-480. | $CF_3$ | $OCH_2F$ | 5-F | CN | H |
| A-481. | $CF_3$ | $OCH_2F$ | 5-$CH_3$ | CN | H |
| A-482. | $CF_3$ | $OCH_2F$ | 5-$OCH_3$ | CN | H |
| A-483. | $CF_3$ | $OCHF_2$ | 3-F | CN | H |
| A-484. | $CF_3$ | $OCHF_2$ | 3-$CH_3$ | CN | H |
| A-485. | $CF_3$ | $OCHF_2$ | 3-$OCH_3$ | CN | H |
| A-486. | $CF_3$ | $OCHF_2$ | 5-F | CN | H |
| A-487. | $CF_3$ | $OCHF_2$ | 5-$CH_3$ | CN | H |
| A-488. | $CF_3$ | $OCHF_2$ | 5-$OCH_3$ | CN | H |
| A-489. | $CF_3$ | $OCF_3$ | 3-F | CN | H |
| A-490. | $CF_3$ | $OCF_3$ | 3-$CH_3$ | CN | H |
| A-491. | $CF_3$ | $OCF_3$ | 3-$OCH_3$ | CN | H |
| A-492. | $CF_3$ | $OCF_3$ | 5-F | CN | H |
| A-493. | $CF_3$ | $OCF_3$ | 5-$CH_3$ | CN | H |
| A-494. | $CF_3$ | $OCF_3$ | 5-$OCH_3$ | CN | H |
| A-495. | $OCH_2F$ | F | 3-F | CN | H |
| A-496. | $OCH_2F$ | F | 3-$CH_3$ | CN | H |
| A-497. | $OCH_2F$ | F | 3-$OCH_3$ | CN | H |
| A-498. | $OCH_2F$ | F | 5-F | CN | H |
| A-499. | $OCH_2F$ | F | 5-$CH_3$ | CN | H |
| A-500. | $OCH_2F$ | F | 5-$OCH_3$ | CN | H |
| A-501. | $OCH_2F$ | $CH_3$ | 3-F | CN | H |
| A-502. | $OCH_2F$ | $CH_3$ | 3-$CH_3$ | CN | H |
| A-503. | $OCH_2F$ | $CH_3$ | 3-$OCH_3$ | CN | H |
| A-504. | $OCH_2F$ | $CH_3$ | 5-F | CN | H |
| A-505. | $OCH_2F$ | $CH_3$ | 5-$CH_3$ | CN | H |
| A-506. | $OCH_2F$ | $CH_3$ | 5-$OCH_3$ | CN | H |
| A-507. | $OCH_2F$ | $OCH_3$ | 3-F | CN | H |
| A-508. | $OCH_2F$ | $OCH_3$ | 3-$CH_3$ | CN | H |
| A-509. | $OCH_2F$ | $OCH_3$ | 3-$OCH_3$ | CN | H |
| A-510. | $OCH_2F$ | $OCH_3$ | 5-F | CN | H |
| A-511. | $OCH_2F$ | $OCH_3$ | 5-$CH_3$ | CN | H |
| A-512. | $OCH_2F$ | $OCH_3$ | 5-$OCH_3$ | CN | H |
| A-513. | $OCH_2F$ | CN | 3-F | CN | H |
| A-514. | $OCH_2F$ | CN | 3-$CH_3$ | CN | H |
| A-515. | $OCH_2F$ | CN | 3-$OCH_3$ | CN | H |
| A-516. | $OCH_2F$ | CN | 5-F | CN | H |
| A-517. | $OCH_2F$ | CN | 5-$CH_3$ | CN | H |
| A-518. | $OCH_2F$ | CN | 5-$OCH_3$ | CN | H |
| A-519. | $OCH_2F$ | $CH_2F$ | 3-F | CN | H |
| A-520. | $OCH_2F$ | $CH_2F$ | 3-$CH_3$ | CN | H |
| A-521. | $OCH_2F$ | $CH_2F$ | 3-$OCH_3$ | CN | H |
| A-522. | $OCH_2F$ | $CH_2F$ | 5-F | CN | H |
| A-523. | $OCH_2F$ | $CH_2F$ | 5-$CH_3$ | CN | H |
| A-524. | $OCH_2F$ | $CH_2F$ | 5-$OCH_3$ | CN | H |
| A-525. | $OCH_2F$ | $CHF_2$ | 3-F | CN | H |
| A-526. | $OCH_2F$ | $CHF_2$ | 3-$CH_3$ | CN | H |
| A-527. | $OCH_2F$ | $CHF_2$ | 3-$OCH_3$ | CN | H |
| A-528. | $OCH_2F$ | $CHF_2$ | 5-F | CN | H |
| A-529. | $OCH_2F$ | $CHF_2$ | 5-$CH_3$ | CN | H |
| A-530. | $OCH_2F$ | $CHF_2$ | 5-$OCH_3$ | CN | H |
| A-531. | $OCH_2F$ | $CF_3$ | 3-F | CN | H |
| A-532. | $OCH_2F$ | $CF_3$ | 3-$CH_3$ | CN | H |
| A-533. | $OCH_2F$ | $CF_3$ | 3-$OCH_3$ | CN | H |
| A-534. | $OCH_2F$ | $CF_3$ | 5-F | CN | H |
| A-535. | $OCH_2F$ | $CF_3$ | 5-$CH_3$ | CN | H |
| A-536. | $OCH_2F$ | $CF_3$ | 5-$OCH_3$ | CN | H |
| A-537. | $OCH_2F$ | $OCH_2F$ | 3-F | CN | H |
| A-538. | $OCH_2F$ | $OCH_2F$ | 3-$CH_3$ | CN | H |
| A-539. | $OCH_2F$ | $OCH_2F$ | 3-$OCH_3$ | CN | H |
| A-540. | $OCH_2F$ | $OCH_2F$ | 5-F | CN | H |
| A-541. | $OCH_2F$ | $OCH_2F$ | 5-$CH_3$ | CN | H |
| A-542. | $OCH_2F$ | $OCH_2F$ | 5-$OCH_3$ | CN | H |
| A-543. | $OCH_2F$ | $OCHF_2$ | 3-F | CN | H |
| A-544. | $OCH_2F$ | $OCHF_2$ | 3-$CH_3$ | CN | H |
| A-545. | $OCH_2F$ | $OCHF_2$ | 3-$OCH_3$ | CN | H |
| A-546. | $OCH_2F$ | $OCHF_2$ | 5-F | CN | H |
| A-547. | $OCH_2F$ | $OCHF_2$ | 5-$CH_3$ | CN | H |
| A-548. | $OCH_2F$ | $OCHF_2$ | 5-$OCH_3$ | CN | H |
| A-549. | $OCH_2F$ | $OCF_3$ | 3-F | CN | H |
| A-550. | $OCH_2F$ | $OCF_3$ | 3-$CH_3$ | CN | H |
| A-551. | $OCH_2F$ | $OCF_3$ | 3-$OCH_3$ | CN | H |
| A-552. | $OCH_2F$ | $OCF_3$ | 5-F | CN | H |
| A-553. | $OCH_2F$ | $OCF_3$ | 5-$CH_3$ | CN | H |
| A-554. | $OCH_2F$ | $OCF_3$ | 5-$OCH_3$ | CN | H |
| A-555. | $OCHF_2$ | F | 3-F | CN | H |
| A-556. | $OCHF_2$ | F | 3-$CH_3$ | CN | H |
| A-557. | $OCHF_2$ | F | 3-$OCH_3$ | CN | H |
| A-558. | $OCHF_2$ | F | 5-F | CN | H |
| A-559. | $OCHF_2$ | F | 5-$CH_3$ | CN | H |
| A-560. | $OCHF_2$ | F | 5-$OCH_3$ | CN | H |
| A-561. | $OCHF_2$ | $CH_3$ | 3-F | CN | H |
| A-562. | $OCHF_2$ | $CH_3$ | 3-$CH_3$ | CN | H |
| A-563. | $OCHF_2$ | $CH_3$ | 3-$OCH_3$ | CN | H |
| A-564. | $OCHF_2$ | $CH_3$ | 5-F | CN | H |
| A-565. | $OCHF_2$ | $CH_3$ | 5-$CH_3$ | CN | H |
| A-566. | $OCHF_2$ | $CH_3$ | 5-$OCH_3$ | CN | H |
| A-567. | $OCHF_2$ | $OCH_3$ | 3-F | CN | H |
| A-568. | $OCHF_2$ | $OCH_3$ | 3-$CH_3$ | CN | H |
| A-569. | $OCHF_2$ | $OCH_3$ | 3-$OCH_3$ | CN | H |
| A-570. | $OCHF_2$ | $OCH_3$ | 5-F | CN | H |
| A-571. | $OCHF_2$ | $OCH_3$ | 5-$CH_3$ | CN | H |
| A-572. | $OCHF_2$ | $OCH_3$ | 5-$OCH_3$ | CN | H |
| A-573. | $OCHF_2$ | CN | 3-F | CN | H |
| A-574. | $OCHF_2$ | CN | 3-$CH_3$ | CN | H |
| A-575. | $OCHF_2$ | CN | 3-$OCH_3$ | CN | H |
| A-576. | $OCHF_2$ | CN | 5-F | CN | H |
| A-577. | $OCHF_2$ | CN | 5-$CH_3$ | CN | H |
| A-578. | $OCHF_2$ | CN | 5-$OCH_3$ | CN | H |
| A-579. | $OCHF_2$ | $CH_2F$ | 3-F | CN | H |
| A-580. | $OCHF_2$ | $CH_2F$ | 3-$CH_3$ | CN | H |
| A-581. | $OCHF_2$ | $CH_2F$ | 3-$OCH_3$ | CN | H |
| A-582. | $OCHF_2$ | $CH_2F$ | 5-F | CN | H |
| A-583. | $OCHF_2$ | $CH_2F$ | 5-$CH_3$ | CN | H |
| A-584. | $OCHF_2$ | $CH_2F$ | 5-$OCH_3$ | CN | H |
| A-585. | $OCHF_2$ | $CHF_2$ | 3-F | CN | H |
| A-586. | $OCHF_2$ | $CHF_2$ | 3-$CH_3$ | CN | H |
| A-587. | $OCHF_2$ | $CHF_2$ | 3-$OCH_3$ | CN | H |
| A-588. | $OCHF_2$ | $CHF_2$ | 5-F | CN | H |
| A-589. | $OCHF_2$ | $CHF_2$ | 5-$CH_3$ | CN | H |
| A-590. | $OCHF_2$ | $CHF_2$ | 5-$OCH_3$ | CN | H |
| A-591. | $OCHF_2$ | $CF_3$ | 3-F | CN | H |
| A-592. | $OCHF_2$ | $CF_3$ | 3-$CH_3$ | CN | H |
| A-593. | $OCHF_2$ | $CF_3$ | 3-$OCH_3$ | CN | H |

TABLE A-continued

| Example No. | $R^{8a}$ | $R^{8b}$ | $R^{8c}$ | $R^1$ | $R^2$ |
|---|---|---|---|---|---|
| A-594. | OCHF$_2$ | CF$_3$ | 5-F | CN | H |
| A-595. | OCHF$_2$ | CF$_3$ | 5-CH$_3$ | CN | H |
| A-596. | OCHF$_2$ | CF$_3$ | 5-OCH$_3$ | CN | H |
| A-597. | OCHF$_2$ | OCH$_2$F | 3-F | CN | H |
| A-598. | OCHF$_2$ | OCH$_2$F | 3-CH$_3$ | CN | H |
| A-599. | OCHF$_2$ | OCH$_2$F | 3-OCH$_3$ | CN | H |
| A-600. | OCHF$_2$ | OCH$_2$F | 5-F | CN | H |
| A-601. | OCHF$_2$ | OCH$_2$F | 5-CH$_3$ | CN | H |
| A-602. | OCHF$_2$ | OCH$_2$F | 5-OCH$_3$ | CN | H |
| A-603. | OCHF$_2$ | OCHF$_2$ | 3-F | CN | H |
| A-604. | OCHF$_2$ | OCHF$_2$ | 3-CH$_3$ | CN | H |
| A-605. | OCHF$_2$ | OCHF$_2$ | 3-OCH$_3$ | CN | H |
| A-606. | OCHF$_2$ | OCHF$_2$ | 5-F | CN | H |
| A-607. | OCHF$_2$ | OCHF$_2$ | 5-CH$_3$ | CN | H |
| A-608. | OCHF$_2$ | OCHF$_2$ | 5-OCH$_3$ | CN | H |
| A-609. | OCHF$_2$ | OCF$_3$ | 3-F | CN | H |
| A-610. | OCHF$_2$ | OCF$_3$ | 3-CH$_3$ | CN | H |
| A-611. | OCHF$_2$ | OCF$_3$ | 3-OCH$_3$ | CN | H |
| A-612. | OCHF$_2$ | OCF$_3$ | 5-F | CN | H |
| A-613. | OCHF$_2$ | OCF$_3$ | 5-CH$_3$ | CN | H |
| A-614. | OCHF$_2$ | OCF$_3$ | 5-OCH$_3$ | CN | H |
| A-615. | OCF$_3$ | F | 3-F | CN | H |
| A-616. | OCF$_3$ | F | 3-CH$_3$ | CN | H |
| A-617. | OCF$_3$ | F | 3-OCH$_3$ | CN | H |
| A-618. | OCF$_3$ | F | 5-F | CN | H |
| A-619. | OCF$_3$ | F | 5-CH$_3$ | CN | H |
| A-620. | OCF$_3$ | F | 5-OCH$_3$ | CN | H |
| A-621. | OCF$_3$ | CH$_3$ | 3-F | CN | H |
| A-622. | OCF$_3$ | CH$_3$ | 3-CH$_3$ | CN | H |
| A-623. | OCF$_3$ | CH$_3$ | 3-OCH$_3$ | CN | H |
| A-624. | OCF$_3$ | CH$_3$ | 5-F | CN | H |
| A-625. | OCF$_3$ | CH$_3$ | 5-CH$_3$ | CN | H |
| A-626. | OCF$_3$ | CH$_3$ | 5-OCH$_3$ | CN | H |
| A-627. | OCF$_3$ | OCH$_3$ | 3-F | CN | H |
| A-628. | OCF$_3$ | OCH$_3$ | 3-CH$_3$ | CN | H |
| A-629. | OCF$_3$ | OCH$_3$ | 3-OCH$_3$ | CN | H |
| A-630. | OCF$_3$ | OCH$_3$ | 5-F | CN | H |
| A-631. | OCF$_3$ | OCH$_3$ | 5-CH$_3$ | CN | H |
| A-632. | OCF$_3$ | OCH$_3$ | 5-OCH$_3$ | CN | H |
| A-633. | OCF$_3$ | CN | 3-F | CN | H |
| A-634. | OCF$_3$ | CN | 3-CH$_3$ | CN | H |
| A-635. | OCF$_3$ | CN | 3-OCH$_3$ | CN | H |
| A-636. | OCF$_3$ | CN | 5-F | CN | H |
| A-637. | OCF$_3$ | CN | 5-CH$_3$ | CN | H |
| A-638. | OCF$_3$ | CN | 5-OCH$_3$ | CN | H |
| A-639. | OCF$_3$ | CH$_2$F | 3-F | CN | H |
| A-640. | OCF$_3$ | CH$_2$F | 3-CH$_3$ | CN | H |
| A-641. | OCF$_3$ | CH$_2$F | 3-OCH$_3$ | CN | H |
| A-642. | OCF$_3$ | CH$_2$F | 5-F | CN | H |
| A-643. | OCF$_3$ | CH$_2$F | 5-CH$_3$ | CN | H |
| A-644. | OCF$_3$ | CH$_2$F | 5-OCH$_3$ | CN | H |
| A-645. | OCF$_3$ | CHF$_2$ | 3-F | CN | H |
| A-646. | OCF$_3$ | CHF$_2$ | 3-CH$_3$ | CN | H |
| A-647. | OCF$_3$ | CHF$_2$ | 3-OCH$_3$ | CN | H |
| A-648. | OCF$_3$ | CHF$_2$ | 5-F | CN | H |
| A-649. | OCF$_3$ | CHF$_2$ | 5-CH$_3$ | CN | H |
| A-650. | OCF$_3$ | CHF$_2$ | 5-OCH$_3$ | CN | H |
| A-651. | OCF$_3$ | CF$_3$ | 3-F | CN | H |
| A-652. | OCF$_3$ | CF$_3$ | 3-CH$_3$ | CN | H |
| A-653. | OCF$_3$ | CF$_3$ | 3-OCH$_3$ | CN | H |
| A-654. | OCF$_3$ | CF$_3$ | 5-F | CN | H |
| A-655. | OCF$_3$ | CF$_3$ | 5-CH$_3$ | CN | H |
| A-656. | OCF$_3$ | CF$_3$ | 5-OCH$_3$ | CN | H |
| A-657. | OCF$_3$ | OCH$_2$F | 3-F | CN | H |
| A-658. | OCF$_3$ | OCH$_2$F | 3-CH$_3$ | CN | H |
| A-659. | OCF$_3$ | OCH$_2$F | 3-OCH$_3$ | CN | H |
| A-660. | OCF$_3$ | OCH$_2$F | 5-F | CN | H |
| A-661. | OCF$_3$ | OCH$_2$F | 5-CH$_3$ | CN | H |
| A-662. | OCF$_3$ | OCH$_2$F | 5-OCH$_3$ | CN | H |
| A-663. | OCF$_3$ | OCHF$_2$ | 3-F | CN | H |
| A-664. | OCF$_3$ | OCHF$_2$ | 3-CH$_3$ | CN | H |
| A-665. | OCF$_3$ | OCHF$_2$ | 3-OCH$_3$ | CN | H |
| A-666. | OCF$_3$ | OCHF$_2$ | 5-F | CN | H |
| A-667. | OCF$_3$ | OCHF$_2$ | 5-CH$_3$ | CN | H |
| A-668. | OCF$_3$ | OCHF$_2$ | 5-OCH$_3$ | CN | H |
| A-669. | OCF$_3$ | OCF$_3$ | 3-F | CN | H |
| A-670. | OCF$_3$ | OCF$_3$ | 3-CH$_3$ | CN | H |
| A-671. | OCF$_3$ | OCF$_3$ | 3-OCH$_3$ | CN | H |
| A-672. | OCF$_3$ | OCF$_3$ | 5-F | CN | H |
| A-673. | OCF$_3$ | OCF$_3$ | 5-CH$_3$ | CN | H |
| A-674. | OCF$_3$ | OCF$_3$ | 5-OCH$_3$ | CN | H |
| A-675. | H | H | H | F | H |
| A-676. | F | H | H | F | H |
| A-677. | CH$_3$ | H | H | F | H |
| A-678. | OCH$_3$ | H | H | F | H |
| A-679. | CH$_2$F | H | H | F | H |
| A-680. | CHF$_2$ | H | H | F | H |
| A-681. | CF$_3$ | H | H | F | H |
| A-682. | OCH$_2$F | H | H | F | H |
| A-683. | OCHF$_2$ | H | H | F | H |
| A-684. | OCF$_3$ | H | H | F | H |
| A-685. | H | F | H | F | H |
| A-686. | H | CH$_3$ | H | F | H |
| A-687. | H | OCH$_3$ | H | F | H |
| A-688. | H | CN | H | F | H |
| A-689. | H | CH$_2$F | H | F | H |
| A-690. | H | CHF$_2$ | H | F | H |
| A-691. | H | CF$_3$ | H | F | H |
| A-692. | H | OCH$_2$F | H | F | H |
| A-693. | H | OCHF$_2$ | H | F | H |
| A-694. | H | OCF$_3$ | H | F | H |
| A-695. | H | H | 3-F | F | H |
| A-696. | H | H | 3-CH$_3$ | F | H |
| A-697. | H | H | 3-OCH$_3$ | F | H |
| A-698. | H | H | 5-F | F | H |
| A-699. | H | H | 5-CH$_3$ | F | H |
| A-700. | H | H | 5-OCH$_3$ | F | H |
| A-701. | F | F | H | F | H |
| A-702. | F | CH$_3$ | H | F | H |
| A-703. | F | OCH$_3$ | H | F | H |
| A-704. | F | CN | H | F | H |
| A-705. | F | CH$_2$F | H | F | H |
| A-706. | F | CHF$_2$ | H | F | H |
| A-707. | F | CF$_3$ | H | F | H |
| A-708. | F | OCH$_2$F | H | F | H |
| A-709. | F | OCHF$_2$ | H | F | H |
| A-710. | F | OCF$_3$ | H | F | H |
| A-711. | F | H | 3-F | F | H |
| A-712. | F | H | 3-CH$_3$ | F | H |
| A-713. | F | H | 3-OCH$_3$ | F | H |
| A-714. | F | H | 5-F | F | H |
| A-715. | F | H | 5-CH$_3$ | F | H |
| A-716. | F | H | 5-OCH$_3$ | F | H |
| A-717. | CH$_3$ | F | H | F | H |
| A-718. | CH$_3$ | CH$_3$ | H | F | H |
| A-719. | CH$_3$ | OCH$_3$ | H | F | H |
| A-720. | CH$_3$ | CN | H | F | H |
| A-721. | CH$_3$ | CH$_2$F | H | F | H |
| A-722. | CH$_3$ | CHF$_2$ | H | F | H |
| A-723. | CH$_3$ | CF$_3$ | H | F | H |
| A-724. | CH$_3$ | OCH$_2$F | H | F | H |
| A-725. | CH$_3$ | OCHF$_2$ | H | F | H |
| A-726. | CH$_3$ | OCF$_3$ | H | F | H |
| A-727. | CH$_3$ | H | 3-F | F | H |
| A-728. | CH$_3$ | H | 3-CH$_3$ | F | H |
| A-729. | CH$_3$ | H | 3-OCH$_3$ | F | H |
| A-730. | CH$_3$ | H | 5-F | F | H |
| A-731. | CH$_3$ | H | 5-CH$_3$ | F | H |
| A-732. | CH$_3$ | H | 5-OCH$_3$ | F | H |
| A-733. | OCH$_3$ | F | H | F | H |
| A-734. | OCH$_3$ | CH$_3$ | H | F | H |
| A-735. | OCH$_3$ | OCH$_3$ | H | F | H |
| A-736. | OCH$_3$ | CN | H | F | H |
| A-737. | OCH$_3$ | CH$_2$F | H | F | H |
| A-738. | OCH$_3$ | CHF$_2$ | H | F | H |
| A-739. | OCH$_3$ | CF$_3$ | H | F | H |
| A-740. | OCH$_3$ | OCH$_2$F | H | F | H |
| A-741. | OCH$_3$ | OCHF$_2$ | H | F | H |
| A-742. | OCH$_3$ | OCF$_3$ | H | F | H |
| A-743. | OCH$_3$ | H | 3-F | F | H |
| A-744. | OCH$_3$ | H | 3-CH$_3$ | F | H |
| A-745. | OCH$_3$ | H | 3-OCH$_3$ | F | H |
| A-746. | OCH$_3$ | H | 5-F | F | H |
| A-747. | OCH$_3$ | H | 5-CH$_3$ | F | H |
| A-748. | OCH$_3$ | H | 5-OCH$_3$ | F | H |
| A-749. | H | F | 3-F | F | H |

TABLE A-continued

| Example No. | $R^{8a}$ | $R^{8b}$ | $R^{8c}$ | $R^1$ | $R^2$ |
|---|---|---|---|---|---|
| A-750. | H | F | 3-CH$_3$ | F | H |
| A-751. | H | F | 3-OCH$_3$ | F | H |
| A-752. | H | F | 5-F | F | H |
| A-753. | H | F | 5-CH$_3$ | F | H |
| A-754. | H | F | 5-OCH$_3$ | F | H |
| A-755. | H | CH$_3$ | 3-F | F | H |
| A-756. | H | CH$_3$ | 3-CH$_3$ | F | H |
| A-757. | H | CH$_3$ | 3-OCH$_3$ | F | H |
| A-758. | H | CH$_3$ | 5-F | F | H |
| A-759. | H | CH$_3$ | 5-CH$_3$ | F | H |
| A-760. | H | CH$_3$ | 5-OCH$_3$ | F | H |
| A-761. | H | OCH$_3$ | 3-F | F | H |
| A-762. | H | OCH$_3$ | 3-CH$_3$ | F | H |
| A-763. | H | OCH$_3$ | 3-OCH$_3$ | F | H |
| A-764. | H | OCH$_3$ | 5-F | F | H |
| A-765. | H | OCH$_3$ | 5-CH$_3$ | F | H |
| A-766. | H | OCH$_3$ | 5-OCH$_3$ | F | H |
| A-767. | H | CN | 3-F | F | H |
| A-768. | H | CN | 3-CH$_3$ | F | H |
| A-769. | H | CN | 3-OCH$_3$ | F | H |
| A-770. | H | CN | 5-F | F | H |
| A-771. | H | CN | 5-CH$_3$ | F | H |
| A-772. | H | CN | 5-OCH$_3$ | F | H |
| A-773. | H | CH$_2$F | 3-F | F | H |
| A-774. | H | CH$_2$F | 3-CH$_3$ | F | H |
| A-775. | H | CH$_2$F | 3-OCH$_3$ | F | H |
| A-776. | H | CH$_2$F | 5-F | F | H |
| A-777. | H | CH$_2$F | 5-CH$_3$ | F | H |
| A-778. | H | CH$_2$F | 5-OCH$_3$ | F | H |
| A-779. | H | CHF$_2$ | 3-F | F | H |
| A-780. | H | CHF$_2$ | 3-CH$_3$ | F | H |
| A-781. | H | CHF$_2$ | 3-OCH$_3$ | F | H |
| A-782. | H | CHF$_2$ | 5-F | F | H |
| A-783. | H | CHF$_2$ | 5-CH$_3$ | F | H |
| A-784. | H | CHF$_2$ | 5-OCH$_3$ | F | H |
| A-785. | H | CF$_3$ | 3-F | F | H |
| A-786. | H | CF$_3$ | 3-CH$_3$ | F | H |
| A-787. | H | CF$_3$ | 3-OCH$_3$ | F | H |
| A-788. | H | CF$_3$ | 5-F | F | H |
| A-789. | H | CF$_3$ | 5-CH$_3$ | F | H |
| A-790. | H | CF$_3$ | 5-OCH$_3$ | F | H |
| A-791. | H | OCH$_2$F | 3-F | F | H |
| A-792. | H | OCH$_2$F | 3-CH$_3$ | F | H |
| A-793. | H | OCH$_2$F | 3-OCH$_3$ | F | H |
| A-794. | H | OCH$_2$F | 5-F | F | H |
| A-795. | H | OCH$_2$F | 5-CH$_3$ | F | H |
| A-796. | H | OCH$_2$F | 5-OCH$_3$ | F | H |
| A-797. | H | OCHF$_2$ | 3-F | F | H |
| A-798. | H | OCHF$_2$ | 3-CH$_3$ | F | H |
| A-799. | H | OCHF$_2$ | 3-OCH$_3$ | F | H |
| A-800. | H | OCHF$_2$ | 5-F | F | H |
| A-801. | H | OCHF$_2$ | 5-CH$_3$ | F | H |
| A-802. | H | OCHF$_2$ | 5-OCH$_3$ | F | H |
| A-803. | H | OCF$_3$ | 3-F | F | H |
| A-804. | H | OCF$_3$ | 3-CH$_3$ | F | H |
| A-805. | H | OCF$_3$ | 3-OCH$_3$ | F | H |
| A-806. | H | OCF$_3$ | 5-F | F | H |
| A-807. | H | OCF$_3$ | 5-CH$_3$ | F | H |
| A-808. | H | OCF$_3$ | 5-OCH$_3$ | F | H |
| A-809. | F | F | 3-F | F | H |
| A-810. | F | F | 3-CH$_3$ | F | H |
| A-811. | F | F | 3-OCH$_3$ | F | H |
| A-812. | F | F | 5-F | F | H |
| A-813. | F | F | 5-CH$_3$ | F | H |
| A-814. | F | F | 5-OCH$_3$ | F | H |
| A-815. | F | CH$_3$ | 3-F | F | H |
| A-816. | F | CH$_3$ | 3-CH$_3$ | F | H |
| A-817. | F | CH$_3$ | 3-OCH$_3$ | F | H |
| A-818. | F | CH$_3$ | 5-F | F | H |
| A-819. | F | CH$_3$ | 5-CH$_3$ | F | H |
| A-820. | F | CH$_3$ | 5-OCH$_3$ | F | H |
| A-821. | F | OCH$_3$ | 3-F | F | H |
| A-822. | F | OCH$_3$ | 3-CH$_3$ | F | H |
| A-823. | F | OCH$_3$ | 3-OCH$_3$ | F | H |
| A-824. | F | OCH$_3$ | 5-F | F | H |
| A-825. | F | OCH$_3$ | 5-CH$_3$ | F | H |
| A-826. | F | OCH$_3$ | 5-OCH$_3$ | F | H |
| A-827. | F | CN | 3-F | F | H |
| A-828. | F | CN | 3-CH$_3$ | F | H |
| A-829. | F | CN | 3-OCH$_3$ | F | H |
| A-830. | F | CN | 5-F | F | H |
| A-831. | F | CN | 5-CH$_3$ | F | H |
| A-832. | F | CN | 5-OCH$_3$ | F | H |
| A-833. | F | CH$_2$F | 3-F | F | H |
| A-834. | F | CH$_2$F | 3-CH$_3$ | F | H |
| A-835. | F | CH$_2$F | 3-OCH$_3$ | F | H |
| A-836. | F | CH$_2$F | 5-F | F | H |
| A-837. | F | CH$_2$F | 5-CH$_3$ | F | H |
| A-838. | F | CH$_2$F | 5-OCH$_3$ | F | H |
| A-839. | F | CHF$_2$ | 3-F | F | H |
| A-840. | F | CHF$_2$ | 3-CH$_3$ | F | H |
| A-841. | F | CHF$_2$ | 3-OCH$_3$ | F | H |
| A-842. | F | CHF$_2$ | 5-F | F | H |
| A-843. | F | CHF$_2$ | 5-CH$_3$ | F | H |
| A-844. | F | CHF$_2$ | 5-OCH$_3$ | F | H |
| A-845. | F | CF$_3$ | 3-F | F | H |
| A-846. | F | CF$_3$ | 3-CH$_3$ | F | H |
| A-847. | F | CF$_3$ | 3-OCH$_3$ | F | H |
| A-848. | F | CF$_3$ | 5-F | F | H |
| A-849. | F | CF$_3$ | 5-CH$_3$ | F | H |
| A-850. | F | CF$_3$ | 5-OCH$_3$ | F | H |
| A-851. | F | OCH$_2$F | 3-F | F | H |
| A-852. | F | OCH$_2$F | 3-CH$_3$ | F | H |
| A-853. | F | OCH$_2$F | 3-OCH$_3$ | F | H |
| A-854. | F | OCH$_2$F | 5-F | F | H |
| A-855. | F | OCH$_2$F | 5-CH$_3$ | F | H |
| A-856. | F | OCH$_2$F | 5-OCH$_3$ | F | H |
| A-857. | F | OCHF$_2$ | 3-F | F | H |
| A-858. | F | OCHF$_2$ | 3-CH$_3$ | F | H |
| A-859. | F | OCHF$_2$ | 3-OCH$_3$ | F | H |
| A-860. | F | OCHF$_2$ | 5-F | F | H |
| A-861. | F | OCHF$_2$ | 5-CH$_3$ | F | H |
| A-862. | F | OCHF$_2$ | 5-OCH$_3$ | F | H |
| A-863. | F | OCF$_3$ | 3-F | F | H |
| A-864. | F | OCF$_3$ | 3-CH$_3$ | F | H |
| A-865. | F | OCF$_3$ | 3-OCH$_3$ | F | H |
| A-866. | F | OCF$_3$ | 5-F | F | H |
| A-867. | F | OCF$_3$ | 5-CH$_3$ | F | H |
| A-868. | F | OCF$_3$ | 5-OCH$_3$ | F | H |
| A-869. | CH$_3$ | F | 3-F | F | H |
| A-870. | CH$_3$ | F | 3-CH$_3$ | F | H |
| A-871. | CH$_3$ | F | 3-OCH$_3$ | F | H |
| A-872. | CH$_3$ | F | 5-F | F | H |
| A-873. | CH$_3$ | F | 5-CH$_3$ | F | H |
| A-874. | CH$_3$ | F | 5-OCH$_3$ | F | H |
| A-875. | CH$_3$ | CH$_3$ | 3-F | F | H |
| A-876. | CH$_3$ | CH$_3$ | 3-CH$_3$ | F | H |
| A-877. | CH$_3$ | CH$_3$ | 3-OCH$_3$ | F | H |
| A-878. | CH$_3$ | CH$_3$ | 5-F | F | H |
| A-879. | CH$_3$ | CH$_3$ | 5-CH$_3$ | F | H |
| A-880. | CH$_3$ | CH$_3$ | 5-OCH$_3$ | F | H |
| A-881. | CH$_3$ | OCH$_3$ | 3-F | F | H |
| A-882. | CH$_3$ | OCH$_3$ | 3-CH$_3$ | F | H |
| A-883. | CH$_3$ | OCH$_3$ | 3-OCH$_3$ | F | H |
| A-884. | CH$_3$ | OCH$_3$ | 5-F | F | H |
| A-885. | CH$_3$ | OCH$_3$ | 5-CH$_3$ | F | H |
| A-886. | CH$_3$ | OCH$_3$ | 5-OCH$_3$ | F | H |
| A-887. | CH$_3$ | CN | 3-F | F | H |
| A-888. | CH$_3$ | CN | 3-CH$_3$ | F | H |
| A-889. | CH$_3$ | CN | 3-OCH$_3$ | F | H |
| A-890. | CH$_3$ | CN | 5-F | F | H |
| A-891. | CH$_3$ | CN | 5-CH$_3$ | F | H |
| A-892. | CH$_3$ | CN | 5-OCH$_3$ | F | H |
| A-893. | CH$_3$ | CH$_2$F | 3-F | F | H |
| A-894. | CH$_3$ | CH$_2$F | 3-CH$_3$ | F | H |
| A-895. | CH$_3$ | CH$_2$F | 3-OCH$_3$ | F | H |
| A-896. | CH$_3$ | CH$_2$F | 5-F | F | H |
| A-897. | CH$_3$ | CH$_2$F | 5-CH$_3$ | F | H |
| A-898. | CH$_3$ | CH$_2$F | 5-OCH$_3$ | F | H |
| A-899. | CH$_3$ | CHF$_2$ | 3-F | F | H |
| A-900. | CH$_3$ | CHF$_2$ | 3-CH$_3$ | F | H |
| A-901. | CH$_3$ | CHF$_2$ | 3-OCH$_3$ | F | H |
| A-902. | CH$_3$ | CHF$_2$ | 5-F | F | H |
| A-903. | CH$_3$ | CHF$_2$ | 5-CH$_3$ | F | H |
| A-904. | CH$_3$ | CHF$_2$ | 5-OCH$_3$ | F | H |
| A-905. | CH$_3$ | CF$_3$ | 3-F | F | H |

TABLE A-continued

| Example No. | $R^{8a}$ | $R^{8b}$ | $R^{8c}$ | $R^1$ | $R^2$ |
|---|---|---|---|---|---|
| A-906. | CH₃ | CF₃ | 3-CH₃ | F | H |
| A-907. | CH₃ | CF₃ | 3-OCH₃ | F | H |
| A-908. | CH₃ | CF₃ | 5-F | F | H |
| A-909. | CH₃ | CF₃ | 5-CH₃ | F | H |
| A-910. | CH₃ | CF₃ | 5-OCH₃ | F | H |
| A-911. | CH₃ | OCH₂F | 3-F | F | H |
| A-912. | CH₃ | OCH₂F | 3-CH₃ | F | H |
| A-913. | CH₃ | OCH₂F | 3-OCH₃ | F | H |
| A-914. | CH₃ | OCH₂F | 5-F | F | H |
| A-915. | CH₃ | OCH₂F | 5-CH₃ | F | H |
| A-916. | CH₃ | OCH₂F | 5-OCH₃ | F | H |
| A-917. | CH₃ | OCHF₂ | 3-F | F | H |
| A-918. | CH₃ | OCHF₂ | 3-CH₃ | F | H |
| A-919. | CH₃ | OCHF₂ | 3-OCH₃ | F | H |
| A-920. | CH₃ | OCHF₂ | 5-F | F | H |
| A-921. | CH₃ | OCHF₂ | 5-CH₃ | F | H |
| A-922. | CH₃ | OCHF₂ | 5-OCH₃ | F | H |
| A-923. | CH₃ | OCF₃ | 3-F | F | H |
| A-924. | CH₃ | OCF₃ | 3-CH₃ | F | H |
| A-925. | CH₃ | OCF₃ | 3-OCH₃ | F | H |
| A-926. | CH₃ | OCF₃ | 5-F | F | H |
| A-927. | CH₃ | OCF₃ | 5-CH₃ | F | H |
| A-928. | CH₃ | OCF₃ | 5-OCH₃ | F | H |
| A-929. | OCH₃ | F | 3-F | F | H |
| A-930. | OCH₃ | F | 3-CH₃ | F | H |
| A-931. | OCH₃ | F | 3-OCH₃ | F | H |
| A-932. | OCH₃ | F | 5-F | F | H |
| A-933. | OCH₃ | F | 5-CH₃ | F | H |
| A-934. | OCH₃ | F | 5-OCH₃ | F | H |
| A-935. | OCH₃ | CH₃ | 3-F | F | H |
| A-936. | OCH₃ | CH₃ | 3-CH₃ | F | H |
| A-937. | OCH₃ | CH₃ | 3-OCH₃ | F | H |
| A-938. | OCH₃ | CH₃ | 5-F | F | H |
| A-939. | OCH₃ | CH₃ | 5-CH₃ | F | H |
| A-940. | OCH₃ | CH₃ | 5-OCH₃ | F | H |
| A-941. | OCH₃ | OCH₃ | 3-F | F | H |
| A-942. | OCH₃ | OCH₃ | 3-CH₃ | F | H |
| A-943. | OCH₃ | OCH₃ | 3-OCH₃ | F | H |
| A-944. | OCH₃ | OCH₃ | 5-F | F | H |
| A-945. | OCH₃ | OCH₃ | 5-CH₃ | F | H |
| A-946. | OCH₃ | OCH₃ | 5-OCH₃ | F | H |
| A-947. | OCH₃ | CN | 3-F | F | H |
| A-948. | OCH₃ | CN | 3-CH₃ | F | H |
| A-949. | OCH₃ | CN | 3-OCH₃ | F | H |
| A-950. | OCH₃ | CN | 5-F | F | H |
| A-951. | OCH₃ | CN | 5-CH₃ | F | H |
| A-952. | OCH₃ | CN | 5-OCH₃ | F | H |
| A-953. | OCH₃ | CH₂F | 3-F | F | H |
| A-954. | OCH₃ | CH₂F | 3-CH₃ | F | H |
| A-955. | OCH₃ | CH₂F | 3-OCH₃ | F | H |
| A-956. | OCH₃ | CH₂F | 5-F | F | H |
| A-957. | OCH₃ | CH₂F | 5-CH₃ | F | H |
| A-958. | OCH₃ | CH₂F | 5-OCH₃ | F | H |
| A-959. | OCH₃ | CHF₂ | 3-F | F | H |
| A-960. | OCH₃ | CHF₂ | 3-CH₃ | F | H |
| A-961. | OCH₃ | CHF₂ | 3-OCH₃ | F | H |
| A-962. | OCH₃ | CHF₂ | 5-F | F | H |
| A-963. | OCH₃ | CHF₂ | 5-CH₃ | F | H |
| A-964. | OCH₃ | CHF₂ | 5-OCH₃ | F | H |
| A-965. | OCH₃ | CF₃ | 3-F | F | H |
| A-966. | OCH₃ | CF₃ | 3-CH₃ | F | H |
| A-967. | OCH₃ | CF₃ | 3-OCH₃ | F | H |
| A-968. | OCH₃ | CF₃ | 5-F | F | H |
| A-969. | OCH₃ | CF₃ | 5-CH₃ | F | H |
| A-970. | OCH₃ | CF₃ | 5-OCH₃ | F | H |
| A-971. | OCH₃ | OCH₂F | 3-F | F | H |
| A-972. | OCH₃ | OCH₂F | 3-CH₃ | F | H |
| A-973. | OCH₃ | OCH₂F | 3-OCH₃ | F | H |
| A-974. | OCH₃ | OCH₂F | 5-F | F | H |
| A-975. | OCH₃ | OCH₂F | 5-CH₃ | F | H |
| A-976. | OCH₃ | OCH₂F | 5-OCH₃ | F | H |
| A-977. | OCH₃ | OCHF₂ | 3-F | F | H |
| A-978. | OCH₃ | OCHF₂ | 3-CH₃ | F | H |
| A-979. | OCH₃ | OCHF₂ | 3-OCH₃ | F | H |
| A-980. | OCH₃ | OCHF₂ | 5-F | F | H |
| A-981. | OCH₃ | OCHF₂ | 5-CH₃ | F | H |
| A-982. | OCH₃ | OCHF₂ | 5-OCH₃ | F | H |
| A-983. | OCH₃ | OCF₃ | 3-F | F | H |
| A-984. | OCH₃ | OCF₃ | 3-CH₃ | F | H |
| A-985. | OCH₃ | OCF₃ | 3-OCH₃ | F | H |
| A-986. | OCH₃ | OCF₃ | 5-F | F | H |
| A-987. | OCH₃ | OCF₃ | 5-CH₃ | F | H |
| A-988. | OCH₃ | OCF₃ | 5-OCH₃ | F | H |
| A-989. | CH₂F | F | 3-F | F | H |
| A-990. | CH₂F | F | 3-CH₃ | F | H |
| A-991. | CH₂F | F | 3-OCH₃ | F | H |
| A-992. | CH₂F | F | 5-F | F | H |
| A-993. | CH₂F | F | 5-CH₃ | F | H |
| A-994. | CH₂F | F | 5-OCH₃ | F | H |
| A-995. | CH₂F | CH₃ | 3-F | F | H |
| A-996. | CH₂F | CH₃ | 3-CH₃ | F | H |
| A-997. | CH₂F | CH₃ | 3-OCH₃ | F | H |
| A-998. | CH₂F | CH₃ | 5-F | F | H |
| A-999. | CH₂F | CH₃ | 5-CH₃ | F | H |
| A-1000. | CH₂F | CH₃ | 5-OCH₃ | F | H |
| A-1001. | CH₂F | OCH₃ | 3-F | F | H |
| A-1002. | CH₂F | OCH₃ | 3-CH₃ | F | H |
| A-1003. | CH₂F | OCH₃ | 3-OCH₃ | F | H |
| A-1004. | CH₂F | OCH₃ | 5-F | F | H |
| A-1005. | CH₂F | OCH₃ | 5-CH₃ | F | H |
| A-1006. | CH₂F | OCH₃ | 5-OCH₃ | F | H |
| A-1007. | CH₂F | CN | 3-F | F | H |
| A-1008. | CH₂F | CN | 3-CH₃ | F | H |
| A-1009. | CH₂F | CN | 3-OCH₃ | F | H |
| A-1010. | CH₂F | CN | 5-F | F | H |
| A-1011. | CH₂F | CN | 5-CH₃ | F | H |
| A-1012. | CH₂F | CN | 5-OCH₃ | F | H |
| A-1013. | CH₂F | CH₂F | 3-F | F | H |
| A-1014. | CH₂F | CH₂F | 3-CH₃ | F | H |
| A-1015. | CH₂F | CH₂F | 3-OCH₃ | F | H |
| A-1016. | CH₂F | CH₂F | 5-F | F | H |
| A-1017. | CH₂F | CH₂F | 5-CH₃ | F | H |
| A-1018. | CH₂F | CH₂F | 5-OCH₃ | F | H |
| A-1019. | CH₂F | CHF₂ | 3-F | F | H |
| A-1020. | CH₂F | CHF₂ | 3-CH₃ | F | H |
| A-1021. | CH₂F | CHF₂ | 3-OCH₃ | F | H |
| A-1022. | CH₂F | CHF₂ | 5-F | F | H |
| A-1023. | CH₂F | CHF₂ | 5-CH₃ | F | H |
| A-1024. | CH₂F | CHF₂ | 5-OCH₃ | F | H |
| A-1025. | CH₂F | CF₃ | 3-F | F | H |
| A-1026. | CH₂F | CF₃ | 3-CH₃ | F | H |
| A-1027. | CH₂F | CF₃ | 3-OCH₃ | F | H |
| A-1028. | CH₂F | CF₃ | 5-F | F | H |
| A-1029. | CH₂F | CF₃ | 5-CH₃ | F | H |
| A-1030. | CH₂F | CF₃ | 5-OCH₃ | F | H |
| A-1031. | CH₂F | OCH₂F | 3-F | F | H |
| A-1032. | CH₂F | OCH₂F | 3-CH₃ | F | H |
| A-1033. | CH₂F | OCH₂F | 3-OCH₃ | F | H |
| A-1034. | CH₂F | OCH₂F | 5-F | F | H |
| A-1035. | CH₂F | OCH₂F | 5-CH₃ | F | H |
| A-1036. | CH₂F | OCH₂F | 5-OCH₃ | F | H |
| A-1037. | CH₂F | OCHF₂ | 3-F | F | H |
| A-1038. | CH₂F | OCHF₂ | 3-CH₃ | F | H |
| A-1039. | CH₂F | OCHF₂ | 3-OCH₃ | F | H |
| A-1040. | CH₂F | OCHF₂ | 5-F | F | H |
| A-1041. | CH₂F | OCHF₂ | 5-CH₃ | F | H |
| A-1042. | CH₂F | OCHF₂ | 5-OCH₃ | F | H |
| A-1043. | CH₂F | OCF₃ | 3-F | F | H |
| A-1044. | CH₂F | OCF₃ | 3-CH₃ | F | H |
| A-1045. | CH₂F | OCF₃ | 3-OCH₃ | F | H |
| A-1046. | CH₂F | OCF₃ | 5-F | F | H |
| A-1047. | CH₂F | OCF₃ | 5-CH₃ | F | H |
| A-1048. | CH₂F | OCF₃ | 5-OCH₃ | F | H |
| A-1049. | CHF₂ | F | 3-F | F | H |
| A-1050. | CHF₂ | F | 3-CH₃ | F | H |
| A-1051. | CHF₂ | F | 3-OCH₃ | F | H |
| A-1052. | CHF₂ | F | 5-F | F | H |
| A-1053. | CHF₂ | F | 5-CH₃ | F | H |
| A-1054. | CHF₂ | F | 5-OCH₃ | F | H |
| A-1055. | CHF₂ | CH₃ | 3-F | F | H |
| A-1056. | CHF₂ | CH₃ | 3-CH₃ | F | H |
| A-1057. | CHF₂ | CH₃ | 3-OCH₃ | F | H |
| A-1058. | CHF₂ | CH₃ | 5-F | F | H |
| A-1059. | CHF₂ | CH₃ | 5-CH₃ | F | H |
| A-1060. | CHF₂ | CH₃ | 5-OCH₃ | F | H |
| A-1061. | CHF₂ | OCH₃ | 3-F | F | H |

TABLE A-continued

| Example No. | $R^{8a}$ | $R^{8b}$ | $R^{8c}$ | $R^1$ | $R^2$ |
| --- | --- | --- | --- | --- | --- |
| A-1062. | $CHF_2$ | $OCH_3$ | 3-$CH_3$ | F | H |
| A-1063. | $CHF_2$ | $OCH_3$ | 3-$OCH_3$ | F | H |
| A-1064. | $CHF_2$ | $OCH_3$ | 5-F | F | H |
| A-1065. | $CHF_2$ | $OCH_3$ | 5-$CH_3$ | F | H |
| A-1066. | $CHF_2$ | $OCH_3$ | 5-$OCH_3$ | F | H |
| A-1067. | $CHF_2$ | CN | 3-F | F | H |
| A-1068. | $CHF_2$ | CN | 3-$CH_3$ | F | H |
| A-1069. | $CHF_2$ | CN | 3-$OCH_3$ | F | H |
| A-1070. | $CHF_2$ | CN | 5-F | F | H |
| A-1071. | $CHF_2$ | CN | 5-$CH_3$ | F | H |
| A-1072. | $CHF_2$ | CN | 5-$OCH_3$ | F | H |
| A-1073. | $CHF_2$ | $CH_2F$ | 3-F | F | H |
| A-1074. | $CHF_2$ | $CH_2F$ | 3-$CH_3$ | F | H |
| A-1075. | $CHF_2$ | $CH_2F$ | 3-$OCH_3$ | F | H |
| A-1076. | $CHF_2$ | $CH_2F$ | 5-F | F | H |
| A-1077. | $CHF_2$ | $CH_2F$ | 5-$CH_3$ | F | H |
| A-1078. | $CHF_2$ | $CH_2F$ | 5-$OCH_3$ | F | H |
| A-1079. | $CHF_2$ | $CHF_2$ | 3-F | F | H |
| A-1080. | $CHF_2$ | $CHF_2$ | 3-$CH_3$ | F | H |
| A-1081. | $CHF_2$ | $CHF_2$ | 3-$OCH_3$ | F | H |
| A-1082. | $CHF_2$ | $CHF_2$ | 5-F | F | H |
| A-1083. | $CHF_2$ | $CHF_2$ | 5-$CH_3$ | F | H |
| A-1084. | $CHF_2$ | $CHF_2$ | 5-$OCH_3$ | F | H |
| A-1085. | $CHF_2$ | $CF_3$ | 3-F | F | H |
| A-1086. | $CHF_2$ | $CF_3$ | 3-$CH_3$ | F | H |
| A-1087. | $CHF_2$ | $CF_3$ | 3-$OCH_3$ | F | H |
| A-1088. | $CHF_2$ | $CF_3$ | 5-F | F | H |
| A-1089. | $CHF_2$ | $CF_3$ | 5-$CH_3$ | F | H |
| A-1090. | $CHF_2$ | $CF_3$ | 5-$OCH_3$ | F | H |
| A-1091. | $CHF_2$ | $OCH_2F$ | 3-F | F | H |
| A-1092. | $CHF_2$ | $OCH_2F$ | 3-$CH_3$ | F | H |
| A-1093. | $CHF_2$ | $OCH_2F$ | 3-$OCH_3$ | F | H |
| A-1094. | $CHF_2$ | $OCH_2F$ | 5-F | F | H |
| A-1095. | $CHF_2$ | $OCH_2F$ | 5-$CH_3$ | F | H |
| A-1096. | $CHF_2$ | $OCH_2F$ | 5-$OCH_3$ | F | H |
| A-1097. | $CHF_2$ | $OCHF_2$ | 3-F | F | H |
| A-1098. | $CHF_2$ | $OCHF_2$ | 3-$CH_3$ | F | H |
| A-1099. | $CHF_2$ | $OCHF_2$ | 3-$OCH_3$ | F | H |
| A-1100. | $CHF_2$ | $OCHF_2$ | 5-F | F | H |
| A-1101. | $CHF_2$ | $OCHF_2$ | 5-$CH_3$ | F | H |
| A-1102. | $CHF_2$ | $OCHF_2$ | 5-$OCH_3$ | F | H |
| A-1103. | $CHF_2$ | $OCF_3$ | 3-F | F | H |
| A-1104. | $CHF_2$ | $OCF_3$ | 3-$CH_3$ | F | H |
| A-1105. | $CHF_2$ | $OCF_3$ | 3-$OCH_3$ | F | H |
| A-1106. | $CHF_2$ | $OCF_3$ | 5-F | F | H |
| A-1107. | $CHF_2$ | $OCF_3$ | 5-$CH_3$ | F | H |
| A-1108. | $CHF_2$ | $OCF_3$ | 5-$OCH_3$ | F | H |
| A-1109. | $CF_3$ | F | 3-F | F | H |
| A-1110. | $CF_3$ | F | 3-$CH_3$ | F | H |
| A-1111. | $CF_3$ | F | 3-$OCH_3$ | F | H |
| A-1112. | $CF_3$ | F | 5-F | F | H |
| A-1113. | $CF_3$ | F | 5-$CH_3$ | F | H |
| A-1114. | $CF_3$ | F | 5-$OCH_3$ | F | H |
| A-1115. | $CF_3$ | $CH_3$ | 3-F | F | H |
| A-1116. | $CF_3$ | $CH_3$ | 3-$CH_3$ | F | H |
| A-1117. | $CF_3$ | $CH_3$ | 3-$OCH_3$ | F | H |
| A-1118. | $CF_3$ | $CH_3$ | 5-F | F | H |
| A-1119. | $CF_3$ | $CH_3$ | 5-$CH_3$ | F | H |
| A-1120. | $CF_3$ | $CH_3$ | 5-$OCH_3$ | F | H |
| A-1121. | $CF_3$ | $OCH_3$ | 3-F | F | H |
| A-1122. | $CF_3$ | $OCH_3$ | 3-$CH_3$ | F | H |
| A-1123. | $CF_3$ | $OCH_3$ | 3-$OCH_3$ | F | H |
| A-1124. | $CF_3$ | $OCH_3$ | 5-F | F | H |
| A-1125. | $CF_3$ | $OCH_3$ | 5-$CH_3$ | F | H |
| A-1126. | $CF_3$ | $OCH_3$ | 5-$OCH_3$ | F | H |
| A-1127. | $CF_3$ | CN | 3-F | F | H |
| A-1128. | $CF_3$ | CN | 3-$CH_3$ | F | H |
| A-1129. | $CF_3$ | CN | 3-$OCH_3$ | F | H |
| A-1130. | $CF_3$ | CN | 5-F | F | H |
| A-1131. | $CF_3$ | CN | 5-$CH_3$ | F | H |
| A-1132. | $CF_3$ | CN | 5-$OCH_3$ | F | H |
| A-1133. | $CF_3$ | $CH_2F$ | 3-F | F | H |
| A-1134. | $CF_3$ | $CH_2F$ | 3-$CH_3$ | F | H |
| A-1135. | $CF_3$ | $CH_2F$ | 3-$OCH_3$ | F | H |
| A-1136. | $CF_3$ | $CH_2F$ | 5-F | F | H |
| A-1137. | $CF_3$ | $CH_2F$ | 5-$CH_3$ | F | H |
| A-1138. | $CF_3$ | $CH_2F$ | 5-$OCH_3$ | F | H |
| A-1139. | $CF_3$ | $CHF_2$ | 3-F | F | H |
| A-1140. | $CF_3$ | $CHF_2$ | 3-$CH_3$ | F | H |
| A-1141. | $CF_3$ | $CHF_2$ | 3-$OCH_3$ | F | H |
| A-1142. | $CF_3$ | $CHF_2$ | 5-F | F | H |
| A-1143. | $CF_3$ | $CHF_2$ | 5-$CH_3$ | F | H |
| A-1144. | $CF_3$ | $CHF_2$ | 5-$OCH_3$ | F | H |
| A-1145. | $CF_3$ | $CF_3$ | 3-F | F | H |
| A-1146. | $CF_3$ | $CF_3$ | 3-$CH_3$ | F | H |
| A-1147. | $CF_3$ | $CF_3$ | 3-$OCH_3$ | F | H |
| A-1148. | $CF_3$ | $CF_3$ | 5-F | F | H |
| A-1149. | $CF_3$ | $CF_3$ | 5-$CH_3$ | F | H |
| A-1150. | $CF_3$ | $CF_3$ | 5-$OCH_3$ | F | H |
| A-1151. | $CF_3$ | $OCH_2F$ | 3-F | F | H |
| A-1152. | $CF_3$ | $OCH_2F$ | 3-$CH_3$ | F | H |
| A-1153. | $CF_3$ | $OCH_2F$ | 3-$OCH_3$ | F | H |
| A-1154. | $CF_3$ | $OCH_2F$ | 5-F | F | H |
| A-1155. | $CF_3$ | $OCH_2F$ | 5-$CH_3$ | F | H |
| A-1156. | $CF_3$ | $OCH_2F$ | 5-$OCH_3$ | F | H |
| A-1157. | $CF_3$ | $OCHF_2$ | 3-F | F | H |
| A-1158. | $CF_3$ | $OCHF_2$ | 3-$CH_3$ | F | H |
| A-1159. | $CF_3$ | $OCHF_2$ | 3-$OCH_3$ | F | H |
| A-1160. | $CF_3$ | $OCHF_2$ | 5-F | F | H |
| A-1161. | $CF_3$ | $OCHF_2$ | 5-$CH_3$ | F | H |
| A-1162. | $CF_3$ | $OCHF_2$ | 5-$OCH_3$ | F | H |
| A-1163. | $CF_3$ | $OCF_3$ | 3-F | F | H |
| A-1164. | $CF_3$ | $OCF_3$ | 3-$CH_3$ | F | H |
| A-1165. | $CF_3$ | $OCF_3$ | 3-$OCH_3$ | F | H |
| A-1166. | $CF_3$ | $OCF_3$ | 5-F | F | H |
| A-1167. | $CF_3$ | $OCF_3$ | 5-$CH_3$ | F | H |
| A-1168. | $CF_3$ | $OCF_3$ | 5-$OCH_3$ | F | H |
| A-1169. | $OCH_2F$ | F | 3-F | F | H |
| A-1170. | $OCH_2F$ | F | 3-$CH_3$ | F | H |
| A-1171. | $OCH_2F$ | F | 3-$OCH_3$ | F | H |
| A-1172. | $OCH_2F$ | F | 5-F | F | H |
| A-1173. | $OCH_2F$ | F | 5-$CH_3$ | F | H |
| A-1174. | $OCH_2F$ | F | 5-$OCH_3$ | F | H |
| A-1175. | $OCH_2F$ | $CH_3$ | 3-F | F | H |
| A-1176. | $OCH_2F$ | $CH_3$ | 3-$CH_3$ | F | H |
| A-1177. | $OCH_2F$ | $CH_3$ | 3-$OCH_3$ | F | H |
| A-1178. | $OCH_2F$ | $CH_3$ | 5-F | F | H |
| A-1179. | $OCH_2F$ | $CH_3$ | 5-$CH_3$ | F | H |
| A-1180. | $OCH_2F$ | $CH_3$ | 5-$OCH_3$ | F | H |
| A-1181. | $OCH_2F$ | $OCH_3$ | 3-F | F | H |
| A-1182. | $OCH_2F$ | $OCH_3$ | 3-$CH_3$ | F | H |
| A-1183. | $OCH_2F$ | $OCH_3$ | 3-$OCH_3$ | F | H |
| A-1184. | $OCH_2F$ | $OCH_3$ | 5-F | F | H |
| A-1185. | $OCH_2F$ | $OCH_3$ | 5-$CH_3$ | F | H |
| A-1186. | $OCH_2F$ | $OCH_3$ | 5-$OCH_3$ | F | H |
| A-1187. | $OCH_2F$ | CN | 3-F | F | H |
| A-1188. | $OCH_2F$ | CN | 3-$CH_3$ | F | H |
| A-1189. | $OCH_2F$ | CN | 3-$OCH_3$ | F | H |
| A-1190. | $OCH_2F$ | CN | 5-F | F | H |
| A-1191. | $OCH_2F$ | CN | 5-$CH_3$ | F | H |
| A-1192. | $OCH_2F$ | CN | 5-$OCH_3$ | F | H |
| A-1193. | $OCH_2F$ | $CH_2F$ | 3-F | F | H |
| A-1194. | $OCH_2F$ | $CH_2F$ | 3-$CH_3$ | F | H |
| A-1195. | $OCH_2F$ | $CH_2F$ | 3-$OCH_3$ | F | H |
| A-1196. | $OCH_2F$ | $CH_2F$ | 5-F | F | H |
| A-1197. | $OCH_2F$ | $CH_2F$ | 5-$CH_3$ | F | H |
| A-1198. | $OCH_2F$ | $CH_2F$ | 5-$OCH_3$ | F | H |
| A-1199. | $OCH_2F$ | $CHF_2$ | 3-F | F | H |
| A-1200. | $OCH_2F$ | $CHF_2$ | 3-$CH_3$ | F | H |
| A-1201. | $OCH_2F$ | $CHF_2$ | 3-$OCH_3$ | F | H |
| A-1202. | $OCH_2F$ | $CHF_2$ | 5-F | F | H |
| A-1203. | $OCH_2F$ | $CHF_2$ | 5-$CH_3$ | F | H |
| A-1204. | $OCH_2F$ | $CHF_2$ | 5-$OCH_3$ | F | H |
| A-1205. | $OCH_2F$ | $CF_3$ | 3-F | F | H |
| A-1206. | $OCH_2F$ | $CF_3$ | 3-$CH_3$ | F | H |
| A-1207. | $OCH_2F$ | $CF_3$ | 3-$OCH_3$ | F | H |
| A-1208. | $OCH_2F$ | $CF_3$ | 5-F | F | H |
| A-1209. | $OCH_2F$ | $CF_3$ | 5-$CH_3$ | F | H |
| A-1210. | $OCH_2F$ | $CF_3$ | 5-$OCH_3$ | F | H |
| A-1211. | $OCH_2F$ | $OCH_2F$ | 3-F | F | H |
| A-1212. | $OCH_2F$ | $OCH_2F$ | 3-$CH_3$ | F | H |
| A-1213. | $OCH_2F$ | $OCH_2F$ | 3-$OCH_3$ | F | H |
| A-1214. | $OCH_2F$ | $OCH_2F$ | 5-F | F | H |
| A-1215. | $OCH_2F$ | $OCH_2F$ | 5-$CH_3$ | F | H |
| A-1216. | $OCH_2F$ | $OCH_2F$ | 5-$OCH_3$ | F | H |
| A-1217. | $OCH_2F$ | $OCHF_2$ | 3-F | F | H |

TABLE A-continued

| Example No. | $R^{8a}$ | $R^{8b}$ | $R^{8c}$ | $R^1$ | $R^2$ |
|---|---|---|---|---|---|
| A-1218. | OCH$_2$F | OCHF$_2$ | 3-CH$_3$ | F | H |
| A-1219. | OCH$_2$F | OCHF$_2$ | 3-OCH$_3$ | F | H |
| A-1220. | OCH$_2$F | OCHF$_2$ | 5-F | F | H |
| A-1221. | OCH$_2$F | OCHF$_2$ | 5-CH$_3$ | F | H |
| A-1222. | OCH$_2$F | OCHF$_2$ | 5-OCH$_3$ | F | H |
| A-1223. | OCH$_2$F | OCF$_3$ | 3-F | F | H |
| A-1224. | OCH$_2$F | OCF$_3$ | 3-CH$_3$ | F | H |
| A-1225. | OCH$_2$F | OCF$_3$ | 3-OCH$_3$ | F | H |
| A-1226. | OCH$_2$F | OCF$_3$ | 5-F | F | H |
| A-1227. | OCH$_2$F | OCF$_3$ | 5-CH$_3$ | F | H |
| A-1228. | OCH$_2$F | OCF$_3$ | 5-OCH$_3$ | F | H |
| A-1229. | OCHF$_2$ | F | 3-F | F | H |
| A-1230. | OCHF$_2$ | F | 3-CH$_3$ | F | H |
| A-1231. | OCHF$_2$ | F | 3-OCH$_3$ | F | H |
| A-1232. | OCHF$_2$ | F | 5-F | F | H |
| A-1233. | OCHF$_2$ | F | 5-CH$_3$ | F | H |
| A-1234. | OCHF$_2$ | F | 5-OCH$_3$ | F | H |
| A-1235. | OCHF$_2$ | CH$_3$ | 3-F | F | H |
| A-1236. | OCHF$_2$ | CH$_3$ | 3-CH$_3$ | F | H |
| A-1237. | OCHF$_2$ | CH$_3$ | 3-OCH$_3$ | F | H |
| A-1238. | OCHF$_2$ | CH$_3$ | 5-F | F | H |
| A-1239. | OCHF$_2$ | CH$_3$ | 5-CH$_3$ | F | H |
| A-1240. | OCHF$_2$ | CH$_3$ | 5-OCH$_3$ | F | H |
| A-1241. | OCHF$_2$ | OCH$_3$ | 3-F | F | H |
| A-1242. | OCHF$_2$ | OCH$_3$ | 3-CH$_3$ | F | H |
| A-1243. | OCHF$_2$ | OCH$_3$ | 3-OCH$_3$ | F | H |
| A-1244. | OCHF$_2$ | OCH$_3$ | 5-F | F | H |
| A-1245. | OCHF$_2$ | OCH$_3$ | 5-CH$_3$ | F | H |
| A-1246. | OCHF$_2$ | OCH$_3$ | 5-OCH$_3$ | F | H |
| A-1247. | OCHF$_2$ | CN | 3-F | F | H |
| A-1248. | OCHF$_2$ | CN | 3-CH$_3$ | F | H |
| A-1249. | OCHF$_2$ | CN | 3-OCH$_3$ | F | H |
| A-1250. | OCHF$_2$ | CN | 5-F | F | H |
| A-1251. | OCHF$_2$ | CN | 5-CH$_3$ | F | H |
| A-1252. | OCHF$_2$ | CN | 5-OCH$_3$ | F | H |
| A-1253. | OCHF$_2$ | CH$_2$F | 3-F | F | H |
| A-1254. | OCHF$_2$ | CH$_2$F | 3-CH$_3$ | F | H |
| A-1255. | OCHF$_2$ | CH$_2$F | 3-OCH$_3$ | F | H |
| A-1256. | OCHF$_2$ | CH$_2$F | 5-F | F | H |
| A-1257. | OCHF$_2$ | CH$_2$F | 5-CH$_3$ | F | H |
| A-1258. | OCHF$_2$ | CH$_2$F | 5-OCH$_3$ | F | H |
| A-1259. | OCHF$_2$ | CHF$_2$ | 3-F | F | H |
| A-1260. | OCHF$_2$ | CHF$_2$ | 3-CH$_3$ | F | H |
| A-1261. | OCHF$_2$ | CHF$_2$ | 3-OCH$_3$ | F | H |
| A-1262. | OCHF$_2$ | CHF$_2$ | 5-F | F | H |
| A-1263. | OCHF$_2$ | CHF$_2$ | 5-CH$_3$ | F | H |
| A-1264. | OCHF$_2$ | CHF$_2$ | 5-OCH$_3$ | F | H |
| A-1265. | OCHF$_2$ | CF$_3$ | 3-F | F | H |
| A-1266. | OCHF$_2$ | CF$_3$ | 3-CH$_3$ | F | H |
| A-1267. | OCHF$_2$ | CF$_3$ | 3-OCH$_3$ | F | H |
| A-1268. | OCHF$_2$ | CF$_3$ | 5-F | F | H |
| A-1269. | OCHF$_2$ | CF$_3$ | 5-CH$_3$ | F | H |
| A-1270. | OCHF$_2$ | CF$_3$ | 5-OCH$_3$ | F | H |
| A-1271. | OCHF$_2$ | OCH$_2$F | 3-F | F | H |
| A-1272. | OCHF$_2$ | OCH$_2$F | 3-CH$_3$ | F | H |
| A-1273. | OCHF$_2$ | OCH$_2$F | 3-OCH$_3$ | F | H |
| A-1274. | OCHF$_2$ | OCH$_2$F | 5-F | F | H |
| A-1275. | OCHF$_2$ | OCH$_2$F | 5-CH$_3$ | F | H |
| A-1276. | OCHF$_2$ | OCH$_2$F | 5-OCH$_3$ | F | H |
| A-1277. | OCHF$_2$ | OCHF$_2$ | 3-F | F | H |
| A-1278. | OCHF$_2$ | OCHF$_2$ | 3-CH$_3$ | F | H |
| A-1279. | OCHF$_2$ | OCHF$_2$ | 3-OCH$_3$ | F | H |
| A-1280. | OCHF$_2$ | OCHF$_2$ | 5-F | F | H |
| A-1281. | OCHF$_2$ | OCHF$_2$ | 5-CH$_3$ | F | H |
| A-1282. | OCHF$_2$ | OCHF$_2$ | 5-OCH$_3$ | F | H |
| A-1283. | OCHF$_2$ | OCF$_3$ | 3-F | F | H |
| A-1284. | OCHF$_2$ | OCF$_3$ | 3-CH$_3$ | F | H |
| A-1285. | OCHF$_2$ | OCF$_3$ | 3-OCH$_3$ | F | H |
| A-1286. | OCHF$_2$ | OCF$_3$ | 5-F | F | H |
| A-1287. | OCHF$_2$ | OCF$_3$ | 5-CH$_3$ | F | H |
| A-1288. | OCHF$_2$ | OCF$_3$ | 5-OCH$_3$ | F | H |
| A-1289. | OCF$_3$ | F | 3-F | F | H |
| A-1290. | OCF$_3$ | F | 3-CH$_3$ | F | H |
| A-1291. | OCF$_3$ | F | 3-OCH$_3$ | F | H |
| A-1292. | OCF$_3$ | F | 5-F | F | H |
| A-1293. | OCF$_3$ | F | 5-CH$_3$ | F | H |
| A-1294. | OCF$_3$ | F | 5-OCH$_3$ | F | H |
| A-1295. | OCF$_3$ | CH$_3$ | 3-F | F | H |
| A-1296. | OCF$_3$ | CH$_3$ | 3-CH$_3$ | F | H |
| A-1297. | OCF$_3$ | CH$_3$ | 3-OCH$_3$ | F | H |
| A-1298. | OCF$_3$ | CH$_3$ | 5-F | F | H |
| A-1299. | OCF$_3$ | CH$_3$ | 5-CH$_3$ | F | H |
| A-1300. | OCF$_3$ | CH$_3$ | 5-OCH$_3$ | F | H |
| A-1301. | OCF$_3$ | OCH$_3$ | 3-F | F | H |
| A-1302. | OCF$_3$ | OCH$_3$ | 3-CH$_3$ | F | H |
| A-1303. | OCF$_3$ | OCH$_3$ | 3-OCH$_3$ | F | H |
| A-1304. | OCF$_3$ | OCH$_3$ | 5-F | F | H |
| A-1305. | OCF$_3$ | OCH$_3$ | 5-CH$_3$ | F | H |
| A-1306. | OCF$_3$ | OCH$_3$ | 5-OCH$_3$ | F | H |
| A-1307. | OCF$_3$ | CN | 3-F | F | H |
| A-1308. | OCF$_3$ | CN | 3-CH$_3$ | F | H |
| A-1309. | OCF$_3$ | CN | 3-OCH$_3$ | F | H |
| A-1310. | OCF$_3$ | CN | 5-F | F | H |
| A-1311. | OCF$_3$ | CN | 5-CH$_3$ | F | H |
| A-1312. | OCF$_3$ | CN | 5-OCH$_3$ | F | H |
| A-1313. | OCF$_3$ | CH$_2$F | 3-F | F | H |
| A-1314. | OCF$_3$ | CH$_2$F | 3-CH$_3$ | F | H |
| A-1315. | OCF$_3$ | CH$_2$F | 3-OCH$_3$ | F | H |
| A-1316. | OCF$_3$ | CH$_2$F | 5-F | F | H |
| A-1317. | OCF$_3$ | CH$_2$F | 5-CH$_3$ | F | H |
| A-1318. | OCF$_3$ | CH$_2$F | 5-OCH$_3$ | F | H |
| A-1319. | OCF$_3$ | CHF$_2$ | 3-F | F | H |
| A-1320. | OCF$_3$ | CHF$_2$ | 3-CH$_3$ | F | H |
| A-1321. | OCF$_3$ | CHF$_2$ | 3-OCH$_3$ | F | H |
| A-1322. | OCF$_3$ | CHF$_2$ | 5-F | F | H |
| A-1323. | OCF$_3$ | CHF$_2$ | 5-CH$_3$ | F | H |
| A-1324. | OCF$_3$ | CHF$_2$ | 5-OCH$_3$ | F | H |
| A-1325. | OCF$_3$ | CF$_3$ | 3-F | F | H |
| A-1326. | OCF$_3$ | CF$_3$ | 3-CH$_3$ | F | H |
| A-1327. | OCF$_3$ | CF$_3$ | 3-OCH$_3$ | F | H |
| A-1328. | OCF$_3$ | CF$_3$ | 5-F | F | H |
| A-1329. | OCF$_3$ | CF$_3$ | 5-CH$_3$ | F | H |
| A-1330. | OCF$_3$ | CF$_3$ | 5-OCH$_3$ | F | H |
| A-1331. | OCF$_3$ | OCH$_2$F | 3-F | F | H |
| A-1332. | OCF$_3$ | OCH$_2$F | 3-CH$_3$ | F | H |
| A-1333. | OCF$_3$ | OCH$_2$F | 3-OCH$_3$ | F | H |
| A-1334. | OCF$_3$ | OCH$_2$F | 5-F | F | H |
| A-1335. | OCF$_3$ | OCH$_2$F | 5-CH$_3$ | F | H |
| A-1336. | OCF$_3$ | OCH$_2$F | 5-OCH$_3$ | F | H |
| A-1337. | OCF$_3$ | OCHF$_2$ | 3-F | F | H |
| A-1338. | OCF$_3$ | OCHF$_2$ | 3-CH$_3$ | F | H |
| A-1339. | OCF$_3$ | OCHF$_2$ | 3-OCH$_3$ | F | H |
| A-1340. | OCF$_3$ | OCHF$_2$ | 5-F | F | H |
| A-1341. | OCF$_3$ | OCHF$_2$ | 5-CH$_3$ | F | H |
| A-1342. | OCF$_3$ | OCHF$_2$ | 5-OCH$_3$ | F | H |
| A-1343. | OCF$_3$ | OCF$_3$ | 3-F | F | H |
| A-1344. | OCF$_3$ | OCF$_3$ | 3-CH$_3$ | F | H |
| A-1345. | OCF$_3$ | OCF$_3$ | 3-OCH$_3$ | F | H |
| A-1346. | OCF$_3$ | OCF$_3$ | 5-F | F | H |
| A-1347. | OCF$_3$ | OCF$_3$ | 5-CH$_3$ | F | H |
| A-1348. | OCF$_3$ | OCF$_3$ | 5-OCH$_3$ | F | H |
| A-1349. | H | H | H | Cl | H |
| A-1350. | F | H | H | Cl | H |
| A-1351. | CH$_3$ | H | H | Cl | H |
| A-1352. | OCH$_3$ | H | H | Cl | H |
| A-1353. | CH$_2$F | H | H | Cl | H |
| A-1354. | CHF$_2$ | H | H | Cl | H |
| A-1355. | CF$_3$ | H | H | Cl | H |
| A-1356. | OCH$_2$F | H | H | Cl | H |
| A-1357. | OCHF$_2$ | H | H | Cl | H |
| A-1358. | OCF$_3$ | H | H | Cl | H |
| A-1359. | H | F | H | Cl | H |
| A-1360. | H | CH$_3$ | H | Cl | H |
| A-1361. | H | OCH$_3$ | H | Cl | H |
| A-1362. | H | CN | H | Cl | H |
| A-1363. | H | CH$_2$F | H | Cl | H |
| A-1364. | H | CHF$_2$ | H | Cl | H |
| A-1365. | H | CF$_3$ | H | Cl | H |
| A-1366. | H | OCH$_2$F | H | Cl | H |
| A-1367. | H | OCHF$_2$ | H | Cl | H |
| A-1368. | H | OCF$_3$ | H | Cl | H |
| A-1369. | H | H | 3-F | Cl | H |
| A-1370. | H | H | 3-CH$_3$ | Cl | H |
| A-1371. | H | H | 3-OCH$_3$ | Cl | H |
| A-1372. | H | H | 5-F | Cl | H |
| A-1373. | H | H | 5-CH$_3$ | Cl | H |

TABLE A-continued

| Example No. | $R^{8a}$ | $R^{8b}$ | $R^{8c}$ | $R^1$ | $R^2$ |
|---|---|---|---|---|---|
| A-1374. | H | H | 5-OCH$_3$ | Cl | H |
| A-1375. | F | F | H | Cl | H |
| A-1376. | F | CH$_3$ | H | Cl | H |
| A-1377. | F | OCH$_3$ | H | Cl | H |
| A-1378. | F | CN | H | Cl | H |
| A-1379. | F | CH$_2$F | H | Cl | H |
| A-1380. | F | CHF$_2$ | H | Cl | H |
| A-1381. | F | CF$_3$ | H | Cl | H |
| A-1382. | F | OCH$_2$F | H | Cl | H |
| A-1383. | F | OCHF$_2$ | H | Cl | H |
| A-1384. | F | OCF$_3$ | H | Cl | H |
| A-1385. | F | H | 3-F | Cl | H |
| A-1386. | F | H | 3-CH$_3$ | Cl | H |
| A-1387. | F | H | 3-OCH$_3$ | Cl | H |
| A-1388. | F | H | 5-F | Cl | H |
| A-1389. | F | H | 5-CH$_3$ | Cl | H |
| A-1390. | F | H | 5-OCH$_3$ | Cl | H |
| A-1391. | CH$_3$ | F | H | Cl | H |
| A-1392. | CH$_3$ | CH$_3$ | H | Cl | H |
| A-1393. | CH$_3$ | OCH$_3$ | H | Cl | H |
| A-1394. | CH$_3$ | CN | H | Cl | H |
| A-1395. | CH$_3$ | CH$_2$F | H | Cl | H |
| A-1396. | CH$_3$ | CHF$_2$ | H | Cl | H |
| A-1397. | CH$_3$ | CF$_3$ | H | Cl | H |
| A-1398. | CH$_3$ | OCH$_2$F | H | Cl | H |
| A-1399. | CH$_3$ | OCHF$_2$ | H | Cl | H |
| A-1400. | CH$_3$ | OCF$_3$ | H | Cl | H |
| A-1401. | CH$_3$ | H | 3-F | Cl | H |
| A-1402. | CH$_3$ | H | 3-CH$_3$ | Cl | H |
| A-1403. | CH$_3$ | H | 3-OCH$_3$ | Cl | H |
| A-1404. | CH$_3$ | H | 5-F | Cl | H |
| A-1405. | CH$_3$ | H | 5-CH$_3$ | Cl | H |
| A-1406. | CH$_3$ | H | 5-OCH$_3$ | Cl | H |
| A-1407. | OCH$_3$ | F | H | Cl | H |
| A-1408. | OCH$_3$ | CH$_3$ | H | Cl | H |
| A-1409. | OCH$_3$ | OCH$_3$ | H | Cl | H |
| A-1410. | OCH$_3$ | CN | H | Cl | H |
| A-1411. | OCH$_3$ | CH$_2$F | H | Cl | H |
| A-1412. | OCH$_3$ | CHF$_2$ | H | Cl | H |
| A-1413. | OCH$_3$ | CF$_3$ | H | Cl | H |
| A-1414. | OCH$_3$ | OCH$_2$F | H | Cl | H |
| A-1415. | OCH$_3$ | OCHF$_2$ | H | Cl | H |
| A-1416. | OCH$_3$ | OCF$_3$ | H | Cl | H |
| A-1417. | OCH$_3$ | H | 3-F | Cl | H |
| A-1418. | OCH$_3$ | H | 3-CH$_3$ | Cl | H |
| A-1419. | OCH$_3$ | H | 3-OCH$_3$ | Cl | H |
| A-1420. | OCH$_3$ | H | 5-F | Cl | H |
| A-1421. | OCH$_3$ | H | 5-CH$_3$ | Cl | H |
| A-1422. | OCH$_3$ | H | 5-OCH$_3$ | Cl | H |
| A-1423. | H | F | 3-F | Cl | H |
| A-1424. | H | F | 3-CH$_3$ | Cl | H |
| A-1425. | H | F | 3-OCH$_3$ | Cl | H |
| A-1426. | H | F | 5-F | Cl | H |
| A-1427. | H | F | 5-CH$_3$ | Cl | H |
| A-1428. | H | F | 5-OCH$_3$ | Cl | H |
| A-1429. | H | CH$_3$ | 3-F | Cl | H |
| A-1430. | H | CH$_3$ | 3-CH$_3$ | Cl | H |
| A-1431. | H | CH$_3$ | 3-OCH$_3$ | Cl | H |
| A-1432. | H | CH$_3$ | 5-F | Cl | H |
| A-1433. | H | CH$_3$ | 5-CH$_3$ | Cl | H |
| A-1434. | H | CH$_3$ | 5-OCH$_3$ | Cl | H |
| A-1435. | H | OCH$_3$ | 3-F | Cl | H |
| A-1436. | H | OCH$_3$ | 3-CH$_3$ | Cl | H |
| A-1437. | H | OCH$_3$ | 3-OCH$_3$ | Cl | H |
| A-1438. | H | OCH$_3$ | 5-F | Cl | H |
| A-1439. | H | OCH$_3$ | 5-CH$_3$ | Cl | H |
| A-1440. | H | OCH$_3$ | 5-OCH$_3$ | Cl | H |
| A-1441. | H | CN | 3-F | Cl | H |
| A-1442. | H | CN | 3-CH$_3$ | Cl | H |
| A-1443. | H | CN | 3-OCH$_3$ | Cl | H |
| A-1444. | H | CN | 5-F | Cl | H |
| A-1445. | H | CN | 5-CH$_3$ | Cl | H |
| A-1446. | H | CN | 5-OCH$_3$ | Cl | H |
| A-1447. | H | CH$_2$F | 3-F | Cl | H |
| A-1448. | H | CH$_2$F | 3-CH$_3$ | Cl | H |
| A-1449. | H | CH$_2$F | 3-OCH$_3$ | Cl | H |
| A-1450. | H | CH$_2$F | 5-F | Cl | H |
| A-1451. | H | CH$_2$F | 5-CH$_3$ | Cl | H |
| A-1452. | H | CH$_2$F | 5-OCH$_3$ | Cl | H |
| A-1453. | H | CHF$_2$ | 3-F | Cl | H |
| A-1454. | H | CHF$_2$ | 3-CH$_3$ | Cl | H |
| A-1455. | H | CHF$_2$ | 3-OCH$_3$ | Cl | H |
| A-1456. | H | CHF$_2$ | 5-F | Cl | H |
| A-1457. | H | CHF$_2$ | 5-CH$_3$ | Cl | H |
| A-1458. | H | CHF$_2$ | 5-OCH$_3$ | Cl | H |
| A-1459. | H | CF$_3$ | 3-F | Cl | H |
| A-1460. | H | CF$_3$ | 3-CH$_3$ | Cl | H |
| A-1461. | H | CF$_3$ | 3-OCH$_3$ | Cl | H |
| A-1462. | H | CF$_3$ | 5-F | Cl | H |
| A-1463. | H | CF$_3$ | 5-CH$_3$ | Cl | H |
| A-1464. | H | CF$_3$ | 5-OCH$_3$ | Cl | H |
| A-1465. | H | OCH$_2$F | 3-F | Cl | H |
| A-1466. | H | OCH$_2$F | 3-CH$_3$ | Cl | H |
| A-1467. | H | OCH$_2$F | 3-OCH$_3$ | Cl | H |
| A-1468. | H | OCH$_2$F | 5-F | Cl | H |
| A-1469. | H | OCH$_2$F | 5-CH$_3$ | Cl | H |
| A-1470. | H | OCH$_2$F | 5-OCH$_3$ | Cl | H |
| A-1471. | H | OCHF$_2$ | 3-F | Cl | H |
| A-1472. | H | OCHF$_2$ | 3-CH$_3$ | Cl | H |
| A-1473. | H | OCHF$_2$ | 3-OCH$_3$ | Cl | H |
| A-1474. | H | OCHF$_2$ | 5-F | Cl | H |
| A-1475. | H | OCHF$_2$ | 5-CH$_3$ | Cl | H |
| A-1476. | H | OCHF$_2$ | 5-OCH$_3$ | Cl | H |
| A-1477. | H | OCF$_3$ | 3-F | Cl | H |
| A-1478. | H | OCF$_3$ | 3-CH$_3$ | Cl | H |
| A-1479. | H | OCF$_3$ | 3-OCH$_3$ | Cl | H |
| A-1480. | H | OCF$_3$ | 5-F | Cl | H |
| A-1481. | H | OCF$_3$ | 5-CH$_3$ | Cl | H |
| A-1482. | H | OCF$_3$ | 5-OCH$_3$ | Cl | H |
| A-1483. | F | F | 3-F | Cl | H |
| A-1484. | F | F | 3-CH$_3$ | Cl | H |
| A-1485. | F | F | 3-OCH$_3$ | Cl | H |
| A-1486. | F | F | 5-F | Cl | H |
| A-1487. | F | F | 5-CH$_3$ | Cl | H |
| A-1488. | F | F | 5-OCH$_3$ | Cl | H |
| A-1489. | F | CH$_3$ | 3-F | Cl | H |
| A-1490. | F | CH$_3$ | 3-CH$_3$ | Cl | H |
| A-1491. | F | CH$_3$ | 3-OCH$_3$ | Cl | H |
| A-1492. | F | CH$_3$ | 5-F | Cl | H |
| A-1493. | F | CH$_3$ | 5-CH$_3$ | Cl | H |
| A-1494. | F | CH$_3$ | 5-OCH$_3$ | Cl | H |
| A-1495. | F | OCH$_3$ | 3-F | Cl | H |
| A-1496. | F | OCH$_3$ | 3-CH$_3$ | Cl | H |
| A-1497. | F | OCH$_3$ | 3-OCH$_3$ | Cl | H |
| A-1498. | F | OCH$_3$ | 5-F | Cl | H |
| A-1499. | F | OCH$_3$ | 5-CH$_3$ | Cl | H |
| A-1500. | F | OCH$_3$ | 5-OCH$_3$ | Cl | H |
| A-1501. | F | CN | 3-F | Cl | H |
| A-1502. | F | CN | 3-CH$_3$ | Cl | H |
| A-1503. | F | CN | 3-OCH$_3$ | Cl | H |
| A-1504. | F | CN | 5-F | Cl | H |
| A-1505. | F | CN | 5-CH$_3$ | Cl | H |
| A-1506. | F | CN | 5-OCH$_3$ | Cl | H |
| A-1507. | F | CH$_2$F | 3-F | Cl | H |
| A-1508. | F | CH$_2$F | 3-CH$_3$ | Cl | H |
| A-1509. | F | CH$_2$F | 3-OCH$_3$ | Cl | H |
| A-1510. | F | CH$_2$F | 5-F | Cl | H |
| A-1511. | F | CH$_2$F | 5-CH$_3$ | Cl | H |
| A-1512. | F | CH$_2$F | 5-OCH$_3$ | Cl | H |
| A-1513. | F | CHF$_2$ | 3-F | Cl | H |
| A-1514. | F | CHF$_2$ | 3-CH$_3$ | Cl | H |
| A-1515. | F | CHF$_2$ | 3-OCH$_3$ | Cl | H |
| A-1516. | F | CHF$_2$ | 5-F | Cl | H |
| A-1517. | F | CHF$_2$ | 5-CH$_3$ | Cl | H |
| A-1518. | F | CHF$_2$ | 5-OCH$_3$ | Cl | H |
| A-2807. | H | CF$_3$ | 3-F | F | F |
| A-2808. | H | CF$_3$ | 3-CH$_3$ | F | F |
| A-2809. | H | CF$_3$ | 3-OCH$_3$ | F | F |
| A-2810. | H | CF$_3$ | 5-F | F | F |
| A-2811. | H | CF$_3$ | 5-CH$_3$ | F | F |
| A-2812. | H | CF$_3$ | 5-OCH$_3$ | F | F |
| A-2813. | H | OCH$_2$F | 3-F | F | F |
| A-2814. | H | OCH$_2$F | 3-CH$_3$ | F | F |
| A-2815. | H | OCH$_2$F | 3-OCH$_3$ | F | F |
| A-2816. | H | OCH$_2$F | 5-F | F | F |
| A-2817. | H | OCH$_2$F | 5-CH$_3$ | F | F |

TABLE A-continued

| Example No. | $R^{8a}$ | $R^{8b}$ | $R^{8c}$ | $R^1$ | $R^2$ |
|---|---|---|---|---|---|
| A-2818. | H | OCH$_2$F | 5-OCH$_3$ | F | F |
| A-2819. | H | OCHF$_2$ | 3-F | F | F |
| A-2820. | H | OCHF$_2$ | 3-CH$_3$ | F | F |
| A-2821. | H | OCHF$_2$ | 3-OCH$_3$ | F | F |
| A-2822. | H | OCHF$_2$ | 5-F | F | F |
| A-2823. | H | OCHF$_2$ | 5-CH$_3$ | F | F |
| A-2824. | H | OCHF$_2$ | 5-OCH$_3$ | F | F |
| A-2825. | H | OCF$_3$ | 3-F | F | F |
| A-2826. | H | OCF$_3$ | 3-CH$_3$ | F | F |
| A-2827. | H | OCF$_3$ | 3-OCH$_3$ | F | F |
| A-2828. | H | OCF$_3$ | 5-F | F | F |
| A-2829. | H | OCF$_3$ | 5-CH$_3$ | F | F |
| A-2830. | H | OCF$_3$ | 5-OCH$_3$ | F | F |
| A-2831. | F | F | 3-F | F | F |
| A-2832. | F | F | 3-CH$_3$ | F | F |
| A-2833. | F | F | 3-OCH$_3$ | F | F |
| A-2834. | F | F | 5-F | F | F |
| A-2835. | F | F | 5-CH$_3$ | F | F |
| A-2836. | F | F | 5-OCH$_3$ | F | F |
| A-2837. | F | CH$_3$ | 3-F | F | F |
| A-2838. | F | CH$_3$ | 3-CH$_3$ | F | F |
| A-2839. | F | CH$_3$ | 3-OCH$_3$ | F | F |
| A-2840. | F | CH$_3$ | 5-F | F | F |
| A-2841. | F | CH$_3$ | 5-CH$_3$ | F | F |
| A-2842. | F | CH$_3$ | 5-OCH$_3$ | F | F |
| A-2843. | F | OCH$_3$ | 3-F | F | F |
| A-2844. | F | OCH$_3$ | 3-CH$_3$ | F | F |
| A-2845. | F | OCH$_3$ | 3-OCH$_3$ | F | F |
| A-2846. | F | OCH$_3$ | 5-F | F | F |
| A-2847. | F | OCH$_3$ | 5-CH$_3$ | F | F |
| A-2848. | F | OCH$_3$ | 5-OCH$_3$ | F | F |
| A-2849. | F | CN | 3-F | F | F |
| A-2850. | F | CN | 3-CH$_3$ | F | F |
| A-2851. | F | CN | 3-OCH$_3$ | F | F |
| A-2852. | F | CN | 5-F | F | F |
| A-2853. | F | CN | 5-CH$_3$ | F | F |
| A-2854. | F | CN | 5-OCH$_3$ | F | F |
| A-2855. | F | CH$_2$F | 3-F | F | F |
| A-2856. | F | CH$_2$F | 3-CH$_3$ | F | F |
| A-2857. | F | CH$_2$F | 3-OCH$_3$ | F | F |
| A-2858. | F | CH$_2$F | 5-F | F | F |
| A-2859. | F | CH$_2$F | 5-CH$_3$ | F | F |
| A-2860. | F | CH$_2$F | 5-OCH$_3$ | F | F |
| A-2861. | F | CHF$_2$ | 3-F | F | F |
| A-2862. | F | CHF$_2$ | 3-CH$_3$ | F | F |
| A-2863. | F | CHF$_2$ | 3-OCH$_3$ | F | F |
| A-2864. | F | CHF$_2$ | 5-F | F | F |
| A-2865. | F | CHF$_2$ | 5-CH$_3$ | F | F |
| A-2866. | F | CHF$_2$ | 5-OCH$_3$ | F | F |
| A-2867. | F | CF$_3$ | 3-F | F | F |
| A-2868. | F | CF$_3$ | 3-CH$_3$ | F | F |
| A-2869. | F | CF$_3$ | 3-OCH$_3$ | F | F |
| A-2870. | F | CF$_3$ | 5-F | F | F |
| A-2871. | F | CF$_3$ | 5-CH$_3$ | F | F |
| A-2872. | F | CF$_3$ | 5-OCH$_3$ | F | F |
| A-2873. | F | OCH$_2$F | 3-F | F | F |
| A-2874. | F | OCH$_2$F | 3-CH$_3$ | F | F |
| A-2875. | F | OCH$_2$F | 3-OCH$_3$ | F | F |
| A-2876. | F | OCH$_2$F | 5-F | F | F |
| A-2877. | F | OCH$_2$F | 5-CH$_3$ | F | F |
| A-2878. | F | OCH$_2$F | 5-OCH$_3$ | F | F |
| A-2879. | F | OCHF$_2$ | 3-F | F | F |
| A-2880. | F | OCHF$_2$ | 3-CH$_3$ | F | F |
| A-2881. | F | OCHF$_2$ | 3-OCH$_3$ | F | F |
| A-2882. | F | OCHF$_2$ | 5-F | F | F |
| A-2883. | F | OCHF$_2$ | 5-CH$_3$ | F | F |
| A-2884. | F | OCHF$_2$ | 5-OCH$_3$ | F | F |
| A-2885. | F | OCF$_3$ | 3-F | F | F |
| A-2886. | F | OCF$_3$ | 3-CH$_3$ | F | F |
| A-2887. | F | OCF$_3$ | 3-OCH$_3$ | F | F |
| A-2888. | F | OCF$_3$ | 5-F | F | F |
| A-2889. | F | OCF$_3$ | 5-CH$_3$ | F | F |
| A-2890. | F | OCF$_3$ | 5-OCH$_3$ | F | F |
| A-2891. | CH$_3$ | F | 3-F | F | F |
| A-2892. | CH$_3$ | F | 3-CH$_3$ | F | F |
| A-2893. | CH$_3$ | F | 3-OCH$_3$ | F | F |
| A-2894. | CH$_3$ | F | 5-F | F | F |
| A-2895. | CH$_3$ | F | 5-CH$_3$ | F | F |
| A-2896. | CH$_3$ | F | 5-OCH$_3$ | F | F |
| A-2897. | CH$_3$ | CH$_3$ | 3-F | F | F |
| A-2898. | CH$_3$ | CH$_3$ | 3-CH$_3$ | F | F |
| A-2899. | CH$_3$ | CH$_3$ | 3-OCH$_3$ | F | F |
| A-2900. | CH$_3$ | CH$_3$ | 5-F | F | F |
| A-2901. | CH$_3$ | CH$_3$ | 5-CH$_3$ | F | F |
| A-2902. | CH$_3$ | CH$_3$ | 5-OCH$_3$ | F | F |
| A-2903. | CH$_3$ | OCH$_3$ | 3-F | F | F |
| A-2904. | CH$_3$ | OCH$_3$ | 3-CH$_3$ | F | F |
| A-2905. | CH$_3$ | OCH$_3$ | 3-OCH$_3$ | F | F |
| A-2906. | CH$_3$ | OCH$_3$ | 5-F | F | F |
| A-2907. | CH$_3$ | OCH$_3$ | 5-CH$_3$ | F | F |
| A-2908. | CH$_3$ | OCH$_3$ | 5-OCH$_3$ | F | F |
| A-2909. | CH$_3$ | CN | 3-F | F | F |
| A-2910. | CH$_3$ | CN | 3-CH$_3$ | F | F |
| A-2911. | CH$_3$ | CN | 3-OCH$_3$ | F | F |
| A-2912. | CH$_3$ | CN | 5-F | F | F |
| A-2913. | CH$_3$ | CN | 5-CH$_3$ | F | F |
| A-2914. | CH$_3$ | CN | 5-OCH$_3$ | F | F |
| A-2915. | CH$_3$ | CH$_2$F | 3-F | F | F |
| A-2916. | CH$_3$ | CH$_2$F | 3-CH$_3$ | F | F |
| A-2917. | CH$_3$ | CH$_2$F | 3-OCH$_3$ | F | F |
| A-2918. | CH$_3$ | CH$_2$F | 5-F | F | F |
| A-2919. | CH$_3$ | CH$_2$F | 5-CH$_3$ | F | F |
| A-2920. | CH$_3$ | CH$_2$F | 5-OCH$_3$ | F | F |
| A-2921. | CH$_3$ | CHF$_2$ | 3-F | F | F |
| A-2922. | CH$_3$ | CHF$_2$ | 3-CH$_3$ | F | F |
| A-2923. | CH$_3$ | CHF$_2$ | 3-OCH$_3$ | F | F |
| A-2924. | CH$_3$ | CHF$_2$ | 5-F | F | F |
| A-2925. | CH$_3$ | CHF$_2$ | 5-CH$_3$ | F | F |
| A-2926. | CH$_3$ | CHF$_2$ | 5-OCH$_3$ | F | F |
| A-2927. | CH$_3$ | CF$_3$ | 3-F | F | F |
| A-2928. | CH$_3$ | CF$_3$ | 3-CH$_3$ | F | F |
| A-2929. | CH$_3$ | CF$_3$ | 3-OCH$_3$ | F | F |
| A-2930. | CH$_3$ | CF$_3$ | 5-F | F | F |
| A-2931. | CH$_3$ | CF$_3$ | 5-CH$_3$ | F | F |
| A-2932. | CH$_3$ | CF$_3$ | 5-OCH$_3$ | F | F |
| A-2933. | CH$_3$ | OCH$_2$F | 3-F | F | F |
| A-2934. | CH$_3$ | OCH$_2$F | 3-CH$_3$ | F | F |
| A-2935. | CH$_3$ | OCH$_2$F | 3-OCH$_3$ | F | F |
| A-2936. | CH$_3$ | OCH$_2$F | 5-F | F | F |
| A-2937. | CH$_3$ | OCH$_2$F | 5-CH$_3$ | F | F |
| A-2938. | CH$_3$ | OCH$_2$F | 5-OCH$_3$ | F | F |
| A-2939. | CH$_3$ | OCHF$_2$ | 3-F | F | F |
| A-2940. | CH$_3$ | OCHF$_2$ | 3-CH$_3$ | F | F |
| A-2941. | CH$_3$ | OCHF$_2$ | 3-OCH$_3$ | F | F |
| A-2942. | CH$_3$ | OCHF$_2$ | 5-F | F | F |
| A-2943. | CH$_3$ | OCHF$_2$ | 5-CH$_3$ | F | F |
| A-2944. | CH$_3$ | OCHF$_2$ | 5-OCH$_3$ | F | F |
| A-2945. | CH$_3$ | OCF$_3$ | 3-F | F | F |
| A-2946. | CH$_3$ | OCF$_3$ | 3-CH$_3$ | F | F |
| A-2947. | CH$_3$ | OCF$_3$ | 3-OCH$_3$ | F | F |
| A-2948. | CH$_3$ | OCF$_3$ | 5-F | F | F |
| A-2949. | CH$_3$ | OCF$_3$ | 5-CH$_3$ | F | F |
| A-2950. | CH$_3$ | OCF$_3$ | 5-OCH$_3$ | F | F |
| A-2951. | OCH$_3$ | F | 3-F | F | F |
| A-2952. | OCH$_3$ | F | 3-CH$_3$ | F | F |
| A-2953. | OCH$_3$ | F | 3-OCH$_3$ | F | F |
| A-2954. | OCH$_3$ | F | 5-F | F | F |
| A-2955. | OCH$_3$ | F | 5-CH$_3$ | F | F |
| A-2956. | OCH$_3$ | F | 5-OCH$_3$ | F | F |
| A-2957. | OCH$_3$ | CH$_3$ | 3-F | F | F |
| A-2958. | OCH$_3$ | CH$_3$ | 3-CH$_3$ | F | F |
| A-2959. | OCH$_3$ | CH$_3$ | 3-OCH$_3$ | F | F |
| A-2960. | OCH$_3$ | CH$_3$ | 5-F | F | F |
| A-2961. | OCH$_3$ | CH$_3$ | 5-CH$_3$ | F | F |
| A-2962. | OCH$_3$ | CH$_3$ | 5-OCH$_3$ | F | F |
| A-2963. | OCH$_3$ | OCH$_3$ | 3-F | F | F |
| A-2964. | OCH$_3$ | OCH$_3$ | 3-CH$_3$ | F | F |
| A-2965. | OCH$_3$ | OCH$_3$ | 3-OCH$_3$ | F | F |
| A-2966. | OCH$_3$ | OCH$_3$ | 5-F | F | F |
| A-2967. | OCH$_3$ | OCH$_3$ | 5-CH$_3$ | F | F |
| A-2968. | OCH$_3$ | OCH$_3$ | 5-OCH$_3$ | F | F |
| A-2969. | OCH$_3$ | CN | 3-F | F | F |
| A-2970. | OCH$_3$ | CN | 3-CH$_3$ | F | F |
| A-2971. | OCH$_3$ | CN | 3-OCH$_3$ | F | F |
| A-2972. | OCH$_3$ | CN | 5-F | F | F |
| A-2973. | OCH$_3$ | CN | 5-CH$_3$ | F | F |

TABLE A-continued

| Example No. | R^{8a} | R^{8b} | R^{8c} | R^1 | R^2 |
|---|---|---|---|---|---|
| A-2974. | OCH$_3$ | CN | 5-OCH$_3$ | F | F |
| A-2975. | OCH$_3$ | CH$_2$F | 3-F | F | F |
| A-2976. | OCH$_3$ | CH$_2$F | 3-CH$_3$ | F | F |
| A-2977. | OCH$_3$ | CH$_2$F | 3-OCH$_3$ | F | F |
| A-2978. | OCH$_3$ | CH$_2$F | 5-F | F | F |
| A-2979. | OCH$_3$ | CH$_2$F | 5-CH$_3$ | F | F |
| A-2980. | OCH$_3$ | CH$_2$F | 5-OCH$_3$ | F | F |
| A-2981. | OCH$_3$ | CHF$_2$ | 3-F | F | F |
| A-2982. | OCH$_3$ | CHF$_2$ | 3-CH$_3$ | F | F |
| A-2983. | OCH$_3$ | CHF$_2$ | 3-OCH$_3$ | F | F |
| A-2984. | OCH$_3$ | CHF$_2$ | 5-F | F | F |
| A-2985. | OCH$_3$ | CHF$_2$ | 5-CH$_3$ | F | F |
| A-2986. | OCH$_3$ | CHF$_2$ | 5-OCH$_3$ | F | F |
| A-2987. | OCH$_3$ | CF$_3$ | 3-F | F | F |
| A-2988. | OCH$_3$ | CF$_3$ | 3-CH$_3$ | F | F |
| A-2989. | OCH$_3$ | CF$_3$ | 3-OCH$_3$ | F | F |
| A-2990. | OCH$_3$ | CF$_3$ | 5-F | F | F |
| A-2991. | OCH$_3$ | CF$_3$ | 5-CH$_3$ | F | F |
| A-2992. | OCH$_3$ | CF$_3$ | 5-OCH$_3$ | F | F |
| A-2993. | OCH$_3$ | OCH$_2$F | 3-F | F | F |
| A-2994. | OCH$_3$ | OCH$_2$F | 3-CH$_3$ | F | F |
| A-2995. | OCH$_3$ | OCH$_2$F | 3-OCH$_3$ | F | F |
| A-2996. | OCH$_3$ | OCH$_2$F | 5-F | F | F |
| A-2997. | OCH$_3$ | OCH$_2$F | 5-CH$_3$ | F | F |
| A-2998. | OCH$_3$ | OCH$_2$F | 5-OCH$_3$ | F | F |
| A-2999. | OCH$_3$ | OCHF$_2$ | 3-F | F | F |
| A-3000. | OCH$_3$ | OCHF$_2$ | 3-CH$_3$ | F | F |
| A-3001. | OCH$_3$ | OCHF$_2$ | 3-OCH$_3$ | F | F |
| A-3002. | OCH$_3$ | OCHF$_2$ | 5-F | F | F |
| A-3003. | OCH$_3$ | OCHF$_2$ | 5-CH$_3$ | F | F |
| A-3004. | OCH$_3$ | OCHF$_2$ | 5-OCH$_3$ | F | F |
| A-3005. | OCH$_3$ | OCF$_3$ | 3-F | F | F |
| A-3006. | OCH$_3$ | OCF$_3$ | 3-CH$_3$ | F | F |
| A-3007. | OCH$_3$ | OCF$_3$ | 3-OCH$_3$ | F | F |
| A-3008. | OCH$_3$ | OCF$_3$ | 5-F | F | F |
| A-3009. | OCH$_3$ | OCF$_3$ | 5-CH$_3$ | F | F |
| A-3010. | OCH$_3$ | OCF$_3$ | 5-OCH$_3$ | F | F |
| A-3011. | CH$_2$F | F | 3-F | F | F |
| A-3012. | CH$_2$F | F | 3-CH$_3$ | F | F |
| A-3013. | CH$_2$F | F | 3-OCH$_3$ | F | F |
| A-3014. | CH$_2$F | F | 5-F | F | F |
| A-3015. | CH$_2$F | F | 5-CH$_3$ | F | F |
| A-3016. | CH$_2$F | F | 5-OCH$_3$ | F | F |
| A-3017. | CH$_2$F | CH$_3$ | 3-F | F | F |
| A-3018. | CH$_2$F | CH$_3$ | 3-CH$_3$ | F | F |
| A-3019. | CH$_2$F | CH$_3$ | 3-OCH$_3$ | F | F |
| A-3020. | CH$_2$F | CH$_3$ | 5-F | F | F |
| A-3021. | CH$_2$F | CH$_3$ | 5-CH$_3$ | F | F |
| A-3022. | CH$_2$F | CH$_3$ | 5-OCH$_3$ | F | F |
| A-3023. | CH$_2$F | OCH$_3$ | 3-F | F | F |
| A-3024. | CH$_2$F | OCH$_3$ | 3-CH$_3$ | F | F |
| A-3025. | CH$_2$F | OCH$_3$ | 3-OCH$_3$ | F | F |
| A-3026. | CH$_2$F | OCH$_3$ | 5-F | F | F |
| A-3027. | CH$_2$F | OCH$_3$ | 5-CH$_3$ | F | F |
| A-3028. | CH$_2$F | OCH$_3$ | 5-OCH$_3$ | F | F |
| A-3029. | CH$_2$F | CN | 3-F | F | F |
| A-3030. | CH$_2$F | CN | 3-CH$_3$ | F | F |
| A-3031. | CH$_2$F | CN | 3-OCH$_3$ | F | F |
| A-3032. | CH$_2$F | CN | 5-F | F | F |
| A-3033. | CH$_2$F | CN | 5-CH$_3$ | F | F |
| A-3034. | CH$_2$F | CN | 5-OCH$_3$ | F | F |
| A-3035. | CH$_2$F | CH$_2$F | 3-F | F | F |
| A-3036. | CH$_2$F | CH$_2$F | 3-CH$_3$ | F | F |
| A-3037. | CH$_2$F | CH$_2$F | 3-OCH$_3$ | F | F |
| A-3038. | CH$_2$F | CH$_2$F | 5-F | F | F |
| A-3039. | CH$_2$F | CH$_2$F | 5-CH$_3$ | F | F |
| A-3040. | CH$_2$F | CH$_2$F | 5-OCH$_3$ | F | F |
| A-3041. | CH$_2$F | CHF$_2$ | 3-F | F | F |
| A-3042. | CH$_2$F | CHF$_2$ | 3-CH$_3$ | F | F |
| A-3043. | CH$_2$F | CHF$_2$ | 3-OCH$_3$ | F | F |
| A-3044. | CH$_2$F | CHF$_2$ | 5-F | F | F |
| A-3045. | CH$_2$F | CHF$_2$ | 5-CH$_3$ | F | F |
| A-3046. | CH$_2$F | CHF$_2$ | 5-OCH$_3$ | F | F |
| A-3047. | CH$_2$F | CF$_3$ | 3-F | F | F |
| A-3048. | CH$_2$F | CF$_3$ | 3-CH$_3$ | F | F |
| A-3049. | CH$_2$F | CF$_3$ | 3-OCH$_3$ | F | F |
| A-3050. | CH$_2$F | CF$_3$ | 5-F | F | F |
| A-3051. | CH$_2$F | CF$_3$ | 5-CH$_3$ | F | F |
| A-3052. | CH$_2$F | CF$_3$ | 5-OCH$_3$ | F | F |
| A-3053. | CH$_2$F | OCH$_2$F | 3-F | F | F |
| A-3054. | CH$_2$F | OCH$_2$F | 3-CH$_3$ | F | F |
| A-3055. | CH$_2$F | OCH$_2$F | 3-OCH$_3$ | F | F |
| A-3056. | CH$_2$F | OCH$_2$F | 5-F | F | F |
| A-3057. | CH$_2$F | OCH$_2$F | 5-CH$_3$ | F | F |
| A-3058. | CH$_2$F | OCH$_2$F | 5-OCH$_3$ | F | F |
| A-3059. | CH$_2$F | OCHF$_2$ | 3-F | F | F |
| A-3060. | CH$_2$F | OCHF$_2$ | 3-CH$_3$ | F | F |
| A-3061. | CH$_2$F | OCHF$_2$ | 3-OCH$_3$ | F | F |
| A-3062. | CH$_2$F | OCHF$_2$ | 5-F | F | F |
| A-3063. | CH$_2$F | OCHF$_2$ | 5-CH$_3$ | F | F |
| A-3064. | CH$_2$F | OCHF$_2$ | 5-OCH$_3$ | F | F |
| A-3065. | CH$_2$F | OCF$_3$ | 3-F | F | F |
| A-3066. | CH$_2$F | OCF$_3$ | 3-CH$_3$ | F | F |
| A-3067. | CH$_2$F | OCF$_3$ | 3-OCH$_3$ | F | F |
| A-3068. | CH$_2$F | OCF$_3$ | 5-F | F | F |
| A-3069. | CH$_2$F | OCF$_3$ | 5-CH$_3$ | F | F |
| A-3070. | CH$_2$F | OCF$_3$ | 5-OCH$_3$ | F | F |
| A-3071. | CHF$_2$ | F | 3-F | F | F |
| A-3072. | CHF$_2$ | F | 3-CH$_3$ | F | F |
| A-3073. | CHF$_2$ | F | 3-OCH$_3$ | F | F |
| A-3074. | CHF$_2$ | F | 5-F | F | F |
| A-3075. | CHF$_2$ | F | 5-CH$_3$ | F | F |
| A-3076. | CHF$_2$ | F | 5-OCH$_3$ | F | F |
| A-3077. | CHF$_2$ | CH$_3$ | 3-F | F | F |
| A-3078. | CHF$_2$ | CH$_3$ | 3-CH$_3$ | F | F |
| A-3079. | CHF$_2$ | CH$_3$ | 3-OCH$_3$ | F | F |
| A-3080. | CHF$_2$ | CH$_3$ | 5-F | F | F |
| A-3081. | CHF$_2$ | CH$_3$ | 5-CH$_3$ | F | F |
| A-3082. | CHF$_2$ | CH$_3$ | 5-OCH$_3$ | F | F |
| A-3083. | CHF$_2$ | OCH$_3$ | 3-F | F | F |
| A-3084. | CHF$_2$ | OCH$_3$ | 3-CH$_3$ | F | F |
| A-3085. | CHF$_2$ | OCH$_3$ | 3-OCH$_3$ | F | F |
| A-3086. | CHF$_2$ | OCH$_3$ | 5-F | F | F |
| A-3087. | CHF$_2$ | OCH$_3$ | 5-CH$_3$ | F | F |
| A-3088. | CHF$_2$ | OCH$_3$ | 5-OCH$_3$ | F | F |
| A-3089. | CHF$_2$ | CN | 3-F | F | F |
| A-3090. | CHF$_2$ | CN | 3-CH$_3$ | F | F |
| A-3091. | CHF$_2$ | CN | 3-OCH$_3$ | F | F |
| A-3092. | CHF$_2$ | CN | 5-F | F | F |
| A-3093. | CHF$_2$ | CN | 5-CH$_3$ | F | F |
| A-3094. | CHF$_2$ | CN | 5-OCH$_3$ | F | F |
| A-3095. | CHF$_2$ | CH$_2$F | 3-F | F | F |
| A-3096. | CHF$_2$ | CH$_2$F | 3-CH$_3$ | F | F |
| A-3097. | CHF$_2$ | CH$_2$F | 3-OCH$_3$ | F | F |
| A-3098. | CHF$_2$ | CH$_2$F | 5-F | F | F |
| A-3099. | CHF$_2$ | CH$_2$F | 5-CH$_3$ | F | F |
| A-3100. | CHF$_2$ | CH$_2$F | 5-OCH$_3$ | F | F |
| A-3101. | CHF$_2$ | CHF$_2$ | 3-F | F | F |
| A-3102. | CHF$_2$ | CHF$_2$ | 3-CH$_3$ | F | F |
| A-3103. | CHF$_2$ | CHF$_2$ | 3-OCH$_3$ | F | F |
| A-3104. | CHF$_2$ | CHF$_2$ | 5-F | F | F |
| A-3105. | CHF$_2$ | CHF$_2$ | 5-CH$_3$ | F | F |
| A-3106. | CHF$_2$ | CHF$_2$ | 5-OCH$_3$ | F | F |
| A-3107. | CHF$_2$ | CF$_3$ | 3-F | F | F |
| A-3108. | CHF$_2$ | CF$_3$ | 3-CH$_3$ | F | F |
| A-3109. | CHF$_2$ | CF$_3$ | 3-OCH$_3$ | F | F |
| A-3110. | CHF$_2$ | CF$_3$ | 5-F | F | F |
| A-3111. | CHF$_2$ | CF$_3$ | 5-CH$_3$ | F | F |
| A-3112. | CHF$_2$ | CF$_3$ | 5-OCH$_3$ | F | F |
| A-3113. | CHF$_2$ | OCH$_2$F | 3-F | F | F |
| A-3114. | CHF$_2$ | OCH$_2$F | 3-CH$_3$ | F | F |
| A-3115. | CHF$_2$ | OCH$_2$F | 3-OCH$_3$ | F | F |
| A-3116. | CHF$_2$ | OCH$_2$F | 5-F | F | F |
| A-3117. | CHF$_2$ | OCH$_2$F | 5-CH$_3$ | F | F |
| A-3118. | CHF$_2$ | OCH$_2$F | 5-OCH$_3$ | F | F |
| A-3119. | CHF$_2$ | OCHF$_2$ | 3-F | F | F |
| A-3120. | CHF$_2$ | OCHF$_2$ | 3-CH$_3$ | F | F |
| A-3121. | CHF$_2$ | OCHF$_2$ | 3-OCH$_3$ | F | F |
| A-3122. | CHF$_2$ | OCHF$_2$ | 5-F | F | F |
| A-3123. | CHF$_2$ | OCHF$_2$ | 5-CH$_3$ | F | F |
| A-3124. | CHF$_2$ | OCHF$_2$ | 5-OCH$_3$ | F | F |
| A-3125. | CHF$_2$ | OCF$_3$ | 3-F | F | F |
| A-3126. | CHF$_2$ | OCF$_3$ | 3-CH$_3$ | F | F |
| A-3127. | CHF$_2$ | OCF$_3$ | 3-OCH$_3$ | F | F |
| A-3128. | CHF$_2$ | OCF$_3$ | 5-F | F | F |
| A-3129. | CHF$_2$ | OCF$_3$ | 5-CH$_3$ | F | F |

TABLE A-continued

| Example No. | R⁸ᵃ | R⁸ᵇ | R⁸ᶜ | R¹ | R² |
|---|---|---|---|---|---|
| A-3130. | CHF₂ | OCF₃ | 5-OCH₃ | F | F |
| A-3131. | CF₃ | F | 3-F | F | F |
| A-3132. | CF₃ | F | 3-CH₃ | F | F |
| A-3133. | CF₃ | F | 3-OCH₃ | F | F |
| A-3134. | CF₃ | F | 5-F | F | F |
| A-3135. | CF₃ | F | 5-CH₃ | F | F |
| A-3136. | CF₃ | F | 5-OCH₃ | F | F |
| A-3137. | CF₃ | CH₃ | 3-F | F | F |
| A-3138. | CF₃ | CH₃ | 3-CH₃ | F | F |
| A-3139. | CF₃ | CH₃ | 3-OCH₃ | F | F |
| A-3140. | CF₃ | CH₃ | 5-F | F | F |
| A-3141. | CF₃ | CH₃ | 5-CH₃ | F | F |
| A-3142. | CF₃ | CH₃ | 5-OCH₃ | F | F |
| A-3143. | CF₃ | OCH₃ | 3-F | F | F |
| A-3144. | CF₃ | OCH₃ | 3-CH₃ | F | F |
| A-3145. | CF₃ | OCH₃ | 3-OCH₃ | F | F |
| A-3146. | CF₃ | OCH₃ | 5-F | F | F |
| A-3147. | CF₃ | OCH₃ | 5-CH₃ | F | F |
| A-3148. | CF₃ | OCH₃ | 5-OCH₃ | F | F |
| A-3149. | CF₃ | CN | 3-F | F | F |
| A-3150. | CF₃ | CN | 3-CH₃ | F | F |
| A-3151. | CF₃ | CN | 3-OCH₃ | F | F |
| A-3152. | CF₃ | CN | 5-F | F | F |
| A-3153. | CF₃ | CN | 5-CH₃ | F | F |
| A-3154. | CF₃ | CN | 5-OCH₃ | F | F |
| A-3155. | CF₃ | CH₂F | 3-F | F | F |
| A-3156. | CF₃ | CH₂F | 3-CH₃ | F | F |
| A-3157. | CF₃ | CH₂F | 3-OCH₃ | F | F |
| A-3158. | CF₃ | CH₂F | 5-F | F | F |
| A-3159. | CF₃ | CH₂F | 5-CH₃ | F | F |
| A-3160. | CF₃ | CH₂F | 5-OCH₃ | F | F |
| A-3161. | CF₃ | CHF₂ | 3-F | F | F |
| A-3162. | CF₃ | CHF₂ | 3-CH₃ | F | F |
| A-3163. | CF₃ | CHF₂ | 3-OCH₃ | F | F |
| A-3164. | CF₃ | CHF₂ | 5-F | F | F |
| A-3165. | CF₃ | CHF₂ | 5-CH₃ | F | F |
| A-3166. | CF₃ | CHF₂ | 5-OCH₃ | F | F |
| A-3167. | CF₃ | CF₃ | 3-F | F | F |
| A-3168. | CF₃ | CF₃ | 3-CH₃ | F | F |
| A-3169. | CF₃ | CF₃ | 3-OCH₃ | F | F |
| A-3170. | CF₃ | CF₃ | 5-F | F | F |
| A-3171. | CF₃ | CF₃ | 5-CH₃ | F | F |
| A-3172. | CF₃ | CF₃ | 5-OCH₃ | F | F |
| A-3173. | CF₃ | OCH₂F | 3-F | F | F |
| A-3174. | CF₃ | OCH₂F | 3-CH₃ | F | F |
| A-3175. | CF₃ | OCH₂F | 3-OCH₃ | F | F |
| A-3176. | CF₃ | OCH₂F | 5-F | F | F |
| A-3177. | CF₃ | OCH₂F | 5-CH₃ | F | F |
| A-3178. | CF₃ | OCH₂F | 5-OCH₃ | F | F |
| A-3179. | CF₃ | OCHF₂ | 3-F | F | F |
| A-3180. | CF₃ | OCHF₂ | 3-CH₃ | F | F |
| A-3181. | CF₃ | OCHF₂ | 3-OCH₃ | F | F |
| A-3182. | CF₃ | OCHF₂ | 5-F | F | F |
| A-3183. | CF₃ | OCHF₂ | 5-CH₃ | F | F |
| A-3184. | CF₃ | OCHF₂ | 5-OCH₃ | F | F |
| A-3185. | CF₃ | OCF₃ | 3-F | F | F |
| A-3186. | CF₃ | OCF₃ | 3-CH₃ | F | F |
| A-3187. | CF₃ | OCF₃ | 3-OCH₃ | F | F |
| A-3188. | CF₃ | OCF₃ | 5-F | F | F |
| A-3189. | CF₃ | OCF₃ | 5-CH₃ | F | F |
| A-3190. | CF₃ | OCF₃ | 5-OCH₃ | F | F |
| A-3191. | OCH₂F | F | 3-F | F | F |
| A-3192. | OCH₂F | F | 3-CH₃ | F | F |
| A-3193. | OCH₂F | F | 3-OCH₃ | F | F |
| A-3194. | OCH₂F | F | 5-F | F | F |
| A-3195. | OCH₂F | F | 5-CH₃ | F | F |
| A-3196. | OCH₂F | F | 5-OCH₃ | F | F |
| A-3197. | OCH₂F | CH₃ | 3-F | F | F |
| A-3198. | OCH₂F | CH₃ | 3-CH₃ | F | F |
| A-3199. | OCH₂F | CH₃ | 3-OCH₃ | F | F |
| A-3200. | OCH₂F | CH₃ | 5-F | F | F |
| A-3201. | OCH₂F | CH₃ | 5-CH₃ | F | F |
| A-3202. | OCH₂F | CH₃ | 5-OCH₃ | F | F |
| A-3203. | OCH₂F | OCH₃ | 3-F | F | F |
| A-3204. | OCH₂F | OCH₃ | 3-CH₃ | F | F |
| A-3205. | OCH₂F | OCH₃ | 3-OCH₃ | F | F |
| A-3206. | OCH₂F | OCH₃ | 5-F | F | F |
| A-3207. | OCH₂F | OCH₃ | 5-CH₃ | F | F |
| A-3208. | OCH₂F | OCH₃ | 5-OCH₃ | F | F |
| A-3209. | OCH₂F | CN | 3-F | F | F |
| A-3210. | OCH₂F | CN | 3-CH₃ | F | F |
| A-3211. | OCH₂F | CN | 3-OCH₃ | F | F |
| A-3212. | OCH₂F | CN | 5-F | F | F |
| A-3213. | OCH₂F | CN | 5-CH₃ | F | F |
| A-3214. | OCH₂F | CN | 5-OCH₃ | F | F |
| A-3215. | OCH₂F | CH₂F | 3-F | F | F |
| A-3216. | OCH₂F | CH₂F | 3-CH₃ | F | F |
| A-3217. | OCH₂F | CH₂F | 3-OCH₃ | F | F |
| A-3218. | OCH₂F | CH₂F | 5-F | F | F |
| A-3219. | OCH₂F | CH₂F | 5-CH₃ | F | F |
| A-3220. | OCH₂F | CH₂F | 5-OCH₃ | F | F |
| A-3221. | OCH₂F | CHF₂ | 3-F | F | F |
| A-3222. | OCH₂F | CHF₂ | 3-CH₃ | F | F |
| A-3223. | OCH₂F | CHF₂ | 3-OCH₃ | F | F |
| A-3224. | OCH₂F | CHF₂ | 5-F | F | F |
| A-3225. | OCH₂F | CHF₂ | 5-CH₃ | F | F |
| A-3226. | OCH₂F | CHF₂ | 5-OCH₃ | F | F |
| A-3227. | OCH₂F | CF₃ | 3-F | F | F |
| A-3228. | OCH₂F | CF₃ | 3-CH₃ | F | F |
| A-3229. | OCH₂F | CF₃ | 3-OCH₃ | F | F |
| A-3230. | OCH₂F | CF₃ | 5-F | F | F |
| A-3231. | OCH₂F | CF₃ | 5-CH₃ | F | F |
| A-3232. | OCH₂F | CF₃ | 5-OCH₃ | F | F |
| A-3233. | OCH₂F | OCH₂F | 3-F | F | F |
| A-3234. | OCH₂F | OCH₂F | 3-CH₃ | F | F |
| A-3235. | OCH₂F | OCH₂F | 3-OCH₃ | F | F |
| A-3236. | OCH₂F | OCH₂F | 5-F | F | F |
| A-3237. | OCH₂F | OCH₂F | 5-CH₃ | F | F |
| A-3238. | OCH₂F | OCH₂F | 5-OCH₃ | F | F |
| A-3239. | OCH₂F | OCHF₂ | 3-F | F | F |
| A-3240. | OCH₂F | OCHF₂ | 3-CH₃ | F | F |
| A-3241. | OCH₂F | OCHF₂ | 3-OCH₃ | F | F |
| A-3242. | OCH₂F | OCHF₂ | 5-F | F | F |
| A-3243. | OCH₂F | OCHF₂ | 5-CH₃ | F | F |
| A-3244. | OCH₂F | OCHF₂ | 5-OCH₃ | F | F |
| A-3245. | OCH₂F | OCF₃ | 3-F | F | F |
| A-3246. | OCH₂F | OCF₃ | 3-CH₃ | F | F |
| A-3247. | OCH₂F | OCF₃ | 3-OCH₃ | F | F |
| A-3248. | OCH₂F | OCF₃ | 5-F | F | F |
| A-3249. | OCH₂F | OCF₃ | 5-CH₃ | F | F |
| A-3250. | OCH₂F | OCF₃ | 5-OCH₃ | F | F |
| A-3251. | OCHF₂ | F | 3-F | F | F |
| A-3252. | OCHF₂ | F | 3-CH₃ | F | F |
| A-3253. | OCHF₂ | F | 3-OCH₃ | F | F |
| A-3254. | OCHF₂ | F | 5-F | F | F |
| A-3255. | OCHF₂ | F | 5-CH₃ | F | F |
| A-3256. | OCHF₂ | F | 5-OCH₃ | F | F |
| A-3257. | OCHF₂ | CH₃ | 3-F | F | F |
| A-3258. | OCHF₂ | CH₃ | 3-CH₃ | F | F |
| A-3259. | OCHF₂ | CH₃ | 3-OCH₃ | F | F |
| A-3260. | OCHF₂ | CH₃ | 5-F | F | F |
| A-3261. | OCHF₂ | CH₃ | 5-CH₃ | F | F |
| A-3262. | OCHF₂ | CH₃ | 5-OCH₃ | F | F |
| A-3263. | OCHF₂ | OCH₃ | 3-F | F | F |
| A-3264. | OCHF₂ | OCH₃ | 3-CH₃ | F | F |
| A-3265. | OCHF₂ | OCH₃ | 3-OCH₃ | F | F |
| A-3266. | OCHF₂ | OCH₃ | 5-F | F | F |
| A-3267. | OCHF₂ | OCH₃ | 5-CH₃ | F | F |
| A-3268. | OCHF₂ | OCH₃ | 5-OCH₃ | F | F |
| A-3269. | OCHF₂ | CN | 3-F | F | F |
| A-3270. | OCHF₂ | CN | 3-CH₃ | F | F |
| A-3271. | OCHF₂ | CN | 3-OCH₃ | F | F |
| A-3272. | OCHF₂ | CN | 5-F | F | F |
| A-3273. | OCHF₂ | CN | 5-CH₃ | F | F |
| A-3274. | OCHF₂ | CN | 5-OCH₃ | F | F |
| A-3275. | OCHF₂ | CH₂F | 3-F | F | F |
| A-3276. | OCHF₂ | CH₂F | 3-CH₃ | F | F |
| A-3277. | OCHF₂ | CH₂F | 3-OCH₃ | F | F |
| A-3278. | OCHF₂ | CH₂F | 5-F | F | F |
| A-3279. | OCHF₂ | CH₂F | 5-CH₃ | F | F |
| A-3280. | OCHF₂ | CH₂F | 5-OCH₃ | F | F |
| A-3281. | OCHF₂ | CHF₂ | 3-F | F | F |
| A-3282. | OCHF₂ | CHF₂ | 3-CH₃ | F | F |
| A-3283. | OCHF₂ | CHF₂ | 3-OCH₃ | F | F |
| A-3284. | OCHF₂ | CHF₂ | 5-F | F | F |
| A-3285. | OCHF₂ | CHF₂ | 5-CH₃ | F | F |

TABLE A-continued

| Example No. | $R^{8a}$ | $R^{8b}$ | $R^{8c}$ | $R^1$ | $R^2$ |
|---|---|---|---|---|---|
| A-3286. | OCHF$_2$ | CHF$_2$ | 5-OCH$_3$ | F | F |
| A-3287. | OCHF$_2$ | CF$_3$ | 3-F | F | F |
| A-3288. | OCHF$_2$ | CF$_3$ | 3-CH$_3$ | F | F |
| A-3289. | OCHF$_2$ | CF$_3$ | 3-OCH$_3$ | F | F |
| A-3290. | OCHF$_2$ | CF$_3$ | 5-F | F | F |
| A-3291. | OCHF$_2$ | CF$_3$ | 5-CH$_3$ | F | F |
| A-3292. | OCHF$_2$ | CF$_3$ | 5-OCH$_3$ | F | F |
| A-3293. | OCHF$_2$ | OCH$_2$F | 3-F | F | F |
| A-3294. | OCHF$_2$ | OCH$_2$F | 3-CH$_3$ | F | F |
| A-3295. | OCHF$_2$ | OCH$_2$F | 3-OCH$_3$ | F | F |
| A-3296. | OCHF$_2$ | OCH$_2$F | 5-F | F | F |
| A-3297. | OCHF$_2$ | OCH$_2$F | 5-CH$_3$ | F | F |
| A-3298. | OCHF$_2$ | OCH$_2$F | 5-OCH$_3$ | F | F |
| A-3299. | OCHF$_2$ | OCHF$_2$ | 3-F | F | F |
| A-3300. | OCHF$_2$ | OCHF$_2$ | 3-CH$_3$ | F | F |
| A-3301. | OCHF$_2$ | OCHF$_2$ | 3-OCH$_3$ | F | F |
| A-3302. | OCHF$_2$ | OCHF$_2$ | 5-F | F | F |
| A-3303. | OCHF$_2$ | OCHF$_2$ | 5-CH$_3$ | F | F |
| A-3304. | OCHF$_2$ | OCHF$_2$ | 5-OCH$_3$ | F | F |
| A-3305. | OCHF$_2$ | OCF$_3$ | 3-F | F | F |
| A-3306. | OCHF$_2$ | OCF$_3$ | 3-CH$_3$ | F | F |
| A-3307. | OCHF$_2$ | OCF$_3$ | 3-OCH$_3$ | F | F |
| A-3308. | OCHF$_2$ | OCF$_3$ | 5-F | F | F |
| A-3309. | OCHF$_2$ | OCF$_3$ | 5-CH$_3$ | F | F |
| A-3310. | OCHF$_2$ | OCF$_3$ | 5-OCH$_3$ | F | F |
| A-3311. | OCF$_3$ | F | 3-F | F | F |
| A-3312. | OCF$_3$ | F | 3-CH$_3$ | F | F |
| A-3313. | OCF$_3$ | F | 3-OCH$_3$ | F | F |
| A-3314. | OCF$_3$ | F | 5-F | F | F |
| A-3315. | OCF$_3$ | F | 5-CH$_3$ | F | F |
| A-3316. | OCF$_3$ | F | 5-OCH$_3$ | F | F |
| A-3317. | OCF$_3$ | CH$_3$ | 3-F | F | F |
| A-3318. | OCF$_3$ | CH$_3$ | 3-CH$_3$ | F | F |
| A-3319. | OCF$_3$ | CH$_3$ | 3-OCH$_3$ | F | F |
| A-3320. | OCF$_3$ | CH$_3$ | 5-F | F | F |
| A-3321. | OCF$_3$ | CH$_3$ | 5-CH$_3$ | F | F |
| A-3322. | OCF$_3$ | CH$_3$ | 5-OCH$_3$ | F | F |
| A-3323. | OCF$_3$ | OCH$_3$ | 3-F | F | F |
| A-3324. | OCF$_3$ | OCH$_3$ | 3-CH$_3$ | F | F |
| A-3325. | OCF$_3$ | OCH$_3$ | 3-OCH$_3$ | F | F |
| A-3326. | OCF$_3$ | OCH$_3$ | 5-F | F | F |
| A-3327. | OCF$_3$ | OCH$_3$ | 5-CH$_3$ | F | F |
| A-3328. | OCF$_3$ | OCH$_3$ | 5-OCH$_3$ | F | F |
| A-3329. | OCF$_3$ | CN | 3-F | F | F |
| A-3330. | OCF$_3$ | CN | 3-CH$_3$ | F | F |
| A-3331. | OCF$_3$ | CN | 3-OCH$_3$ | F | F |
| A-3332. | OCF$_3$ | CN | 5-F | F | F |
| A-3333. | OCF$_3$ | CN | 5-CH$_3$ | F | F |
| A-3334. | OCF$_3$ | CN | 5-OCH$_3$ | F | F |
| A-3335. | OCF$_3$ | CH$_2$F | 3-F | F | F |
| A-3336. | OCF$_3$ | CH$_2$F | 3-CH$_3$ | F | F |
| A-3337. | OCF$_3$ | CH$_2$F | 3-OCH$_3$ | F | F |
| A-3338. | OCF$_3$ | CH$_2$F | 5-F | F | F |
| A-3339. | OCF$_3$ | CH$_2$F | 5-CH$_3$ | F | F |
| A-3340. | OCF$_3$ | CH$_2$F | 5-OCH$_3$ | F | F |
| A-3341. | OCF$_3$ | CHF$_2$ | 3-F | F | F |
| A-3342. | OCF$_3$ | CHF$_2$ | 3-CH$_3$ | F | F |
| A-3343. | OCF$_3$ | CHF$_2$ | 3-OCH$_3$ | F | F |
| A-3344. | OCF$_3$ | CHF$_2$ | 5-F | F | F |
| A-3345. | OCF$_3$ | CHF$_2$ | 5-CH$_3$ | F | F |
| A-3346. | OCF$_3$ | CHF$_2$ | 5-OCH$_3$ | F | F |
| A-3347. | OCF$_3$ | CF$_3$ | 3-F | F | F |
| A-3348. | OCF$_3$ | CF$_3$ | 3-CH$_3$ | F | F |
| A-3349. | OCF$_3$ | CF$_3$ | 3-OCH$_3$ | F | F |
| A-3350. | OCF$_3$ | CF$_3$ | 5-F | F | F |
| A-3351. | OCF$_3$ | CF$_3$ | 5-CH$_3$ | F | F |
| A-3352. | OCF$_3$ | CF$_3$ | 5-OCH$_3$ | F | F |
| A-3353. | OCF$_3$ | OCH$_2$F | 3-F | F | F |
| A-3354. | OCF$_3$ | OCH$_2$F | 3-CH$_3$ | F | F |
| A-3355. | OCF$_3$ | OCH$_2$F | 3-OCH$_3$ | F | F |
| A-3356. | OCF$_3$ | OCH$_2$F | 5-F | F | F |
| A-3357. | OCF$_3$ | OCH$_2$F | 5-CH$_3$ | F | F |
| A-3358. | OCF$_3$ | OCH$_2$F | 5-OCH$_3$ | F | F |
| A-3359. | OCF$_3$ | OCHF$_2$ | 3-F | F | F |
| A-3360. | OCF$_3$ | OCHF$_2$ | 3-CH$_3$ | F | F |
| A-3361. | OCF$_3$ | OCHF$_2$ | 3-OCH$_3$ | F | F |
| A-3362. | OCF$_3$ | OCHF$_2$ | 5-F | F | F |
| A-3363. | OCF$_3$ | OCHF$_2$ | 5-CH$_3$ | F | F |
| A-3364. | OCF$_3$ | OCHF$_2$ | 5-OCH$_3$ | F | F |
| A-3365. | OCF$_3$ | OCF$_3$ | 3-F | F | F |
| A-3366. | OCF$_3$ | OCF$_3$ | 3-CH$_3$ | F | F |
| A-3367. | OCF$_3$ | OCF$_3$ | 3-OCH$_3$ | F | F |
| A-3368. | OCF$_3$ | OCF$_3$ | 5-F | F | F |
| A-3369. | OCF$_3$ | OCF$_3$ | 5-CH$_3$ | F | F |
| A-3370. | OCF$_3$ | OCF$_3$ | 5-OCH$_3$ | F | F |
| A-3371. | H | H | H | Cl | F |
| A-3372. | F | H | H | Cl | F |
| A-3373. | CH$_3$ | H | H | Cl | F |
| A-3374. | OCH$_3$ | H | H | Cl | F |
| A-3375. | CH$_2$F | H | H | Cl | F |
| A-3376. | CHF$_2$ | H | H | Cl | F |
| A-3377. | CF$_3$ | H | H | Cl | F |
| A-3378. | OCH$_2$F | H | H | Cl | F |
| A-3379. | OCHF$_2$ | H | H | Cl | F |
| A-3380. | OCF$_3$ | H | H | Cl | F |
| A-3381. | H | F | H | Cl | F |
| A-3382. | H | CH$_3$ | H | Cl | F |
| A-3383. | H | OCH$_3$ | H | Cl | F |
| A-3384. | H | CN | H | Cl | F |
| A-3385. | H | CH$_2$F | H | Cl | F |
| A-3386. | H | CHF$_2$ | H | Cl | F |
| A-3387. | H | CF$_3$ | H | Cl | F |
| A-3388. | H | OCH$_2$F | H | Cl | F |
| A-3389. | H | OCHF$_2$ | H | Cl | F |
| A-3390. | H | OCF$_3$ | H | Cl | F |
| A-3391. | H | H | 3-F | Cl | F |
| A-3392. | H | H | 3-CH$_3$ | Cl | F |
| A-3393. | H | H | 3-OCH$_3$ | Cl | F |
| A-3394. | H | H | 5-F | Cl | F |
| A-3395. | H | H | 5-CH$_3$ | Cl | F |
| A-3396. | H | H | 5-OCH$_3$ | Cl | F |
| A-3397. | F | F | H | Cl | F |
| A-3398. | F | CH$_3$ | H | Cl | F |
| A-3399. | F | OCH$_3$ | H | Cl | F |
| A-3400. | F | CN | H | Cl | F |
| A-3401. | F | CH$_2$F | H | Cl | F |
| A-3402. | F | CHF$_2$ | H | Cl | F |
| A-3403. | F | CF$_3$ | H | Cl | F |
| A-3404. | F | OCH$_2$F | H | Cl | F |
| A-3405. | F | OCHF$_2$ | H | Cl | F |
| A-3406. | F | OCF$_3$ | H | Cl | F |
| A-3407. | F | H | 3-F | Cl | F |
| A-3408. | F | H | 3-CH$_3$ | Cl | F |
| A-3409. | F | H | 3-OCH$_3$ | Cl | F |
| A-3410. | F | H | 5-F | Cl | F |
| A-3411. | F | H | 5-CH$_3$ | Cl | F |
| A-3412. | F | H | 5-OCH$_3$ | Cl | F |
| A-3413. | CH$_3$ | F | H | Cl | F |
| A-3414. | CH$_3$ | CH$_3$ | H | Cl | F |
| A-3415. | CH$_3$ | OCH$_3$ | H | Cl | F |
| A-3416. | CH$_3$ | CN | H | Cl | F |
| A-3417. | CH$_3$ | CH$_2$F | H | Cl | F |
| A-3418. | CH$_3$ | CHF$_2$ | H | Cl | F |
| A-3419. | CH$_3$ | CF$_3$ | H | Cl | F |
| A-3420. | CH$_3$ | OCH$_2$F | H | Cl | F |
| A-3421. | CH$_3$ | OCHF$_2$ | H | Cl | F |
| A-3422. | CH$_3$ | OCF$_3$ | H | Cl | F |
| A-3423. | CH$_3$ | H | 3-F | Cl | F |
| A-3424. | CH$_3$ | H | 3-CH$_3$ | Cl | F |
| A-3425. | CH$_3$ | H | 3-OCH$_3$ | Cl | F |
| A-3426. | CH$_3$ | H | 5-F | Cl | F |
| A-3427. | CH$_3$ | H | 5-CH$_3$ | Cl | F |
| A-3428. | CH$_3$ | H | 5-OCH$_3$ | Cl | F |
| A-3429. | OCH$_3$ | F | H | Cl | F |
| A-3430. | OCH$_3$ | CH$_3$ | H | Cl | F |
| A-3431. | OCH$_3$ | OCH$_3$ | H | Cl | F |
| A-3432. | OCH$_3$ | CN | H | Cl | F |
| A-3433. | OCH$_3$ | CH$_2$F | H | Cl | F |
| A-3434. | OCH$_3$ | CHF$_2$ | H | Cl | F |
| A-3435. | OCH$_3$ | CF$_3$ | H | Cl | F |
| A-3436. | OCH$_3$ | OCH$_2$F | H | Cl | F |
| A-3437. | OCH$_3$ | OCHF$_2$ | H | Cl | F |
| A-3438. | OCH$_3$ | OCF$_3$ | H | Cl | F |
| A-3439. | OCH$_3$ | H | 3-F | Cl | F |
| A-3440. | OCH$_3$ | H | 3-CH$_3$ | Cl | F |
| A-3441. | OCH$_3$ | H | 3-OCH$_3$ | Cl | F |

TABLE A-continued

| Example No. | $R^{8a}$ | $R^{8b}$ | $R^{8c}$ | $R^1$ | $R^2$ |
|---|---|---|---|---|---|
| A-3442. | OCH₃ | H | 5-F | Cl | F |
| A-3443. | OCH₃ | H | 5-CH₃ | Cl | F |
| A-3444. | OCH₃ | H | 5-OCH₃ | Cl | F |
| A-3445. | H | F | 3-F | Cl | F |
| A-3446. | H | F | 3-CH₃ | Cl | F |
| A-3447. | H | F | 3-OCH₃ | Cl | F |
| A-3448. | H | F | 5-F | Cl | F |
| A-3449. | H | F | 5-CH₃ | Cl | F |
| A-3450. | H | F | 5-OCH₃ | Cl | F |
| A-3451. | H | CH₃ | 3-F | Cl | F |
| A-3452. | H | CH₃ | 3-CH₃ | Cl | F |
| A-3453. | H | CH₃ | 3-OCH₃ | Cl | F |
| A-3454. | H | CH₃ | 5-F | Cl | F |
| A-3455. | H | CH₃ | 5-CH₃ | Cl | F |
| A-3456. | H | CH₃ | 5-OCH₃ | Cl | F |
| A-3457. | H | OCH₃ | 3-F | Cl | F |
| A-3458. | H | OCH₃ | 3-CH₃ | Cl | F |
| A-3459. | H | OCH₃ | 3-OCH₃ | Cl | F |
| A-3460. | H | OCH₃ | 5-F | Cl | F |
| A-3461. | H | OCH₃ | 5-CH₃ | Cl | F |
| A-3462. | H | OCH₃ | 5-OCH₃ | Cl | F |
| A-3463. | H | CN | 3-F | Cl | F |
| A-3464. | H | CN | 3-CH₃ | Cl | F |
| A-3465. | H | CN | 3-OCH₃ | Cl | F |
| A-3466. | H | CN | 5-F | Cl | F |
| A-3467. | H | CN | 5-CH₃ | Cl | F |
| A-3468. | H | CN | 5-OCH₃ | Cl | F |
| A-3469. | H | CH₂F | 3-F | Cl | F |
| A-3470. | H | CH₂F | 3-CH₃ | Cl | F |
| A-3471. | H | CH₂F | 3-OCH₃ | Cl | F |
| A-3472. | H | CH₂F | 5-F | Cl | F |
| A-3473. | H | CH₂F | 5-CH₃ | Cl | F |
| A-3474. | H | CH₂F | 5-OCH₃ | Cl | F |
| A-3475. | H | CHF₂ | 3-F | Cl | F |
| A-3476. | H | CHF₂ | 3-CH₃ | Cl | F |
| A-3477. | H | CHF₂ | 3-OCH₃ | Cl | F |
| A-3478. | H | CHF₂ | 5-F | Cl | F |
| A-3479. | H | CHF₂ | 5-CH₃ | Cl | F |
| A-3480. | H | CHF₂ | 5-OCH₃ | Cl | F |
| A-3481. | H | CF₃ | 3-F | Cl | F |
| A-3482. | H | CF₃ | 3-CH₃ | Cl | F |
| A-3483. | H | CF₃ | 3-OCH₃ | Cl | F |
| A-3484. | H | CF₃ | 5-F | Cl | F |
| A-3485. | H | CF₃ | 5-CH₃ | Cl | F |
| A-3486. | H | CF₃ | 5-OCH₃ | Cl | F |
| A-3487. | H | OCH₂F | 3-F | Cl | F |
| A-3488. | H | OCH₂F | 3-CH₃ | Cl | F |
| A-3489. | H | OCH₂F | 3-OCH₃ | Cl | F |
| A-3490. | H | OCH₂F | 5-F | Cl | F |
| A-3491. | H | OCH₂F | 5-CH₃ | Cl | F |
| A-3492. | H | OCH₂F | 5-OCH₃ | Cl | F |
| A-3493. | H | OCHF₂ | 3-F | Cl | F |
| A-3494. | H | OCHF₂ | 3-CH₃ | Cl | F |
| A-3495. | H | OCHF₂ | 3-OCH₃ | Cl | F |
| A-3496. | H | OCHF₂ | 5-F | Cl | F |
| A-3497. | H | OCHF₂ | 5-CH₃ | Cl | F |
| A-3498. | H | OCHF₂ | 5-OCH₃ | Cl | F |
| A-3499. | H | OCF₃ | 3-F | Cl | F |
| A-3500. | H | OCF₃ | 3-CH₃ | Cl | F |
| A-3501. | H | OCF₃ | 3-OCH₃ | Cl | F |
| A-3502. | H | OCF₃ | 5-F | Cl | F |
| A-3503. | H | OCF₃ | 5-CH₃ | Cl | F |
| A-3504. | H | OCF₃ | 5-OCH₃ | Cl | F |
| A-3505. | F | F | 3-F | Cl | F |
| A-3506. | F | F | 3-CH₃ | Cl | F |
| A-3507. | F | F | 3-OCH₃ | Cl | F |
| A-3508. | F | F | 5-F | Cl | F |
| A-3509. | F | F | 5-CH₃ | Cl | F |
| A-3510. | F | F | 5-OCH₃ | Cl | F |
| A-3511. | F | CH₃ | 3-F | Cl | F |
| A-3512. | F | CH₃ | 3-CH₃ | Cl | F |
| A-3513. | F | CH₃ | 3-OCH₃ | Cl | F |
| A-3514. | F | CH₃ | 5-F | Cl | F |
| A-3515. | F | CH₃ | 5-CH₃ | Cl | F |
| A-3516. | F | CH₃ | 5-OCH₃ | Cl | F |
| A-3517. | F | OCH₃ | 3-F | Cl | F |
| A-3518. | F | OCH₃ | 3-CH₃ | Cl | F |
| A-3519. | F | OCH₃ | 3-OCH₃ | Cl | F |
| A-3520. | F | OCH₃ | 5-F | Cl | F |
| A-3521. | F | OCH₃ | 5-CH₃ | Cl | F |
| A-3522. | F | OCH₃ | 5-OCH₃ | Cl | F |
| A-3523. | F | CN | 3-F | Cl | F |
| A-3524. | F | CN | 3-CH₃ | Cl | F |
| A-3525. | F | CN | 3-OCH₃ | Cl | F |
| A-3526. | F | CN | 5-F | Cl | F |
| A-3527. | F | CN | 5-CH₃ | Cl | F |
| A-3528. | F | CN | 5-OCH₃ | Cl | F |
| A-3529. | F | CH₂F | 3-F | Cl | F |
| A-3530. | F | CH₂F | 3-CH₃ | Cl | F |
| A-3531. | F | CH₂F | 3-OCH₃ | Cl | F |
| A-3532. | F | CH₂F | 5-F | Cl | F |
| A-3533. | F | CH₂F | 5-CH₃ | Cl | F |
| A-3534. | F | CH₂F | 5-OCH₃ | Cl | F |
| A-3535. | F | CHF₂ | 3-F | Cl | F |
| A-3536. | F | CHF₂ | 3-CH₃ | Cl | F |
| A-3537. | F | CHF₂ | 3-OCH₃ | Cl | F |
| A-3538. | F | CHF₂ | 5-F | Cl | F |
| A-3539. | F | CHF₂ | 5-CH₃ | Cl | F |
| A-3540. | F | CHF₂ | 5-OCH₃ | Cl | F |
| A-3541. | F | CF₃ | 3-F | Cl | F |
| A-3542. | F | CF₃ | 3-CH₃ | Cl | F |
| A-3543. | F | CF₃ | 3-OCH₃ | Cl | F |
| A-3544. | F | CF₃ | 5-F | Cl | F |
| A-3545. | F | CF₃ | 5-CH₃ | Cl | F |
| A-3546. | F | CF₃ | 5-OCH₃ | Cl | F |
| A-3547. | F | OCH₂F | 3-F | Cl | F |
| A-3548. | F | OCH₂F | 3-CH₃ | Cl | F |
| A-3549. | F | OCH₂F | 3-OCH₃ | Cl | F |
| A-3550. | F | OCH₂F | 5-F | Cl | F |
| A-3551. | F | OCH₂F | 5-CH₃ | Cl | F |
| A-3552. | F | OCH₂F | 5-OCH₃ | Cl | F |
| A-3553. | F | OCHF₂ | 3-F | Cl | F |
| A-3554. | F | OCHF₂ | 3-CH₃ | Cl | F |
| A-3555. | F | OCHF₂ | 3-OCH₃ | Cl | F |
| A-3556. | F | OCHF₂ | 5-F | Cl | F |
| A-3557. | F | OCHF₂ | 5-CH₃ | Cl | F |
| A-3558. | F | OCHF₂ | 5-OCH₃ | Cl | F |
| A-3559. | F | OCF₃ | 3-F | Cl | F |
| A-3560. | F | OCF₃ | 3-CH₃ | Cl | F |
| A-3561. | F | OCF₃ | 3-OCH₃ | Cl | F |
| A-3562. | F | OCF₃ | 5-F | Cl | F |
| A-3563. | F | OCF₃ | 5-CH₃ | Cl | F |
| A-3564. | F | OCF₃ | 5-OCH₃ | Cl | F |
| A-3565. | CH₃ | F | 3-F | Cl | F |
| A-3566. | CH₃ | F | 3-CH₃ | Cl | F |
| A-3567. | CH₃ | F | 3-OCH₃ | Cl | F |
| A-3568. | CH₃ | F | 5-F | Cl | F |
| A-3569. | CH₃ | F | 5-CH₃ | Cl | F |
| A-3570. | CH₃ | F | 5-OCH₃ | Cl | F |
| A-3571. | CH₃ | CH₃ | 3-F | Cl | F |
| A-3572. | CH₃ | CH₃ | 3-CH₃ | Cl | F |
| A-3573. | CH₃ | CH₃ | 3-OCH₃ | Cl | F |
| A-3574. | CH₃ | CH₃ | 5-F | Cl | F |
| A-3575. | CH₃ | CH₃ | 5-CH₃ | Cl | F |
| A-3576. | CH₃ | CH₃ | 5-OCH₃ | Cl | F |
| A-3577. | CH₃ | OCH₃ | 3-F | Cl | F |
| A-3578. | CH₃ | OCH₃ | 3-CH₃ | Cl | F |
| A-3579. | CH₃ | OCH₃ | 3-OCH₃ | Cl | F |
| A-3580. | CH₃ | OCH₃ | 5-F | Cl | F |
| A-3581. | CH₃ | OCH₃ | 5-CH₃ | Cl | F |
| A-3582. | CH₃ | OCH₃ | 5-OCH₃ | Cl | F |
| A-3583. | CH₃ | CN | 3-F | Cl | F |
| A-3584. | CH₃ | CN | 3-CH₃ | Cl | F |
| A-3585. | CH₃ | CN | 3-OCH₃ | Cl | F |
| A-3586. | CH₃ | CN | 5-F | Cl | F |
| A-3587. | CH₃ | CN | 5-CH₃ | Cl | F |
| A-3588. | CH₃ | CN | 5-OCH₃ | Cl | F |
| A-3589. | CH₃ | CH₂F | 3-F | Cl | F |
| A-3590. | CH₃ | CH₂F | 3-CH₃ | Cl | F |
| A-3591. | CH₃ | CH₂F | 3-OCH₃ | Cl | F |
| A-3592. | CH₃ | CH₂F | 5-F | Cl | F |
| A-3593. | CH₃ | CH₂F | 5-CH₃ | Cl | F |
| A-3594. | CH₃ | CH₂F | 5-OCH₃ | Cl | F |
| A-3595. | CH₃ | CHF₂ | 3-F | Cl | F |
| A-3596. | CH₃ | CHF₂ | 3-CH₃ | Cl | F |
| A-3597. | CH₃ | CHF₂ | 3-OCH₃ | Cl | F |

TABLE A-continued

| Example No. | $R^{8a}$ | $R^{8b}$ | $R^{8c}$ | $R^1$ | $R^2$ |
|---|---|---|---|---|---|
| A-3598. | CH₃ | CHF₂ | 5-F | Cl | F |
| A-3599. | CH₃ | CHF₂ | 5-CH₃ | Cl | F |
| A-3600. | CH₃ | CHF₂ | 5-OCH₃ | Cl | F |
| A-3601. | CH₃ | CF₃ | 3-F | Cl | F |
| A-3602. | CH₃ | CF₃ | 3-CH₃ | Cl | F |
| A-3603. | CH₃ | CF₃ | 3-OCH₃ | Cl | F |
| A-3604. | CH₃ | CF₃ | 5-F | Cl | F |
| A-3605. | CH₃ | CF₃ | 5-CH₃ | Cl | F |
| A-3606. | CH₃ | CF₃ | 5-OCH₃ | Cl | F |
| A-3607. | CH₃ | OCH₂F | 3-F | Cl | F |
| A-3608. | CH₃ | OCH₂F | 3-CH₃ | Cl | F |
| A-3609. | CH₃ | OCH₂F | 3-OCH₃ | Cl | F |
| A-3610. | CH₃ | OCH₂F | 5-F | Cl | F |
| A-3611. | CH₃ | OCH₂F | 5-CH₃ | Cl | F |
| A-3612. | CH₃ | OCH₂F | 5-OCH₃ | Cl | F |
| A-3613. | CH₃ | OCHF₂ | 3-F | Cl | F |
| A-3614. | CH₃ | OCHF₂ | 3-CH₃ | Cl | F |
| A-3615. | CH₃ | OCHF₂ | 3-OCH₃ | Cl | F |
| A-3616. | CH₃ | OCHF₂ | 5-F | Cl | F |
| A-3617. | CH₃ | OCHF₂ | 5-CH₃ | Cl | F |
| A-3618. | CH₃ | OCHF₂ | 5-OCH₃ | Cl | F |
| A-3619. | CH₃ | OCF₃ | 3-F | Cl | F |
| A-3620. | CH₃ | OCF₃ | 3-CH₃ | Cl | F |
| A-3621. | CH₃ | OCF₃ | 3-OCH₃ | Cl | F |
| A-3622. | CH₃ | OCF₃ | 5-F | Cl | F |
| A-3623. | CH₃ | OCF₃ | 5-CH₃ | Cl | F |
| A-3624. | CH₃ | OCF₃ | 5-OCH₃ | Cl | F |
| A-3625. | OCH₃ | F | 3-F | Cl | F |
| A-3626. | OCH₃ | F | 3-CH₃ | Cl | F |
| A-3627. | OCH₃ | F | 3-OCH₃ | Cl | F |
| A-3628. | OCH₃ | F | 5-F | Cl | F |
| A-3629. | OCH₃ | F | 5-CH₃ | Cl | F |
| A-3630. | OCH₃ | F | 5-OCH₃ | Cl | F |
| A-3631. | OCH₃ | CH₃ | 3-F | Cl | F |
| A-3632. | OCH₃ | CH₃ | 3-CH₃ | Cl | F |
| A-3633. | OCH₃ | CH₃ | 3-OCH₃ | Cl | F |
| A-3634. | OCH₃ | CH₃ | 5-F | Cl | F |
| A-3635. | OCH₃ | CH₃ | 5-CH₃ | Cl | F |
| A-3636. | OCH₃ | CH₃ | 5-OCH₃ | Cl | F |
| A-3637. | OCH₃ | OCH₃ | 3-F | Cl | F |
| A-3638. | OCH₃ | OCH₃ | 3-CH₃ | Cl | F |
| A-3639. | OCH₃ | OCH₃ | 3-OCH₃ | Cl | F |
| A-3640. | OCH₃ | OCH₃ | 5-F | Cl | F |
| A-3641. | OCH₃ | OCH₃ | 5-CH₃ | Cl | F |
| A-3642. | OCH₃ | OCH₃ | 5-OCH₃ | Cl | F |
| A-3643. | OCH₃ | CN | 3-F | Cl | F |
| A-3644. | OCH₃ | CN | 3-CH₃ | Cl | F |
| A-3645. | OCH₃ | CN | 3-OCH₃ | Cl | F |
| A-3646. | OCH₃ | CN | 5-F | Cl | F |
| A-3647. | OCH₃ | CN | 5-CH₃ | Cl | F |
| A-3648. | OCH₃ | CN | 5-OCH₃ | Cl | F |
| A-3649. | OCH₃ | CH₂F | 3-F | Cl | F |
| A-3650. | OCH₃ | CH₂F | 3-CH₃ | Cl | F |
| A-3651. | OCH₃ | CH₂F | 3-OCH₃ | Cl | F |
| A-3652. | OCH₃ | CH₂F | 5-F | Cl | F |
| A-3653. | OCH₃ | CH₂F | 5-CH₃ | Cl | F |
| A-3654. | OCH₃ | CH₂F | 5-OCH₃ | Cl | F |
| A-3655. | OCH₃ | CHF₂ | 3-F | Cl | F |
| A-3656. | OCH₃ | CHF₂ | 3-CH₃ | Cl | F |
| A-3657. | OCH₃ | CHF₂ | 3-OCH₃ | Cl | F |
| A-3658. | OCH₃ | CHF₂ | 5-F | Cl | F |
| A-3659. | OCH₃ | CHF₂ | 5-CH₃ | Cl | F |
| A-3660. | OCH₃ | CHF₂ | 5-OCH₃ | Cl | F |
| A-3661. | OCH₃ | CF₃ | 3-F | Cl | F |
| A-3662. | OCH₃ | CF₃ | 3-CH₃ | Cl | F |
| A-3663. | OCH₃ | CF₃ | 3-OCH₃ | Cl | F |
| A-3664. | OCH₃ | CF₃ | 5-F | Cl | F |
| A-3665. | OCH₃ | CF₃ | 5-CH₃ | Cl | F |
| A-3666. | OCH₃ | CF₃ | 5-OCH₃ | Cl | F |
| A-3667. | OCH₃ | OCH₂F | 3-F | Cl | F |
| A-3668. | OCH₃ | OCH₂F | 3-CH₃ | Cl | F |
| A-3669. | OCH₃ | OCH₂F | 3-OCH₃ | Cl | F |
| A-3670. | OCH₃ | OCH₂F | 5-F | Cl | F |
| A-3671. | OCH₃ | OCH₂F | 5-CH₃ | Cl | F |
| A-3672. | OCH₃ | OCH₂F | 5-OCH₃ | Cl | F |
| A-3673. | OCH₃ | OCHF₂ | 3-F | Cl | F |
| A-3674. | OCH₃ | OCHF₂ | 3-CH₃ | Cl | F |
| A-3675. | OCH₃ | OCHF₂ | 3-OCH₃ | Cl | F |
| A-3676. | OCH₃ | OCHF₂ | 5-F | Cl | F |
| A-3677. | OCH₃ | OCHF₂ | 5-CH₃ | Cl | F |
| A-3678. | OCH₃ | OCHF₂ | 5-OCH₃ | Cl | F |
| A-3679. | OCH₃ | OCF₃ | 3-F | Cl | F |
| A-3680. | OCH₃ | OCF₃ | 3-CH₃ | Cl | F |
| A-3681. | OCH₃ | OCF₃ | 3-OCH₃ | Cl | F |
| A-3682. | OCH₃ | OCF₃ | 5-F | Cl | F |
| A-3683. | OCH₃ | OCF₃ | 5-CH₃ | Cl | F |
| A-3684. | OCH₃ | OCF₃ | 5-OCH₃ | Cl | F |
| A-3685. | CH₂F | F | 3-F | Cl | F |
| A-3686. | CH₂F | F | 3-CH₃ | Cl | F |
| A-3687. | CH₂F | F | 3-OCH₃ | Cl | F |
| A-3688. | CH₂F | F | 5-F | Cl | F |
| A-3689. | CH₂F | F | 5-CH₃ | Cl | F |
| A-3690. | CH₂F | F | 5-OCH₃ | Cl | F |
| A-3691. | CH₂F | CH₃ | 3-F | Cl | F |
| A-3692. | CH₂F | CH₃ | 3-CH₃ | Cl | F |
| A-3693. | CH₂F | CH₃ | 3-OCH₃ | Cl | F |
| A-3694. | CH₂F | CH₃ | 5-F | Cl | F |
| A-3695. | CH₂F | CH₃ | 5-CH₃ | Cl | F |
| A-3696. | CH₂F | CH₃ | 5-OCH₃ | Cl | F |
| A-3697. | CH₂F | OCH₃ | 3-F | Cl | F |
| A-3698. | CH₂F | OCH₃ | 3-CH₃ | Cl | F |
| A-3699. | CH₂F | OCH₃ | 3-OCH₃ | Cl | F |
| A-3700. | CH₂F | OCH₃ | 5-F | Cl | F |
| A-3701. | CH₂F | OCH₃ | 5-CH₃ | Cl | F |
| A-3702. | CH₂F | OCH₃ | 5-OCH₃ | Cl | F |
| A-3703. | CH₂F | CN | 3-F | Cl | F |
| A-3704. | CH₂F | CN | 3-CH₃ | Cl | F |
| A-3705. | CH₂F | CN | 3-OCH₃ | Cl | F |
| A-3706. | CH₂F | CN | 5-F | Cl | F |
| A-3707. | CH₂F | CN | 5-CH₃ | Cl | F |
| A-3708. | CH₂F | CN | 5-OCH₃ | Cl | F |
| A-3709. | CH₂F | CH₂F | 3-F | Cl | F |
| A-3710. | CH₂F | CH₂F | 3-CH₃ | Cl | F |
| A-3711. | CH₂F | CH₂F | 3-OCH₃ | Cl | F |
| A-3712. | CH₂F | CH₂F | 5-F | Cl | F |
| A-3713. | CH₂F | CH₂F | 5-CH₃ | Cl | F |
| A-3714. | CH₂F | CH₂F | 5-OCH₃ | Cl | F |
| A-3715. | CH₂F | CHF₂ | 3-F | Cl | F |
| A-3716. | CH₂F | CHF₂ | 3-CH₃ | Cl | F |
| A-3717. | CH₂F | CHF₂ | 3-OCH₃ | Cl | F |
| A-3718. | CH₂F | CHF₂ | 5-F | Cl | F |
| A-3719. | CH₂F | CHF₂ | 5-CH₃ | Cl | F |
| A-3720. | CH₂F | CHF₂ | 5-OCH₃ | Cl | F |
| A-3721. | CH₂F | CF₃ | 3-F | Cl | F |
| A-3722. | CH₂F | CF₃ | 3-CH₃ | Cl | F |
| A-3723. | CH₂F | CF₃ | 3-OCH₃ | Cl | F |
| A-3724. | CH₂F | CF₃ | 5-F | Cl | F |
| A-3725. | CH₂F | CF₃ | 5-CH₃ | Cl | F |
| A-3726. | CH₂F | CF₃ | 5-OCH₃ | Cl | F |
| A-3727. | CH₂F | OCH₂F | 3-F | Cl | F |
| A-3728. | CH₂F | OCH₂F | 3-CH₃ | Cl | F |
| A-3729. | CH₂F | OCH₂F | 3-OCH₃ | Cl | F |
| A-3730. | CH₂F | OCH₂F | 5-F | Cl | F |
| A-3731. | CH₂F | OCH₂F | 5-CH₃ | Cl | F |
| A-3732. | CH₂F | OCH₂F | 5-OCH₃ | Cl | F |
| A-3733. | CH₂F | OCHF₂ | 3-F | Cl | F |
| A-3734. | CH₂F | OCHF₂ | 3-CH₃ | Cl | F |
| A-3735. | CH₂F | OCHF₂ | 3-OCH₃ | Cl | F |
| A-3736. | CH₂F | OCHF₂ | 5-F | Cl | F |
| A-3737. | CH₂F | OCHF₂ | 5-CH₃ | Cl | F |
| A-3738. | CH₂F | OCHF₂ | 5-OCH₃ | Cl | F |
| A-3739. | CH₂F | OCF₃ | 3-F | Cl | F |
| A-3740. | CH₂F | OCF₃ | 3-CH₃ | Cl | F |
| A-3741. | CH₂F | OCF₃ | 3-OCH₃ | Cl | F |
| A-3742. | CH₂F | OCF₃ | 5-F | Cl | F |
| A-3743. | CH₂F | OCF₃ | 5-CH₃ | Cl | F |
| A-3744. | CH₂F | OCF₃ | 5-OCH₃ | Cl | F |
| A-3745. | CHF₂ | F | 3-F | Cl | F |
| A-3746. | CHF₂ | F | 3-CH₃ | Cl | F |
| A-3747. | CHF₂ | F | 3-OCH₃ | Cl | F |
| A-3748. | CHF₂ | F | 5-F | Cl | F |
| A-3749. | CHF₂ | F | 5-CH₃ | Cl | F |
| A-3750. | CHF₂ | F | 5-OCH₃ | Cl | F |
| A-3751. | CHF₂ | CH₃ | 3-F | Cl | F |
| A-3752. | CHF₂ | CH₃ | 3-CH₃ | Cl | F |
| A-3753. | CHF₂ | CH₃ | 3-OCH₃ | Cl | F |

TABLE A-continued

| Example No. | $R^{8a}$ | $R^{8b}$ | $R^{8c}$ | $R^1$ | $R^2$ |
|---|---|---|---|---|---|
| A-3754. | $CHF_2$ | $CH_3$ | 5-F | Cl | F |
| A-3755. | $CHF_2$ | $CH_3$ | 5-$CH_3$ | Cl | F |
| A-3756. | $CHF_2$ | $CH_3$ | 5-$OCH_3$ | Cl | F |
| A-3757. | $CHF_2$ | $OCH_3$ | 3-F | Cl | F |
| A-3758. | $CHF_2$ | $OCH_3$ | 3-$CH_3$ | Cl | F |
| A-3759. | $CHF_2$ | $OCH_3$ | 3-$OCH_3$ | Cl | F |
| A-3760. | $CHF_2$ | $OCH_3$ | 5-F | Cl | F |
| A-3761. | $CHF_2$ | $OCH_3$ | 5-$CH_3$ | Cl | F |
| A-3762. | $CHF_2$ | $OCH_3$ | 5-$OCH_3$ | Cl | F |
| A-3763. | $CHF_2$ | CN | 3-F | Cl | F |
| A-3764. | $CHF_2$ | CN | 3-$CH_3$ | Cl | F |
| A-3765. | $CHF_2$ | CN | 3-$OCH_3$ | Cl | F |
| A-3766. | $CHF_2$ | CN | 5-F | Cl | F |
| A-3767. | $CHF_2$ | CN | 5-$CH_3$ | Cl | F |
| A-3768. | $CHF_2$ | CN | 5-$OCH_3$ | Cl | F |
| A-3769. | $CHF_2$ | $CH_2F$ | 3-F | Cl | F |
| A-3770. | $CHF_2$ | $CH_2F$ | 3-$CH_3$ | Cl | F |
| A-3771. | $CHF_2$ | $CH_2F$ | 3-$OCH_3$ | Cl | F |
| A-3772. | $CHF_2$ | $CH_2F$ | 5-F | Cl | F |
| A-3773. | $CHF_2$ | $CH_2F$ | 5-$CH_3$ | Cl | F |
| A-3774. | $CHF_2$ | $CH_2F$ | 5-$OCH_3$ | Cl | F |
| A-3775. | $CHF_2$ | $CHF_2$ | 3-F | Cl | F |
| A-3776. | $CHF_2$ | $CHF_2$ | 3-$CH_3$ | Cl | F |
| A-3777. | $CHF_2$ | $CHF_2$ | 3-$OCH_3$ | Cl | F |
| A-3778. | $CHF_2$ | $CHF_2$ | 5-F | Cl | F |
| A-3779. | $CHF_2$ | $CHF_2$ | 5-$CH_3$ | Cl | F |
| A-3780. | $CHF_2$ | $CHF_2$ | 5-$OCH_3$ | Cl | F |
| A-3781. | $CHF_2$ | $CF_3$ | 3-F | Cl | F |
| A-3782. | $CHF_2$ | $CF_3$ | 3-$CH_3$ | Cl | F |
| A-3783. | $CHF_2$ | $CF_3$ | 3-$OCH_3$ | Cl | F |
| A-3784. | $CHF_2$ | $CF_3$ | 5-F | Cl | F |
| A-3785. | $CHF_2$ | $CF_3$ | 5-$CH_3$ | Cl | F |
| A-3786. | $CHF_2$ | $CF_3$ | 5-$OCH_3$ | Cl | F |
| A-3787. | $CHF_2$ | $OCH_2F$ | 3-F | Cl | F |
| A-3788. | $CHF_2$ | $OCH_2F$ | 3-$CH_3$ | Cl | F |
| A-3789. | $CHF_2$ | $OCH_2F$ | 3-$OCH_3$ | Cl | F |
| A-3790. | $CHF_2$ | $OCH_2F$ | 5-F | Cl | F |
| A-3791. | $CHF_2$ | $OCH_2F$ | 5-$CH_3$ | Cl | F |
| A-3792. | $CHF_2$ | $OCH_2F$ | 5-$OCH_3$ | Cl | F |
| A-3793. | $CHF_2$ | $OCHF_2$ | 3-F | Cl | F |
| A-3794. | $CHF_2$ | $OCHF_2$ | 3-$CH_3$ | Cl | F |
| A-3795. | $CHF_2$ | $OCHF_2$ | 3-$OCH_3$ | Cl | F |
| A-3796. | $CHF_2$ | $OCHF_2$ | 5-F | Cl | F |
| A-3797. | $CHF_2$ | $OCHF_2$ | 5-$CH_3$ | Cl | F |
| A-3798. | $CHF_2$ | $OCHF_2$ | 5-$OCH_3$ | Cl | F |
| A-3799. | $CHF_2$ | $OCF_3$ | 3-F | Cl | F |
| A-3800. | $CHF_2$ | $OCF_3$ | 3-$CH_3$ | Cl | F |
| A-3801. | $CHF_2$ | $OCF_3$ | 3-$OCH_3$ | Cl | F |
| A-3802. | $CHF_2$ | $OCF_3$ | 5-F | Cl | F |
| A-3803. | $CHF_2$ | $OCF_3$ | 5-$CH_3$ | Cl | F |
| A-3804. | $CHF_2$ | $OCF_3$ | 5-$OCH_3$ | Cl | F |
| A-3805. | $CF_3$ | F | 3-F | Cl | F |
| A-3806. | $CF_3$ | F | 3-$CH_3$ | Cl | F |
| A-3807. | $CF_3$ | F | 3-$OCH_3$ | Cl | F |
| A-3808. | $CF_3$ | F | 5-F | Cl | F |
| A-3809. | $CF_3$ | F | 5-$CH_3$ | Cl | F |
| A-3810. | $CF_3$ | F | 5-$OCH_3$ | Cl | F |
| A-3811. | $CF_3$ | $CH_3$ | 3-F | Cl | F |
| A-3812. | $CF_3$ | $CH_3$ | 3-$CH_3$ | Cl | F |
| A-3813. | $CF_3$ | $CH_3$ | 3-$OCH_3$ | Cl | F |
| A-3814. | $CF_3$ | $CH_3$ | 5-F | Cl | F |
| A-3815. | $CF_3$ | $CH_3$ | 5-$CH_3$ | Cl | F |
| A-3816. | $CF_3$ | $CH_3$ | 5-$OCH_3$ | Cl | F |
| A-3817. | $CF_3$ | $OCH_3$ | 3-F | Cl | F |
| A-3818. | $CF_3$ | $OCH_3$ | 3-$CH_3$ | Cl | F |
| A-3819. | $CF_3$ | $OCH_3$ | 3-$OCH_3$ | Cl | F |
| A-3820. | $CF_3$ | $OCH_3$ | 5-F | Cl | F |
| A-3821. | $CF_3$ | $OCH_3$ | 5-$CH_3$ | Cl | F |
| A-3822. | $CF_3$ | $OCH_3$ | 5-$OCH_3$ | Cl | F |
| A-3823. | $CF_3$ | CN | 3-F | Cl | F |
| A-3824. | $CF_3$ | CN | 3-$CH_3$ | Cl | F |
| A-3825. | $CF_3$ | CN | 3-$OCH_3$ | Cl | F |
| A-3826. | $CF_3$ | CN | 5-F | Cl | F |
| A-3827. | $CF_3$ | CN | 5-$CH_3$ | Cl | F |
| A-3828. | $CF_3$ | CN | 5-$OCH_3$ | Cl | F |
| A-3829. | $CF_3$ | $CH_2F$ | 3-F | Cl | F |
| A-3830. | $CF_3$ | $CH_2F$ | 3-$CH_3$ | Cl | F |
| A-3831. | $CF_3$ | $CH_2F$ | 3-$OCH_3$ | Cl | F |
| A-3832. | $CF_3$ | $CH_2F$ | 5-F | Cl | F |
| A-3833. | $CF_3$ | $CH_2F$ | 5-$CH_3$ | Cl | F |
| A-3834. | $CF_3$ | $CH_2F$ | 5-$OCH_3$ | Cl | F |
| A-3835. | $CF_3$ | $CHF_2$ | 3-F | Cl | F |
| A-3836. | $CF_3$ | $CHF_2$ | 3-$CH_3$ | Cl | F |
| A-3837. | $CF_3$ | $CHF_2$ | 3-$OCH_3$ | Cl | F |
| A-3838. | $CF_3$ | $CHF_2$ | 5-F | Cl | F |
| A-3839. | $CF_3$ | $CHF_2$ | 5-$CH_3$ | Cl | F |
| A-3840. | $CF_3$ | $CHF_2$ | 5-$OCH_3$ | Cl | F |
| A-3841. | $CF_3$ | $CF_3$ | 3-F | Cl | F |
| A-3842. | $CF_3$ | $CF_3$ | 3-$CH_3$ | Cl | F |
| A-3843. | $CF_3$ | $CF_3$ | 3-$OCH_3$ | Cl | F |
| A-3844. | $CF_3$ | $CF_3$ | 5-F | Cl | F |
| A-3845. | $CF_3$ | $CF_3$ | 5-$CH_3$ | Cl | F |
| A-3846. | $CF_3$ | $CF_3$ | 5-$OCH_3$ | Cl | F |
| A-3847. | $CF_3$ | $OCH_2F$ | 3-F | Cl | F |
| A-3848. | $CF_3$ | $OCH_2F$ | 3-$CH_3$ | Cl | F |
| A-3849. | $CF_3$ | $OCH_2F$ | 3-$OCH_3$ | Cl | F |
| A-3850. | $CF_3$ | $OCH_2F$ | 5-F | Cl | F |
| A-3851. | $CF_3$ | $OCH_2F$ | 5-$CH_3$ | Cl | F |
| A-3852. | $CF_3$ | $OCH_2F$ | 5-$OCH_3$ | Cl | F |
| A-3853. | $CF_3$ | $OCHF_2$ | 3-F | Cl | F |
| A-3854. | $CF_3$ | $OCHF_2$ | 3-$CH_3$ | Cl | F |
| A-3855. | $CF_3$ | $OCHF_2$ | 3-$OCH_3$ | Cl | F |
| A-3856. | $CF_3$ | $OCHF_2$ | 5-F | Cl | F |
| A-3857. | $CF_3$ | $OCHF_2$ | 5-$CH_3$ | Cl | F |
| A-3858. | $CF_3$ | $OCHF_2$ | 5-$OCH_3$ | Cl | F |
| A-3859. | $CF_3$ | $OCF_3$ | 3-F | Cl | F |
| A-3860. | $CF_3$ | $OCF_3$ | 3-$CH_3$ | Cl | F |
| A-3861. | $CF_3$ | $OCF_3$ | 3-$OCH_3$ | Cl | F |
| A-3862. | $CF_3$ | $OCF_3$ | 5-F | Cl | F |
| A-3863. | $CF_3$ | $OCF_3$ | 5-$CH_3$ | Cl | F |
| A-3864. | $CF_3$ | $OCF_3$ | 5-$OCH_3$ | Cl | F |
| A-3865. | $OCH_2F$ | F | 3-F | Cl | F |
| A-3866. | $OCH_2F$ | F | 3-$CH_3$ | Cl | F |
| A-3867. | $OCH_2F$ | F | 3-$OCH_3$ | Cl | F |
| A-3868. | $OCH_2F$ | F | 5-F | Cl | F |
| A-3869. | $OCH_2F$ | F | 5-$CH_3$ | Cl | F |
| A-3870. | $OCH_2F$ | F | 5-$OCH_3$ | Cl | F |
| A-3871. | $OCH_2F$ | $CH_3$ | 3-F | Cl | F |
| A-3872. | $OCH_2F$ | $CH_3$ | 3-$CH_3$ | Cl | F |
| A-3873. | $OCH_2F$ | $CH_3$ | 3-$OCH_3$ | Cl | F |
| A-3874. | $OCH_2F$ | $CH_3$ | 5-F | Cl | F |
| A-3875. | $OCH_2F$ | $CH_3$ | 5-$CH_3$ | Cl | F |
| A-3876. | $OCH_2F$ | $CH_3$ | 5-$OCH_3$ | Cl | F |
| A-3877. | $OCH_2F$ | $OCH_3$ | 3-F | Cl | F |
| A-3878. | $OCH_2F$ | $OCH_3$ | 3-$CH_3$ | Cl | F |
| A-3879. | $OCH_2F$ | $OCH_3$ | 3-$OCH_3$ | Cl | F |
| A-3880. | $OCH_2F$ | $OCH_3$ | 5-F | Cl | F |
| A-3881. | $OCH_2F$ | $OCH_3$ | 5-$CH_3$ | Cl | F |
| A-3882. | $OCH_2F$ | $OCH_3$ | 5-$OCH_3$ | Cl | F |
| A-3883. | $OCH_2F$ | CN | 3-F | Cl | F |
| A-3884. | $OCH_2F$ | CN | 3-$CH_3$ | Cl | F |
| A-3885. | $OCH_2F$ | CN | 3-$OCH_3$ | Cl | F |
| A-3886. | $OCH_2F$ | CN | 5-F | Cl | F |
| A-3887. | $OCH_2F$ | CN | 5-$CH_3$ | Cl | F |
| A-3888. | $OCH_2F$ | CN | 5-$OCH_3$ | Cl | F |
| A-3889. | $OCH_2F$ | $CH_2F$ | 3-F | Cl | F |
| A-3890. | $OCH_2F$ | $CH_2F$ | 3-$CH_3$ | Cl | F |
| A-3891. | $OCH_2F$ | $CH_2F$ | 3-$OCH_3$ | Cl | F |
| A-3892. | $OCH_2F$ | $CH_2F$ | 5-F | Cl | F |
| A-3893. | $OCH_2F$ | $CH_2F$ | 5-$CH_3$ | Cl | F |
| A-3894. | $OCH_2F$ | $CH_2F$ | 5-$OCH_3$ | Cl | F |
| A-3895. | $OCH_2F$ | $CHF_2$ | 3-F | Cl | F |
| A-3896. | $OCH_2F$ | $CHF_2$ | 3-$CH_3$ | Cl | F |
| A-3897. | $OCH_2F$ | $CHF_2$ | 3-$OCH_3$ | Cl | F |
| A-3898. | $OCH_2F$ | $CHF_2$ | 5-F | Cl | F |
| A-3899. | $OCH_2F$ | $CHF_2$ | 5-$CH_3$ | Cl | F |
| A-3900. | $OCH_2F$ | $CHF_2$ | 5-$OCH_3$ | Cl | F |
| A-3901. | $OCH_2F$ | $CF_3$ | 3-F | Cl | F |
| A-3902. | $OCH_2F$ | $CF_3$ | 3-$CH_3$ | Cl | F |
| A-3903. | $OCH_2F$ | $CF_3$ | 3-$OCH_3$ | Cl | F |
| A-3904. | $OCH_2F$ | $CF_3$ | 5-F | Cl | F |
| A-3905. | $OCH_2F$ | $CF_3$ | 5-$CH_3$ | Cl | F |
| A-3906. | $OCH_2F$ | $CF_3$ | 5-$OCH_3$ | Cl | F |
| A-3907. | $OCH_2F$ | $OCH_2F$ | 3-F | Cl | F |
| A-3908. | $OCH_2F$ | $OCH_2F$ | 3-$CH_3$ | Cl | F |
| A-3909. | $OCH_2F$ | $OCH_2F$ | 3-$OCH_3$ | Cl | F |

TABLE A-continued

| Example No. | R$^{8a}$ | R$^{8b}$ | R$^{8c}$ | R$^1$ | R$^2$ |
|---|---|---|---|---|---|
| A-3910. | OCH$_2$F | OCH$_2$F | 5-F | Cl | F |
| A-3911. | OCH$_2$F | OCH$_2$F | 5-CH$_3$ | Cl | F |
| A-3912. | OCH$_2$F | OCH$_2$F | 5-OCH$_3$ | Cl | F |
| A-3913. | OCH$_2$F | OCHF$_2$ | 3-F | Cl | F |
| A-3914. | OCH$_2$F | OCHF$_2$ | 3-CH$_3$ | Cl | F |
| A-3915. | OCH$_2$F | OCHF$_2$ | 3-OCH$_3$ | Cl | F |
| A-3916. | OCH$_2$F | OCHF$_2$ | 5-F | Cl | F |
| A-3917. | OCH$_2$F | OCHF$_2$ | 5-CH$_3$ | Cl | F |
| A-3918. | OCH$_2$F | OCHF$_2$ | 5-OCH$_3$ | Cl | F |
| A-3919. | OCH$_2$F | OCF$_3$ | 3-F | Cl | F |
| A-3920. | OCH$_2$F | OCF$_3$ | 3-CH$_3$ | Cl | F |
| A-3921. | OCH$_2$F | OCF$_3$ | 3-OCH$_3$ | Cl | F |
| A-3922. | OCH$_2$F | OCF$_3$ | 5-F | Cl | F |
| A-3923. | OCH$_2$F | OCF$_3$ | 5-CH$_3$ | Cl | F |
| A-3924. | OCH$_2$F | OCF$_3$ | 5-OCH$_3$ | Cl | F |
| A-3925. | OCHF$_2$ | F | 3-F | Cl | F |
| A-3926. | OCHF$_2$ | F | 3-CH$_3$ | Cl | F |
| A-3927. | OCHF$_2$ | F | 3-OCH$_3$ | Cl | F |
| A-3928. | OCHF$_2$ | F | 5-F | Cl | F |
| A-3929. | OCHF$_2$ | F | 5-CH$_3$ | Cl | F |
| A-3930. | OCHF$_2$ | F | 5-OCH$_3$ | Cl | F |
| A-3931. | OCHF$_2$ | CH$_3$ | 3-F | Cl | F |
| A-3932. | OCHF$_2$ | CH$_3$ | 3-CH$_3$ | Cl | F |
| A-3933. | OCHF$_2$ | CH$_3$ | 3-OCH$_3$ | Cl | F |
| A-3934. | OCHF$_2$ | CH$_3$ | 5-F | Cl | F |
| A-3935. | OCHF$_2$ | CH$_3$ | 5-CH$_3$ | Cl | F |
| A-3936. | OCHF$_2$ | CH$_3$ | 5-OCH$_3$ | Cl | F |
| A-3937. | OCHF$_2$ | OCH$_3$ | 3-F | Cl | F |
| A-3938. | OCHF$_2$ | OCH$_3$ | 3-CH$_3$ | Cl | F |
| A-3939. | OCHF$_2$ | OCH$_3$ | 3-OCH$_3$ | Cl | F |
| A-3940. | OCHF$_2$ | OCH$_3$ | 5-F | Cl | F |
| A-3941. | OCHF$_2$ | OCH$_3$ | 5-CH$_3$ | Cl | F |
| A-3942. | OCHF$_2$ | OCH$_3$ | 5-OCH$_3$ | Cl | F |
| A-3943. | OCHF$_2$ | CN | 3-F | Cl | F |
| A-3944. | OCHF$_2$ | CN | 3-CH$_3$ | Cl | F |
| A-3945. | OCHF$_2$ | CN | 3-OCH$_3$ | Cl | F |
| A-3946. | OCHF$_2$ | CN | 5-F | Cl | F |
| A-3947. | OCHF$_2$ | CN | 5-CH$_3$ | Cl | F |
| A-3948. | OCHF$_2$ | CN | 5-OCH$_3$ | Cl | F |
| A-3949. | OCHF$_2$ | CH$_2$F | 3-F | Cl | F |
| A-3950. | OCHF$_2$ | CH$_2$F | 3-CH$_3$ | Cl | F |
| A-3951. | OCHF$_2$ | CH$_2$F | 3-OCH$_3$ | Cl | F |
| A-3952. | OCHF$_2$ | CH$_2$F | 5-F | Cl | F |
| A-3953. | OCHF$_2$ | CH$_2$F | 5-CH$_3$ | Cl | F |
| A-3954. | OCHF$_2$ | CH$_2$F | 5-OCH$_3$ | Cl | F |
| A-3955. | OCHF$_2$ | CHF$_2$ | 3-F | Cl | F |
| A-3956. | OCHF$_2$ | CHF$_2$ | 3-CH$_3$ | Cl | F |
| A-3957. | OCHF$_2$ | CHF$_2$ | 3-OCH$_3$ | Cl | F |
| A-3958. | OCHF$_2$ | CHF$_2$ | 5-F | Cl | F |
| A-3959. | OCHF$_2$ | CHF$_2$ | 5-CH$_3$ | Cl | F |
| A-3960. | OCHF$_2$ | CHF$_2$ | 5-OCH$_3$ | Cl | F |
| A-3961. | OCHF$_2$ | CF$_3$ | 3-F | Cl | F |
| A-3962. | OCHF$_2$ | CF$_3$ | 3-CH$_3$ | Cl | F |
| A-3963. | OCHF$_2$ | CF$_3$ | 3-OCH$_3$ | Cl | F |
| A-3964. | OCHF$_2$ | CF$_3$ | 5-F | Cl | F |
| A-3965. | OCHF$_2$ | CF$_3$ | 5-CH$_3$ | Cl | F |
| A-3966. | OCHF$_2$ | CF$_3$ | 5-OCH$_3$ | Cl | F |
| A-3967. | OCHF$_2$ | OCH$_2$F | 3-F | Cl | F |
| A-3968. | OCHF$_2$ | OCH$_2$F | 3-CH$_3$ | Cl | F |
| A-3969. | OCHF$_2$ | OCH$_2$F | 3-OCH$_3$ | Cl | F |
| A-3970. | OCHF$_2$ | OCH$_2$F | 5-F | Cl | F |
| A-3971. | OCHF$_2$ | OCH$_2$F | 5-CH$_3$ | Cl | F |
| A-3972. | OCHF$_2$ | OCH$_2$F | 5-OCH$_3$ | Cl | F |
| A-3973. | OCHF$_2$ | OCHF$_2$ | 3-F | Cl | F |
| A-3974. | OCHF$_2$ | OCHF$_2$ | 3-CH$_3$ | Cl | F |
| A-3975. | OCHF$_2$ | OCHF$_2$ | 3-OCH$_3$ | Cl | F |
| A-3976. | OCHF$_2$ | OCHF$_2$ | 5-F | Cl | F |
| A-3977. | OCHF$_2$ | OCHF$_2$ | 5-CH$_3$ | Cl | F |
| A-3978. | OCHF$_2$ | OCHF$_2$ | 5-OCH$_3$ | Cl | F |
| A-3979. | OCHF$_2$ | OCF$_3$ | 3-F | Cl | F |
| A-3980. | OCHF$_2$ | OCF$_3$ | 3-CH$_3$ | Cl | F |
| A-3981. | OCHF$_2$ | OCF$_3$ | 3-OCH$_3$ | Cl | F |
| A-3982. | OCHF$_2$ | OCF$_3$ | 5-F | Cl | F |
| A-3983. | OCHF$_2$ | OCF$_3$ | 5-CH$_3$ | Cl | F |
| A-3984. | OCHF$_2$ | OCF$_3$ | 5-OCH$_3$ | Cl | F |
| A-3985. | OCF$_3$ | F | 3-F | Cl | F |
| A-3986. | OCF$_3$ | F | 3-CH$_3$ | Cl | F |
| A-3987. | OCF$_3$ | F | 3-OCH$_3$ | Cl | F |
| A-3988. | OCF$_3$ | F | 5-F | Cl | F |
| A-3989. | OCF$_3$ | F | 5-CH$_3$ | Cl | F |
| A-3990. | OCF$_3$ | F | 5-OCH$_3$ | Cl | F |
| A-3991. | OCF$_3$ | CH$_3$ | 3-F | Cl | F |
| A-3992. | OCF$_3$ | CH$_3$ | 3-CH$_3$ | Cl | F |
| A-3993. | OCF$_3$ | CH$_3$ | 3-OCH$_3$ | Cl | F |
| A-3994. | OCF$_3$ | CH$_3$ | 5-F | Cl | F |
| A-3995. | OCF$_3$ | CH$_3$ | 5-CH$_3$ | Cl | F |
| A-3996. | OCF$_3$ | CH$_3$ | 5-OCH$_3$ | Cl | F |
| A-3997. | OCF$_3$ | OCH$_3$ | 3-F | Cl | F |
| A-3998. | OCF$_3$ | OCH$_3$ | 3-CH$_3$ | Cl | F |
| A-3999. | OCF$_3$ | OCH$_3$ | 3-OCH$_3$ | Cl | F |
| A-4000. | OCF$_3$ | OCH$_3$ | 5-F | Cl | F |
| A-4001. | OCF$_3$ | OCH$_3$ | 5-CH$_3$ | Cl | F |
| A-4002. | OCF$_3$ | OCH$_3$ | 5-OCH$_3$ | Cl | F |
| A-4003. | OCF$_3$ | CN | 3-F | Cl | F |
| A-4004. | OCF$_3$ | CN | 3-CH$_3$ | Cl | F |
| A-4005. | OCF$_3$ | CN | 3-OCH$_3$ | Cl | F |
| A-4006. | OCF$_3$ | CN | 5-F | Cl | F |
| A-4007. | OCF$_3$ | CN | 5-CH$_3$ | Cl | F |
| A-4008. | OCF$_3$ | CN | 5-OCH$_3$ | Cl | F |
| A-4009. | OCF$_3$ | CH$_2$F | 3-F | Cl | F |
| A-4010. | OCF$_3$ | CH$_2$F | 3-CH$_3$ | Cl | F |
| A-4011. | OCF$_3$ | CH$_2$F | 3-OCH$_3$ | Cl | F |
| A-4012. | OCF$_3$ | CH$_2$F | 5-F | Cl | F |
| A-4013. | OCF$_3$ | CH$_2$F | 5-CH$_3$ | Cl | F |
| A-4014. | OCF$_3$ | CH$_2$F | 5-OCH$_3$ | Cl | F |
| A-4015. | OCF$_3$ | CHF$_2$ | 3-F | Cl | F |
| A-4016. | OCF$_3$ | CHF$_2$ | 3-CH$_3$ | Cl | F |
| A-4017. | OCF$_3$ | CHF$_2$ | 3-OCH$_3$ | Cl | F |
| A-4018. | OCF$_3$ | CHF$_2$ | 5-F | Cl | F |
| A-4019. | OCF$_3$ | CHF$_2$ | 5-CH$_3$ | Cl | F |
| A-4020. | OCF$_3$ | CHF$_2$ | 5-OCH$_3$ | Cl | F |
| A-4021. | OCF$_3$ | CF$_3$ | 3-F | Cl | F |
| A-4022. | OCF$_3$ | CF$_3$ | 3-CH$_3$ | Cl | F |
| A-4023. | OCF$_3$ | CF$_3$ | 3-OCH$_3$ | Cl | F |
| A-4024. | OCF$_3$ | CF$_3$ | 5-F | Cl | F |
| A-4025. | OCF$_3$ | CF$_3$ | 5-CH$_3$ | Cl | F |
| A-4026. | OCF$_3$ | CF$_3$ | 5-OCH$_3$ | Cl | F |
| A-4027. | OCF$_3$ | OCH$_2$F | 3-F | Cl | F |
| A-4028. | OCF$_3$ | OCH$_2$F | 3-CH$_3$ | Cl | F |
| A-4029. | OCF$_3$ | OCH$_2$F | 3-OCH$_3$ | Cl | F |
| A-4030. | OCF$_3$ | OCH$_2$F | 5-F | Cl | F |
| A-4031. | OCF$_3$ | OCH$_2$F | 5-CH$_3$ | Cl | F |
| A-4032. | OCF$_3$ | OCH$_2$F | 5-OCH$_3$ | Cl | F |
| A-4033. | OCF$_3$ | OCHF$_2$ | 3-F | Cl | F |
| A-4034. | OCF$_3$ | OCHF$_2$ | 3-CH$_3$ | Cl | F |
| A-4035. | OCF$_3$ | OCHF$_2$ | 3-OCH$_3$ | Cl | F |
| A-4036. | OCF$_3$ | OCHF$_2$ | 5-F | Cl | F |
| A-4037. | OCF$_3$ | OCHF$_2$ | 5-CH$_3$ | Cl | F |
| A-4038. | OCF$_3$ | OCHF$_2$ | 5-OCH$_3$ | Cl | F |
| A-4039. | OCF$_3$ | OCF$_3$ | 3-F | Cl | F |
| A-4040. | OCF$_3$ | OCF$_3$ | 3-CH$_3$ | Cl | F |
| A-4041. | OCF$_3$ | OCF$_3$ | 3-OCH$_3$ | Cl | F |
| A-4042. | OCF$_3$ | OCF$_3$ | 5-F | Cl | F |
| A-4043. | OCF$_3$ | OCF$_3$ | 5-CH$_3$ | Cl | F |
| A-4044. | OCF$_3$ | OCF$_3$ | 5-OCH$_3$ | Cl | F |

TABLE B

| Example No. | R$^{8b}$ | R$^{8c}$ | R$^1$ | R$^2$ |
|---|---|---|---|---|
| B-1. | H | H | CN | H |
| B-2. | F | H | CN | H |
| B-3. | CH$_3$ | H | CN | H |
| B-4. | OCH$_3$ | H | CN | H |
| B-5. | CN | H | CN | H |
| B-6. | CH$_2$F | H | CN | H |
| B-7. | CHF$_2$ | H | CN | H |
| B-8. | CF$_3$ | H | CN | H |
| B-9. | OCH$_2$F | H | CN | H |
| B-10. | OCHF$_2$ | H | CN | H |
| B-11. | OCF$_3$ | H | CN | H |
| B-12. | H | 3-F | CN | H |
| B-13. | H | 3-CH$_3$ | CN | H |

TABLE B-continued

| Example No. | $R^{8b}$ | $R^{8c}$ | $R^1$ | $R^2$ |
|---|---|---|---|---|
| B-14. | H | 3-OCH$_3$ | CN | H |
| B-15. | H | 5-F | CN | H |
| B-16. | H | 5-CH$_3$ | CN | H |
| B-17. | H | 5-OCH$_3$ | CN | H |
| B-18. | H | 6-F | CN | H |
| B-19. | H | 6-CH$_3$ | CN | H |
| B-20. | H | 6-OCH$_3$ | CN | H |
| B-21. | F | 3-F | CN | H |
| B-22. | F | 3-CH$_3$ | CN | H |
| B-23. | F | 3-OCH$_3$ | CN | H |
| B-24. | F | 5-F | CN | H |
| B-25. | F | 5-CH$_3$ | CN | H |
| B-26. | F | 5-OCH$_3$ | CN | H |
| B-27. | F | 6-F | CN | H |
| B-28. | F | 6-CH$_3$ | CN | H |
| B-29. | F | 6-OCH$_3$ | CN | H |
| B-30. | CH$_3$ | 3-F | CN | H |
| B-31. | CH$_3$ | 3-CH$_3$ | CN | H |
| B-32. | CH$_3$ | 3-OCH$_3$ | CN | H |
| B-33. | CH$_3$ | 5-F | CN | H |
| B-34. | CH$_3$ | 5-CH$_3$ | CN | H |
| B-35. | CH$_3$ | 5-OCH$_3$ | CN | H |
| B-36. | CH$_3$ | 6-F | CN | H |
| B-37. | CH$_3$ | 6-CH$_3$ | CN | H |
| B-38. | CH$_3$ | 6-OCH$_3$ | CN | H |
| B-39. | OCH$_3$ | 3-F | CN | H |
| B-40. | OCH$_3$ | 3-CH$_3$ | CN | H |
| B-41. | OCH$_3$ | 3-OCH$_3$ | CN | H |
| B-42. | OCH$_3$ | 5-F | CN | H |
| B-43. | OCH$_3$ | 5-CH$_3$ | CN | H |
| B-44. | OCH$_3$ | 5-OCH$_3$ | CN | H |
| B-45. | OCH$_3$ | 6-F | CN | H |
| B-46. | OCH$_3$ | 6-CH$_3$ | CN | H |
| B-47. | OCH$_3$ | 6-OCH$_3$ | CN | H |
| B-48. | CN | 3-F | CN | H |
| B-49. | CN | 3-CH$_3$ | CN | H |
| B-50. | CN | 3-OCH$_3$ | CN | H |
| B-51. | CN | 5-F | CN | H |
| B-52. | CN | 5-CH$_3$ | CN | H |
| B-53. | CN | 5-OCH$_3$ | CN | H |
| B-54. | CN | 6-F | CN | H |
| B-55. | CN | 6-CH$_3$ | CN | H |
| B-56. | CN | 6-OCH$_3$ | CN | H |
| B-57. | CH$_2$F | 3-F | CN | H |
| B-58. | CH$_2$F | 3-CH$_3$ | CN | H |
| B-59. | CH$_2$F | 3-OCH$_3$ | CN | H |
| B-60. | CH$_2$F | 5-F | CN | H |
| B-61. | CH$_2$F | 5-CH$_3$ | CN | H |
| B-62. | CH$_2$F | 5-OCH$_3$ | CN | H |
| B-63. | CH$_2$F | 6-F | CN | H |
| B-64. | CH$_2$F | 6-CH$_3$ | CN | H |
| B-65. | CH$_2$F | 6-OCH$_3$ | CN | H |
| B-66. | CHF$_2$ | 3-F | CN | H |
| B-67. | CHF$_2$ | 3-CH$_3$ | CN | H |
| B-68. | CHF$_2$ | 3-OCH$_3$ | CN | H |
| B-69. | CHF$_2$ | 5-F | CN | H |
| B-70. | CHF$_2$ | 5-CH$_3$ | CN | H |
| B-71. | CHF$_2$ | 5-OCH$_3$ | CN | H |
| B-72. | CHF$_2$ | 6-F | CN | H |
| B-73. | CHF$_2$ | 6-CH$_3$ | CN | H |
| B-74. | CHF$_2$ | 6-OCH$_3$ | CN | H |
| B-75. | CF$_3$ | 3-F | CN | H |
| B-76. | CF$_3$ | 3-CH$_3$ | CN | H |
| B-77. | CF$_3$ | 3-OCH$_3$ | CN | H |
| B-78. | CF$_3$ | 5-F | CN | H |
| B-79. | CF$_3$ | 5-CH$_3$ | CN | H |
| B-80. | CF$_3$ | 5-OCH$_3$ | CN | H |
| B-81. | CF$_3$ | 6-F | CN | H |
| B-82. | CF$_3$ | 6-CH$_3$ | CN | H |
| B-83. | CF$_3$ | 6-OCH$_3$ | CN | H |
| B-84. | OCH$_2$F | 3-F | CN | H |
| B-85. | OCH$_2$F | 3-CH$_3$ | CN | H |
| B-86. | OCH$_2$F | 3-OCH$_3$ | CN | H |
| B-87. | OCH$_2$F | 5-F | CN | H |
| B-88. | OCH$_2$F | 5-CH$_3$ | CN | H |
| B-89. | OCH$_2$F | 5-OCH$_3$ | CN | H |
| B-90. | OCH$_2$F | 6-F | CN | H |
| B-91. | OCH$_2$F | 6-CH$_3$ | CN | H |
| B-92. | OCH$_2$F | 6-OCH$_3$ | CN | H |
| B-93. | OCHF$_2$ | 3-F | CN | H |
| B-94. | OCHF$_2$ | 3-CH$_3$ | CN | H |
| B-95. | OCHF$_2$ | 3-OCH$_3$ | CN | H |
| B-96. | OCHF$_2$ | 5-F | CN | H |
| B-97. | OCHF$_2$ | 5-CH$_3$ | CN | H |
| B-98. | OCHF$_2$ | 5-OCH$_3$ | CN | H |
| B-99. | OCHF$_2$ | 6-F | CN | H |
| B-100. | OCHF$_2$ | 6-CH$_3$ | CN | H |
| B-101. | OCHF$_2$ | 6-OCH$_3$ | CN | H |
| B-102. | OCF$_3$ | 3-F | CN | H |
| B-103. | OCF$_3$ | 3-CH$_3$ | CN | H |
| B-104. | OCF$_3$ | 3-OCH$_3$ | CN | H |
| B-105. | OCF$_3$ | 5-F | CN | H |
| B-106. | OCF$_3$ | 5-CH$_3$ | CN | H |
| B-107. | OCF$_3$ | 5-OCH$_3$ | CN | H |
| B-108. | OCF$_3$ | 6-F | CN | H |
| B-109. | OCF$_3$ | 6-CH$_3$ | CN | H |
| B-110. | OCF$_3$ | 6-OCH$_3$ | CN | H |
| B-111. | H | H | F | H |
| B-112. | F | H | F | H |
| B-113. | CH$_3$ | H | F | H |
| B-114. | OCH$_3$ | H | F | H |
| B-115. | CN | H | F | H |
| B-116. | CH$_2$F | H | F | H |
| B-117. | CHF$_2$ | H | F | H |
| B-118. | CF$_3$ | H | F | H |
| B-119. | OCH$_2$F | H | F | H |
| B-120. | OCHF$_2$ | H | F | H |
| B-121. | OCF$_3$ | H | F | H |
| B-122. | H | 3-F | F | H |
| B-123. | H | 3-CH$_3$ | F | H |
| B-124. | H | 3-OCH$_3$ | F | H |
| B-125. | H | 5-F | F | H |
| B-126. | H | 5-CH$_3$ | F | H |
| B-127. | H | 5-OCH$_3$ | F | H |
| B-128. | H | 6-F | F | H |
| B-129. | H | 6-CH$_3$ | F | H |
| B-130. | H | 6-OCH$_3$ | F | H |
| B-131. | F | 3-F | F | H |
| B-132. | F | 3-CH$_3$ | F | H |
| B-133. | F | 3-OCH$_3$ | F | H |
| B-134. | F | 5-F | F | H |
| B-135. | F | 5-CH$_3$ | F | H |
| B-136. | F | 5-OCH$_3$ | F | H |
| B-137. | F | 6-F | F | H |
| B-138. | F | 6-CH$_3$ | F | H |
| B-139. | F | 6-OCH$_3$ | F | H |
| B-140. | CH$_3$ | 3-F | F | H |
| B-141. | CH$_3$ | 3-CH$_3$ | F | H |
| B-142. | CH$_3$ | 3-OCH$_3$ | F | H |
| B-143. | CH$_3$ | 5-F | F | H |
| B-144. | CH$_3$ | 5-CH$_3$ | F | H |
| B-145. | CH$_3$ | 5-OCH$_3$ | F | H |
| B-146. | CH$_3$ | 6-F | F | H |
| B-147. | CH$_3$ | 6-CH$_3$ | F | H |
| B-148. | CH$_3$ | 6-OCH$_3$ | F | H |
| B-149. | OCH$_3$ | 3-F | F | H |
| B-150. | OCH$_3$ | 3-CH$_3$ | F | H |
| B-151. | OCH$_3$ | 3-OCH$_3$ | F | H |
| B-152. | OCH$_3$ | 5-F | F | H |
| B-153. | OCH$_3$ | 5-CH$_3$ | F | H |
| B-154. | OCH$_3$ | 5-OCH$_3$ | F | H |
| B-155. | OCH$_3$ | 6-F | F | H |
| B-156. | OCH$_3$ | 6-CH$_3$ | F | H |
| B-157. | OCH$_3$ | 6-OCH$_3$ | F | H |
| B-158. | CN | 3-F | F | H |
| B-159. | CN | 3-CH$_3$ | F | H |
| B-160. | CN | 3-OCH$_3$ | F | H |
| B-161. | CN | 5-F | F | H |
| B-162. | CN | 5-CH$_3$ | F | H |
| B-163. | CN | 5-OCH$_3$ | F | H |
| B-164. | CN | 6-F | F | H |
| B-165. | CN | 6-CH$_3$ | F | H |
| B-166. | CN | 6-OCH$_3$ | F | H |
| B-167. | CH$_2$F | 3-F | F | H |
| B-168. | CH$_2$F | 3-CH$_3$ | F | H |
| B-169. | CH$_2$F | 3-OCH$_3$ | F | H |

TABLE B-continued

| Example No. | $R^{8b}$ | $R^{8c}$ | $R^1$ | $R^2$ |
|---|---|---|---|---|
| B-170. | $CH_2F$ | 5-F | F | H |
| B-171. | $CH_2F$ | 5-$CH_3$ | F | H |
| B-172. | $CH_2F$ | 5-$OCH_3$ | F | H |
| B-173. | $CH_2F$ | 6-F | F | H |
| B-174. | $CH_2F$ | 6-$CH_3$ | F | H |
| B-175. | $CH_2F$ | 6-$OCH_3$ | F | H |
| B-176. | $CHF_2$ | 3-F | F | H |
| B-177. | $CHF_2$ | 3-$CH_3$ | F | H |
| B-178. | $CHF_2$ | 3-$OCH_3$ | F | H |
| B-179. | $CHF_2$ | 5-F | F | H |
| B-180. | $CHF_2$ | 5-$CH_3$ | F | H |
| B-181. | $CHF_2$ | 5-$OCH_3$ | F | H |
| B-182. | $CHF_2$ | 6-F | F | H |
| B-183. | $CHF_2$ | 6-$CH_3$ | F | H |
| B-184. | $CHF_2$ | 6-$OCH_3$ | F | H |
| B-185. | $CF_3$ | 3-F | F | H |
| B-186. | $CF_3$ | 3-$CH_3$ | F | H |
| B-187. | $CF_3$ | 3-$OCH_3$ | F | H |
| B-188. | $CF_3$ | 5-F | F | H |
| B-189. | $CF_3$ | 5-$CH_3$ | F | H |
| B-190. | $CF_3$ | 5-$OCH_3$ | F | H |
| B-191. | $CF_3$ | 6-F | F | H |
| B-192. | $CF_3$ | 6-$CH_3$ | F | H |
| B-193. | $CF_3$ | 6-$OCH_3$ | F | H |
| B-194. | $OCH_2F$ | 3-F | F | H |
| B-195. | $OCH_2F$ | 3-$CH_3$ | F | H |
| B-196. | $OCH_2F$ | 3-$OCH_3$ | F | H |
| B-197. | $OCH_2F$ | 5-F | F | H |
| B-198. | $OCH_2F$ | 5-$CH_3$ | F | H |
| B-199. | $OCH_2F$ | 5-$OCH_3$ | F | H |
| B-200. | $OCH_2F$ | 6-F | F | H |
| B-201. | $OCH_2F$ | 6-$CH_3$ | F | H |
| B-202. | $OCH_2F$ | 6-$OCH_3$ | F | H |
| B-203. | $OCHF_2$ | 3-F | F | H |
| B-204. | $OCHF_2$ | 3-$CH_3$ | F | H |
| B-205. | $OCHF_2$ | 3-$OCH_3$ | F | H |
| B-206. | $OCHF_2$ | 5-F | F | H |
| B-207. | $OCHF_2$ | 5-$CH_3$ | F | H |
| B-208. | $OCHF_2$ | 5-$OCH_3$ | F | H |
| B-209. | $OCHF_2$ | 6-F | F | H |
| B-210. | $OCHF_2$ | 6-$CH_3$ | F | H |
| B-211. | $OCHF_2$ | 6-$OCH_3$ | F | H |
| B-212. | $OCF_3$ | 3-F | F | H |
| B-213. | $OCF_3$ | 3-$CH_3$ | F | H |
| B-214. | $OCF_3$ | 3-$OCH_3$ | F | H |
| B-215. | $OCF_3$ | 5-F | F | H |
| B-216. | $OCF_3$ | 5-$CH_3$ | F | H |
| B-217. | $OCF_3$ | 5-$OCH_3$ | F | H |
| B-218. | $OCF_3$ | 6-F | F | H |
| B-219. | $OCF_3$ | 6-$CH_3$ | F | H |
| B-220. | $OCF_3$ | 6-$OCH_3$ | F | H |
| B-221. | H | H | Cl | H |
| B-222. | F | H | Cl | H |
| B-223. | $CH_3$ | H | Cl | H |
| B-224. | $OCH_3$ | H | Cl | H |
| B-225. | CN | H | Cl | H |
| B-226. | $CH_2F$ | H | Cl | H |
| B-227. | $CHF_2$ | H | Cl | H |
| B-228. | $CF_3$ | H | Cl | H |
| B-229. | $OCH_2F$ | H | Cl | H |
| B-230. | $OCHF_2$ | H | Cl | H |
| B-231. | $OCF_3$ | H | Cl | H |
| B-232. | H | 3-F | Cl | H |
| B-233. | H | 3-$CH_3$ | Cl | H |
| B-234. | H | 3-$OCH_3$ | Cl | H |
| B-235. | H | 5-F | Cl | H |
| B-236. | H | 5-$CH_3$ | Cl | H |
| B-237. | H | 5-$OCH_3$ | Cl | H |
| B-238. | H | 6-F | Cl | H |
| B-239. | H | 6-$CH_3$ | Cl | H |
| B-240. | H | 6-$OCH_3$ | Cl | H |
| B-241. | F | 3-F | Cl | H |
| B-242. | F | 3-$CH_3$ | Cl | H |
| B-243. | F | 3-$OCH_3$ | Cl | H |
| B-244. | F | 5-F | Cl | H |
| B-245. | F | 5-$CH_3$ | Cl | H |
| B-246. | F | 5-$OCH_3$ | Cl | H |
| B-247. | F | 6-F | Cl | H |
| B-248. | F | 6-$CH_3$ | Cl | H |
| B-249. | F | 6-$OCH_3$ | Cl | H |
| B-250. | $CH_3$ | 3-F | Cl | H |
| B-251. | $CH_3$ | 3-$CH_3$ | Cl | H |
| B-252. | $CH_3$ | 3-$OCH_3$ | Cl | H |
| B-253. | $CH_3$ | 5-F | Cl | H |
| B-254. | $CH_3$ | 5-$CH_3$ | Cl | H |
| B-255. | $CH_3$ | 5-$OCH_3$ | Cl | H |
| B-256. | $CH_3$ | 6-F | Cl | H |
| B-257. | $CH_3$ | 6-$CH_3$ | Cl | H |
| B-258. | $CH_3$ | 6-$OCH_3$ | Cl | H |
| B-259. | $OCH_3$ | 3-F | Cl | H |
| B-260. | $OCH_3$ | 3-$CH_3$ | Cl | H |
| B-261. | $OCH_3$ | 3-$OCH_3$ | Cl | H |
| B-262. | $OCH_3$ | 5-F | Cl | H |
| B-263. | $OCH_3$ | 5-$CH_3$ | Cl | H |
| B-264. | $OCH_3$ | 5-$OCH_3$ | Cl | H |
| B-265. | $OCH_3$ | 6-F | Cl | H |
| B-266. | $OCH_3$ | 6-$CH_3$ | Cl | H |
| B-267. | $OCH_3$ | 6-$OCH_3$ | Cl | H |
| B-268. | CN | 3-F | Cl | H |
| B-269. | CN | 3-$CH_3$ | Cl | H |
| B-270. | CN | 3-$OCH_3$ | Cl | H |
| B-271. | CN | 5-F | Cl | H |
| B-272. | CN | 5-$CH_3$ | Cl | H |
| B-273. | CN | 5-$OCH_3$ | Cl | H |
| B-274. | CN | 6-F | Cl | H |
| B-275. | CN | 6-$CH_3$ | Cl | H |
| B-276. | CN | 6-$OCH_3$ | Cl | H |
| B-277. | $CH_2F$ | 3-F | Cl | H |
| B-278. | $CH_2F$ | 3-$CH_3$ | Cl | H |
| B-279. | $CH_2F$ | 3-$OCH_3$ | Cl | H |
| B-280. | $CH_2F$ | 5-F | Cl | H |
| B-281. | $CH_2F$ | 5-$CH_3$ | Cl | H |
| B-282. | $CH_2F$ | 5-$OCH_3$ | Cl | H |
| B-283. | $CH_2F$ | 6-F | Cl | H |
| B-284. | $CH_2F$ | 6-$CH_3$ | Cl | H |
| B-285. | $CH_2F$ | 6-$OCH_3$ | Cl | H |
| B-286. | $CHF_2$ | 3-F | Cl | H |
| B-287. | $CHF_2$ | 3-$CH_3$ | Cl | H |
| B-288. | $CHF_2$ | 3-$OCH_3$ | Cl | H |
| B-289. | $CHF_2$ | 5-F | Cl | H |
| B-290. | $CHF_2$ | 5-$CH_3$ | Cl | H |
| B-291. | $CHF_2$ | 5-$OCH_3$ | Cl | H |
| B-292. | $CHF_2$ | 6-F | Cl | H |
| B-293. | $CHF_2$ | 6-$CH_3$ | Cl | H |
| B-294. | $CHF_2$ | 6-$OCH_3$ | Cl | H |
| B-295. | $CF_3$ | 3-F | Cl | H |
| B-296. | $CF_3$ | 3-$CH_3$ | Cl | H |
| B-297. | $CF_3$ | 3-$OCH_3$ | Cl | H |
| B-298. | $CF_3$ | 5-F | Cl | H |
| B-299. | $CF_3$ | 5-$CH_3$ | Cl | H |
| B-300. | $CF_3$ | 5-$OCH_3$ | Cl | H |
| B-301. | $CF_3$ | 6-F | Cl | H |
| B-302. | $CF_3$ | 6-$CH_3$ | Cl | H |
| B-303. | $CF_3$ | 6-$OCH_3$ | Cl | H |
| B-304. | $OCH_2F$ | 3-F | Cl | H |
| B-305. | $OCH_2F$ | 3-$CH_3$ | Cl | H |
| B-306. | $OCH_2F$ | 3-$OCH_3$ | Cl | H |
| B-307. | $OCH_2F$ | 5-F | Cl | H |
| B-308. | $OCH_2F$ | 5-$CH_3$ | Cl | H |
| B-309. | $OCH_2F$ | 5-$OCH_3$ | Cl | H |
| B-310. | $OCH_2F$ | 6-F | Cl | H |
| B-311. | $OCH_2F$ | 6-$CH_3$ | Cl | H |
| B-312. | $OCH_2F$ | 6-$OCH_3$ | Cl | H |
| B-313. | $OCHF_2$ | 3-F | Cl | H |
| B-314. | $OCHF_2$ | 3-$CH_3$ | Cl | H |
| B-315. | $OCHF_2$ | 3-$OCH_3$ | Cl | H |
| B-316. | $OCHF_2$ | 5-F | Cl | H |
| B-317. | $OCHF_2$ | 5-$CH_3$ | Cl | H |
| B-318. | $OCHF_2$ | 5-$OCH_3$ | Cl | H |
| B-319. | $OCHF_2$ | 6-F | Cl | H |
| B-320. | $OCHF_2$ | 6-$CH_3$ | Cl | H |
| B-321. | $OCHF_2$ | 6-$OCH_3$ | Cl | H |
| B-322. | $OCF_3$ | 3-F | Cl | H |
| B-323. | $OCF_3$ | 3-$CH_3$ | Cl | H |
| B-324. | $OCF_3$ | 3-$OCH_3$ | Cl | H |
| B-325. | $OCF_3$ | 5-F | Cl | H |

TABLE B-continued

| Example No. | R$^{8b}$ | R$^{8c}$ | R$^1$ | R$^2$ |
|---|---|---|---|---|
| B-326. | OCF$_3$ | 5-CH$_3$ | Cl | H |
| B-327. | OCF$_3$ | 5-OCH$_3$ | Cl | H |
| B-328. | OCF$_3$ | 6-F | Cl | H |
| B-329. | OCF$_3$ | 6-CH$_3$ | Cl | H |
| B-330. | OCF$_3$ | 6-OCH$_3$ | Cl | H |
| B-331. | H | H | CN | F |
| B-332. | F | H | CN | F |
| B-333. | CH$_3$ | H | CN | F |
| B-334. | OCH$_3$ | H | CN | F |
| B-335. | CN | H | CN | F |
| B-336. | CH$_2$F | H | CN | F |
| B-337. | CHF$_2$ | H | CN | F |
| B-338. | CF$_3$ | H | CN | F |
| B-339. | OCH$_2$F | H | CN | F |
| B-340. | OCHF$_2$ | H | CN | F |
| B-341. | OCF$_3$ | H | CN | F |
| B-342. | H | 3-F | CN | F |
| B-343. | H | 3-CH$_3$ | CN | F |
| B-344. | H | 3-OCH$_3$ | CN | F |
| B-345. | H | 5-F | CN | F |
| B-346. | H | 5-CH$_3$ | CN | F |
| B-347. | H | 5-OCH$_3$ | CN | F |
| B-348. | H | 6-F | CN | F |
| B-349. | H | 6-CH$_3$ | CN | F |
| B-350. | H | 6-OCH$_3$ | CN | F |
| B-351. | F | 3-F | CN | F |
| B-352. | F | 3-CH$_3$ | CN | F |
| B-353. | F | 3-OCH$_3$ | CN | F |
| B-354. | F | 5-F | CN | F |
| B-355. | F | 5-CH$_3$ | CN | F |
| B-356. | F | 5-OCH$_3$ | CN | F |
| B-357. | F | 6-F | CN | F |
| B-358. | F | 6-CH$_3$ | CN | F |
| B-359. | F | 6-OCH$_3$ | CN | F |
| B-360. | CH$_3$ | 3-F | CN | F |
| B-361. | CH$_3$ | 3-CH$_3$ | CN | F |
| B-362. | CH$_3$ | 3-OCH$_3$ | CN | F |
| B-363. | CH$_3$ | 5-F | CN | F |
| B-364. | CH$_3$ | 5-CH$_3$ | CN | F |
| B-365. | CH$_3$ | 5-OCH$_3$ | CN | F |
| B-366. | CH$_3$ | 6-F | CN | F |
| B-367. | CH$_3$ | 6-CH$_3$ | CN | F |
| B-368. | CH$_3$ | 6-OCH$_3$ | CN | F |
| B-369. | OCH$_3$ | 3-F | CN | F |
| B-370. | OCH$_3$ | 3-CH$_3$ | CN | F |
| B-371. | OCH$_3$ | 3-OCH$_3$ | CN | F |
| B-372. | OCH$_3$ | 5-F | CN | F |
| B-373. | OCH$_3$ | 5-CH$_3$ | CN | F |
| B-374. | OCH$_3$ | 5-OCH$_3$ | CN | F |
| B-375. | OCH$_3$ | 6-F | CN | F |
| B-376. | OCH$_3$ | 6-CH$_3$ | CN | F |
| B-377. | OCH$_3$ | 6-OCH$_3$ | CN | F |
| B-378. | CN | 3-F | CN | F |
| B-379. | CN | 3-CH$_3$ | CN | F |
| B-380. | CN | 3-OCH$_3$ | CN | F |
| B-381. | CN | 5-F | CN | F |
| B-382. | CN | 5-CH$_3$ | CN | F |
| B-383. | CN | 5-OCH$_3$ | CN | F |
| B-384. | CN | 6-F | CN | F |
| B-385. | CN | 6-CH$_3$ | CN | F |
| B-386. | CN | 6-OCH$_3$ | CN | F |
| B-387. | CH$_2$F | 3-F | CN | F |
| B-388. | CH$_2$F | 3-CH$_3$ | CN | F |
| B-389. | CH$_2$F | 3-OCH$_3$ | CN | F |
| B-390. | CH$_2$F | 5-F | CN | F |
| B-391. | CH$_2$F | 5-CH$_3$ | CN | F |
| B-392. | CH$_2$F | 5-OCH$_3$ | CN | F |
| B-393. | CH$_2$F | 6-F | CN | F |
| B-394. | CH$_2$F | 6-CH$_3$ | CN | F |
| B-395. | CH$_2$F | 6-OCH$_3$ | CN | F |
| B-396. | CHF$_2$ | 3-F | CN | F |
| B-397. | CHF$_2$ | 3-CH$_3$ | CN | F |
| B-398. | CHF$_2$ | 3-OCH$_3$ | CN | F |
| B-399. | CHF$_2$ | 5-F | CN | F |
| B-400. | CHF$_2$ | 5-CH$_3$ | CN | F |
| B-401. | CHF$_2$ | 5-OCH$_3$ | CN | F |
| B-402. | CHF$_2$ | 6-F | CN | F |
| B-403. | CHF$_2$ | 6-CH$_3$ | CN | F |
| B-404. | CHF$_2$ | 6-OCH$_3$ | CN | F |
| B-405. | CF$_3$ | 3-F | CN | F |
| B-406. | CF$_3$ | 3-CH$_3$ | CN | F |
| B-407. | CF$_3$ | 3-OCH$_3$ | CN | F |
| B-408. | CF$_3$ | 5-F | CN | F |
| B-409. | CF$_3$ | 5-CH$_3$ | CN | F |
| B-410. | CF$_3$ | 5-OCH$_3$ | CN | F |
| B-411. | CF$_3$ | 6-F | CN | F |
| B-412. | CF$_3$ | 6-CH$_3$ | CN | F |
| B-413. | CF$_3$ | 6-OCH$_3$ | CN | F |
| B-414. | OCH$_2$F | 3-F | CN | F |
| B-415. | OCH$_2$F | 3-CH$_3$ | CN | F |
| B-416. | OCH$_2$F | 3-OCH$_3$ | CN | F |
| B-417. | OCH$_2$F | 5-F | CN | F |
| B-418. | OCH$_2$F | 5-CH$_3$ | CN | F |
| B-419. | OCH$_2$F | 5-OCH$_3$ | CN | F |
| B-420. | OCH$_2$F | 6-F | CN | F |
| B-421. | OCH$_2$F | 6-CH$_3$ | CN | F |
| B-422. | OCH$_2$F | 6-OCH$_3$ | CN | F |
| B-423. | OCHF$_2$ | 3-F | CN | F |
| B-424. | OCHF$_2$ | 3-CH$_3$ | CN | F |
| B-425. | OCHF$_2$ | 3-OCH$_3$ | CN | F |
| B-426. | OCHF$_2$ | 5-F | CN | F |
| B-427. | OCHF$_2$ | 5-CH$_3$ | CN | F |
| B-428. | OCHF$_2$ | 5-OCH$_3$ | CN | F |
| B-429. | OCHF$_2$ | 6-F | CN | F |
| B-430. | OCHF$_2$ | 6-CH$_3$ | CN | F |
| B-431. | OCHF$_2$ | 6-OCH$_3$ | CN | F |
| B-432. | OCF$_3$ | 3-F | CN | F |
| B-433. | OCF$_3$ | 3-CH$_3$ | CN | F |
| B-434. | OCF$_3$ | 3-OCH$_3$ | CN | F |
| B-435. | OCF$_3$ | 5-F | CN | F |
| B-436. | OCF$_3$ | 5-CH$_3$ | CN | F |
| B-437. | OCF$_3$ | 5-OCH$_3$ | CN | F |
| B-438. | OCF$_3$ | 6-F | CN | F |
| B-439. | OCF$_3$ | 6-CH$_3$ | CN | F |
| B-440. | OCF$_3$ | 6-OCH$_3$ | CN | F |
| B-441. | H | H | F | F |
| B-442. | F | H | F | F |
| B-443. | CH$_3$ | H | F | F |
| B-444. | OCH$_3$ | H | F | F |
| B-445. | CN | H | F | F |
| B-446. | CH$_2$F | H | F | F |
| B-447. | CHF$_2$ | H | F | F |
| B-448. | CF$_3$ | H | F | F |
| B-449. | OCH$_2$F | H | F | F |
| B-450. | OCHF$_2$ | H | F | F |
| B-451. | OCF$_3$ | H | F | F |
| B-452. | H | 3-F | F | F |
| B-453. | H | 3-CH$_3$ | F | F |
| B-454. | H | 3-OCH$_3$ | F | F |
| B-455. | H | 5-F | F | F |
| B-456. | H | 5-CH$_3$ | F | F |
| B-457. | H | 5-OCH$_3$ | F | F |
| B-458. | H | 6-F | F | F |
| B-459. | H | 6-CH$_3$ | F | F |
| B-460. | H | 6-OCH$_3$ | F | F |
| B-461. | F | 3-F | F | F |
| B-462. | F | 3-CH$_3$ | F | F |
| B-463. | F | 3-OCH$_3$ | F | F |
| B-464. | F | 5-F | F | F |
| B-465. | F | 5-CH$_3$ | F | F |
| B-466. | F | 5-OCH$_3$ | F | F |
| B-467. | F | 6-F | F | F |
| B-468. | F | 6-CH$_3$ | F | F |
| B-469. | F | 6-OCH$_3$ | F | F |
| B-470. | CH$_3$ | 3-F | F | F |
| B-471. | CH$_3$ | 3-CH$_3$ | F | F |
| B-472. | CH$_3$ | 3-OCH$_3$ | F | F |
| B-473. | CH$_3$ | 5-F | F | F |
| B-474. | CH$_3$ | 5-CH$_3$ | F | F |
| B-475. | CH$_3$ | 5-OCH$_3$ | F | F |
| B-476. | CH$_3$ | 6-F | F | F |
| B-477. | CH$_3$ | 6-CH$_3$ | F | F |
| B-478. | CH$_3$ | 6-OCH$_3$ | F | F |
| B-479. | OCH$_3$ | 3-F | F | F |
| B-480. | OCH$_3$ | 3-CH$_3$ | F | F |
| B-481. | OCH$_3$ | 3-OCH$_3$ | F | F |

TABLE B-continued

| Example No. | $R^{8b}$ | $R^{8c}$ | $R^1$ | $R^2$ |
|---|---|---|---|---|
| B-482. | OCH$_3$ | 5-F | F | F |
| B-483. | OCH$_3$ | 5-CH$_3$ | F | F |
| B-484. | OCH$_3$ | 5-OCH$_3$ | F | F |
| B-485. | OCH$_3$ | 6-F | F | F |
| B-486. | OCH$_3$ | 6-CH$_3$ | F | F |
| B-487. | OCH$_3$ | 6-OCH$_3$ | F | F |
| B-488. | CN | 3-F | F | F |
| B-489. | CN | 3-CH$_3$ | F | F |
| B-490. | CN | 3-OCH$_3$ | F | F |
| B-491. | CN | 5-F | F | F |
| B-492. | CN | 5-CH$_3$ | F | F |
| B-493. | CN | 5-OCH$_3$ | F | F |
| B-494. | CN | 6-F | F | F |
| B-495. | CN | 6-CH$_3$ | F | F |
| B-496. | CN | 6-OCH$_3$ | F | F |
| B-497. | CH$_2$F | 3-F | F | F |
| B-498. | CH$_2$F | 3-CH$_3$ | F | F |
| B-499. | CH$_2$F | 3-OCH$_3$ | F | F |
| B-500. | CH$_2$F | 5-F | F | F |
| B-501. | CH$_2$F | 5-CH$_3$ | F | F |
| B-502. | CH$_2$F | 5-OCH$_3$ | F | F |
| B-503. | CH$_2$F | 6-F | F | F |
| B-504. | CH$_2$F | 6-CH$_3$ | F | F |
| B-505. | CH$_2$F | 6-OCH$_3$ | F | F |
| B-506. | CHF$_2$ | 3-F | F | F |
| B-507. | CHF$_2$ | 3-CH$_3$ | F | F |
| B-508. | CHF$_2$ | 3-OCH$_3$ | F | F |
| B-509. | CHF$_2$ | 5-F | F | F |
| B-510. | CHF$_2$ | 5-CH$_3$ | F | F |
| B-511. | CHF$_2$ | 5-OCH$_3$ | F | F |
| B-512. | CHF$_2$ | 6-F | F | F |
| B-513. | CHF$_2$ | 6-CH$_3$ | F | F |
| B-514. | CHF$_2$ | 6-OCH$_3$ | F | F |
| B-515. | CF$_3$ | 3-F | F | F |
| B-516. | CF$_3$ | 3-CH$_3$ | F | F |
| B-517. | CF$_3$ | 3-OCH$_3$ | F | F |
| B-518. | CF$_3$ | 5-F | F | F |
| B-519. | CF$_3$ | 5-CH$_3$ | F | F |
| B-520. | CF$_3$ | 5-OCH$_3$ | F | F |
| B-521. | CF$_3$ | 6-F | F | F |
| B-522. | CF$_3$ | 6-CH$_3$ | F | F |
| B-523. | CF$_3$ | 6-OCH$_3$ | F | F |
| B-524. | OCH$_2$F | 3-F | F | F |
| B-525. | OCH$_2$F | 3-CH$_3$ | F | F |
| B-526. | OCH$_2$F | 3-OCH$_3$ | F | F |
| B-527. | OCH$_2$F | 5-F | F | F |
| B-528. | OCH$_2$F | 5-CH$_3$ | F | F |
| B-529. | OCH$_2$F | 5-OCH$_3$ | F | F |
| B-530. | OCH$_2$F | 6-F | F | F |
| B-531. | OCH$_2$F | 6-CH$_3$ | F | F |
| B-532. | OCH$_2$F | 6-OCH$_3$ | F | F |
| B-533. | OCHF$_2$ | 3-F | F | F |
| B-534. | OCHF$_2$ | 3-CH$_3$ | F | F |
| B-535. | OCHF$_2$ | 3-OCH$_3$ | F | F |
| B-536. | OCHF$_2$ | 5-F | F | F |
| B-537. | OCHF$_2$ | 5-CH$_3$ | F | F |
| B-538. | OCHF$_2$ | 5-OCH$_3$ | F | F |
| B-539. | OCHF$_2$ | 6-F | F | F |
| B-540. | OCHF$_2$ | 6-CH$_3$ | F | F |
| B-541. | OCHF$_2$ | 6-OCH$_3$ | F | F |
| B-542. | OCF$_3$ | 3-F | F | F |
| B-543. | OCF$_3$ | 3-CH$_3$ | F | F |
| B-544. | OCF$_3$ | 3-OCH$_3$ | F | F |
| B-545. | OCF$_3$ | 5-F | F | F |
| B-546. | OCF$_3$ | 5-CH$_3$ | F | F |
| B-547. | OCF$_3$ | 5-OCH$_3$ | F | F |
| B-548. | OCF$_3$ | 6-F | F | F |
| B-549. | OCF$_3$ | 6-CH$_3$ | F | F |
| B-550. | OCF$_3$ | 6-OCH$_3$ | F | F |
| B-551. | H | H | Cl | F |
| B-552. | F | H | Cl | F |
| B-553. | CH$_3$ | H | Cl | F |
| B-554. | OCH$_3$ | H | Cl | F |
| B-555. | CN | H | Cl | F |
| B-556. | CH$_2$F | H | Cl | F |
| B-557. | CHF$_2$ | H | Cl | F |
| B-558. | CF$_3$ | H | Cl | F |
| B-559. | OCH$_2$F | H | Cl | F |
| B-560. | OCHF$_2$ | H | Cl | F |
| B-561. | OCF$_3$ | H | Cl | F |
| B-562. | H | 3-F | Cl | F |
| B-563. | H | 3-CH$_3$ | Cl | F |
| B-564. | H | 3-OCH$_3$ | Cl | F |
| B-565. | H | 5-F | Cl | F |
| B-566. | H | 5-CH$_3$ | Cl | F |
| B-567. | H | 5-OCH$_3$ | Cl | F |
| B-568. | H | 6-F | Cl | F |
| B-569. | H | 6-CH$_3$ | Cl | F |
| B-570. | H | 6-OCH$_3$ | Cl | F |
| B-571. | F | 3-F | Cl | F |
| B-572. | F | 3-CH$_3$ | Cl | F |
| B-573. | F | 3-OCH$_3$ | Cl | F |
| B-574. | F | 5-F | Cl | F |
| B-575. | F | 5-CH$_3$ | Cl | F |
| B-576. | F | 5-OCH$_3$ | Cl | F |
| B-577. | F | 6-F | Cl | F |
| B-578. | F | 6-CH$_3$ | Cl | F |
| B-579. | F | 6-OCH$_3$ | Cl | F |
| B-580. | CH$_3$ | 3-F | Cl | F |
| B-581. | CH$_3$ | 3-CH$_3$ | Cl | F |
| B-582. | CH$_3$ | 3-OCH$_3$ | Cl | F |
| B-583. | CH$_3$ | 5-F | Cl | F |
| B-584. | CH$_3$ | 5-CH$_3$ | Cl | F |
| B-585. | CH$_3$ | 5-OCH$_3$ | Cl | F |
| B-586. | CH$_3$ | 6-F | Cl | F |
| B-587. | CH$_3$ | 6-CH$_3$ | Cl | F |
| B-588. | CH$_3$ | 6-OCH$_3$ | Cl | F |
| B-589. | OCH$_3$ | 3-F | Cl | F |
| B-590. | OCH$_3$ | 3-CH$_3$ | Cl | F |
| B-591. | OCH$_3$ | 3-OCH$_3$ | Cl | F |
| B-592. | OCH$_3$ | 5-F | Cl | F |
| B-593. | OCH$_3$ | 5-CH$_3$ | Cl | F |
| B-594. | OCH$_3$ | 5-OCH$_3$ | Cl | F |
| B-595. | OCH$_3$ | 6-F | Cl | F |
| B-596. | OCH$_3$ | 6-CH$_3$ | Cl | F |
| B-597. | OCH$_3$ | 6-OCH$_3$ | Cl | F |
| B-598. | CN | 3-F | Cl | F |
| B-599. | CN | 3-CH$_3$ | Cl | F |
| B-600. | CN | 3-OCH$_3$ | Cl | F |
| B-601. | CN | 5-F | Cl | F |
| B-602. | CN | 5-CH$_3$ | Cl | F |
| B-603. | CN | 5-OCH$_3$ | Cl | F |
| B-604. | CN | 6-F | Cl | F |
| B-605. | CN | 6-CH$_3$ | Cl | F |
| B-606. | CN | 6-OCH$_3$ | Cl | F |
| B-607. | CH$_2$F | 3-F | Cl | F |
| B-608. | CH$_2$F | 3-CH$_3$ | Cl | F |
| B-609. | CH$_2$F | 3-OCH$_3$ | Cl | F |
| B-610. | CH$_2$F | 5-F | Cl | F |
| B-611. | CH$_2$F | 5-CH$_3$ | Cl | F |
| B-612. | CH$_2$F | 5-OCH$_3$ | Cl | F |
| B-613. | CH$_2$F | 6-F | Cl | F |
| B-614. | CH$_2$F | 6-CH$_3$ | Cl | F |
| B-615. | CH$_2$F | 6-OCH$_3$ | Cl | F |
| B-616. | CHF$_2$ | 3-F | Cl | F |
| B-617. | CHF$_2$ | 3-CH$_3$ | Cl | F |
| B-618. | CHF$_2$ | 3-OCH$_3$ | Cl | F |
| B-619. | CHF$_2$ | 5-F | Cl | F |
| B-620. | CHF$_2$ | 5-CH$_3$ | Cl | F |
| B-621. | CHF$_2$ | 5-OCH$_3$ | Cl | F |
| B-622. | CHF$_2$ | 6-F | Cl | F |
| B-623. | CHF$_2$ | 6-CH$_3$ | Cl | F |
| B-624. | CHF$_2$ | 6-OCH$_3$ | Cl | F |
| B-625. | CF$_3$ | 3-F | Cl | F |
| B-626. | CF$_3$ | 3-CH$_3$ | Cl | F |
| B-627. | CF$_3$ | 3-OCH$_3$ | Cl | F |
| B-628. | CF$_3$ | 5-F | Cl | F |
| B-629. | CF$_3$ | 5-CH$_3$ | Cl | F |
| B-630. | CF$_3$ | 5-OCH$_3$ | Cl | F |
| B-631. | CF$_3$ | 6-F | Cl | F |
| B-632. | CF$_3$ | 6-CH$_3$ | Cl | F |
| B-633. | CF$_3$ | 6-OCH$_3$ | Cl | F |
| B-634. | OCH$_2$F | 3-F | Cl | F |
| B-635. | OCH$_2$F | 3-CH$_3$ | Cl | F |
| B-636. | OCH$_2$F | 3-OCH$_3$ | Cl | F |
| B-637. | OCH$_2$F | 5-F | Cl | F |

TABLE B-continued

| Example No. | $R^{8b}$ | $R^{8c}$ | $R^1$ | $R^2$ |
|---|---|---|---|---|
| B-638. | OCH$_2$F | 5-CH$_3$ | Cl | F |
| B-639. | OCH$_2$F | 5-OCH$_3$ | Cl | F |
| B-640. | OCH$_2$F | 6-F | Cl | F |
| B-641. | OCH$_2$F | 6-CH$_3$ | Cl | F |
| B-642. | OCH$_2$F | 6-OCH$_3$ | Cl | F |
| B-643. | OCHF$_2$ | 3-F | Cl | F |
| B-644. | OCHF$_2$ | 3-CH$_3$ | Cl | F |
| B-645. | OCHF$_2$ | 3-OCH$_3$ | Cl | F |
| B-646. | OCHF$_2$ | 5-F | Cl | F |
| B-647. | OCHF$_2$ | 5-CH$_3$ | Cl | F |
| B-648. | OCHF$_2$ | 5-OCH$_3$ | Cl | F |
| B-649. | OCHF$_2$ | 6-F | Cl | F |
| B-650. | OCHF$_2$ | 6-CH$_3$ | Cl | F |
| B-651. | OCHF$_2$ | 6-OCH$_3$ | Cl | F |
| B-652. | OCF$_3$ | 3-F | Cl | F |
| B-653. | OCF$_3$ | 3-CH$_3$ | Cl | F |
| B-654. | OCF$_3$ | 3-OCH$_3$ | Cl | F |
| B-655. | OCF$_3$ | 5-F | Cl | F |
| B-656. | OCF$_3$ | 5-CH$_3$ | Cl | F |
| B-657. | OCF$_3$ | 5-OCH$_3$ | Cl | F |
| B-658. | OCF$_3$ | 6-F | Cl | F |
| B-659. | OCF$_3$ | 6-CH$_3$ | Cl | F |
| B-660. | OCF$_3$ | 6-OCH$_3$ | Cl | F |

The positions (e.g. 3-/5-/6-) of $R^3$ are relative to the 2- and 4-positions of radicals $R^1$ and $R^2$ and to the 1-position of the attachment point of the ring to the SO$_2$ group.

The preferred compounds among the compounds I.1 to I.128 mentioned above are those of the formulae I.1, I.2, I.3, I.4, I.5, I.9, I.13, I.15, I.17, I.19, I.33, I.35, I.49, I.51, I.65, I.67, I.81, I.83, I.97, I.99, I.113 and I.115. More preferred are those of formulae I.1, I.3, I.17, I.19, I.33, I.35, I.49, I.51, I.65, I.67, I.81, I.83, I.97, I.99, I.113 and I.115. Particularly preferred are compounds of the formulae I.1 and I.3.

In a specific embodiment, the compounds I are selected from the compounds specified in the examples, either as a free base or in form of a pharmaceutically acceptable salt, an N-oxide or a stereoisomer or the racemate or any mixture of stereoisomers thereof.

The compounds I of the invention have a center of chirality in position 3 of the 2-oxindole ring. The compounds of the invention may therefore be in the form of a 1:1 mixture of enantiomers (racemate) or of a nonracemic mixture of enantiomers in which one of the two enantiomers, either the enantiomer which rotates the plane of vibration of linearly polarized light to the left (i e minus rotation) (hereinafter (−) enantiomer) or the enantiomer which rotates the plane of vibration of linearly polarized light to the right (i.e. plus rotation) (hereinafter (+) enantiomer), is enriched, or of substantially enantiopure compounds, that is to say of substantially enantiopure (−) enantiomer or (+) enantiomer. Since the compounds of the invention have a single center of asymmetry and no axis/plane of chirality, a nonracemic mixture can also be defined as a mixture of enantiomers in which either the R or the S enantiomer predominates. Substantially enantiopure compounds can accordingly also be defined as substantially enantiopure R enantiomer or substantially enantiopure S enantiomer.

"Substantially enantiopure compounds" means in the context of the present invention those compounds having an enantiomeric excess (ee; % ee=(R−S)/(R+S)×100 or (S−R)/(S+R)×100) of at least 80% ee, preferably at least 85% ee, more preferably at least 90% ee, even more preferably at least 95% ee and in particular at least 98% ee.

In one embodiment of the invention, the compounds of the invention are in the form of substantially enantiopure compounds. Particularly preferred compounds have an enantiomeric excess of at least 85% ee, more preferably of at least 90% ee, even more preferably of at least 95% ee and in particular of at least 98% ee.

The invention thus relates both to the pure enantiomers and to mixtures thereof, e.g. mixtures in which one enantiomer is present in enriched form, but also to the racemates. The invention also relates to the pharmaceutically acceptable salts of the pure enantiomers of compounds I, and the mixtures of enantiomers in the form of the pharmaceutically acceptable salts of compounds I.

Preferred embodiments of the invention are compounds of the formula I as detailed above which are characterized in that they are in optically active form, and the enantiomer of the relevant compound of the formula I is the S-enantiomer, in the form of a free base, or a pharmaceutically acceptable salt thereof.

Particularly preference is given to compounds of the general formula I and their pharmaceutically acceptable salts as detailed above in which the corresponding S-enantiomer is present in an optical purity (enantiomeric excess, ee) of more than 50% ee, particularly preferably of at least 80% ee, more preferably of at least 90% ee and even more preferably of at least 95% ee and in particular of at least 98% ee.

Likewise preferred embodiments of the invention are compounds of the general formula I as detailed above which are characterized in that they are in optically inactive form, i.e. in the form of the racemate, or in the form of a pharmaceutically acceptable salt of the racemate.

Examples of synthetic routes for preparing the oxindole derivatives of the invention are described below.

The compounds of the invention can be prepared by using methods described in WO 2005/030755 and WO 2006/005609 for synthesizing analogous compounds, and the preparation is outlined by way of example in synthesis schemes 1 to 4. If not indicated otherwise, the variables in these synthetic schemes have the same meanings as in formula I.

The 3-hydroxy-1,3-dihydroindol-2-ones IV can be obtained by addition of metallated benzenes or heterocycles III onto the 3-keto group of the isatins II. The metallated benzenes or heterocycles, such as, for example, the corresponding Grignard (Mg) or organyllithium compound, can be obtained in any conventional way from halogen or hydrocarbon compounds. Examples of methods are present in Houben-Weyl, Methoden der Organischen Chemie, vol. 13, 1-2, chapter on Mg and Li compounds. The isatins II are either commercially available or were prepared in analogy to methods described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

The 3-hydroxyoxindoles IV which comprise an iodine in the 6-membered aromatic ring, for example in position 5 or 6, i.e. in the position of the radicals $R^1$ or $R^2$, can be converted with KCN or Zn(CN)$_2$ with Pd(0) catalysis in solvents such as dimethylformamide or tetrahydrofuran, where appropriate also with addition of bases such as K$_2$CO$_3$ or other carbonates or amines, at elevated temperature into the analogous cyan-containing 3-hydroxyoxindole IV. Pd(0) salts which can be taken are for example transition metal complexes which are prepared in situ from PdCl$_2$ or PdOAc$_2$ by addition of phosphines such as tris(orthotolyl) phosphine. It is likewise possible to employ commercial palladium complexes such as, for example, the catalyst tetrakis(triphenylphosphine)palladium(0) and/or additions of phosphine ligands.

The 3-hydroxyoxindoles IV can be converted into the compounds V which have a leaving group LG' in position 3, where the leaving group LG' is a conventional leaving group such as, for example, chlorine or bromide. The intermediate V with for example LG'=chlorine can be prepared by treating the alcohol IV with thionyl chloride in the presence of a base such as, for example, pyridine, in a suitable solvent such as, for example, dichloromethane.

The compounds V can subsequently be reacted with amines, such as, for example, ammonia, in a substitution reaction to give the amines VI. The compounds VI can subsequently be converted by treatment with sulfonyl chlorides VII after deprotonation with a strong base such as, for example, potassium tert-butoxide or sodium hydride in DMF into the sulfonylated product VIII. The sulfonyl chlorides VII employed can either be purchased or be prepared by known processes (for example J. Med. Chem. 40, 1149 (1997)).

The compounds of the invention of the general formula I which have a urea group in position 3 (in other words: compounds I wherein $X^1$ is NH and $X^2$ is N) can be prepared as described in WO 2005/030755 and WO 2006/005609, and shown in synthesis scheme 1, in a two-stage process: firstly, the compounds VIII are reacted with phenyl chloroformate in the presence of a base such as, for example, pyridine to give the corresponding phenyl carbamate IX.

Subsequent reaction with amines X, where appropriate at elevated temperature and with the addition of auxiliary bases such as, for example, triethylamine or diisopropylethylamine, leads to the compounds of the invention of the general formula (I) with a urea bridge ($X^1$=NH). The amines X can be either purchased or prepared by methods known from the literature. Compounds I of the invention with $R^3$=H can be prepared by using appropriate Boc-protected amines ($R^3$=Boc). The Boc protective group can subsequently be removed, for example by treatment with trifluoroacetic acid in dichloromethane.

Synthesis Scheme 1

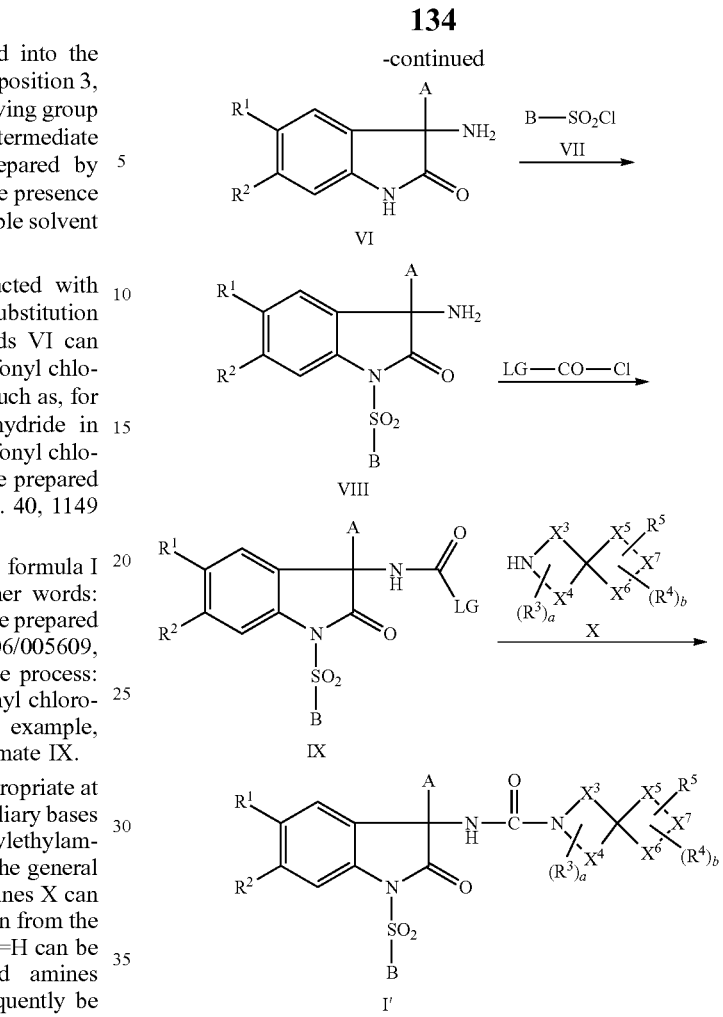

Ph = Phenyl
LG' = leaving group, such as for example Cl
LG = leaving group, such as for example PhO (Phenoxy)

The compounds of the invention of the general formula I having a carbamate group in position 3 (in other words: compounds I wherein $X^1$ is O and $X^2$ is N) can be prepared as described in WO 2006/005609 and shown in synthesis scheme 2: firstly, the 3-hydroxy compound IV is reacted with phenyl chloroformate to give the phenyl carbonate derivatives XIa and/or XIb. The carbamate derivatives XII are obtained with an excess of amine X and can subsequently be converted under the usual conditions (deprotonation with a strong base such as, for example, sodium hydride or potassium tert-butoxide in a suitable solvent such as, for example, DMF, followed by treatment with sulfonyl chlorides VII) into the compounds I of the invention with a carbamate bridge.

Synthesis Scheme 2

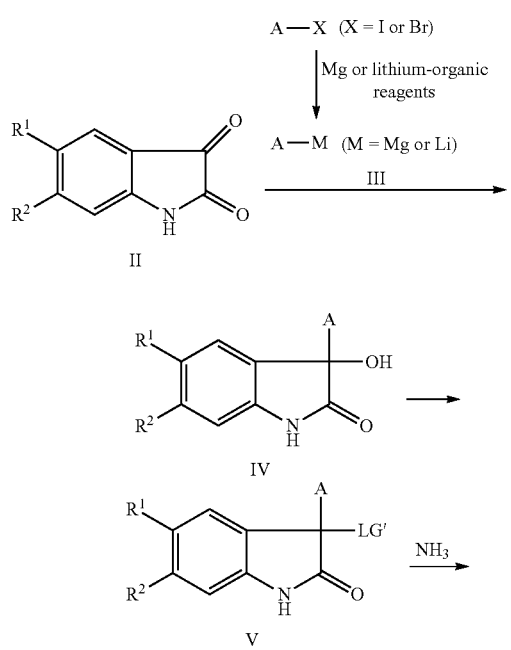

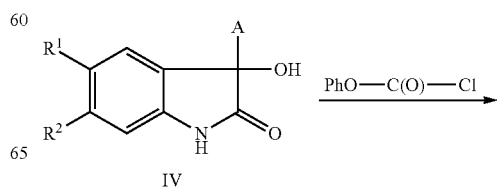

Synthesis Scheme 3

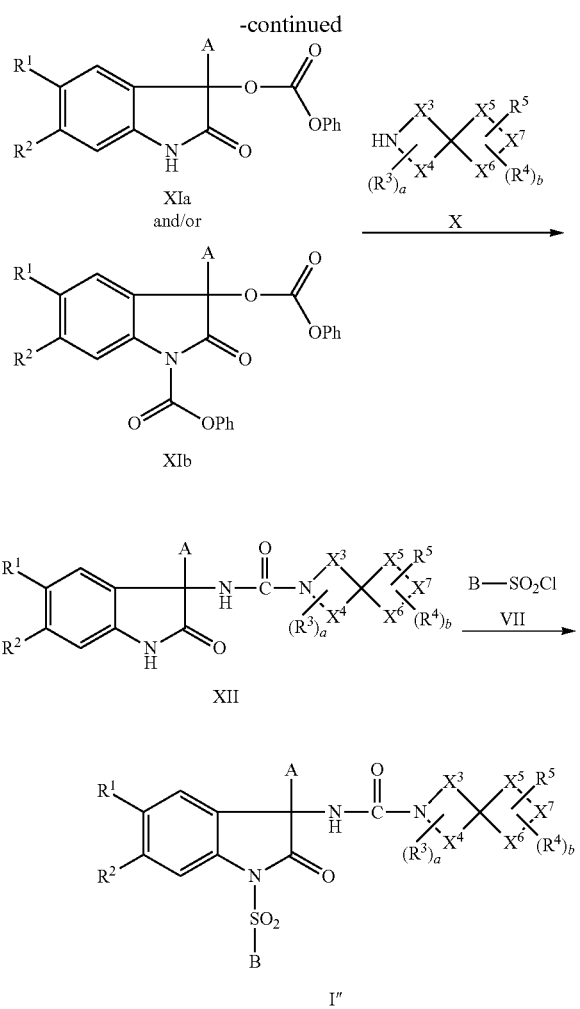

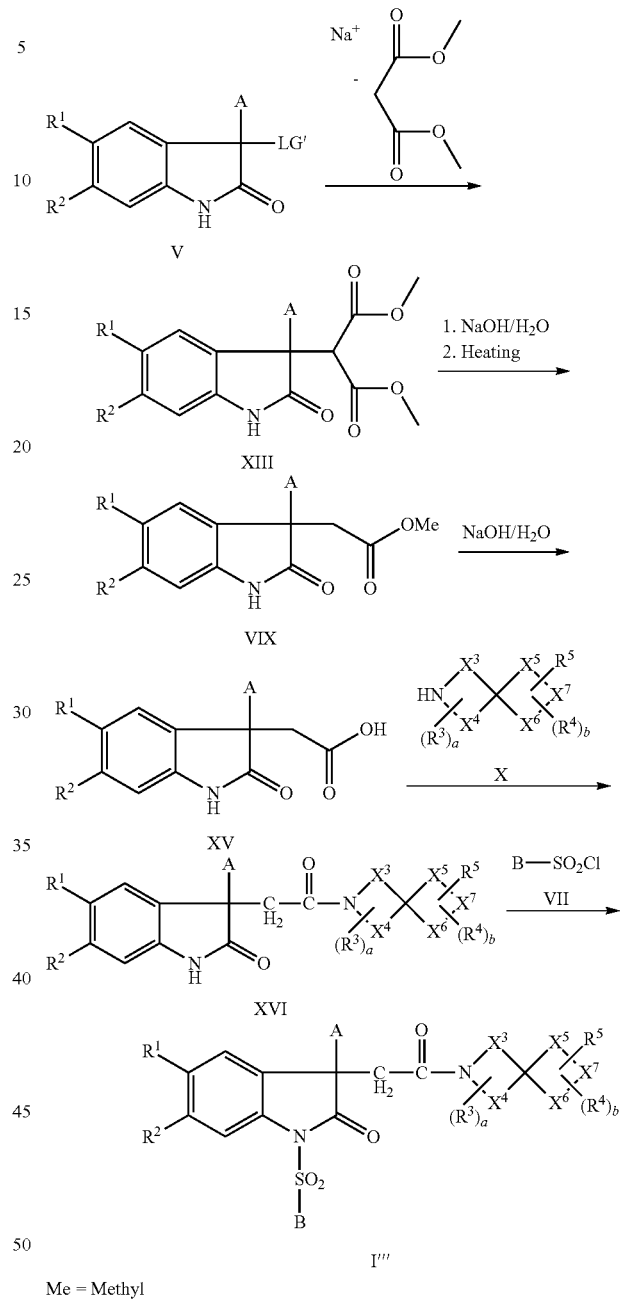

Ph = Phenyl

Me = Methyl

The compounds of the invention of the general formula I which have a 2-oxo-ethyl group in position 3 (in other words: compounds I wherein $X^1$ is $CH_2$ and $X^2$ is N) can be prepared as shown in synthesis scheme 3. Introduction of the acetic acid group can take place as described in WO 2006/005609 in a 4-stage sequence (1. replacement of the leaving group LG' in V by the sodium salt of dimethyl malonate, 2. hydrolysis of the first ester group, 3. thermal decarboxylation, 4. hydrolysis of the second ester group). The amine side chain X can be coupled to the carboxylic acid XV using standard coupling reagents known in peptide chemistry, such as, for example, EDC (N-(3-dimethylaminopropyl)-N'-ethylcarbodiimide hydrochloride) and HOBT (1-hydroxybenzotriazole) in a solvent such as, for example, N,N-dimethylformamide, or BOP (1-benzotriazolyloxytris(dimethylamino)phosphonium hexafluorophosphate) in the presence of a base such as triethylamine or diisopropyethylamine. The sulfonylation can take place by deprotonation of the coupling product XVI with a strong base such as, for example, sodium hydride or potassium tert-butoxide, and subsequent treatment with sulfonyl chlorides VII in a solvent such as, for example, DMF, and leads to the compounds I of the invention with an amide bridge.

Compounds I wherein $X^1$ is NH or O and $X^2$ is CH can be prepared as shown in synthesis scheme 4 in a standard amidation or esterification process. Amidation (when $X^1$ is NH) can be carried out by reacting the amine XVII with the acid XVIII under heating and removal of reaction water, but is preferably carried out by activation of the carboxylic acid XVIII with oxalylchloride [(COCl)$_2$] or thionylchloride (SOCl$_2$) to the respective acid chloride, followed by reaction with amine XVII. Alternatively, amidation is carried out in the presence of a coupling reagent. Suitable coupling reagent (activators) are well known and are for instance selected from carbodiimides, such as DCC (dicyclohexylcarbodiimide) and DIC (diisopropylcarbodiimide), benzotriazole derivatives, such as HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino)methylene]-5-chlorotetrafluoroborate) and phosphonium-derived activators, such as BOP ((benzotriazol-1-yloxy)-tris(dimethylamino)phosphonium hexafluorophosphate), Py-BOP ((benzotriazol-1-yloxy)-tripyrrolidinphosphonium hexafluorophosphate) and Py-BrOP (bromotripyrrolidinphosphonium hexafluorophosphate). Generally, the activator is used in excess. The benzotriazole and phosphonium coupling reagents are generally used in a basic medium. Alike, esterification (when $X^1$ is O) can be carried out by reacting the alcohol XVII with the acid XVIII under heating and removal of reaction water, but is preferably carried out by activation of the carboxylic acid XVIII with oxalylchloride [$(COCl)_2$] or thionylchloride ($SOCl_2$) to the respective acid chloride, followed by reaction with alcohol XVII.

Synthesis Scheme 4

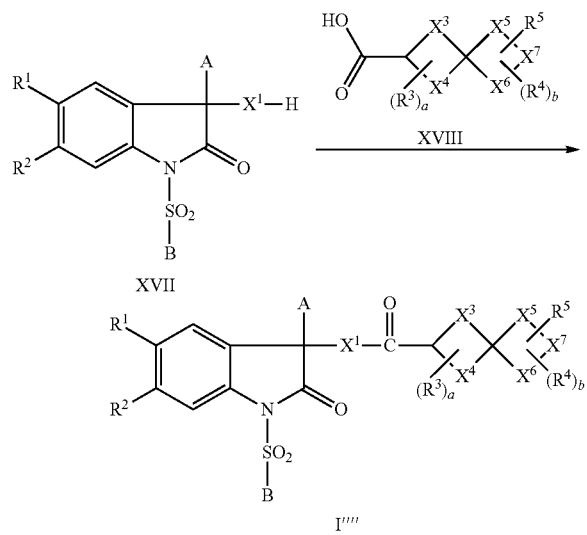

Compounds I wherein $X^1$ is $CH_2$ and $X^2$ is CH can be prepared in analogy to the synthetic routes described in Organic and Biomolecular Chemistry 2013, 11(40), 6984-6993 starting either from isatin II and the Grignard reagent A-M (III) or starting from the oxindole compounds IV or V and reacting these with either XIX or XX.

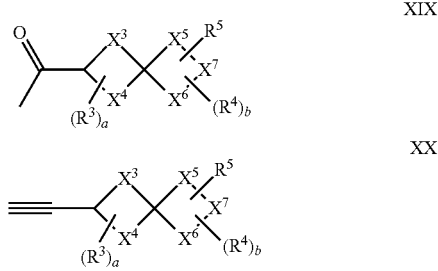

In case that XIX is used, $Cu(CF_3SO_3)_2$ is suitably used as catalyst, and in case that XX is used, $Sn(CF_3SO_3)_2$ is a suitable catalyst.

Compounds I wherein $X^1$ is $CH_2$ and $X^2$ is CH can also be prepared in analogy to the synthetic route described in J. Org. Chem. 2012, 77(24), 11325-11332 by decarboxylating β-ketoacid XXI in the presence of an oxindole compound V.

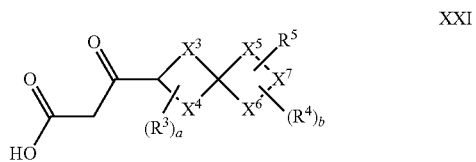

The sequence of reaction steps can be varied. For instance, in schemes 1 to 3, the (het)arylsulfonyl group B—$SO_2$— can be introduced earlier than shown, e.g. by reacting yet II, IV or V with VII in scheme 1, by reacting yet IV, XIa or XIb with VII in scheme 2 or by reacting yet V, XIII, XIV or XV with VII in scheme 3; or can be introduced later, e.g. after the introduction of X in scheme 1 or by reacting a compound XVII, which does however not carry the B—$SO_2$— group, with XVIII and only then with VII. Spiro compounds X can be used in protected form, if required, e.g. if one of $X^3$, $X^4$, $X^5$, $X^6$ and/or $X^7$ is NH and is not substituted by a radical $R^3$, $R^4$ or $R^5$ which confers protection to this nitrogen ring atom. Suitable protective groups are, for example, $C_1$-$C_4$-alkoxycarbonyl groups, such as tert-butoxycarbonyl (Boc), $C_1$-$C_4$-alkylcarbonyl groups, such as acetyl, $C_1$-$C_4$-alkylsulfonyl, phenylsulfonyl or benzyl. Usually, Boc is used. Moreover, radical $R^5$ (if not hydrogen) can be introduced at a later point of time; especially if bound to $X^7$. In this case, a compound I', I'', I''' or I'''', which does however not carry the radical $R^5$ and in which $X^7$ is NH, is reacted with a suitable precursor compound of $R^5$ (especially if $R^5$ is optionally substituted alkyl, alkenyl, alkynyl or cycloalkyl), such as $R^5$—Y wherein Y is a suitable leaving group such as Cl, Br, I or the triflate group. Phenyl or heterocyclyl groups $R^5$ can be introduced in a Buchwald-Hartwig reaction using a Pd catalyst.

In analogy to the findings described by Y. Naruse et al. in Tetrahedron Asymmetry 2013, 24, 169-171, the above synthetic routes may result in the formation of two conformers. If the (het)arylsulfonyl group B—$SO_2$— is introduced in the last step; i.e. after the spiro ring has been introduced, mostly only one conformer is obtained.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the preparation methods are within routine techniques.

Suitable protecting groups and the methods for protecting and deprotecting different substituents using such suitable protecting groups are well known to those skilled in the art; examples of which may be found in T. Greene and P. Wuts, Protective Groups in Organic Synthesis (3rd ed.), John Wiley & Sons, NY (1999), which is incorporated herein by reference in its entirety. Synthesis of the compounds of the invention may be accomplished by methods analogous to those described in the synthetic scheme described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

The present invention moreover relates to compounds of formula I as defined above, wherein at least one of the atoms has been replaced by its stable, non-radioactive isotope (e.g., hydrogen by deuterium, $^{12}C$ by $^{13}C$, $^{14}N$ by $^{15}N$, $^{16}O$ by $^{18}O$) and preferably wherein at least one hydrogen atom has been replaced by a deuterium atom.

Of course, the unlabeled compounds according to the invention might naturally include certain amounts of these respective isotopes. Therefore, when referring to compounds I, wherein at least one of the atoms has been replaced by its stable, non-radioactive isotope, it will be understood that the isotope is present in a higher amount than would naturally occur.

Stable isotopes (e.g., deuterium, $^{13}C$, $^{15}N$, $^{18}O$) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. J. Pharm. Sci. 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. Labelled Comp. Radiopharmaceut., 36(10): 927-932 (1995); Kushner et al., Can. J. Physiol. Pharmacol., 77, 79-88 (1999).

Incorporation of a heavy atom, particularly substitution of deuterium for hydrogen, can give rise to an isotope effect that could alter the pharmacokinetics of the drug.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as D2SO4/D2O. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., Drugs Fut, 21(11), 1116 (1996); Brickner, S J et al., J Med Chem, 39(3), 673 (1996); Mallesham, B et al., Org Lett, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

A further aspect of the present invention relates to a pharmaceutical composition comprising at least one compound of the general formula I and/or an N-oxide, a stereoisomer or a pharmaceutically acceptable salt thereof as detailed above, and a pharmaceutically acceptable carrier; or comprising at least one compound I wherein at least one of the atoms has been replaced by its stable, non-radioactive isotope, preferably wherein at least one hydrogen atom has been replaced by a deuterium atom, in combination with at least one pharmaceutically acceptable carrier and/or auxiliary substance. Suitable carriers depend inter alia on the dosage form of the composition and are known in principle to the skilled worker. Some suitable carriers are described hereinafter.

The present invention furthermore relates to a compound I as defined above or an N-oxide, a stereoisomer or a pharmaceutically acceptable salt thereof for use as a medicament. The present invention also relates to a compound I as defined above or an N-oxide, a stereoisomer or a pharmaceutically acceptable salt thereof for the treatment of vasopressin-related diseases, especially of disorders which respond to the modulation of the vasopressin receptor and in particular of the V1b receptor.

A further aspect of the present invention relates to the use of compounds of the formula I and/or of an N-oxide, a stereoisomer or of pharmaceutically acceptable salts thereof for the manufacture of a medicament for the treatment and/or prophylaxis of vasopressin-related diseases, especially of disorders which respond to the modulation of the vasopressin receptor and in particular of the V1b receptor.

Vasopressin-related diseases are those in which the progress of the disease is at least partly dependent on vasopressin, i.e. diseases which show an elevated vasopressin level which may contribute directly or indirectly to the pathological condition. In other words, vasopressin-related diseases are those which can be influenced by modulating the vasopressin receptor, for example by administration of a vasopressin receptor ligand (agonist, antagonist, partial antagonist/agonist, inverse agonist etc.).

Affective disorders have been related to excessive vasopressin function. Therefore, treatment with compounds targeting the vasopressin system, such as vasopressin antagonists are likely to benefit patients suffering from affective disorders (see for example Surget A., Belzung C., Involvement of vasopressin in affective disorders, Eur. J. Pharm. 2008, 583, 340-349). Affective disorders (mood disorders) include depressive disorders, anxiety disorders, obsessive-compulsive and related disorders, trauma and stressor-related disorders as well as bipolar and related disorders. V1b antagonist have been shown to have anti-drug abuse effects and reduce drug withdrawal effect (see e.g. Zhou Y., Leri F., Cummins E., Hoeschele M., Kreek M. J., Involvement of arginine vasopressin and V1b receptor in heroin withdrawal and heroin seeking precipitated by stress and by heroin. Neuropsychopharmacology, 2008, 33, 226-236). Therefore, compounds targeting the vasopressin system, such as vasopressin antagonists, are thought to be effective for treatment of substance-related and addictive disorders. V1b receptors play a role in a range of emotional responses such as aggression. Attenuating V1b receptor function genetically or with antagonist reduces aggressive behavior (Blanchard R. J., Griebel G., Farrokhi C., Markham C., Yang M., Blanchard D. C., AVP V1b selective antagonist SSR149415 blocks aggressive behaviors in hamsters. Pharmacol. Biochem. Behay. 2005, 80, 189-194; Wersinger S. R., Ginns E. I., O'Carroll A. M., Lolait S. J., Young W. S., III, Vasopressin V1b receptor knockout reduces aggressive behavior in male mice. Mol. Psychiatry, 2002, 7, 975-984). Therefore, attenuating V1b antagonists functioning is likely to reduce aggression and agitation in disorders such as Alzheimer's disease and schizophrenia and other psychiatric and neurological disorders in which aggressive behavior occurs, such as Alzheimer's disease, schizophrenia, bipolar disorder, frontal lobe injuries or substance use disorders.

High cortisol levels have been correlated to reduced cognitive performance in elderly and AD (Alzheimer's disease) patients, and such correlations are more pronounced in subjects carrying the APOϵ4 allele, which is a risk factor for AD (see for example Lee B. K., Glass T. A., Wand G. S., McAtee M. J., Bandeen-Roche K., Bolla K. I., Schwartz B. S., Apolipoprotein e genotype, cortisol, and cognitive function in community-dwelling older adults. Am. J. Psychiatry 2008, 165, 1456-1464). Furthermore, increased plasma cortisol has been associated with more rapid disease progression in AD patients. Animal studies show an interaction between glucocorticoids and AD pathology, including amyloid precursor protein and tau accumulation (see for example Budas G., Coughlan C. M., Seckl J. R., Breen K. C., The effect of corticosteroids on amyloid beta precursor protein/amyloid precursor-like protein expression and processing in vivo. Neurosci. Lett., 1999, 276, 61-64). Cognitive performance can be impaired by stress or exposure to high doses of corticosterone in laboratory animals (for review see Roozendaal B., Systems mediating acute glucocorticoid effects on memory consolidation and retrieval. Prog. Neuropsychopharmacol. Biol. Psychiatry, 2003, 27, 1213-1223). Therefore, lowering cortisol by treatment with V1b antagonist may enhance cognition or prevent/slow down the pathology or cognitive decline Alzheimer's disease patients and in patients with other cognitive impairment such as schizophrenia and depression.

In a preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from diabetes, insulin resistance, nocturnal enuresis, incontinence and diseases in which impairments of blood clotting occur, and/or for delaying micturition; as well as to compounds of the invention of the formula I or of an N-oxide, a stereoisomer or of pharmaceutically acceptable salts thereof for the treatment and/or prophylaxis of the above-listed diseases. The term "diabetes" means all types of diabetes, especially diabetes mellitus (including type I and especially type II), diabetes renalis and in particular diabetes insipidus. The types of diabetes are preferably diabetes mellitus of type II (with insulin resistance) or diabetes insipidus.

In a further preferred embodiment, the present invention relates to the use of compounds of the invention of the formula I or of an N-oxide, a stereoisomer or of pharmaceutically acceptable salts thereof for the manufacture of a medicament for the treatment and/or prophylaxis of diseases selected from hypertension, pulmonary hypertension, heart failure, myocardial infarction, coronary spasm, unstable angina, PTCA (percutaneous transluminal coronary angioplasty), ischemias of the heart, impairments of the renal system, edemas, renal vasospasm, necrosis of the renal cortex, hyponatremia, hypokalemia, Schwartz-Bartter syndrome, impairments of the gastrointestinal tract, gastritic vasospasm, hepatocirrhosis, gastric and intestinal ulcers, emesis, emesis occurring during chemotherapy, and travel sickness; as well as to compounds of the invention of the formula I or of an N-oxide, a stereoisomer or of pharmaceutically acceptable salts thereof for the treatment and/or prophylaxis of the above-listed diseases.

The compounds of the invention of the formula I or their N-oxides, stereoisomers or pharmaceutically acceptable salts or the pharmaceutical composition of the invention can also be used for the treatment of various vasopressin-related complaints which have central nervous causes or alterations in the HPA axis (hypothalamic pituitary adrenal axis), for example for affective disorders such as depressive disorders, anxiety disorders, obsessive-compulsive and related disorders, trauma and stressor-related disorders, and bipolar and related disorders. Depressive disorders include for example dysthymic disorders, major depression, seasonal depression, treatment-resistant depression disorders, disruptive mood dysregulation disorder, premenstrual dysphoric disorder, substance/medication-induced depressive disorder, depressive disorder due to another medical condition, or childhood onset mood disorders. Anxiety disorders include for example phobias, specific phobias, general anxiety disorders, panic disorders, drug withdrawal-induced anxiety disorders, separation anxiety disorder, selective mutism, social anxiety disorder, agoraphobia, substance/medication-induced anxiety disorder and anxiety disorder due to another medical condition. Obsessive-compulsive and related disorders include for example obsessive-compulsive disorder, body dysmorphic disorder, hoarding disorder, trichotillomania, excoriation disorder, substance/medication-induced obsessive-compulsive and related disorder and other specified obsessive-compulsive and related disorders. Trauma and stressor-related disorders include for example reactive attachment disorder, disinhibited social engagement disorder, post-traumatic stress disorder, acute stress disorder, adjustment disorder and other specified trauma- and stressor-related disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder.

Vasopressin-related complaints which have central nervous causes or alterations in the HPA axis are further cognitive disorders such as Alzheimer's disease, MCI (Mild Cognitive Impairment) and CIAS (Cognitive Impairment Associated with Schizophrenia).

The compounds of the invention of the formula I and their N-oxides, a stereoisomers or pharmaceutically acceptable salts or the pharmaceutical composition of the invention can likewise be employed for the treatment of anxiety disorders and stress-dependent anxiety disorders, such as, for example, generalized anxiety disorders, phobias, specific phobias, post-traumatic anxiety disorders, panic anxiety disorders, obsessive-compulsive anxiety disorders, acute stress-dependent anxiety disorders, drug withdrawal-induced anxiety disorders, separation anxiety disorder, selective mutism, social anxiety disorder, agoraphobia, substance/medication-induced anxiety disorder and anxiety disorder due to another medical condition and social phobia. The compounds of the invention of the formula I and their N-oxides, a stereoisomers or pharmaceutically acceptable salts or the pharmaceutical composition of the invention can likewise be employed for the treatment of obsessive-compulsive and related disorders, including, for example, obsessive-compulsive disorder, body dysmorphic disorder, hoarding disorder, trichotillomania, excoriation disorder, substance/medication-induced obsessive-compulsive and related disorder and other specified obsessive-compulsive and related disorders. The compounds of the invention of the formula I and their N-oxides, a stereoisomers or pharmaceutically acceptable salts or the pharmaceutical composition of the invention can likewise be employed for the treatment of trauma and stressor-related disorders, including, for example, reactive attachment disorder, disinhibited social engagement disorder, post-traumatic stress disorder, acute stress disorder, adjustment disorder and other specified trauma- and stressor-related disorders.

The compounds of the invention of the formula I and their N-oxides, stereoisomers or pharmaceutically acceptable salts or the pharmaceutical composition of the invention can likewise be employed for the treatment and/or prophylaxis of social impairment, such as autism or social impairment related with schizophrenia.

The compounds of the invention of the formula I and their N-oxides, stereoisomers or pharmaceutically acceptable salts or the pharmaceutical composition of the invention can likewise be employed for the treatment and/or prophylaxis of increased aggression in conditions selected from Alzheimer's disease, schizophrenia, bipolar disorder, frontal lobe injuries and substance use disorders.

The compounds of the invention can furthermore also be employed for the treatment of memory impairments, Alzheimer's disease, psychoses, psychotic disorders, sleep disorders and/or Cushing's syndrome, and all stress-dependent diseases.

Accordingly, a further preferred embodiment of the present invention relates to the use of compounds of the invention of the formula I or of an N-oxide, a stereoisomer or pharmaceutically acceptable salts thereof for the manufacture of a medicament for the treatment of affective disorders; as well as to compounds of the invention of the formula I or of an N-oxide, a stereoisomer or of pharmaceutically acceptable salts thereof for the treatment of affective disorders.

In a further preferred embodiment, the present invention relates to the use of compounds of the invention of the formula I or of an N-oxide, a stereoisomer or pharmaceutically acceptable salts thereof for the manufacture of a medicament for the treatment of anxiety disorders and/or stress-dependent anxiety disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of memory impairments and/or Alzheimer's disease; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of psychoses and/or psychotic disorders; as well as to compounds of the invention of the formula I or of an N-oxide, a stereoisomer or of pharmaceutically acceptable salts thereof for the treatment of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment of Cushing's syndrome or other stress-dependent diseases; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment of sleep disorders; as well as to compounds of the invention of the formula I or of an N-oxide, a stereoisomer or of pharmaceutically acceptable salts thereof for the treatment of sleep disorders.

In a further preferred embodiment, the present invention relates to the use of compounds of the invention of the formula I or of an N-oxide, a stereoisomer or pharmaceutically acceptable salts thereof for the manufacture of a medicament for the treatment of depressive disorders; as well as to compounds of the invention of the formula I or of an N-oxide, a stereoisomer or of pharmaceutically acceptable salts thereof for the treatment and/or prophylaxis of depressive disorders. In the case of depressive disorders, specific mention is to be made of childhood onset mood disorders, i.e. depressive moods having their onset in childhood, but also of major depression, seasonal depression, bipolar and related disorders, dysthymic disorders, disruptive mood dysregulation disorder, premenstrual dysphoric disorder, substance/medication-induced depressive disorder, and depressive disorder due to another medical condition, and especially of major depression and seasonal depression as well as of the depressive phases of bipolar disorders. Bipolar and related disorders include for example bipolar I disorder, bipolar II disorder, cyclothymic disorder, substance/medication-induced bipolar and related disorder, bipolar and related disorder due to another medical condition and unspecified bipolar and related disorder. The invention also relates to compounds of the formula I or N-oxides, stereoisomers or pharmaceutically acceptable salts thereof for the manufacture of a medicament for the treatment of treatment-resistant depression disorders and for the use in an add-on therapy of depressive disorders.

In a further preferred embodiment, the present invention relates to the use of compounds of the invention of the formula I or of an N-oxide, a stereoisomer or pharmaceutically acceptable salts thereof for the manufacture of a medicament for the treatment of vasomotor symptoms and/or thermoregulatory dysfunctions such as, for example, the hot flush symptom; as well as to compounds of the invention of the formula I or of an N-oxide, a stereoisomer or of pharmaceutically acceptable salts thereof for the treatment of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of drug or pharmaceutical dependencies and/or dependencies mediated by other factors, for the treatment of drug-use disorders, for the treatment and/or prophylaxis of stress caused by withdrawal of one or more factors mediating the dependence and/or for the treatment and/or prophylaxis of stress-induced relapses into drug or pharmaceutical dependencies and/or dependencies mediated by other factors; as well as to compounds of the invention of the formula I or of an N-oxide, a stereoisomer or of pharmaceutically acceptable salts thereof for the treatment and/or prophylaxis of the above-listed diseases. To be more precise, the present invention relates to the use of compounds of the invention of the formula I or of an N-oxide, a stereoisomer or pharmaceutically acceptable salts thereof for the manufacture of a medicament for the treatment and/or prophylaxis of substance-related and addictive disorders such as substance use disorder, substance-induced disorder, alcohol use disorder, alcohol intoxication, alcohol withdrawal, unspecified alcohol-related disorder, caffeine intoxication, caffeine withdrawal, unspecified caffeine disorder, cannabis use disorder, cannabis withdrawal, unspecified cannabis-related disorder, phencyclidine use disorder, other hallucinogen use disorders, phencyclidine intoxication, other hallucinogen disorders, hallucinogen persisting perception disorder, unspecified phencyclidine disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, unspecified tobacco-related disorder, other (or unknown) substance use disorders, other (or unknown) substance intoxication, other (or unknown) substance withdrawal, other (or unknown) substance related disorder and gambling disorder; as well as to compounds of the invention of the formula I or of an N-oxide, a stereoisomer or of pharmaceutically acceptable salts thereof for the treatment and/or prophylaxis of the above-listed diseases.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of schizophrenia and/or psychosis; as well as to compounds of the invention of the formula I or of an N-oxide, a stereoisomer or of pharmaceutically acceptable salts thereof for the treatment and/or prophylaxis of the above-listed disorders.

In a further preferred embodiment, the present invention relates to the use of compounds of the invention of the formula I or of an N-oxide, a stereoisomer or pharmaceutically acceptable salts thereof for the manufacture of a medicament for the treatment and/or prophylaxis of pain, e.g. acute or chronic pain, preferably chronic pain, especially neuropathic pain; as well as to compounds of the invention of the formula I or of an N-oxide, a stereoisomer or of pharmaceutically acceptable salts thereof for the treatment and/or prophylaxis of the above-listed disorders. Chronic pain may be a complex regional pain syndrome, pain arising from peripheral neuropathies, post-operative pain, chronic fatigue syndrome pain, tension-type headache, pain arising from mechanical nerve injury and severe pain associated with diseases such as cancer, metabolic disease, neurotropic viral disease, neurotoxicity, inflammation, multiple sclerosis or any pain arising as a consequence of or associated with stress or depressive illness.

A further aspect of the invention relates to a compound I or pharmaceutically acceptable salts thereof for use as a medicament, and to a compound I or an N-oxide, a stereoisomer or pharmaceutically acceptable salts thereof for the manufacture of a medicament for the treatment and/or prophylaxis of the above-defined diseases.

A further aspect of the invention relates to a method for the treatment and/or prophylaxis of vasopressin-related diseases, in which an effective amount of at least one compound of the invention of the formula I or of an N-oxide, a stereoisomer or of at least one pharmaceutically acceptable salt thereof or of a pharmaceutical composition of the invention is administered to a patient in need thereof.

Concerning the definition of vasopressin-related diseases, reference is made to the above statements made in context with the use according to the invention. Thus, preferred embodiments of the method of the invention correspond to preferred embodiments of the use according to the invention.

The patient to be treated prophylactically or therapeutically with the method of the invention is preferably a mammal, for example a human or a nonhuman mammal or a nonhuman transgenic mammal Specifically it is a human.

The compounds of the general formula I and their pharmaceutically acceptable salts as detailed above can be prepared by a skilled worker with knowledge of the technical teaching of the invention in implementing and/or in analogous implementation of process steps known per se.

The compounds I and/or their pharmaceutically acceptable salts, N-oxides and their stereoisomers are distinguished by having a selectivity for the vasopressin V1b receptor subtype vis-à-vis at least one of the closely related vasopressin/oxytocin receptor subtypes (for example vasopressin V1a, vasopressin V2 and/or oxytocin).

Alternatively, or preferably in addition, the compounds I and/or their pharmaceutically acceptable salts, N-oxides and a stereoisomers are distinguished by having an improved metabolic stability.

The metabolic stability of a compound can be measured for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible in this connection to conclude from an observed longer half-life that the metabolic stability of the compound is improved. The stability in the presence of human liver microsomes is of particular interest because it makes it possible to predict the metabolic degradation of the compound in the human liver. Compounds with increased metabolic stability (measured in the liver microsome test) are therefore probably also degraded more slowly in the liver. The slower metabolic degradation in the liver may lead to higher and/or longer-lasting concentrations (active levels) of the compound in the body, so that the elimination half-life of the compounds of the invention is increased. Increased and/or longer-lasting active levels may lead to a better activity of the compound in the treatment or prophylaxis of various vasopressin-related diseases. In addition, an improved metabolic stability may lead to an increased bioavailability after oral administration, because the compound is subject, after absorption in the intestine, to less metabolic degradation in the liver (so-called first pass effect). An increased oral bioavailability may, owing to an increased concentration (active level) of the compound, lead to a better activity of the compound after oral administration.

The compounds of the invention are effective after administration by various routes. Possible examples are intravenous, intramuscular, subcutaneous, topical, intratracheal, intranasal, transdermal, vaginal, rectal, sublingual, buccal or oral administration, and administration is frequently intravenous, intramuscular or, in particular, oral.

The present invention also relates to pharmaceutical compositions which comprise an effective dose of a compound I of the invention and/or an N-oxide, a stereoisomer and/or a pharmaceutically acceptable salt thereof and suitable pharmaceutical carriers (drug carriers).

These drug carriers are chosen according to the pharmaceutical form and the desired mode of administration and are known in principle to the skilled worker.

The compounds of the invention of the formula I, their N-oxides, stereoisomers or optionally suitable salts of these compounds can be used to produce pharmaceutical compositions for oral, sublingual, buccal, subcutaneous, intramuscular, intravenous, topical, intratracheal, intranasal, transdermal, vaginal or rectal administration, and be administered to animals or humans in uniform administration forms, mixed with conventional pharmaceutical carriers, for the prophylaxis or treatment of the above disorders or diseases.

The suitable administration forms (dose units) include forms for oral administration such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose can be administered once to 5 times a day, so that a daily dose of from 0.5 to 25 000 mg, preferably 1 to 5000 mg, is administered.

If a solid composition is prepared in the form of tablets, the active ingredient is mixed with a solid pharmaceutical carrier such as gelatin, starch, lactose, magnesium stearate, talc, silicon dioxide or the like.

The tablets can be coated with sucrose, a cellulose derivative or another suitable substance or be treated otherwise in order to display a sustained or delayed activity and to release a predetermined amount of the active ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may contain active ingredients together with a sweetener, which is preferably calorie-free, methylparaben or propylparaben as antiseptics, a flavoring and a suitable coloring substance.

Water-dispersible powders or granules may comprise the active ingredients mixed with dispersants, wetting agents or suspending agents, such as polyvinylpyrrolidones, and sweeteners or masking flavors.

Rectal or vaginal administration is achieved by using suppositories which are prepared with binders which melt at rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active ingredient may also be formulated as microcapsules or centrosomes, if suitable with one or more carriers or additives.

The compositions of the invention may, in addition to the compounds of the invention, comprise other active ingredients which may be beneficial for the treatment of the disorders or diseases indicated above.

The present invention thus further relates to pharmaceutical compositions in which a plurality of active ingredients are present together, where at least one of these is a compound I of the invention, or salt thereof.

The invention is explained in more detail below by means of examples, but the examples are not to be understood to be restrictive.

The compounds of the invention can be prepared by various synthetic routes. The methods mentioned, as described accordingly in synthesis schemes 1 to 4, are explained in greater detail merely by way of example using the given examples without being exclusively restricted to synthesis routes 1 to 4 or analogous methods.

EXPERIMENTAL SECTION

Abbreviations used:
rt room temperature (20-25° C.)
h hour(s)
min minute(s)
d day(s)
quant. quantitative
eq. equivalents)
conc. concentrated
TLC thin layer chromatography
RP reversed phase
aq. aqueous
MeOH methanol
EtOH ethanol
THF: tetrahydrofuran
DMF dimethylformamide
DMSO: dimethyl sulfoxide
EtOAc ethyl acetate
TFA: trifluoroacetic acid
DIPEA diisopropylethyl amine
p: pseudo (for example pt pseudo triplet)
b: broad (for example bs broad singlet)
s: singlet
d: doublet
t: triplet
m: multiplet
dd: doublet of doublets
dt: doublet of triplets
tt: triplet of triplets I. Preparation of Compounds of Formula I Example 1

N-[(3S)-5-Cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ and $R^{8c}$ are H and $R^{8b}$ is methoxy)

1.1 (S)-Phenyl (5-cyano-3-(2-ethoxypyridin-3-yl)-1-((4-methoxyphenyl)sulfonyl)-2-oxoindolin-3-yl) carbamate The title compound was prepared as described in WO2009/071691.
ESI-MS: [M+K$^+$]=623.2; [M+Na$^+$]=608.2; [M+H$^+$]= 585.2

1.2 (S)-tert-Butyl 6-((5-cyano-3-(2-ethoxypyridin-3-yl)-1-((4-methoxyphenyl)sulfonyl)-2-oxoindolin-3-yl)carbamoyl)-2,6-diazaspiro[3.3]heptane-2-carboxylate DIPEA (2.05 mmol, 0.36 ml) was added to a suspension of tert-butyl 2,6-diazaspiro[3.3]-heptane-2-carboxylate oxalate (0.41 mmol, 118 mg) in CH$_2$Cl$_2$ (10 ml). Once in solution, (S)-phenyl (5-cyano-3-(2-ethoxypyridin-3-yl)-1-((4-methoxyphenyl)sulfonyl)-2-oxoindolin-3-yl)carbamate (0.41 mmol, 240 mg) was added and the mixture was stirred for 12 h. The mixture was poured into cold 5% aq. K$_2$CO$_3$ (10 ml) and extracted with CH$_2$Cl$_2$ (3×10 ml); and the organic phases were combined, washed with water (3×10 ml), dried on Na$_2$SO$_4$, filtered, evaporated, and finally passed through a silicagel column (eluent: EtOAc). Yield: 205.5 mg (73%).
ESI-MS: [M$^+$–55 (isobutene)]=633.2; [M+H$^+$]=689.2

1.3 (S)-N-(5-Cyano-3-(2-ethoxypyridin-3-yl)-1-((4-methoxyphenyl)sulfonyl)-2-oxoindolin-3-yl)-2,6-diazaspiro[3.3]heptane-2-carboxamide TFA (20 eq., 5.95 mmol, 0.46 ml) was added to a solution of (S)-tert-butyl 6-((5-cyano-3-(2-ethoxypyridin-3-yl)-1-((4-methoxyphenyl)sulfonyl)-2-oxoindolin-3-yl)carbamoyl)-2,6-diazaspiro[3.3]heptane-2-carboxylate (0.30 mmol, 205 mg) in CH$_2$Cl$_2$ (10 ml). The mixture was stirred at rt for 1 h, poured into cold 5% aq. K$_2$CO$_3$ (10 ml) and extracted with CH$_2$Cl$_2$ (3×10 ml). The organic phases were combined, washed with water (3×10 ml), dried on Na$_2$SO$_4$, filtered, evaporated and finally passed through a silicagel column (eluent: CH$_2$Cl$_2$:2M NH$_3$/EtOH 17:3). Yield: 52.7 mg (30%).

ESI-MS: [M+H$^+$]=589.3

1.4 N-[(3S)-5-Cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide (S)-N-(5-cyano-3-(2-ethoxypyridin-3-yl)-1-((4-methoxyphenyl)sulfonyl)-2-oxo-indolin-3-yl)-2,6-diazaspiro[3.3]heptane-2-carboxamide (0.04 mmol, 25 mg), 2-morpholinoacetaldehyde (NaHSO$_3$-salt, 0.04 mmol, 10 mg), sodium acetate (0.09 mmol, 7 mg) and acetic acid (conc., 0.09 mmol, 5 mg) were dissolved in EtOH (1.5 ml) and stirred for 1 h. NaCNBH$_3$ (0.05 mmol, 3.2 mg) was added portionwise and stirred at rt for 12 h. The mixture was poured into cold 5% aq. K$_2$CO$_3$ (5 ml) and extracted with ethyl acetate (3×5 ml); the organic phases were combined, washed with water (3×5 ml) and dried on Na$_2$SO$_4$, filtered, evaporated and finally passed through a silicagel column (eluent: CH$_2$Cl$_2$: 2M NH$_3$/EtOH 19:1). Solvents were evaporated, the residue precipitated in water and the filtrate evaporated in vacuo. Yield: 4.81 mg (16%).

ESI-MS: [M+H$^+$]=702.3

The product was obtained in form of two conformers. These conformers were separated via RP-HPLC with following column: LUNA C18 Axia 100A 5µ 75×30; flow 40 ml/min; eluent gradient H$_2$O/10-90% methanol+0.1% trifluoroacetic acid.

Conformer 1A of N-[(3S)-5-cyano-3-(2-ethoxy-3-pyridyl)-1-(4-methoxyphenyl)-sulfonyl-2-oxo-indolin-3-yl]-2-(2-morpholinoethyl)-2,6-diazaspiro[3.3]heptane-6-carboxamide; 2,2,2-trifluoroacetic acid

ESI-MS: [M+H$^+$]=702.2

$^1$H NMR (CDCl$_3$, 600 MHz): d=8.22 (d, 1H), 7.85-7.78 (m, 2H), 7.78-7.72 (m, 2H), 7.37 (s br, 1H), 7.00 (s br, 1H), 6.94-6.85 (m br, 4H incl. 6.89 d), 4.41 (m sym., 2H), 4.35-4.30 (m, 2H), 4.30-4.22 (m, 3H), 4.17-4.03 (m br, 2H), 3.94-3.84 (m, 7H incl 3.87 s), 3.71 (br. s., 1H), 3.54-3.45 (m, 2H incl. 3.50 s), 3.16 (s br., 2H), 3.04 (br. s., 4H), 1.23 (m sym., 4H)

Conformer 1B of N-[(3S)-5-cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide; 2,2,2-trifluoroacetic acid

ESI-MS: [M+H$^+$]=702.2

$^1$H NMR (CDCl$_3$, 600 MHz): d=8.13 (d, 1H), 8.05 (d, 2H), 8.00 (d, 1H), 7.64 (s, 1H), 7.61 (d, 1H), 6.99 (d, 2H), 6.85 (m sym., 1H), 6.44 (s, 1H), 4.52 (m sym., 2H), 4.26 (dd, 4H), 4.06 (s br, 4H), 3.94 (m, 4H), 3.88 (s, 3H), 3.59 (m sym., 2H), 3.24 (m sym., 2H), 3.10 (br. s., 4H), 1.46 (t, 3H).

The following compounds were prepared analogously:

Example 2

N-[(3S)-5-Cyano-3-(2-ethoxy-3-pyridyl)-1-(4-methoxyphenyl)sulfonyl-2-oxo-indolin-3-yl]-2-(3-morpholinopropyl)-2,6-diazaspiro[3.3]heptane-6-carboxamide (S-enantiomer of compound of formula I.1, wherein X$^1$ is NH, R$^1$ is CN, R$^2$ is H, R$^5$ is 3-(morpholin-4-yl)-n-propyl, R$^{8a}$ and R$^{8c}$ are H and R$^{8b}$ is methoxy)

ESI-MS: [M+H$^+$]=716.3

The product was obtained in form of two conformers. These conformers were identified via HPLC (Column: Zorbax Extended C18, 50×2.1 mm ID, 1.8µ, System: Acetonitrile/Formic acid, Flow: 0.7 ml/min, Inj. Vol: 1 µl Temp: 65° C.):

Conformer 2A: retention time: 1.38 min
Conformer 2B: retention time: 1.46 min

Example 3

N-[(3S)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide (S-enantiomer of compound of formula I.1, wherein X$^1$ is NH, R$^1$ is CN, R$^2$ is H, R$^5$ is 2-(morpholin-4-yl)-ethyl, R$^{8a}$ is methoxy, R$^{8b}$ is F and R$^{8c}$ is H)

ESI-MS: [M+H$^+$]=720.3

The product was obtained in form of two conformers. These conformers were identified via HPLC (Column: Zorbax Extended C18, 50×2.1 mm ID, 1.8µ, System: Acetonitrile/Formic acid, Flow: 0.7 ml/min, Inj. Vol: 1 µl Temp: 65° C.):

Conformer 3A: retention time: 1.52 min
Conformer 3B: retention time: 1.61 min

Example 4

N-[(3S)-5-Cyano-3-(2-ethoxy-3-pyridyl)-1-[(5-methoxy-2-pyridyl)sulfonyl]-2-oxo-indolin-3-yl]-2-(2-morpholinoethyl)-2,6-diazaspiro[3.3]heptane-6-carboxamide (S-enantiomer of compound of formula I.65, wherein X$^1$ is NH, R$^1$ is CN, R$^2$ is H, R$^5$ is 2-(morpholin-4-yl)-ethyl, R$^{8b}$ is methoxy and R$^{8c}$ is H)

ESI-MS: [M+H$^+$]=703.3

The product was obtained in form of two conformers. These conformers were identified via HPLC (Column: Zorbax Extended C18, 50×2.1 mm ID, 1.8µ, System: Acetonitrile/Formic acid, Flow: 0.7 ml/min, Inj. Vol: 1 µl Temp: 65° C.):

Conformer 4A: retention time: 1.48 min
Conformer 4B: retention time: 1.55 min

Example 5

N-[(3S)-5-cyano-1-(4-cyanophenyl)sulfonyl-3-(2-ethoxy-3-pyridyl)-2-oxo-indolin-3-yl]-2-(2-morpholinoethyl)-2,6-diazaspiro[3.3]heptane-6-carboxamide (S-enantiomer of compound of formula I.1, wherein X$^1$ is NH, R$^1$ is CN, R$^2$ is H, R$^5$ is 2-(morpholin-4-yl)-ethyl, R$^{8a}$ is H, R$^{8b}$ is CN and R$^{8c}$ is H)

ESI-MS: [M+H$^+$]=697.3

Example 6

N-[(3S)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide; 2,2,2-trifluoroacetic acid (S-enantiomer of compound of formula I.1, wherein $X^1$ is NH, $R^1$ is CN, $R^2$ is H, $R^5$ is 2-(morpholin-4-yl)-ethyl, $R^{8a}$ is F, $R^{8b}$ is methoxy and $R^{8c}$ is H)
ESI-MS: [M+H$^+$]=720.2
The product was obtained in form of two conformers. These conformers were identified via HPLC (Column: Zorbax Extended C18, 50×2.1 mm ID, 1.8μ, System: Acetonitrile/Formic acid, Flow: 0.7 ml/min, Inj. Vol: 1 μl Temp: 65° C.):
Conformer 6A: retention time: 1.54 min
Conformer 6B: retention time: 1.66 min

Example 7

N-[(3S)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is methoxy, $R^{8b}$ is methoxy and $R^{8c}$ is H)
ESI-MS: [M+H$^+$]=732.3
The product was obtained in form of two conformers. These conformers were identified via HPLC (Column: Zorbax Extended C18, 50×2.1 mm ID, 1.8μ, System: Acetonitrile/Formic acid, Flow: 0.7 ml/min, Inj. Vol: 1 μl Temp: 65° C.):
Conformer 7A: retention time: 3.99 min
Conformer 7B: retention time: 4.60 min

Example 8

N-[(3S)-5-Cyano-3-(2-ethoxy-3-pyridyl)-1-(4-fluorophenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is H, $R^{8b}$ is F and $R^{8c}$ is H)
ESI-MS: [M+H$^+$]=690.3
The product was obtained in form of two conformers. These conformers were identified via HPLC (Column: Zorbax Extended C18, 50×2.1 mm ID, 1.8μ, System: Acetonitrile/Formic acid, Flow: 0.7 ml/min, Inj. Vol: 1 μl Temp: 65° C.):
Conformer 8A: retention time: 3.78 min
Conformer 8B: retention time: 4.89 min

Example 9

N-[(3S)-5-Cyano-3-(2-ethoxy-3-pyridyl)-1-(4-methoxyphenyl)sulfonyl-2-oxo-indolin-3-yl]-2-(2-diethylaminoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(diethylamino)-ethyl, $R^{8a}$ is H, $R^{8b}$ is methoxy and $R^{8c}$ is H)

9.1 N,N-Diethyl-2-(2,6-diazaspiro[3.3]heptan-2-yl)ethanamine tris(2,2,2-trifluoroacetate)

tert-Butyl 6-(2-(diethylamino)ethyl)-2,6-diazaspiro[3.3]heptane-2-carboxylate was deprotected with TFA as described in step 1.3 of example 1. The product was further reacted immediately in order to avoid degradation.

9.2 N-[(3S)-5-Cyano-3-(2-ethoxy-3-pyridyl)-1-(4-methoxyphenyl)sulfonyl-2-oxo-indolin-3-yl]-2-(2-diethylaminoethyl)-2,6-diazaspiro[3.3]heptane-6-carboxamide (S)-Phenyl (5-cyano-3-(2-ethoxypyridin-3-yl)-1-((4-methoxyphenyl)sulfonyl)-2-oxoindolin-3-yl)carbamate and N,N-diethyl-2-(2,6-diazaspiro[3.3]heptan-2-yl)ethanamine tris(2,2,2-trifluoroacetate) were reacted as described in step 1.2 of example 1.
ESI-MS: [M+Na$^+$]=710.5; [M+H$^+$]=688.3;

Example 10

N-[(3S)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide; 2,2,2-trifluoroacetic acid (S-enantiomer of compound of formula I.1, wherein $X^1$ is NH, $R^1$ is CN, $R^2$ is H, $R^5$ is 2-(morpholin-4-yl)-ethyl, $R^{8a}$ is H, $R^{8b}$ is methyl and $R^{8c}$ is H)
ESI-MS: [M+H$^+$]=686.2

Example 11

N-[(3S)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide; 2,2,2-trifluoroacetic acid (S-enantiomer of compound of formula I.1, wherein $X^1$ is NH, $R^1$ is CN, $R^2$ is H, $R^5$ is 2-(morpholin-4-yl)-ethyl, $R^{8a}$ is methoxy, $R^{8b}$ is H and $R^{8c}$ is H)
ESI-MS: [M+H$^+$]=702.3

Example 12

N-[(3S)-5-Cyano-1-(4-methoxyphenyl)sulfonyl-3-(2-methoxy-3-pyridyl)-2-oxo-indolin-3-yl]-2-(2-morpholinoethyl)-2,6-diazaspiro[3.3]heptane-6-carboxamide; 2,2,2-trifluoroacetic acid (S-enantiomer of compound of formula I.17, wherein $X^1$ is NH, $R^1$ is CN, $R^2$ is H, $R^5$ is 2-(morpholin-4-yl)-ethyl, $R^{8a}$ is H, $R^{8b}$ is methoxy and $R^{8c}$ is H)
The title compound was prepared from (S)-phenyl (5-cyano-1-((4-methoxyphenyl)sulfonyl)-3-(2-methoxypyridin-3-yl)-2-oxoindolin-3-yl)carbamate as described in step 1.2 of example 1.
ESI-MS: [M+H$^+$]=688.2

Example 13

N-[(3S)-5-Cyano-3-(2-ethoxy-3-pyridyl)-1-(4-methoxyphenyl)sulfonyl-2-oxo-indolin-3-yl]-2-[2-(1-piperidyl)ethyl]-2,6-diazaspiro[3.3]heptane-6-carboxamide (S-enantiomer of compound of formula I.1, wherein $X^1$ is NH, $R^1$ is CN, $R^2$ is H, $R^5$ is 2-(piperidin-1-yl)-ethyl, $R^{8a}$ is H, $R^{8b}$ is methoxy and $R^{8c}$ is H)

13.1 2-(2-(Piperidin-1-yl)ethyl)-2,6-diazaspiro[3.3]heptane tris(2,2,2-trifluoroacetate)

The title compounds was prepared from tert-butyl 6-(2-(piperidin-1-yl)ethyl)-2,6-diazaspiro[3.3]heptane-2-carboxylate as described in step 9.1 of example 9.

13.2 (S)-N-(5-Cyano-3-(2-ethoxypyridin-3-yl)-2-oxoindolin-3-yl)-6-(2-(piperidin-1-yl)ethyl)-2,6-diazaspiro[3.3]heptane-2-carboxamide The title compounds was prepared from (S)-phenyl (5-cyano-3-(2-ethoxypyridin-3-yl)-2-oxoindolin-3-yl)carbamate and 2-(2-(piperidin-1-yl)ethyl)-2,6-diazaspiro[3.3]heptane tris(2,2,2-trifluoroacetate) as described in step 1.2 of example 1.
ESI-MS: [M+H$^+$]=544.3

13.3 N-[(3S)-5-Cyano-3-(2-ethoxy-3-pyridyl)-1-(4-methoxyphenyl)sulfonyl-2-oxo-indolin-3-yl]-2-[2-(1-piperidyl)ethyl]-2,6-diazaspiro[3.3]heptane-6-carboxamide Potassium tert-butanolate (0.08 mmol, 8 mg) was added to a solution of (S)-N-(5-cyano-3-(2-ethoxypyridin-3-yl)-2-oxoindolin-3-yl)-6-(2-(piperidin-1-yl)ethyl)-2,6-diazaspiro[3.3]heptane-2-carboxamide from step 13.2 (0.06 mmol, 33 mg) in THF (1.5 ml) cooled down to 0° C.; and the mixture was further stirred for 1 h at 0° C. Then 4-methoxybenzene-1-sulfonyl chloride (0.07 mmol, 14 mg) was added and stirred for 12 h. The mixture was poured into cold 5% aq. K$_2$CO$_3$ (5 ml) and extracted with CH$_2$Cl$_2$ (3×5 ml). The organic phases were combined, washed with water (3×5 ml), dried on Na$_2$SO$_4$, filtered, evaporated, and finally passed through a silicagel column (eluent: CH$_2$Cl$_2$:MeOH 9:1). Yield: 11 mg (25%).
ESI-MS: [M+H$^+$]=700.3
The product was obtained in form of two conformers. These conformers were identified via HPLC (Column: Zorbax Extended C18, 50×2.1 mm ID, 1.8μ, System: Acetonitrile/Formic acid, Flow: 0.7 ml/min, Inj. Vol: 1 μl Temp: 65° C.):
Conformer 13A: retention time: 1.47 min
Conformer 13B: retention time: 1.57 min
In examples 14 to 18 only one conformer was observed.

Example 14

N-[(3S)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is methoxy, $R^{8b}$ is H and $R^{8c}$ is H)

14.1 tert-Butyl 6-(2-morpholinoethyl)-2,6-diazaspiro[3.3]heptane-2-carboxylate K$_2$CO$_3$ (52.0 mmol, 7.2 g) was added to a suspension of tert-butyl 2,6-diazaspiro[3.3]heptane-2-carboxylate oxalate (10.4 mmol, 3.0 g) in DMF (90 ml). After 1 h stirring at rt, 4-(2-bromoethyl)morpholine hydrochloride (11.5 mmol, 2.6 g) was added portionwise and the mixture was stirred at rt for 12 h. The precipitate was filtered off, and the filtrate evaporated in vacuo. The residue was passed through a silicagel column (eluent: CH$_2$Cl$_2$:MeOH 9:1). Yield: 1.9 g (59%).

14.2 4-(2-(2,6-Diazaspiro[3.3]heptan-2-yl)ethyl)morpholine tris(2,2,2-trifluoroacetate)

TFA (61 mmol, 4.7 ml) was added to a solution of tert-butyl 6-(2-morpholinoethyl)-2,6-diazaspiro[3.3]heptane-2-carboxylate from step 14.1 (6.1 mmol, 1.9 g) in CH$_2$Cl$_2$ (15 ml). The mixture was stirred at rt for 1 h, and solvents were removed under vacuo. The residue was crystallized by addition of a few drops of diethyl ether to the solution in MeOH. Yield: 2.2 g (65%).

14.3 (S)-N-(5-Cyano-3-(2-ethoxypyridin-3-yl)-2-oxoindolin-3-yl)-6-(2-morpholinoethyl)-2,6-diazaspiro[3.3]heptane-2-carboxamide DIPEA (21.7 mmol, 3.8 ml) was added to a suspension of 4-(2-(2,6-diazaspiro[3.3]heptan-2-yl)ethyl)morpholine tris(2,2,2-trifluoroacetate) from step 14.2 (4.3 mmol, 2.4 g) in CH$_2$Cl$_2$ (50 ml). Once in solution, (S)-phenyl-(5-cyano-3-(2-ethoxypyridin-3-yl)-2-oxoindolin-3-yl)carbamate (4.3 mmol, 1.8 g) was added and the mixture was further stirred for 12 h. The mixture was then poured into cold 5% aq. K$_2$CO$_3$ (50 ml) and extracted with CH$_2$Cl$_2$ (3×50 ml). The organic phases were combined, washed with water (3×50 ml), dried on Na$_2$SO$_4$, filtered and evaporated. The residue was precipitated in ether, filtered off, washed with ether, and dried in vacuo.
Yield: 2.13 g (92%).
ESI-MS: [M+H$^+$]=532.2

14.4 N-[(3S)-5-cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide The title compound was obtained in analogy to example 13 from (S)-N-(5-cyano-3-(2-ethoxypyridin-3-yl)-2-oxoindolin-3-yl)-6-(2-morpholinoethyl)-2,6-diazaspiro[3.3]heptane-2-carboxamide from step 14.3 and 2-methoxybenzene-1-sulfonyl chloride.
ESI-MS: [M+H$^+$]=702.3 (only 1 conformer observed)

Example 15

N-[(3S)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is methoxy, $R^{8b}$ is methoxy and $R^{8c}$ is H)

The title compound was obtained in analogy to example 13 from (S)-N-(5-cyano-3-(2-ethoxypyridin-3-yl)-2-oxoindolin-3-yl)-6-(2-morpholinoethyl)-2,6-diazaspiro[3.3]heptane-2-carboxamide from step 14.3 and 2,4-dimethoxybenzene-1-sulfonyl chloride.

ESI-MS: [M+H$^+$]=732.3 (only 1 conformer observed)

Example 16

N-[(3S)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is H, $R^{8b}$ is methyl and $R^{8c}$ is H)

The title compound was obtained in analogy to example 13 from (S)-N-(5-cyano-3-(2-ethoxypyridin-3-yl)-2-oxoindolin-3-yl)-6-(2-morpholinoethyl)-2,6-diazaspiro[3.3]heptane-2-carboxamide from step 14.3 and 4-methylbenzene-1-sulfonyl chloride.

ESI-MS: [M+H$^+$]=686.3 (1 conformer)

Example 17

N-[(3S)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is methoxy, $R^{8b}$ is F and $R^{8c}$ is H)

The title compound was obtained in analogy to example 13 from (S)-N-(5-cyano-3-(2-ethoxypyridin-3-yl)-2-oxoindolin-3-yl)-6-(2-morpholinoethyl)-2,6-diazaspiro[3.3]heptane-2-carboxamide from step 14.3 and 4-fluoro-2-methoxybenzene-1-sulfonyl chloride.

ESI-MS: [M+H$^+$]=720.3 (only 1 conformer observed)

Example 18

N-[(3S)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is H, $R^5$ is 2-(morpholin-4-yl)-ethyl, $R^{8a}$ is F, $R^{8b}$ is methoxy and $R^{8c}$ is H)

The title compound was obtained in analogy to example 13 from (S)-N-(5-cyano-3-(2-ethoxypyridin-3-yl)-2-oxoindolin-3-yl)-6-(2-morpholinoethyl)-2,6-diazaspiro[3.3]heptane-2-carboxamide from step 14.3 and 2-fluoro-4-methoxybenzene-1-sulfonyl chloride.

ESI-MS: [M+H$^+$]=720.3 (only 1 conformer observed)

Example 19

N-[(3S)-5-Cyano-3-(2-ethoxy-3-pyridyl)-6-fluoro-1-(4-methoxyphenyl)sulfonyl-2-oxo-indolin-3-yl]-2-(2-morpholinoethyl)-2,6-diazaspiro[3.3]heptane-6-carboxamide (S-enantiomer of compound of formula I.1, wherein $X^1$ is NH, $R^1$ is CN, $R^2$ is F, $R^5$ is 2-(morpholin-4-yl)-ethyl, $R^{8a}$ is H, $R^{8b}$ is methoxy and $R^{8c}$ is H)

19.1 (S)-Phenyl (5-cyano-3-(2-ethoxypyridin-3-yl)-6-fluoro-1-((4-methoxyphenyl)sulfonyl)-2-oxoindolin-3-yl)carbamate Pyridine (1.5 mmol, 0.1 ml) was added to a solution of (S)-3-amino-3-(2-ethoxypyridin-3-yl)-6-fluoro-1-((4-methoxyphenyl)sulfonyl)-2-oxoindoline-5-carbonitrile (described in WO2009/071690, 0.15 mmol, 72 mg) in CH$_2$Cl$_2$ (5 ml) cooled at 5° C. Phenyl chloroformate (0.16 mmol, 26 mg) was added dropwise and the mixture stirred for 1 h at 0° C. The reaction was monitored by TLC (eluted with MeOH (5%)/CH$_2$Cl$_2$). The mixture was poured into cold water (5 ml) and extracted with CH$_2$Cl$_2$ (3×5 ml). The combined organic phases were washed with water (3×5 ml), dried on Na$_2$SO$_4$, filtered and evaporated in vacuo. The residue was used in the next step without further purification.

19.2 N-[(3S)-5-Cyano-3-(2-ethoxy-3-pyridyl)-6-fluoro-1-(4-methoxyphenyl)sulfonyl-2-oxo-indolin-3-yl]-2-(2-morpholinoethyl)-2,6-diazaspiro[3.3]heptane-6-carboxamide The title compound was obtained in analogy to step 1.2 of example 1 from (S)-phenyl (5-cyano-3-(2-ethoxypyridin-3-yl)-6-fluoro-1-((4-methoxyphenyl)sulfonyl)-2-oxoindolin-3-yl)carbamate from step 19.2 and 4-(2-(2,6-diazaspiro[3.3]heptan-2-yl)ethyl)morpholine tris(2,2,2-trifluoroacetate) (see step 14.2 of example 14; 0.1 mmol, 65 mg).

ESI-MS: [M+H$^+$]=720.30

Example 20

3-(2-Ethoxy-3-pyridyl)-1-(4-methoxyphenyl)sulfonyl-3-[2-[2-(2-morpholinoethyl)-2,6-diazaspiro[3.3]heptan-6-yl]-2-oxo-ethyl]-2-oxo-indoline-5-carbonitrile (Compound of formula I.1, wherein $X^1$ is CH$_2$, $R^1$ is CN, $R^2$ is H, $R^5$ is 2-(morpholin-4-yl)-ethyl, $R^{8a}$ is H, $R^{8b}$ is methoxy and $R^{8c}$ is H)

DIPEA (0.9 mmol, 121 mg) was added to a solution of (2-(5-cyano-3-(2-ethoxypyridin-3-yl)-1-((4-methoxyphenyl)sulfonyl)-2-oxoindolin-3-yl)acetic acid (synthesis described in WO2009/071687, 0.1 mmol, 68 mg) and 4-(2-(2,6-diazaspiro[3.3]heptan-2-yl)ethyl)-morpholine tris(2,2,2-trifluoroacetate) (see step 14.2 of example 14, 0.2 mmol, 89 mg) in CH$_2$Cl$_2$ (20 ml). Then 2-(3H-[1,2,3]triazolo[4,5-b]pyridin-3-yl)-1,1,3,3-tetramethylisouronium hexafluorophosphate(V) (HATU, 0.3 mmol, 127 mg) was added and the mixture stirred at room temperature for 12 h. The reaction was monitored by TLC (eluted with MeOH (5%)/CH$_2$Cl$_2$). The reaction mixture was diluted with CH$_2$Cl$_2$ and washed with water (20 mL each). The organic phase was dried on Na$_2$SO$_4$, filtered and evaporated. It was passed through a silicagel column (eluent: MeOH (2%)/CH$_2$Cl$_2$). Yield: 55 mg (59%).

ESI-MS: [M+K$^+$]=739.20; [M+Na$^+$]=723.25; [M+H$^+$]=701.20

The two enantiomers 20A and 20B were separated by chiral HPLC from the racemic title compound on following column: DAICEL Chiralpak IC 2×25 cm; flow 12 ml/min; eluent n-heptane/ethanol/triethylamine 300:700:1.

Example 21

N-[(3S)-5-Cyano-3-(2-ethoxy-3-pyridyl)-1-(4-methoxyphenyl)sulfonyl-2-oxo-indolin-3-yl]-2-(2-morpholinoethoxy)-6-azaspiro[3.3]heptane-6-carboxamide (S-enantiomer of compound of formula I.2, wherein $X^1$ is NH, $R^1$ is CN, $R^2$ is H, $R^5$ is 2-(morpholin-4-yl)-ethoxy, $R^{8a}$ is H, $R^{8b}$ is methoxy and $R^{8c}$ is H)

21.1 tert-Butyl 6-(2-morpholinoethoxy)-2-azaspiro[3.3]heptane-2-carboxylate

Potassium tert-butanolate (1.7 mmol, 188 mg) was added portionwise to a solution of tert-butyl 6-hydroxy-2-azaspiro[3.3]heptane-2-carboxylate (1.5 mmol, 325 mg) in DMF abs. (2 ml) cooled at 0° C. After stirring for 1 h at 0° C., 4-(2-bromoethyl)morpholine hydrobromide (0.7 mmol, 199 mg) was added and the mixture was stirred for 12 h at rt. It was poured onto cold NaHCO$_3$ conc. (5 ml) and extracted with ether (3×5 ml). The organic phases were combined and washed once with NaHCO$_3$ conc. (5 ml) and dried on Na$_2$SO$_4$, filtered and evaporated. The residue was passed through a silicagel column (eluent: 1.) neat EtOAc; 2.) EtOAc:MeOH 1:1). Yield: 67.5 mg (27%).

21.2 4-(2-(2-Azaspiro[3.3]heptan-6-yloxy)ethyl)morpholine bis(2,2,2-trifluoroacetate)

tert-Butyl 6-(2-morpholinoethoxy)-2-azaspiro[3.3]heptane-2-carboxylate from step 21.1 (0.2 mmol, 66 mg) was deprotected with TFA (10 eq., 20 mmol, 231 mg) in CH$_2$Cl$_2$ (5 ml) at rt for 1 h. The product was used in the next step without further purification. Yield: 92 mg (quant).

21.3 N-[(3S)-5-Cyano-3-(2-ethoxy-3-pyridyl)-1-(4-methoxyphenyl)sulfonyl-2-oxo-indolin-3-yl]-2-(2-morpholinoethoxy)-6-azaspiro[3.3]heptane-6-carboxamide The title compound was prepared in analogy to step 1.2 of example 1 from (S)-phenyl (5-cyano-3-(2-ethoxypyridin-3-yl)-1-((4-methoxyphenyl)sulfonyl)-2-oxoindolin-3-yl)carbamate and 4-(2-(2-azaspiro[3.3]heptan-6-yloxy)ethyl)morpholine bis(2,2,2-trifluoroacetate).

The filtrate was passed through a silicagel column (eluent: EtOAc:MeOH 17:3), which afforded two conformers of the title compound. Yield: Conformer 21A: 38 mg, 27%; conformer 21B: 28 mg, 20% (85% purity).

ESI-MS: [M+H$^+$]=717.40

These two conformers were identified via HPLC (Column: Zorbax Extended C18, 50×2.1 mm ID, 1.8μ, System: Acetonitrile/Formic acid, Flow: 0.7 ml/min, Inj. Vol: 1 μl Temp: 65° C.):
Conformer 21A: retention time: 1.39 min
Conformer 21B: retention time: 1.25 min

Example 22

(±)-N-[5-Cyano-1-(2,4-dimethoxyphenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide (Compound of formula I.1, wherein $X^1$ is NH, $R^1$ is CN, $R^2$ is H, $R^5$ is 1-isopropylpiperidin-4-yl, $R^{8a}$ is methoxy, $R^{8b}$ is methoxy and $R^{8c}$ is H)

Zinc(II) chloride (0.01 mmol, 1.5 mg) was added to a solution of (±)-N-(5-cyano-1-((2,4-dimethoxyphenyl)sulfonyl)-3-(2-ethoxypyridin-3-yl)-2-oxoindolin-3-yl)-6-(piperidin-4-yl)-2,6-diazaspiro[3.3]heptane-2-carboxamide 2,2,2-trifluoroacetate (0.02 mmol, 15 mg) and propan-2-one (0.03 mmol, 1.6 mg) in methanol (5 ml). The solution was stirred for 30 min at rt. Sodium cyanotrihydroborate (0.02 mmol, 1.4 mg) was added and the whole mixture was stirred for 2 d at rt. The reaction was monitored by TLC (eluent: 5% MeOH/CH$_2$Cl$_2$). The mixture was poured onto cold 5% aq. K$_2$CO$_3$ (30 mL) and extracted three times with 20 mL ethyl acetate. The combined organic phases were washed with water (3×20 mL), dried on Na$_2$SO$_4$, filtered and evaporated. The crude was purified using preparative TLC (eluent: 10% MeOH/CH$_2$Cl$_2$). Yield: 5 mg (37%).

ESI-MS: [M+H$^+$]=744.30

Example 23

(±)-N-[5-Cyano-1-(2,4-dimethoxyphenyl)sulfonyl-3-(2-ethoxy-3-pyridyl)-2-oxo-indolin-3-yl]-2-(1-methyl-4-piperidyl)-2,6-diazaspiro[3.3]heptane-6-carboxamide (Compound of formula I.1, wherein $X^1$ is NH, $R^1$ is CN, $R^2$ is H, $R^5$ is 1-methylpiperidin-4-yl, $R^{8a}$ is methoxy, $R^{8b}$ is methoxy and $R^{8c}$ is H)

23.1 tert-Butyl 6-(1-methylpiperidin-4-yl)-2,6-diazaspiro[3.3]heptane-2-carboxylate Acetic acid (10.4 mmol, 0.6 ml) and sodium triacetoxyhydroborate (10.4 mmol, 2.2 g, portionwise) were added to tert-butyl 2,6-diazaspiro[3.3]heptane-2-carboxylate oxalate (1.04 mmol, 300 mg) dissolved in THF (45 ml) under N$_2$. The mixture was stirred overnight, poured onto 5% K$_2$CO$_3$ aq. (50 ml), then extracted with EtOAc (3×50 ml), and chloroform (3×50 ml). The organic phases were combined, dried on Na$_2$SO$_4$, filtrated and concentrated in vacuo. The product was passed through a silicagel column (eluent: EtOAc:MeOH: 25% NH$_3$ aq. 15:3:2). Yield: 123 mg (40%).

23.2 2-(1-Methylpiperidin-4-yl)-2,6-diazaspiro[3.3]heptane trihydrochloride tert-Butyl 6-(1-methylpiperidin-4-yl)-2,6-diazaspiro[3.3]heptane-2-carboxylate from step 23.1 (0.42 mmol, 123 mg) was dissolved in HCl (2M in diethylether, 10 ml). The reaction mixture was stirred at rt for 12 h. The precipitate was filtrated, taken up in MeOH and evaporated. Yield: 75.1 mg (92%).

23.3 (±)-Phenyl (5-cyano-1-((2,4-dimethoxyphenyl)sulfonyl)-3-(2-ethoxypyridin-3-yl)-2-oxoindolin-3-yl)carbamate Phenyl chloroformate (1.3 eq., 2 mmol, 309 mg) was added dropwise over 10 min to a solution of 3-amino-1-(2,4-dimethoxyphenylsulfonyl)-3-(2-ethoxypyridin-3-yl)-2-oxoindoline-5-carbonitrile (1.5 mmol, 750 mg) and pyridine (15.2 mmol, 1.2 g) in CH$_2$Cl$_2$ (100 ml) cooled at 5° C. The mixture was allowed to warm up to room temperature and stirred for 12 h. 2 additional eq. of phenyl chloroformate (3 mmol, 475 mg) were added and the mixture was further stirred for 5 h at room temperature. The reaction was monitored by TLC eluted with 5% MeOH/CH$_2$Cl$_2$. The mixture was diluted with CH$_2$Cl$_2$ (50 ml) and water was added (100 ml). The phases were separated and the organic layer was washed with sat. aq. $Na_2CO_3$ and water (1×200 ml), dried on $Na_2SO_4$, filtered and evaporated. The crude product was taken up into a small amount of $CH_2Cl_2$ and treated with diisopropyl ether. The mixture was stirred for 2 h and the precipitate filtered off and dried in vacuo (30° C.). Yield: 920 mg (quant.) ESI-MS: $[M+K^+]$=653.00; $[M+Na^+]$=637.10; $[M+H^+]$=615.10

23.4 (±)-N-[5-Cyano-1-(2,4-dimethoxyphenyl)sulfonyl-3-(2-ethoxy-3-pyridyl)-2-oxo-indolin-3-yl]-2-(1-methyl-4-piperidyl)-2,6-diazaspiro[3.3]heptane-6-carboxamide Triethylamine (0.13 mmol, 13 mg) was added to a solution of 2-(1-methylpiperidin-4-yl)-2,6-diazaspiro[3.3]heptane trihydrochloride from step 23.2 (0.04 mmol, 11 mg) and (±)-phenyl (5-cyano-1-((2,4-dimethoxyphenyl)sulfonyl)-3-(2-ethoxypyridin-3-yl)-2-oxoindolin-3-yl)carbamate from step 23.3 (0.02 mmol, 10 mg) in THF (1.5 ml). The mixture was stirred at room temperature for 12 h, poured onto cold 5% aq. $K_2CO_3$ and extracted three times with ethyl acetate (2 ml). The organic phases were combined and washed with water (3×2 ml), dried on $Na_2SO_4$, filtered and evaporated. The residue was purified by preparative TLC (eluent: 17:3 $CH_2Cl_2$/2M $NH_3$ in EtOH). Yield: 3.91 mg (34%).

ESI-MS: $[M+H^+]$=716.30 (ca 90% purity)

Example 24

N-[(3S)-5-cyano-1-(4-cyanophenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-isopropylpiperidin4-yl, $R^{8a}$ is H, $R^{8b}$ is cyano and $R^{8c}$ is H)

24.1 (S)-N-(5-Cyano-3-(2-ethoxypyridin-3-yl)-2-oxoindolin-3-yl)-6-(1-isopropylpiperidin-4-yl)-2,6-diazaspiro[3.3]heptane-2-carboxamide DIPEA (2.4 mmol, 0.4 ml) was added to a suspension of 2-(1-isopropylpiperidin-4-yl)-2,6-diazaspiro[3.3]heptane tris(2,2,2-trifluoroacetate) (0.48 mmol, 273 mg) in $CH_2Cl_2$ (10 ml). Once solved, (S)-phenyl (5-cyano-3-(2-ethoxypyridin-3-yl)-2-oxoindolin-3-yl)carbamate (0.48 mmol, 200 mg) was added and the mixture was stirred for 12 h. The mixture was poured onto cold 5% aq. $K_2CO_3$ (10 ml) and extracted with $CH_2Cl_2$ (3×10 ml). The organic phases were combined, washed with water (3×10 ml) and dried with $Na_2SO_4$, filtered and evaporated. The residue was passed through a silicagel column (eluent: $CH_2Cl_2$:2M $NH_3$/EtOH 1:1). Yield: 127.4 mg (49%).

24.2 N-[(3S)-5-cyano-1-(4-cyanophenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide Potassium tert-butanolate (0.06 mmol, 6 mg) was added to (S)-N-(5-cyano-3-(2-ethoxypyridin-3-yl)-2-oxoindolin-3-yl)-6-(1-isopropylpiperidin-4-yl)-2,6-diazaspiro[3.3]heptane-2-carboxamide from step 24.1 (0.06 mmol, 30 mg) dissolved in THF (1 ml) at 0° C. After 1 h stirring at 0° C., 4-cyanobenzene-1-sulfonyl chloride (0.06 mmol, 11 mg) was added and the mixture stirred for 2 d at rt. The mixture was poured onto cold 5% aq. $K_2CO_3$ (5 ml) and extracted with EtOAc (3×5 ml). The organic phases were combined, washed with water (3×5 ml), dried on $Na_2SO_4$, filtered and evaporated. The residue was passed on a silicagel column (eluent: $CH_2Cl_2$:2M $NH_3$/EtOH 17:3). Yield: 12.12 mg (31%).

ESI-MS: $[M+H^+]$=709.30 (ca 90% purity)

Example 25

N-[(3S)-5-Cyano-3-(2-ethoxy-3-pyridyl)-2-oxo-1-(p-tolylsulfonyl)indolin-3-yl]-2-(1-isopropyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-isopropylpiperidin-4-yl, $R^{8a}$ is H, $R^{8b}$ is methyl and $R^{8c}$ is H)

The title compound was prepared in analogy to example 24 using 4-methylbenzene-1-sulfonyl chloride.

ESI-MS: $[M+H^+]$=698.30

Example 26

N-[(3S)-5-Cyano-3-(2-ethoxy-3-pyridyl)-2-oxo-1-(p-tolylsulfonyl)indolin-3-yl]-2-(oxetan-3-yl)-2,6-diazaspiro[3.3]heptane-6-carboxamide (S-enantiomer of compound of formula I.1, wherein $X^1$ is NH, $R^1$ is CN, $R^2$ is H, $R^5$ is oxetan-3-yl, $R^{8a}$ is H, $R^{8b}$ is methyl and $R^{8c}$ is H)

26.1 (S)-N-(5-Cyano-3-(2-ethoxypyridin-3-yl)-2-oxoindolin-3-yl)-6-(oxetan-3-yl)-2,6-diazaspiro[3.3]heptane-2-carboxamide The title compound was prepared in analogy to example 24.1 using 2-(oxetan-3-yl)-2,6-diazaspiro[3.3]heptane bis(2,2,2-trifluoroacetate).

ESI-MS: $[M+H^+]$=475.20

26.2 N-[(3S)-5-Cyano-3-(2-ethoxy-3-pyridyl)-2-oxo-1-(p-tolylsulfonyl)indolin-3-yl]-2-(oxetan-3-yl)-2,6-diazaspiro[3.3]heptane-6-carboxamide The title compound was prepared in analogy to example 24.2 using (S)-N-(5-cyano-3-(2-ethoxypyridin-3-yl)-2-oxoindolin-3-yl)-6-(oxetan-3-yl)-2,6-diazaspiro[3.3]heptane-2-carboxamide and 4-methylbenzene-1-sulfonyl chloride.

ESI-MS: $[M+H^+]$=629.30

Example 27

N-[(3S)-5-Cyano-3-(2-ethoxy-3-pyridyl)-1-(4-fluorophenyl)sulfonyl-2-oxo-indolin-3-yl]-2-(1-isopropyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-isopropylpiperidin-4-yl, $R^{8a}$ is H, $R^{8b}$ is F and $R^{8c}$ is H)

ESI-MS: $[M+H^+]$=702.30 (90% purity)

Example 28

N-[(3S)-5-Cyano-3-(2-ethoxy-3-pyridyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide (S-enantiomer of compound of formula I.1, wherein $X^1$ is NH, $R^1$ is CN, $R^2$ is H, $R^5$ is oxetan-3-yl, $R^{8a}$ is H, $R^{8b}$ is F and $R^{8c}$ is H)

28.1 (S)-N-(5-Cyano-3-(2-ethoxypyridin-3-yl)-2-oxoindolin-3-yl)-2,6-diazaspiro[3.3]heptane-2-carboxamide 2,2,2-trifluoroacetate (S)-tert-Butyl 6-((5-cyano-3-(2-ethoxypyridin-3-yl)-2-oxoindolin-3-yl)carbamoyl)-2,6-diazaspiro[3.3]heptane-2-carboxylate (0.1 mmol, 58 mg) was deprotected with TFA (20 eq., 2.2 mmol, 255 mg) in $CH_2Cl_2$ (10 ml). Yield: 56.3 mg (95%)

ESI-MS: [M+H$^+$]=419, 20

28.2 (S)-tert-Butyl 4-(6-((5-cyano-3-(2-ethoxypyridin-3-yl)-2-oxoindolin-3-yl)carbamoyl)-2,6-diazaspiro[3.3]heptan-2-yl)piperidine-1-carboxylate (S)-N-(5-Cyano-3-(2-ethoxypyridin-3-yl)-2-oxoindolin-3-yl)-2,6-diazaspiro[3.3]heptane-2-carboxamide 2,2,2-trifluoroacetate from step 28.1 (0.09 mmol, 50 mg), tert-butyl 4-oxopiperidine-1-carboxylate (0.09 mmol, 19 mg), sodium acetate (0.09 mmol, 8 mg) and conc. acetic acid (2 eq., 0.19 mmol, 11 µl) were dissolved in EtOH (5 ml) and stirred for 1 h. Sodium cyanotrihydroborate (0.11 mmol, 7 mg) was added portionswise and the mixture was stirred for 12 h at rt. The mixture was poured onto cold 5% aq. $K_2CO_3$ (5 ml) and extracted with ethyl acetate (3×5 ml). The organic phases were combined, washed with water (3×5 ml) and dried on $Na_2SO_4$, filtered and evaporated. Yield: 51.2 mg (91%).

ESI-MS: [M+H$^+$]=602.30

28.3 (S)-N-(5-Cyano-3-(2-ethoxypyridin-3-yl)-2-oxoindolin-3-yl)-6-(piperidin-4-yl)-2,6-diazaspiro[3.3]heptane-2-carboxamide bis(2,2,2-trifluoroacetate)

(S)-tert-Butyl 4-(6-((5-cyano-3-(2-ethoxypyridin-3-yl)-2-oxoindolin-3-yl)carbamoyl)-2,6-diazaspiro[3.3]heptan-2-yl)piperidine-1-carboxylate from step 28.2 (0.08 mmol, 50 mg) was deprotected with TFA (20 eq., 1.7 mmol, 190 mg) in $CH_2Cl_2$ (5 ml). Yield: 59.8 mg (quant.)

ESI-MS: [M+H$^+$]=502.30

28.4 (S)-N-(5-Cyano-3-(2-ethoxypyridin-3-yl)-2-oxoindolin-3-yl)-6-(1-(oxetan-3-yl)piperidin-4-yl)-2,6-diazaspiro[3.3]heptane-2-carboxamide(R-2630)

(S)-N-(5-cyano-3-(2-ethoxypyridin-3-yl)-2-oxoindolin-3-yl)-6-(piperidin-4-yl)-2,6-diazaspiro[3.3]heptane-2-carboxamide bis(2,2,2-trifluoroacetate) from step 28.3 (0.08 mmol, 58 mg), oxetan-3-one (0.08 mmol, 6 mg), sodium acetate (0.16 mmol, 13 mg) and conc. acetic acid were dissolved in EtOH (1.5 ml). The mixture was stirred for 1 h and sodium cyanotrihydroborate (0.1 mmol, 6 mg) was added portionswise, and further stirred for 12 h at rt. The mixture was poured onto cold 5% aq. $K_2CO_3$ (5 ml) and extracted with ethyl acetate (3×5 ml). The organic phases were combined, washed with water (3×5 ml), dried with $Na_2SO_4$, filtered and evaporated. Yield: 34.2 mg (77%).

ESI-MS: [M+H$^+$]=558.30

28.5 N-[(3S)-5-Cyano-3-(2-ethoxy-3-pyridyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide The title compound was prepared in analogy to example 24.2 using (S)-N-(5-cyano-3-(2-ethoxypyridin-3-yl)-2-oxoindolin-3-yl)-6-(1-(oxetan-3-yl)piperidin-4-yl)-2,6-diazaspiro[3.3]heptane-2-carboxamide and 4-fluorobenzene-1-sulfonyl chloride.

ESI-MS: [M+H$^+$]=716.30

Example 29

N-[(3S)-5-Cyano-3-(2-ethoxy-3-pyridyl)-1-(4-methoxyphenyl)sulfonyl-2-oxo-indolin-3-yl]-2-(1-isopropyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-isopropylpiperidin-4-yl, $R^{8a}$ is H, $R^{8b}$ is methoxy and $R^{8c}$ is H)

ESI-MS: [M+H+]=714.30

Example 30

N-[(3S)-5-Cyano-3-(2-ethoxy-3-pyridyl)-2-oxo-1-(p-tolylsulfonyl)indolin-3-yl]-2-[1-(oxetan-3-yl)-4-piperidyl]-2,6-diazaspiro[3.3]heptane-6-carboxamide (S-enantiomer of compound of formula I.1, wherein $X^1$ is NH, $R^1$ is CN, $R^2$ is H, $R^5$ is 1-(oxetan-3-yl)-piperidin-4-yl, $R^{8a}$ is H, $R^{8b}$ is methyl and $R^{8c}$ is H)

ESI-MS: [M+H$^+$]=712.30 (90% purity)

Example 31

N-[(3S)-5-Cyano-3-(2-ethoxy-3-pyridyl)-1-(4-fluorophenyl)sulfonyl-2-oxo-indolin-3-yl]-2-(oxetan-3-yl)-2,6-diazaspiro[3.3]heptane-6-carboxamide (S-enantiomer of compound of formula I.1, wherein $X^1$ is NH, $R^1$ is CN, $R^2$ is H, $R^5$ is oxetan-3-yl, $R^{8a}$ is H, $R^{8b}$ is F and $R^{8c}$ is H)

ESI-MS: [M+H$^+$]=633.20

Example 32

N-[(3S)-5-Cyano-3-(2-ethoxy-3-pyridyl)-1-(2-methoxyphenyl)sulfonyl-2-oxo-indolin-3-yl]-2-(1-methyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-methylpiperidin-4-yl, $R^{8a}$ is methoxy, $R^{8b}$ is H and $R^{8c}$ is H)

The title compound was prepared in analogy to step 24.1 of example 24 using (S)-phenyl (5-cyano-3-(2-ethoxypyridin-3-yl)-1-((2-methoxyphenyl)sulfonyl)-2-oxo-indolin-3-yl)carbamate; ESI-MS: [M+H$^+$]=686.20

The product was obtained in form of two conformers. These conformers were identified with following column: Grace, GROM_SIL 80 ODS 7 pH, 4 μm, 40×2 mm ID, System: Methanol/TFA, Flow: 0.6 ml/min, Inj. Vol: 3 μl Temp: 65° C.
Conformer 32A: retention time: 4.78 min
Conformer 32B: retention time: 4.55 min The conformers were separated via preparative HPLC with following column: xTerra prepMS C18 19×150 mm 5 μm; flow 15 ml/min; eluent gradient H$_2$O/10-100% MeOH+ 0.1% TFA
Conformer 32A: ESI-MS: [M+H$^+$]=686.20
Conformer 32B: ESI-MS: [M+H$^+$]=686.20

Example 33

N-[(3S)-5-Cyano-3-(2-ethoxy-3-pyridyl)-1-(4-methoxyphenyl)sulfonyl-2-oxo-indolin-3-yl]-2-(1-methyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-methylpiperidin-4-yl, $R^{8a}$ is H, $R^{8b}$ is methoxy and $R^{8c}$ is H)

The title compound was prepared in analogy to step 24.1 of example 24 using (S)-phenyl (5-cyano-3-(2-ethoxypyridin-3-yl)-1-((4-methoxyphenyl)sulfonyl)-2-oxo-indolin-3-yl)carbamate; ESI-MS: [M+H$^+$]=686.30

The product was obtained in form of two conformers. These conformers were identified with following column: Grace, GROM_SIL 80 ODS 7 pH, 4 μm, 40×2 mm ID, System: Methanol/TFA, Flow: 0.6 ml/min, Inj. Vol: 3 μl Temp: 65° C.
Conformer 33A: retention time: 4.90 min
Conformer 33B: retention time: 4.64 min The conformers were separated via preparative HPLC with following column: xTerra prepMS C18 19×150 mm 5 μm; flow 15 ml/min; eluent gradient H$_2$O/10-100% MeOH+ 0.1% TFA
Conformer 33A: ESI-MS: [M+H$^+$]=686.30
Conformer 33B: ESI-MS: [M+H$^+$]=686.30

Example 34

N-[(3S)-1-(Benzenesulfonyl)-5-cyano-3-(2-ethoxy-3-pyridyl)-2-oxo-indolin-3-yl]-2-(1-methyl-4-piperidyl)-2,6-diazaspiro[3.3]heptane-6-carboxamide (S-enantiomer of compound of formula I.1, wherein $X^1$ is NH, $R^1$ is CN, $R^2$ is H, $R^5$ is 1-methylpiperidin-4-yl, $R^{8a}$ is H, $R^{8b}$ is H and $R^{8c}$ is H)

The title compound was prepared in analogy to step 24.1 of example 24 using (S)-phenyl (5-cyano-3-(2-ethoxypyridin-3-yl)-2-oxo-1-(phenylsulfonyl)indolin-3-yl)carbamate. ESI-MS: [M+H$^+$]=656.20

The product was obtained in form of two conformers. These conformers were identified with following column: Macherey & Nagel Nucleosil C18 PPN, 100×2,1, System: Methanol/TFA, Flow: 0.2 ml/min, Inj. Vol: 41 Temp: 40° C.
Conformer 34A: retention time: 17.79 min
Conformer 34B: retention time: 19.74 min The conformers were separated via preparative HPLC with following column: xTerra prepMS C18 19×150 mm 5 μm; flow 15 ml/min; eluent gradient H$_2$O/10-100% MeOH+ 0.1% TFA
Conformer 34A: ESI-MS: [M+H$^+$]=656.20
Conformer 34B: ESI-MS: [M+H$^+$]=656.20

Example 35

N-[(3S)-5-Cyano-3-(2-ethoxyphenyl)-1-(4-methoxyphenyl)sulfonyl-2-oxo-indolin-3-yl]-2-[1-(oxetan-3-yl)-4-piperidyl]-2,6-diazaspiro[3.3]heptane-6-carboxamide; 2,2,2-trifluoroacetic acid (S-enantiomer of compound of formula I.49, wherein $X^1$ is NH, $R^1$ is CN, $R^2$ is H, $R^5$ is 1-(oxetan-3-yl)-piperidin-4-yl, $R^{8a}$ is H, $R^{8b}$ is methoxy and $R^{8c}$ is H)

ESI-MS: [M+H$^+$]=727.30

The product was obtained in form of two conformers. These conformers were identified with following column: Zorbax Extended C18, 50×2.1 mm ID, 1.8μ, System: ACN/Formic acid, Flow: 0.7 ml/min, Inj. Vol: 1 μl Temp: 65° C.

Conformer 35A: retention time: 1.48 min

Conformer 35B: retention time: 1.83 min

The conformers were separated via preparative RP-HPLC with following column: LUNA C18 Axia 100A 5μ 75×30; flow 40 ml/min; eluent gradient H2O/10-90% MeOH+0.1% TFA Conformer 35A: ESI-MS: [M+H$^+$]=727.30
Conformer 35B: ESI-MS: [M+H$^+$]=727.30

Example 36

N-[(3S)-5-Cyano-1-(4-cyanophenyl)sulfonyl-3-(2-ethoxyphenyl)-2-oxo-indolin-3-yl]-2-[1-(oxetan-3-yl)-4-piperidyl]-2,6-diazaspiro[3.3]heptane-6-carboxamide; 2,2,2-trifluoroacetic acid (S-enantiomer of compound of formula I.49, wherein $X^1$ is NH, $R^1$ is CN, $R^2$ is H, $R^5$ is 1-(oxetan-3-yl)-piperidin-4-yl, $R^{8a}$ is H, $R^{8b}$ is cyano and $R^{8c}$ is H)

ESI-MS: [M+H$^+$]=722.20

Example 37

N-[(3S)-5-Cyano-3-(2-ethoxyphenyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide; 2,2,2-trifluoroacetic acid (S-enantiomer of compound of formula I.49, wherein $X^1$ is NH, $R^1$ is CN, $R^2$ is H, $R^5$ is 1-(oxetan-3-yl)-piperidin-4-yl, $R^{8a}$ is H, $R^{8b}$ is F and $R^{8c}$ is H)

ESI-MS: [M+H$^+$]=715.30

The product was obtained in form of two conformers. These conformers were identified with following column: Zorbax Extended C18, 50×2.1 mm ID, 1.8μ, System: ACN/Formic acid, Flow: 0.7 ml/min, Inj. Vol: 1 μl Temp: 65° C.

Conformer 37A: retention time: 1.48 min

Conformer 37B: retention time: 1.82 min

The conformers were separated via preparative RP-HPLC with following column: LUNA C18 Axia 100A 5μ 75×30; flow 40 ml/min; eluent gradient H2O/10-90% MeOH+0.1% TFA Conformer 37A: ESI-MS: [M+H$^+$]=715.30
Conformer 37B: ESI-MS: [M+H$^+$]=715.30

Example 38

N-[(3S)-5-Cyano-3-(2-ethoxyphenyl)-2-oxo-1-(p-tolylsulfonyl)indolin-3-yl]-2-[1-(oxetan-3-yl)-4-piperidyl]-2,6-diazaspiro[3.3]heptane-6-carboxamide; 2,2,2-trifluoroacetic acid (S-enantiomer of compound of formula I.49, wherein $X^1$ is NH, $R^1$ is CN, $R^2$ is H, $R^5$ is 1-(oxetan-3-yl)-piperidin-4-yl, $R^{8a}$ is H, $R^{8b}$ is methyl and $R^{8c}$ is H)
ESI-MS: [M+H$^+$]=711.30
The product was obtained in form of two conformers. These conformers were identified with following column: Zorbax Extended C18, 50×2.1 mm ID, 1.8µ, System: ACN/Formic acid, Flow: 0.7 ml/min, Inj. Vol: 1 µl Temp: 65° C.
Conformer 38A: retention time: 1.59 min
Conformer 38B: retention time: 1.80 min
The conformers were separated via preparative RP-HPLC with following column: LUNA C18 Axia 100A 5µ 75×30; flow 40 ml/min; eluent gradient H2O/10-90%
MeOH+0.1% TFA
Conformer 38A: ESI-MS: [M+H$^+$]=711.30
Conformer 38B: ESI-MS: [M+H$^+$]=711.30

Example 39

N-[(3S)-5-Cyano-1-(2,4-dimethoxyphenyl)sulfonyl-3-(2-ethoxyphenyl)-2-oxo-indolin-3-yl]-2-(1-methyl-4-piperidyl)-2,6-diazaspiro[3.3]heptane-6-carboxamide (S-enantiomer of compound of formula I.49, wherein $X^1$ is NH, $R^1$ is CN, $R^2$ is H, $R^5$ is 1-methylpiperidin-4-yl, $R^{8a}$ is methoxy, $R^{8b}$ is methoxy and $R^{8c}$ is H)
ESI-MS: [M+H+]=715.3
The product was obtained in form of two conformers. These conformers were identified with following column: Phenomenex, Kinetex 1.7µ, 100A, C18, 50×2.1, System: MeOH/Formic acid, Flow: 0.6 ml/min, Inj. Vol: 2 µl Temp: 70° C.
Conformer 39A: retention time: 3.32 min
Conformer 39B: retention time: 4.08 min
The conformers were separated via preparative HPLC with following column: xTerra prepMS C18 19×150 mm 5 µm; flow 15 ml/min; eluent gradient H2O/10-90% MeOH+0.1% TFA
Conformer 39A: ESI-MS: [M+H$^+$]=715.30
Conformer 39B: ESI-MS: [M+H$^+$]=715.30

Example 40

N-[(3S)-5-Cyano-3-(2-ethoxyphenyl)-1-(4-methoxyphenyl)sulfonyl-2-oxo-indolin-3-yl]-2-(1-isopropyl-4-piperidyl)-2,6-diazaspiro[3.3]heptane-6-carboxamide (S-enantiomer of compound of formula I.49, wherein $X^1$ is NH, $R^1$ is CN, $R^2$ is H, $R^5$ is 1-isopropylpiperidin-4-yl, $R^{8a}$ is H, $R^{8b}$ is methoxy and $R^{8c}$ is H)
ESI-MS: [M+H$^+$]=713.30

Example 41

N-[(3S)-5-Cyano-3-(2-ethoxyphenyl)-2-oxo-1-(p-tolylsulfonyl)indolin-3-yl]-2-(1-isopropyl-4-piperidyl)-2,6-diazaspiro[3.3]heptane-6-carboxamide (S-enantiomer of compound of formula I.49, wherein $X^1$ is NH, $R^1$ is CN, $R^2$ is H, $R^5$ is 1-isopropylpiperidin-4-yl, $R^{8a}$ is H, $R^{8b}$ is methyl and $R^{8c}$ is H)
ESI-MS: [M+H$^+$]=697.30

The product was obtained in form of two conformers. These conformers were identified with following column: WATERS, XBridge C18, 2.5µ, 20×2.1 mm ID, System: MeOH/Formic acid, Flow: 0.6 ml/min, Inj. Vol: 3 µl Temp: 65° C.
Conformer 41A: retention time: 4.56 min
Conformer 41B: retention time: 4.74 min

Example 42

N-[(3S)-5-Cyano-1-(4-cyanophenyl)sulfonyl-3-(2-ethoxyphenyl)-2-oxo-indolin-3-yl]-2-(1-isopropyl-4-piperidyl)-2,6-diazaspiro[3.3]heptane-6-carboxamide (S-enantiomer of compound of formula I.49, wherein $X^1$ is NH, $R^1$ is CN, $R^2$ is H, $R^5$ is 1-isopropylpiperidin-4-yl, $R^{8a}$ is H, $R^{8b}$ is cyano and $R^{8c}$ is H)
ESI-MS: [M+H$^+$]=708.30
The product was obtained in form of two conformers. These conformers were identified with following column: WATERS, XBridge C18, 2.5µ, 20×2.1 mm ID, System: MeOH/Formic acid, Flow: 0.6 ml/min, Inj. Vol: 3 µl Temp: 65° C.
Conformer 42A: retention time: 4.23 min
Conformer 42B: retention time: 4.63 min

Example 43

N-[(3S)-5-Cyano-3-(2-ethoxyphenyl)-1-(4-fluorophenyl)sulfonyl-2-oxo-indolin-3-yl]-2-(1-isopropyl-4-piperidyl)-2,6-diazaspiro[3.3]heptane-6-carboxamide; 2,2,2-trifluoroacetic acid (S-enantiomer of compound of formula I.49, wherein $X^1$ is NH, $R^1$ is CN, $R^2$ is H, $R^5$ is 1-isopropylpiperidin-4-yl, $R^{8a}$ is H, $R^{8b}$ is F and $R^{8c}$ is H)
The product was obtained in form of two conformers. These conformers were separated with following RP-HPLC column: xTerra prepMS C18 19×150 mm 5 µm; flow 15 ml/min; eluent gradient H$_2$O/30-100% MeOH+0.1% TFA
Conformer 43A: retention time: 14.27 min
Conformer 43B: retention time: 18.36 min

Example 44

N-[(3S)-5-Cyano-3-(2-ethoxy-3-pyridyl)-1-(4-methoxyphenyl)sulfonyl-2-oxo-indolin-3-yl]-6-azaspiro[3.3]heptane-2-carboxamide (S-enantiomer of compound of formula I.3, wherein $X^1$ is NH, $R^1$ is CN, $R^2$ is H, $R^5$ is H, $R^{8a}$ is H, $R^{8b}$ is methoxy and $R^{8c}$ is H)

44.1 (S)-tert-Butyl 6-((5-cyano-3-(2-ethoxypyridin-3-yl)-1-((4-methoxyphenyl)sulfonyl)-2-oxoindolin-3-yl)carbamoyl)-2-azaspiro[3.3]heptane-2-carboxylate N1-((Ethylimino)methylene)-N3,N3-dimethylpropane-1,3-diamine hydrochloride (5.4 mmol, 1.0 g) was added portionwise to a solution of (S)-3-amino-3-(2-ethoxypyridin-3-yl)-1-((4-methoxyphenyl)sulfonyl)-2-oxoindoline-5-carbonitrile (1.1 mmol, 500 mg) and 2-(tert-butoxycarbonyl)-2-azaspiro[3.3]heptane-6-carboxylic acid (1.1 mmol, 260 mg) in pyridine (10 ml). The mixture was stirred for 12 h at rt. The reaction was monitored by TLC (eluent: 5%

MeOH/CH$_2$Cl$_2$). The mixture was poured onto cooled water and the precipitate filtered off. It was washed with cold water and dried in vacuo. The crude product was directly used in the next step without purification.

ESI-MS: [M+H$^+$]=688.20 (90% purity)

44.2 N-[(3S)-5-Cyano-3-(2-ethoxy-3-pyridyl)-1-(4-methoxyphenyl)sulfonyl-2-oxo-indolin-3-yl]-6-azaspiro[3.3]heptane-2-carboxamide (S)-tert-Butyl 6-((5-cyano-3-(2-ethoxypyridin-3-yl)-1-((4-methoxyphenyl)sulfonyl)-2-oxoindolin-3-yl)carbamoyl)-2-azaspiro[3.3]heptane-2-carboxylate (1.0 mmol, 679 mg) was dissolved in CH$_2$Cl$_2$ (10 ml) and then treated with TFA (9.9 mmol, 0.8 ml). The mixture was stirred at room temperature for 2 h. The reaction was monitored by TLC (eluent: 5% MeOH/CH$_2$Cl$_2$). The mixture was concentrated, diluted with ethyl acetate (30 mL) and washed twice with water (20 mL each). The combined organic layers were dried (Na$_2$SO$_4$), filtered and evaporated. The residue was purified using a SiOH-Chromabond (eluent: 0-6% MeOH/CH$_2$Cl$_2$). Yield: 114 mg (20%).

ESI-MS: [M+H$^+$]=588.20

Example 45

N-[(3S)-5-Cyano-3-(2-ethoxy-3-pyridyl)-1-(4-methoxyphenyl)sulfonyl-2-oxo-indolin-3-yl]-6-(1-isopropyl-4-piperidyl)-6-azaspiro[3.3]heptane-2-carboxamide (S-enantiomer of compound of formula I.3, wherein $X^1$ is NH, $R^1$ is CN, $R^2$ is H, $R^5$ is 1-isopropylpiperidin-4-yl, $R^{8a}$ is H, $R^{8b}$ is methoxy and $R^{8c}$ is H)

ESI-MS: [M+H$^+$]=713.35

Example 46

N-[(3S)-5-Cyano-3-(2-ethoxy-3-pyridyl)-1-(4-methoxyphenyl)sulfonyl-2-oxo-indolin-3-yl]-6-(1-methylazetidin-3-yl)-6-azaspiro[3.3]heptane-2-carboxamide (S-enantiomer of compound of formula I.3, wherein $X^1$ is NH, $R^1$ is CN, $R^2$ is H, $R^5$ is 1-methylazetidin-3-yl, $R^{8a}$ is H, $R^{8b}$ is methoxy and $R^{8c}$ is H)

ESI-MS: [M+H$^+$]=657.20

Example 47

N-(5-Cyano-1-(2,4-dimethoxyphenylsulfonyl)-3-(2-ethoxypyridin-3-yl)-2-oxoindolin-3-yl)-3-(piperidin-4-yl)-3-azaspiro[5.5]undecane-9-carboxamide 2,2,2-trifluoroacetate (Compound of formula I.15, wherein $X^1$ is NH, $R^1$ is CN, $R^2$ is H, $R^5$ is piperidin-4-yl, $R^{8a}$ is methoxy, $R^{8b}$ is methoxy and $R^{8c}$ is H)

ESI-MS: 757.30 [M+H]$^+$

Example 48

N-(5-Cyano-1-(2,4-dimethoxyphenylsulfonyl)-3-(2-ethoxypyridin-3-yl)-2-oxoindolin-3-yl)-6-(2,6-diazaspiro[3.3]heptan-2-yl)spiro[3.3]heptane-2-carboxamide 2,2,2-trifluoroacetate (Compound of formula I.4, wherein $X^1$ is NH, $R^1$ is CN, $R^2$ is H, $R^5$ is 2,6-diazaspiro[3.3]heptane-2-yl, $R^{8a}$ is methoxy, $R^{8b}$ is methoxy and $R^{8c}$ is H)

ESI-MS: 713.30 [M+H]$^+$

Example 49A

First stereoisomer of N-(5-cyano-1-(2,4-dimethoxyphenylsulfonyl)-3-(2-ethoxypyridin-3-yl)-2-oxoindolin-3-yl)-7-(piperidin-4-yl)-2,7-diazaspiro[3.5]nonane-2-carboxamide 2,2,2-trifluoroacetate (First stereoisomer of compound of formula I.5, wherein $X^1$ is NH, $R^1$ is CN, $R^2$ is H, $R^5$ is piperidin-4-yl, $R^{8a}$ is methoxy, $R^{8b}$ is methoxy and $R^{8c}$ is H)

ESI-MS: 730.30 [M+H]$^+$

Example 49B

Second stereoisomer of N-(5-cyano-1-(2,4-dimethoxyphenylsulfonyl)-3-(2-ethoxypyridin-3-yl)-2-oxoindolin-3-yl)-7-(piperidin-4-yl)-2,7-diazaspiro[3.5]nonane-2-carboxamide 2,2,2-trifluoroacetate (Second stereoisomer of compound of formula I.5, wherein $X^1$ is NH, $R^1$ is CN, $R^2$ is H, $R^5$ is piperidin-4-yl, $R^{8a}$ is methoxy, $R^{8b}$ is methoxy and $R^{8c}$ is H)

ESI-MS: 730.30 [M+H]+

Example 50

N-(5-Cyano-1-(2,4-dimethoxyphenylsulfonyl)-3-(2-ethoxypyridin-3-yl)-2-oxoindolin-3-yl)-2-(piperidin-4-yl)-2,7-diazaspiro[3.5]nonane-7-carboxamide bis-2,2,2-trifluoroacetate (Compound of formula I.9, wherein $X^1$ is NH, $R^1$ is CN, $R^2$ is H, $R^5$ is piperidin-4-yl, $R^{8a}$ is methoxy, $R^{8b}$ is methoxy and $R^{8c}$ is H)

ESI-MS: 730.30 [M+H]$^+$

Example 51

N-(5-Cyano-1-(2,4-dimethoxyphenylsulfonyl)-3-(2-ethoxypyridin-3-yl)-2-oxoindolin-3-yl)-2,7-diazaspiro[3.5]nonane-7-carboxamide 2,2,2-trifluoroacetate (Compound of formula I.9, wherein $X^1$ is NH, $R^1$ is CN, $R^2$ is H, $R^5$ is H, $R^{8a}$ is methoxy, $R^{8b}$ is methoxy and $R^{8c}$ is H)

ESI-MS: 647.20 [M+H]$^+$

Example 52

N-(5-Cyano-1-(2,4-dimethoxyphenylsulfonyl)-3-(2-ethoxypyridin-3-yl)-2-oxoindolin-3-yl)-3-azaspiro[5.5]undecane-9-carboxamide 2,2,2-trifluoroacetate (Compound of formula I.15, wherein $X^1$ is NH, $R^1$ is CN, $R^2$ is H, $R^5$ is H, $R^{8a}$ is methoxy, $R^{8b}$ is methoxy and $R^{8c}$ is H)

ESI-MS: 674.30 [M+H]$^+$

Example 53

N-(5-Cyano-1-(2,4-dimethoxyphenylsulfonyl)-3-(2-ethoxypyridin-3-yl)-2-oxoindolin-3-yl)-9-methyl-3,9-diazaspiro[5.5]undecane-3-carboxamide 2,2,2-trifluoroacetate (Compound of formula I.13, wherein $X^1$ is NH, $R^1$ is CN, $R^2$ is H, $R^5$ is methyl, $R^{8a}$ is methoxy, $R^{8b}$ is methoxy and $R^{8c}$ is H)
ESI-MS: 689.30 [M+H]$^+$

Example 54

N-(5-Cyano-1-(2,4-dimethoxyphenylsulfonyl)-3-(2-ethoxypyridin-3-yl)-2-oxoindolin-3-yl)-6-(4-ethyl-piperazin-1-yl)spiro[3.3]heptane-2-carboxamide 2,2,2-trifluoroacetate (Compound of formula I.4, wherein $X^1$ is NH, $R^1$ is CN, $R^2$ is H, $R^5$ is 4-ethylpiperazin-1-yl, $R^{8a}$ is methoxy, $R^{8b}$ is methoxy and $R^{8c}$ is H)
ESI-MS: 729.20 [M+H]$^+$

Example 55

N-(5-Cyano-1-(2,4-dimethoxyphenylsulfonyl)-3-(2-ethoxypyridin-3-yl)-2-oxoindolin-3-yl)-7-methyl-2,7-diazaspiro[3.5]nonane-2-carboxamide 2,2,2-trifluoroacetate (Compound of formula I.5, wherein $X^1$ is NH, $R^1$ is CN, $R^2$ is H, $R^5$ is methyl, $R^{8a}$ is methoxy, $R^{8b}$ is methoxy and $R^{8c}$ is H)
ESI-MS: 661.20 [M+H]$^+$

Example 56

N-(5-Cyano-1-(2,4-dimethoxyphenylsulfonyl)-3-(2-ethoxypyridin-3-yl)-2-oxoindolin-3-yl)-9-ethyl-3,9-diazaspiro[5.5]undecane-3-carboxamide 2,2,2-trifluoroacetate (Compound of formula I.13, wherein $X^1$ is NH, $R^1$ is CN, $R^2$ is H, $R^5$ is ethyl, $R^{8a}$ is methoxy, $R^{8b}$ is methoxy and $R^{8c}$ is H)
ESI-MS: 703.20 [M+H]$^+$

Example 57

N-(5-Cyano-1-(2,4-dimethoxyphenylsulfonyl)-3-(2-ethoxypyridin-3-yl)-2-oxoindolin-3-yl)-2-azaspiro[3.3]heptane-6-carboxamide 2,2,2-trifluoroacetate (Compound of formula I.3, wherein $X^1$ is NH, $R^1$ is CN, $R^2$ is H, $R^5$ is H, $R^{8a}$ is methoxy, $R^{8b}$ is methoxy and $R^{8c}$ is H)
ESI-MS: 618.20 [M+H]$^+$

Example 58

N-(5-Cyano-1-(2,4-dimethoxyphenylsulfonyl)-3-(2-ethoxypyridin-3-yl)-2-oxoindolin-3-yl)-2,6-diazaspiro[3.3]heptane-2-carboxamide 2,2,2-trifluoroacetate (Compound of formula I.1, wherein $X^1$ is NH, $R^1$ is CN, $R^2$ is H, $R^5$ is H, $R^{8a}$ is methoxy, $R^{8b}$ is methoxy and $R^{8c}$ is H)
ESI-MS: 619.20 [M+H]$^+$

Example 59

N-(5-Cyano-1-(2,4-dimethoxyphenylsulfonyl)-3-(2-ethoxypyridin-3-yl)-2-oxoindolin-3-yl)-6-(piperidin-4-yl)-2,6-diazaspiro[3.3]heptane-2-carboxamide 2,2,2-trifluoroacetate (Compound of formula I.1, wherein $X^1$ is NH, $R^1$ is CN, $R^2$ is H, $R^5$ is piperidin-4-yl, $R^{8a}$ is methoxy, $R^{8b}$ is methoxy and $R^{8c}$ is H)
ESI-MS: 702.30 [M+H]$^+$

Example 60

N-(5-Cyano-1-(2,4-dimethoxyphenylsulfonyl)-3-(2-ethoxypyridin-3-yl)-2-oxoindolin-3-yl)-2,7-diazaspiro[3.5]nonane-2-carboxamide 2,2,2-trifluoroacetate (Compound of formula I.5, wherein $X^1$ is NH, $R^1$ is CN, $R^2$ is H, $R^5$ is H, $R^{8a}$ is methoxy, $R^{8b}$ is methoxy and $R^{8c}$ is H)
ESI-MS: 647.20 [M+H]$^+$ III. Determination of the Biological Activity
1. Vasopressin V1b Receptor Binding Assay:
Substances:

The test substances were dissolved in a concentration of 5 mM in 100% DMSO and further diluted to $5 \times 10^{-4}$ M to $5 \times 10^{-9}$ M. These serial DMSO predilutions were diluted 1:10 with assay buffer. The substance concentration was further diluted 1:5 in the assay mixture resulting in 2% DMSO in the mixture. All dilutions were performed in a Biomek NX automation workstation (Beckman)

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized and centrifuged as described and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4.

In the assay mixture (200 μl), membranes (26 μg protein in incubation buffer) from CHO-K1 cells with stably expressed human V1b receptors (cell line hV1b_3H2_CHO) were incubated with 1.5 nM $^3$H-AVP (8-Arg-vasopressin, PerkinElmer, NET 800) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 μM AVP (Fluka 94836). All determinations were carried out as duplicate determinations. After incubation (60 minutes at room temperature), the free radioligand was filtered off by vacuum filtration (Tomtec Mach III) through Wathman GF/B glass fiber filter plates (UniFilter, PerkinElmer 6005177). The liquid scintillation measurement took place in a Microbeta TriLux 12 (Wallac).

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant human V1b receptors is 0.4 nM and was used to determine the Ki.

2. Vasopressin V1a Receptor Binding Assay:

Substances:

The test substances were dissolved in a concentration of 5 mM M in DMSO. Further dilution of these DMSO solutions took place as described for V1b.

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) using a Polytron homogenizer at intermediate setting for 2×10 seconds, and subsequently centrifuged at 40 000×g for 1 h. The membrane pellet was again homogenized in a High-Pressure-Homogenizer, Polytec 50K at 1500 PSI (Heinemann, Germany) and subsequently taken up in 50 mM Tris-HCl, pH 7.4, homogenized and stored in aliquots frozen in liquid nitrogen at −190° C.

Binding Assay:

The binding assay was carried out by the method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4.

In the assay mixture (200 µl), membranes (40 µg protein in incubation buffer) from CHO-K1 cells with stably expressed human V1a receptors (cell line hV1a_5_CHO) were incubated with 0.04 nM $^{125}$I-AVP (8-Arg-vasopressin, PerkinElmer NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Fluka 94836). Duplicate determinations were carried out.

After incubation (60 minutes at room temperature), the samples were processed as described for V1b.

Analysis:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki.

3. Oxytocin Receptor Binding Assay

Substances:

The substances were dissolved in a concentration of 5 mM in DMSO and diluted further as described for V1b.

Membrane Preparation:

Confluent HEK-293 cells with transiently expressing recombinant human oxytocin receptors were centrifuged at 750×g at room temperature for 5 minutes. The residue was taken up in ice-cold lysis buffer (50 mM Tris-HCl, 10% glycerol, pH 7.4 and Roche complete protease inhibitor) and subjected to an osmotic shock at 4° C. for 20 minutes. Cell lysates were then centrifuged at 750×g at 4° C. for 20 minutes, the residue was taken up in incubation buffer (50 mM Tris, 10 mM MgCl$_2$, 0.1% BSA, pH 7.4), and aliquots corresponding to 10$^7$ cells/ml were prepared. The aliquots were frozen at −80° C. until use.

Binding Assay:

On the day of the experiment, the cell lysate was thawed, homogenized, and diluted with incubation buffer (50 mM Tris, 10 mM MgCl$_2$, 0.1% BSA, pH 7.4) to the desired concentration. The reaction mixture of 0.200 ml was composed of cell lysate corresponding to 5×10$^4$ cells (HEK-293 cells expressing transiently human OT receptors) and 1 nM 3H-oxytocin (PerkinElmer NET858) in the presence of test substance (displacement experiment) or incubation buffer only (total binding). The nonspecific binding was determined in the presence of 1 µM oxytocin (Bachem AG, H2510). Determinations were carried out in duplicates. After 60 minutes incubation at room temperature, bound and free radioligand were separated by filtration under vacuum on GF/B UniFilter plates (Perkin Elmer #6005177) pre-incubated with 0.3% PEI. The bound radioactivity was determined by liquid scintillation measurement in a Microbeta (Perkin Elmer) plate counter.

Analysis:

The binding parameters were calculated by nonlinear regression analysis (SAS) in analogy to the LIGAND program of Munson and Rodbard (Analytical Biochem 1980; 107: 220-239). The Kd of $^3$H-oxytocin for the recombinant human OT receptors was 7.6 nM and was used to calculate the Ki from competition binding experiments.

4. Determination of the Microsomal Half-life:

The metabolic stability of the compounds of the invention was determined in the following assay.

The test substances were incubated in a concentration of 0.5 µM as follows:

0.5 µM test substance are preincubated together with liver microsomes from different species (from rat, human or other species) (0.25 mg of microsomal protein/ml) in 0.05 M potassium phosphate buffer of pH 7.4 in microtiter plates at 37° C. for 5 min. The reaction is started by adding NADPH (1 mg/mL). After 0, 5, 10, 15, 20 and 30 min, 50 µl aliquots are removed, and the reaction is immediately stopped and cooled with the same volume of acetonitrile. The samples are frozen until analyzed. The remaining concentration of undegraded test substance is determined by MSMS. The half-life (T½) is determined from the gradient of the signal of test substance/unit time plot, it being possible to calculate the half-life of the test substance, assuming first order kinetics, from the decrease in the concentration of the compound with time. The microsomal clearance (mCl) is calculated from mCl=ln 2/T½/(content of microsomal protein in mg/ml)×1000 [ml/min/mg] (modified from references: Di, The Society for Biomolecular Screening, 2003, 453-462; Obach, D M D, 1999 vol 27. N 11, 1350-1359).

5. Methods for in vitro Determination of the Cytochrome P450 (CYP) Inhibition

Luminescent Substrates for 2C9 and 3A4:

0.4 mg/ml human liver microsomes are preincubated with the test substances to be investigated (0-20 µM), the CYP-specific substrates, in 0.05 M potassium phosphate buffer of pH 7.4 at 37° C. for 10 min. The Cyp-specific substrate for CYP 2C9 is luciferin H, and for CYP 3A4 is luciferin BE. The reaction is started by adding NADPH. After incubation at RT for 30 min, the luciferin detection reagent is added, and the resulting luminescence signal is measured (modified from reference: Promega, Technical Bulletin P450-GLO™ Assays).

Midazolam CYP 3A4 Time-dependent Inhibition

The assay consists of 2 parts. Firstly, the test substance is preincubated with the liver microsomes (with NADPH=preincubation, then addition of the substrate; in the second part the substrate and the test substance are added simultaneously=coincubation.

Preincubation:

0.05 mg/ml microsomal protein (human liver microsomes) are preincubated with 0-10 μM (or 50 μM) test substance in 50 mM potassium phosphate buffer for 5 min. The reaction is started with NADPH. After 30 min 4 μM midazolam (final concentration) are added, and incubation is continued for 10 min. 75 μl of the reaction solution are removed after 10 min, and stopped with 150 μl of acetonitrile solution.

Coincubation:

0.05 mg/ml microsomal protein (human liver microsomes) are preincubated with 4 μm midazolam (final concentration) and 0-10 μM (or 50 μM) test substance in 50 mM potassium phosphate buffer for 5 min. The reaction is started with NADPH. 75 μl of the reaction solution are removed after 10 min and stopped with 150 μl of acetonitrile solution. The samples are frozen until the MSMS analysis (modified from references: Obdach, Journal of Pharmacology & Experimental Therapeutics, Vol 316, 1, 336-348, 2006; Walsky, Drug Metabolism and Disposition Vol 32, 6, 647-660, 2004).

6. Method for Determining the Solubility in Water (in mg/ml)

The solubility in water of the compounds of the invention can be determined for example by the so-called shake flask method (as specified in *ASTM International: E* 1148-02, *Standard test methods for measurement of aqueous solubility, Book of Standards Volume* 11.05.). This entails an excess of the solid compound being put into a buffer solution with a particular pH (for example phosphate buffer of pH 7.4), and the resulting mixture being shaken or stirred until equilibrium has been set up (typically 24 or 48 hours, sometimes even up to 7 days). The undissolved solid is then removed by filtration or centrifugation, and the concentration of the dissolved compound is determined by UV spectroscopy or high pressure liquid chromatography (HPLC) by means of an appropriate calibration plot.

7. Results

The results of the receptor binding investigations are expressed as receptor binding constants [$K_i$(V1b)] or selectivities [$K_i$(V1a)/$K_i$(V1b)]. The results of the investigation of the metabolic stability are indicated as microsomal clearance (mCl).

The compounds of the invention show very high affinities for the V1b receptor in these assays (maximally 100 nM, or maximally 10 nM, frequently <1 nM). The compounds also show high selectivities vis-à-vis the V1a receptor and a good metabolic stability, measured as microsomal clearance.

The results are listed in table C. The numbers of the compounds refer to the synthesis examples.

TABLE C

| Example | $K_i$(h-V1b)* [nM] | $K_i$(h-V1a)/$K_i$(h-V1b) |
|---|---|---|
| 1 | ++ | +++ |
| 1B | +++ | +++ |
| 2 | + | +++ |
| 3 | ++ | +++ |
| 4 | ++ | +++ |
| 5 | + | +++ |
| 6 | ++ | ++ |
| 7 | ++ | ++ |
| 8 | + | ++ |
| 9 | ++ | +++ |
| 10 | ++ | ++ |
| 11 | ++ | +++ |
| 12 | ++ | + |
| 13 | +++ | ++ |

TABLE C-continued

| Example | $K_i$(h-V1b)* [nM] | $K_i$(h-V1a)/$K_i$(h-V1b) |
|---|---|---|
| 14 | + | +++ |
| 15 | +++ | +++ |
| 16 | ++ | ++ |
| 17 | ++ | ++ |
| 18 | +++ | +++ |
| 19 | ++ | +++ |
| 20 | ++ | ++ |
| 20A | ++ | ++ |
| 21A | + | +++ |
| 21B | + | +++ |
| 22 | ++ | +++ |
| 24 | + | +++ |
| 25 | + | ++ |
| 27 | + | +++ |
| 29 | ++ | +++ |
| 31 | + | |
| 32 | + | ++ |
| 33 | + | ++ |
| 35B | + | ++ |
| 39B | + | ++ |
| 40 | ++ | +++ |
| 41 | + | +++ |
| 42 | + | +++ |
| 43B | + | +++ |
| 44 | + | |
| 45 | + | + |
| 46 | ++ | + |
| 47 | ++ | |
| 48 | ++ | |
| 50 | + | |
| 51 | + | |
| 52 | ++ | |
| 53 | + | |
| 54 | +++ | |
| 55 | + | |
| 56 | + | |
| 57 | + | |
| 58 | + | ++ |
| 59 | + | +++ |
| 60 | ++ | ++ |

*h = human

Key:

| | $K_i$(h-V1b) | $K_i$(h-V1a)/$K_i$(h-V1b) |
|---|---|---|
| + | >10-100 nM | 10-<25 |
| ++ | 1-10 nM | 25-75 |
| +++ | <1 nM | >75 |

The invention claimed is:

1. A compound of formula I

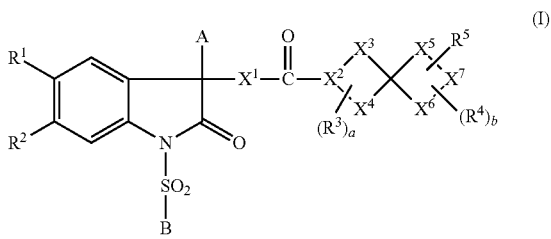

wherein

A is a ring selected from the group consisting of phenyl and 6-membered hetaryl containing 1 or 2 nitrogen atoms as ring members, where ring A carries one substituent $R^6$ and optionally one substituent $R^7$;

B is a ring selected from the group consisting of phenyl, pyridyl and quinolinyl, where ring B may carry 1, 2 or 3 substituents $R^8$;

$X^1$ is NH, $CH_2$ or O;

$X^2$ is N or CH;

$X^3$, $X^4$, $X^5$ and $X^6$, independently of each other, are selected from the group consisting of $—CH_2—$, $—O—$, $—S(O)_c—$, $—NH—$, $—C(O)—$, $—CH_2CH_2—$, $—CH_2O—$, $—OCH_2—$, $—S(O)_cCH_2—$, $—CH_2S(O)_c—$, $CH_2NH—$, $—NHCH_2—$, $—CH_2C(O)—$ and $—C(O)CH_2—$;

$X^7$ is NH, $CH_2$ or O;

$R^1$ is selected from the group consisting of cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^2$ is selected from the group consisting of hydrogen, cyano, halogen, $C_1$-$C_3$-alkyl, fluorinated $C_1$-$C_3$-alkyl, $C_3$-$C_6$-cycloalkyl, fluorinated $C_3$-$C_6$-cycloalkyl, $C_1$-$C_3$-alkoxy and fluorinated $C_1$-$C_3$-alkoxy;

$R^3$ and $R^4$, independently of each other and independently of each occurrence, are selected from the group consisting of hydroxyl, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy and $NR^9R^{10}$, and in case that $R^3$ or $R^4$ are bound to a carbon ring atom, are additionally selected from halogen; or two non-geminal radicals $R^3$ form together a group $—(CH_2)_k—$, where k is 1, 2, 3 or 4, where 1 or 2 hydrogen atoms in this group may be replaced by a methyl group; or two non-geminal radicals $R^4$ form together a group $—(CH_2)_k—$, where k is 1, 2, 3 or 4, where 1 or 2 hydrogen atoms in this group may be replaced by a methyl group; or two geminal radicals $R^3$ form together a group $—(CH_2)_j—$, where j is 2, 3, 4 or 5, where 1 or 2 hydrogen atoms in this group may be replaced by a methyl group; or two geminal radicals $R^4$ form together a group $—(CH_2)_j—$, where j is 2, 3, 4 or 5, where 1 or 2 hydrogen atoms in this group may be replaced by a methyl group;

with the proviso that $R^3$ and $R^4$ are not halogen, hydroxyl, $C_1$-$C_4$-alkoxy or $C_1$-$C_4$-haloalkoxy if they are bound to a carbon atom in α-position to a nitrogen ring atom;

$R^5$ is selected from the group consisting of hydrogen; cyano; $C_1$-$C_6$-alkyl; $C_2$-$C_6$-alkenyl; $C_2$-$C_6$-alkynyl; $C_3$-$C_7$-cycloalkyl, where the four last-mentioned radicals may be partially or fully halogenated and/or may carry one or more substituents $R^{11}$; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$; $—OR^{13}$; $—S(O)_lR^{13}$; $NR^{14}R^{15}$; and $—C(=O)R^{16}$;

$R^6$ and $R^7$, independently of each other, are selected from the group consisting of halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

each $R^8$ is independently selected from the group consisting of halogen, cyano, hydroxyl, $C_1$-$C_3$-alkyl, fluorinated $C_1$-$C_3$-alkyl, $C_1$-$C_3$-hydroxyalkyl, $C_1$-$C_3$-alkoxy and fluorinated $C_1$-$C_3$-alkoxy;

$R^9$ and $R^{10}$, independently of each other, are selected from the group consisting of hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, phenyl and benzyl;

each $R^{11}$ is independently selected from the group consisting of cyano; $—OR^{13}$; $—S(O)_lR^{13}$; $NR^{14}R^{15}$; $—C(=O)R^{16}$; $C_3$-$C_6$-cycloalkyl; $C_3$-$C_6$-halocycloalkyl; phenyl which may carry 1, 2 or 3 substituents $R^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally selected from $C_1$-$C_4$-alkyl or $C_1$-$C_4$-haloalkyl;

each $R^{12}$ is independently selected from the group consisting of halogen; hydroxyl; cyano; nitro; $C_1$-$C_4$-alkyl; $C_1$-$C_4$-haloalkyl; $C_3$-$C_6$-cycloalkyl; $C_3$-$C_6$-halocycloalkyl; $C_1$-$C_4$-alkoxy; $C_1$-$C_4$-haloalkoxy; $C_1$-$C_4$-alkylthio; $C_1$-$C_4$-haloalkylthio; $C_1$-$C_4$-alkylsulfinyl; $C_1$-$C_4$-haloalkylsulfinyl; $C_1$-$C_4$-alkylsulfonyl; $C_1$-$C_4$-haloalkylsulfonyl; phenyl; phenoxy; benzyloxy, where the phenyl moiety in the three last-mentioned radicals may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members, where the heteromonocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

each $R^{13}$ is independently selected from the group consisting of hydrogen; $C_1$-$C_4$-alkyl; $C_1$-$C_4$-haloalkyl; $C_1$-$C_4$-alkyl which carries one substituent $R^{17}$; $C_2$-$C_4$-alkenyl; $C_2$-$C_4$-haloalkenyl; $C_2$-$C_4$-alkynyl; $C_2$-$C_4$-haloalkynyl; $C_3$-$C_6$-cycloalkyl; $C_3$-$C_6$-halocycloalkyl; phenyl which may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and $SO_2$ as ring members, where the heterocyclic ring may carry 1, 2 or 3 substituents selected from the group consisting of halogen, hydroxyl, cyano, $C_1$-$C_4$-alkyl, $C_1$-$C_4$-haloalkyl, $C_1$-$C_4$-alkoxy and $C_1$-$C_4$-haloalkoxy;

R$^{14}$ and R$^{15}$, independently of each other and independently of each occurrence, are selected from the group consisting of hydrogen; C$_1$-C$_4$-alkyl; C$_1$-C$_4$-haloalkyl; C$_3$-C$_6$-cycloalkyl; C$_3$-C$_6$-halocycloalkyl; phenyl which may carry 1, 2 or 3 substituents selected from the group consisting of halogen, hydroxyl, cyano, C$_1$-C$_4$-alkyl, C$_1$-C$_4$-haloalkyl, C$_1$-C$_4$-alkoxy and C$_1$-C$_4$-haloalkoxy; and a 3-, 4-, 5-, 6- or 7-membered saturated, partially unsaturated or maximally unsaturated heterocyclic ring containing 1, 2 or 3 heteroatoms or heteroatom groups selected from the group consisting of O, N, S, NO, SO and SO$_2$ as ring members, where the heterocyclic ring may carry 1, 2 or 3 substituents selected from the group consisting of halogen, hydroxyl, cyano, C$_1$-C$_4$-alkyl, C$_1$-C$_4$-haloalkyl, C$_1$-C$_4$-alkoxy and C$_1$-C$_4$-haloalkoxy, C$_1$-C$_4$-alkylcarbonyl and C$_1$-C$_4$-haloalkylcarbonyl;

each R$^{16}$ is independently selected the group consisting of from hydrogen, C$_1$-C$_4$-alkyl, C$_1$-C$_4$-haloalkyl, C$_3$-C$_6$-cycloalkyl, C$_3$-C$_6$-halocycloalkyl, phenyl, —OR$^{13}$ and NR$^{14}$R$^{15}$;

each R$^{17}$ is independently selected from the group consisting of cyano; hydroxyl; C$_1$-C$_4$-alkoxy; C$_1$-C$_4$-haloalkoxy; C$_1$-C$_4$-alkylthio; C$_1$-C$_4$-haloalkylthio; C$_1$-C$_4$-alkylsulfinyl; C$_1$-C$_4$-haloalkylsulfinyl; C$_1$-C$_4$-alkylsulfonyl; C$_1$-C$_4$-haloalkylsulfonyl; NR$^{14}$R$^{15}$; C$_1$-C$_4$-alkylcarbonyl; C$_1$-C$_4$-haloalkylcarbonyl; C$_3$-C$_6$-cycloalkyl; C$_3$-C$_6$-halocycloalkyl; phenyl which may carry 1, 2 or 3 substituents R$^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and SO$_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and SO$_2$ as ring members, where the heteromonocyclic or heterobicyclic ring may carry 1, 2 or 3 substituents R$^{12}$;

a is 0, 1 or 2;
b is 0, 1 or 2;
c is 0, 1 or 2; and
l is 0, 1 or 2;

or an N-oxide, stereoisomer, or pharmaceutically acceptable salt thereof, or wherein at least one of the atoms has been replaced by its stable, non-radioactive isotope.

2. The compound as claimed in claim 1, wherein at least one hydrogen atom has been replaced by a deuterium atom.

3. The compound as claimed in claim 1, where X$^1$ is NH or CH$_2$.

4. The compound as claimed in claim 1, where X$^3$, X$^4$, X$^5$ and X$^6$, independently of each other, are selected from the group consisting of —CH$_2$— and —CH$_2$CH$_2$—.

5. The compound as claimed in claim 1, where X$^7$ is NH or CH$_2$.

6. The compound as claimed in claim 1, where R$^5$ is bound to X$^7$.

7. The compound as claimed in claim 1, where A is phenyl or pyridyl, where A carries one substituent R$^6$ and optionally one substituent R$^7$.

8. The compound as claimed in claim 7, where A is phenyl or 3-pyridyl, where A carries the radical R$^6$ in 2-position and the radical R$^7$, if present, in 4- or 5-position, relative to the 1-position of the attachment point of A to the remainder of the molecule.

9. The compound as claimed in claim 7, where A is phenyl or 3-pyridyl, where A carries the radical R$^6$ in 2-position and no radical R$^7$.

10. The compound as claimed in claim 1, where B is phenyl or 2-pyridyl, where B may carry 1, 2 or 3 substituents R$^8$.

11. The compound as claimed in claim 1, where R$^1$ is halogen or cyano.

12. The compound as claimed in claim 11, where R$^1$ is selected from the group consisting of cyano, fluorine and chlorine.

13. The compound as claimed in claim 1, where R$^2$ is hydrogen or halogen.

14. The compound as claimed in claim 1, where R$^3$ and R$^4$, independently of each other and independently of each occurrence, are selected from the group consisting of halogen and C$_1$-C$_4$-alkyl, with the proviso that R$^3$ and R$^4$ are not halogen if they are bound to a carbon atom in α-position to a nitrogen ring atom.

15. The compound as claimed in claim 1, where R$^5$ is selected from the group consisting of hydrogen; C$_1$-C$_6$-alkyl; fluorinated C$_1$-C$_6$-alkyl; C$_3$-C$_6$-cycloalkyl; fluorinated C$_3$-C$_6$-cycloalkyl; C$_1$-C$_6$-alkyl which carries one substituent R$^{11}$; phenyl which may carry 1, 2 or 3 substituents R$^{12}$; a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and SO$_2$ as ring members; and a 5-, 6-, 7-, 8-, 9-, 10- or 11-membered saturated, partially unsaturated or maximally unsaturated heterobicyclic ring containing 1, 2 or 3 heteroatoms or heteroatom groups selected from the group consisting of O, N, S, NO, SO and SO$_2$ as ring members, where the heteromonocyclic or heterobicyclic ring may carry 1, 2 or 3 substituents R$^{12}$; and in case that R$^5$ is bound to a carbon ring atom, it is additionally selected from —OR$^{13}$.

16. The compound as claimed in claim 15, where R$^5$ is selected from the group consisting of hydrogen; C$_1$-C$_6$-alkyl; fluorinated C$_1$-C$_6$-alkyl; C$_1$-C$_6$-alkyl which carries one substituent R$^{11}$; a 3-, 4-, 5- or 6-membered saturated heteromonocyclic ring containing 1 or 2 heteroatoms or heteroatom groups selected from the group consisting of O, N, S, NO, SO and SO$_2$ as ring members; and a 7-, 8-, 9-, 10- or 11-membered saturated heterobicyclic ring containing 1 or 2 heteroatoms or heteroatom groups selected from the group consisting of O, N, S, NO, SO and SO$_2$ as ring members, where the heteromonocyclic or heterobicyclic ring may carry 1, 2 or 3 substituents R$^{12}$; and in case that R$^5$ is bound to a carbon ring atom, it is additionally selected from —OR$^{13}$.

17. The compound as claimed in claim 16, where R$^5$ is selected from the group consisting of hydrogen; C$_1$-C$_4$-alkyl; C$_1$-C$_4$-alkyl which carries one substituent R$^{11}$; a 4-, 5- or 6-membered saturated heteromonocyclic ring containing 1 or 2 heteroatoms selected from the group consisting of O, N and S as ring members; and a 7-, 8-, 9-, 10- or 11-membered saturated heterobicyclic spiro ring containing 1 or 2 heteroatoms selected from the group consisting of O, N and S as ring members, where the heteromonocyclic or heterobicyclic ring may carry 1 or 2 substituents R$^{12}$; and in case that R$^5$ is bound to a carbon ring atom, it is additionally selected from —OR$^{13}$.

18. The compound as claimed in claim 1, where R$^{11}$ is selected from the group consisting of cyano; —OR$^{13}$; NR$^{14}$R$^{15}$; a 3-, 4-, 5-, 6- or 7-membered saturated heteromonocyclic ring containing 1, 2 or 3 heteroatoms or heteroatom groups selected from the group consisting of O, N, S, NO, SO and $SO_2$ as ring members; and a 5-, 6-, 7-, 8-, 9-, 10- or 11-membered saturated heterobicyclic ring containing 1, 2 or 3 heteroatoms or heteroatom groups selected from the group consisting of O, N, S, NO, SO and $SO_2$ as ring members, where the heteromonocyclic or heterobicyclic ring may carry 1, 2 or 3 substituents $R^{12}$; and as a substituent on a cycloalkyl ring, $R^{11}$ is additionally selected from the group consisting of $C_1$-$C_4$-alkyl and $C_1$-$C_4$-haloalkyl.

19. The compound as claimed in claim 18, where $R^{11}$ is $NR^{14}R^{15}$, where $R^{14}$ and $R^{15}$ are independently selected from the group consisting of hydrogen and $C_1$-$C_4$-alkyl; or a 4-,5- or 6-membered saturated heteromonocyclic ring containing 1 or 2 heteroatoms or heteroatom groups selected from the group consisting of O, N, S, NO, SO and $SO_2$ as ring members, where the heteromonocyclic ring may carry 1 or 2 or 3 substituents $R^{12}$.

20. The compound as claimed in claim 1, where $R^{12}$ is selected from the group consisting of halogen; cyano; $C_1$-$C_4$-alkyl; fluorinated $C_1$-$C_4$-alkyl; $C_1$-$C_4$-alkoxy; fluorinated $C_1$-$C_4$-alkoxy; phenyl which may carry 1, 2 or 3 substituents selected from the group consisting of halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy; and a 3-, 4-, 5- or 6-membered saturated heteromonocyclic ring containing 1, 2 or 3 heteroatoms or heteroatom groups selected from the group consisting of O, N, S, NO, SO and $SO_2$ as ring members, where the heteromonocyclic ring may carry 1, 2 or 3 substituents selected from the group consisting of halogen, hydroxyl, cyano, $C_1$-$C_4$-alkyl, fluorinated $C_1$-$C_4$-alkyl, $C_1$-$C_4$-alkoxy and fluorinated $C_1$-$C_4$-alkoxy.

21. The compound as claimed in claim 20, where $R^{12}$ is selected from the group consisting of $C_1$-$C_4$-alkyl, fluorinated $C_1$-$C_4$-alkyl, and a 3-, 4-, 5- or 6-membered saturated heteromonocyclic ring containing 1 or 2 heteroatoms selected from the group consisting of O, N and S as ring members.

22. The compound as claimed in claim 1, where $R^{13}$ is selected from the group consisting of hydrogen, $C_1$-$C_4$-alkyl, $C_1$-$C_4$-haloalkyl and $C_1$-$C_4$-alkyl which carries one substituent $R^{17}$.

23. The compound as claimed in claim 1, where $R^{17}$ is selected from $NR^{14}R^{15}$; phenyl which may carry 1, 2 or 3 substituents $R^{12}$; and a 3-, 4-, 5-, 6- or 7-membered saturated, partially unsaturated or maximally unsaturated heteromonocyclic ring containing 1, 2 or 3 heteroatoms or heteroatom groups selected from the group consisting of O, N, S, NO, SO and $SO_2$ as ring members.

24. The compound as claimed in claim 1, where $R^6$ is $C_1$-$C_3$-alkoxy.

25. The compound as claimed in claim 1, where $R^7$ is halogen or $C_1$-$C_3$-alkoxy.

26. The compound as claimed in claim 1, where each $R^8$ is independently selected from the group consisting of halogen, cyano, $C_1$-$C_3$-alkyl, fluorinated $C_1$-$C_3$-alkyl, $C_1$-$C_3$-alkoxy and fluorinated $C_1$-$C_3$-alkoxy.

27. The compound as claimed in claim 26, where each $R^8$ is independently selected from the group consisting of fluorine, cyano, methyl, methoxy and trifluoromethoxy.

28. The compound as claimed in claim 1, where a and b are independently 0 or 1.

29. The compound as claimed in claim 1, of formula IA

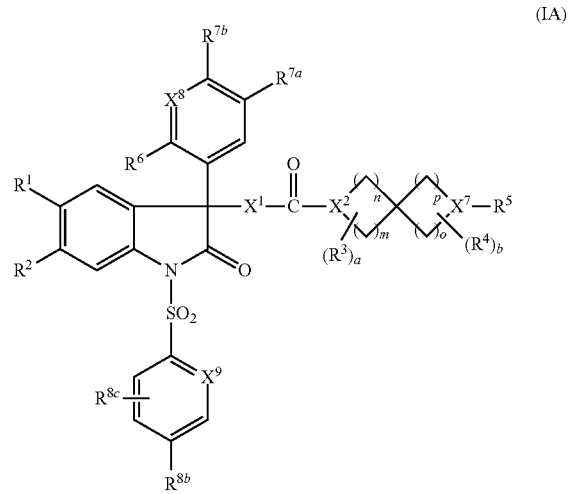

(IA)

where
$X^1$, $X^2$, $X^7$, $R^1$, $R^2$, $R^3$, $R^4$, $R^5$, $R^6$, a and b are as defined in claim 1;
$X^8$ is N or CH;
$X^9$ is N or C—$R^{8a}$;
$R^{7a}$ and $R^{7b}$, independently of each other, are hydrogen or have one of the definitions given for $R^7$ in claim 1, with the proviso that at least one of $R^{7a}$ and $R^{7b}$ is hydrogen;
$R^{8a}$, $R^{8b}$ and $R^{8c}$, independently of each other, are hydrogen or have one of the definitions given for $R^8$ in claim 1; and
m, n, o and p are independently of each other 1 or 2.

30. The compound as claimed in claim 29, where m and n are both 1 or are both 2.

31. The compound as claimed in claim 29, where o and p are both 1 or are both 2.

32. A compound selected from the group consisting of:
N-[5-Cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide;
N-[(3S)-5-Cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide;
N-[(3R)-5-Cyano-3-(2-ethoxy-3-pyridyl)-1-(4-methoxyphenyl)sulfonyl-2-oxo-indolin-3-yl]-2-(2-morpholinoethyl)-2,6-diazaspiro[3.3]heptane-6-carboxamide;
N-[5-Cyano-3-(2-ethoxy-3-pyridyl)-1-(4-methoxyphenyl)sulfonyl-2-oxo-indolin-3-yl]-2-(3-morpholinopropyl)-2,6-diazaspiro[3.3]heptane-6-carboxamide;
N-[(3S)-5-Cyano-3-(2-ethoxy-3-pyridyl)-1-(4-methoxyphenyl)sulfonyl-2-oxo-indolin-3-yl]-2-(3-morpholinopropyl)-2,6-diazaspiro[3.3]heptane-6-carboxamide;
N-[(3R)-5-Cyano-3-(2-ethoxy-3-pyridyl)-1-(4-methoxyphenyl)sulfonyl-2-oxo-indolin-3-yl]-2-(3-morpholinopropyl)-2,6-diazaspiro[3.3]heptane-6-carboxamide;
N-[5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;
N-[(3S)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-1-[(5-methoxy-2-pyridyl)sulfonyl]-2-oxo-indolin-3-yl]-2-(2-morpholinoethyl)-2,6-diazaspiro[3.3]heptane-6-carboxamide;

N-[(3S)-5-Cyano-3-(2-ethoxy-3-pyridyl)-1-[(5-methoxy-2-pyridyl)sulfonyl]-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-[(5-methoxy-2-pyridyl)sulfonyl]-2-oxo-indolin-3-yl]-2-(2-morpholinoethyl)-2,6-diazaspiro[3.3]heptane-6-carboxamide;

N-[5-cyano-1-(4-cyanophenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3S)-5-cyano-1-(4-cyanophenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3R)-5-cyano-1-(4-cyanophenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;

N-[(3S)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;

N-[5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3S)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3R)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-1-(4-fluorophenyl)sulfonyl-2-oxo-indolin-3-yl]-2-(2-morpholinoethyl)-2,6-diazaspiro[3.3]heptane-6-carboxamide;

N-[(3S)-5-Cyano-3-(2-ethoxy-3-pyridyl)-1-(4-fluorophenyl)sulfonyl-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-(4-fluorophenyl)sulfonyl-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-1-(4-methoxyphenyl)sulfonyl-2-oxo-indolin-3-yl]-2-(2-diethylaminoethyl)-2,6-diazaspiro[3.3]heptane-6-carboxamide;

N-[(3S)-5-Cyano-3-(2-ethoxy-3-pyridyl)-1-(4-methoxyphenyl)sulfonyl-2-oxo-indolin-3-yl]-2-(2-diethylaminoethyl)-2,6-diazaspiro[3.3]heptane-6-carboxamide;

N-[(3R)-5-Cyano-3-(2-ethoxy-3-pyridyl)-1-(4-methoxyphenyl)sulfonyl-2-oxo-indolin-3-yl]-2-(2-diethylaminoethyl)-2,6-diazaspiro[3.3]heptane-6-carboxamide;

N-[5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[(3S)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[(3R)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[(3S)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[5-Cyano-1-(4-methoxyphenyl)sulfonyl-3-(2-methoxy-3-pyridyl)-2-oxo-indolin-3-yl]-2-(2-morpholinoethyl)-2,6-diazaspiro[3.3]heptane-6-carboxamide;

N-[(3S)-5-Cyano-1-(4-methoxyphenyl)sulfonyl-3-(2-methoxy-3-pyridyl)-2-oxo-indolin-3-yl]-2-(2-morpholinoethyl)-2,6-diazaspiro[3.3]heptane-6-carboxamide;

N-[(3R)-5-Cyano-1-(4-methoxyphenyl)sulfonyl-3-(2-methoxy-3-pyridyl)-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-1-(4-methoxyphenyl)sulfonyl-2-oxo-indolin-3-yl]-2-[2-(1-piperidyl)ethyl]-2,6-diazaspiro[3.3]heptane-6-carboxamide;

N-[(3S)-5-Cyano-3-(2-ethoxy-3-pyridyl)-1-(4-methoxyphenyl)sulfonyl-2-oxo-indolin-3-yl]-2-[2-(1-piperidyl)ethyl]-2,6-diazaspiro[3.3]heptane-6-carboxamide;

N-[(3R)-5-Cyano-3-(2-ethoxy-3-pyridyl)-1-(4-methoxyphenyl)sulfonyl-2-oxo-indolin-3-yl]-2-[2-(1-piperidyl)ethyl]-2,6-diazaspiro[3.3]heptane-6-carboxamide;

N-[5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[(3S)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[(3R)-5-Cyano-3-(2-ethoxy-3-pyridyl)-1-(2-methoxyphenyl)sulfonyl-2-oxo-indolin-3-yl]-2-(2-morpholinoethyl)-2,6-diazaspiro[3.3]heptane-6-carboxamide;

N-[5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3S)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[(3R)-5-Cyano-1-(2,4-dimethoxyphenyl)sulfonyl-3-(2-ethoxy-3-pyridyl)-2-oxo-indolin-3-yl]-2-(2-morpholinoethyl)-2,6-diazaspiro[3.3]heptane-6-carboxamide;

N-[5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[(3S)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[(3R)-5-Cyano-3-(2-ethoxy-3-pyridyl)-2-oxo-1-(p-tolylsulfonyl)indolin-3-yl]-2-(2-morpholinoethyl)-2,6-diazaspiro[3.3]heptane-6-carboxamide;

N-[5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;
N-[(3S)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;
N-[(3R)-5-Cyano-3-(2-ethoxy-3-pyridyl)-1-(4-fluoro-2-methoxy-phenyl)sulfonyl-2-oxo-indolin-3-yl]-2-(2-morpholinoethyl)-2,6-diazaspiro[3.3]heptane-6-carboxamide;
N-[5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;
N-[(3S)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;
N-[(3R)-5-Cyano-3-(2-ethoxy-3-pyridyl)-1-(2-fluoro-4-methoxy-phenyl)sulfonyl-2-oxo-indolin-3-yl]-2-(2-morpholinoethyl)-2,6-diazaspiro[3.3]heptane-6-carboxamide;
N-[5-Cyano-3-(2-ethoxy-3-pyridyl)-6-fluoro-1-(4-methoxyphenyl)sulfonyl-2-oxo-indolin-3-yl]-2-(2-morpholinoethyl)-2,6-diazaspiro[3.3]heptane-6-carboxamide;
N-[(3S)-5-Cyano-3-(2-ethoxy-3-pyridyl)-6-fluoro-1-(4-methoxyphenyl)sulfonyl-2-oxo-indolin-3-yl]-2-(2-morpholinoethyl)-2,6-diazaspiro[3.3]heptane-6-carboxamide;
N-[(3R)-5-Cyano-3-(2-ethoxy-3-pyridyl)-6-fluoro-1-(4-methoxyphenyl)sulfonyl-2-oxo-indolin-3-yl]-2-(2-morpholinoethyl)-2,6-diazaspiro[3.3]heptane-6-carboxamide;
3-(2-Ethoxy-3-pyridyl)-1-(4-methoxyphenyl)sulfonyl-3-[2-[2-(2-morpholinoethyl)-2,6-diazaspiro[3.3]heptan-6-yl]-2-oxo-ethyl]-2-oxo-indoline-5-carbonitrile;
(3S)-3-(2-Ethoxy-3-pyridyl)-1-(4-methoxyphenyl)sulfonyl-3-[2-[2-(2-morpholinoethyl)-2,6-diazaspiro[3.3]heptan-6-yl]-2-oxo-ethyl]-2-oxo-indoline-5-carbonitrile;
(3R)-3-(2-Ethoxy-3-pyridyl)-1-(4-methoxyphenyl)sulfonyl-3-[2-[2-(2-morpholinoethyl)-2,6-diazaspiro[3.3]heptan-6-yl]-2-oxo-ethyl]-2-oxo-indoline-5-carbonitrile;
N-[5-Cyano-3-(2-ethoxy-3-pyridyl)-1-(4-methoxyphenyl)sulfonyl-2-oxo-indolin-3-yl]-2-(2-morpholinoethoxy)-6-azaspiro[3.3]heptane-6-carboxamide;
N-[(3S)-5-Cyano-3-(2-ethoxy-3-pyridyl)-1-(4-methoxyphenyl)sulfonyl-2-oxo-indolin-3-yl]-2-(2-morpholinoethoxy)-6-azaspiro[3.3]heptane-6-carboxamide;
N-[(3R)-5-Cyano-3-(2-ethoxy-3-pyridyl)-1-(4-methoxyphenyl)sulfonyl-2-oxo-indolin-3-yl]-2-(2-morpholinoethoxy)-6-azaspiro[3.3]heptane-6-carboxamide;
N-[5-Cyano-1-(2,4-dimethoxyphenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
(3S)-N-[5-Cyano-1-(2,4-dimethoxyphenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
(3R)-N-[5-Cyano-1-(2,4-dimethoxyphenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
N-[5-Cyano-1-(2,4-dimethoxyphenyl)sulfonyl-3-(2-ethoxy-3-pyridyl)-2-oxo-indolin-3-yl]-2-(1-methyl-4-piperidyl)-2,6-diazaspiro[3.3]heptane-6-carboxamide;
(3S)-N-[5-Cyano-1-(2,4-dimethoxyphenyl)sulfonyl-3-(2-ethoxy-3-pyridyl)-2-oxo-indolin-3-yl]-2-(1-methyl-4-piperidyl)-2,6-diazaspiro[3.3]heptane-6-carboxamide;
(3R)-N-[5-Cyano-1-(2,4-dimethoxyphenyl)sulfonyl-3-(2-ethoxy-3-pyridyl)-2-oxo-indolin-3-yl]-2-(1-methyl-4-piperidyl)-2,6-diazaspiro[3.3]heptane-6-carboxamide;
N-[5-cyano-1-(4-cyanophenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
N-[(3S)-5-cyano-1-(4-cyanophenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
N-[(3R)-5-cyano-1-(4-cyanophenyl)sulfonyl-3-(2-ethoxy-3-pyridyl)-2-oxo-indolin-3-yl]-2-(1-isopropyl-4-piperidyl)-2,6-diazaspiro[3.3]heptane-6-carboxamide;
N-[5-Cyano-3-(2-ethoxy-3-pyridyl)-2-oxo-1-(p-tolylsulfonyl)indolin-3-yl]-2-(1-isopropyl-4-piperidyl)-2,6-diazaspiro[3.3]heptane-6-carboxamide;
N-[(3S)-5-Cyano-3-(2-ethoxy-3-pyridyl)-2-oxo-1-(p-tolylsulfonyl)indolin-3-yl]-2-(1-isopropyl-4-piperidyl)-2,6-diazaspiro[3.3]heptane-6-carboxamide;
N-[(3R)-5-Cyano-3-(2-ethoxy-3-pyridyl)-2-oxo-1-(p-tolylsulfonyl)indolin-3-yl]-2-(1-isopropyl-4-piperidyl)-2,6-diazaspiro[3.3]heptane-6-carboxamide;
N-[5-Cyano-3-(2-ethoxy-3-pyridyl)-2-oxo-1-(p-tolylsulfonyl)indolin-3-yl]-2-(oxetan-3-yl)-2,6-diazaspiro[3.3]heptane-6-carboxamide;
N-[(3S)-5-Cyano-3-(2-ethoxy-3-pyridyl)-2-oxo-1-(p-tolylsulfonyl)indolin-3-yl]-2-(oxetan-3-yl)-2,6-diazaspiro[3.3]heptane-6-carboxamide;
N-[(3R)-5-Cyano-3-(2-ethoxy-3-pyridyl)-2-oxo-1-(p-tolylsulfonyl)indolin-3-yl]-2-(oxetan-3-yl)-2,6-diazaspiro[3.3]heptane-6-carboxamide;
N-[5-Cyano-3-(2-ethoxy-3-pyridyl)-1-(4-fluorophenyl)sulfonyl-2-oxo-indolin-3-yl]-2-(1-isopropyl-4-piperidyl)-2,6-diazaspiro[3.3]heptane-6-carboxamide;
N-[(3S)-5-Cyano-3-(2-ethoxy-3-pyridyl)-1-(4-fluorophenyl)sulfonyl-2-oxo-indolin-3-yl]-2-(1-isopropyl-4-piperidyl)-2,6-diazaspiro[3.3]heptane-6-carboxamide;
N-[(3R)-5-Cyano-3-(2-ethoxy-3-pyridyl)-1-(4-fluorophenyl)sulfonyl-2-oxo-indolin-3-yl]-2-(1-isopropyl-4-piperidyl)-2,6-diazaspiro[3.3]heptane-6-carboxamide;
N-[5-Cyano-3-(2-ethoxy-3-pyridyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[(3S)-5-Cyano-3-(2-ethoxy-3-pyridyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[(3R)-5-Cyano-3-(2-ethoxy-3-pyridyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[5-Cyano-3-(2-ethoxy-3-pyridyl)-1-(4-methoxyphenyl)sulfonyl-2-oxo-indolin-3-yl]-2-(1-isopropyl-4-piperidyl)-2,6-diazaspiro[3.3]heptane-6-carboxamide;
N-[(3S)-5-Cyano-3-(2-ethoxy-3-pyridyl)-1-(4-methoxyphenyl)sulfonyl-2-oxo-indolin-3-yl]-2-(1-isopropyl-4-piperidyl)-2,6-diazaspiro[3.3]heptane-6-carboxamide;

N-[(3R)-5-Cyano-3-(2-ethoxy-3-pyridyl)-1-(4-methoxyphenyl)sulfonyl-2-oxo-indolin-3-yl]-2-(1-isopropyl-4-piperidyl)-2,6-diazaspiro[3.3]heptane-6-carboxamide;
N-[5-Cyano-3-(2-ethoxy-3-pyridyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[(3S)-5-Cyano-3-(2-ethoxy-3-pyridyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[(3R)-5-Cyano-3-(2-ethoxy-3-pyridyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[5-Cyano-3-(2-ethoxy-3-pyridyl)-1-(4-fluorophenyl)sulfonyl-2-oxo-indolin-3-yl]-2-(oxetan-3-yl)-2,6-diazaspiro[3.3]heptane-6-carboxamide;
N-[(3S)-5-Cyano-3-(2-ethoxy-3-pyridyl)-1-(4-fluorophenyl)sulfonyl-2-oxo-indolin-3-yl]-2-(oxetan-3-yl)-2,6-diazaspiro[3.3]heptane-6-carboxamide;
N-[(3R)-5-Cyano-3-(2-ethoxy-3-pyridyl)-1-(4-fluorophenyl)sulfonyl-2-oxo-indolin-3-yl]-2-(oxetan-3-yl)-2,6-diazaspiro[3.3]heptane-6-carboxamide;
N-[5-Cyano-3-(2-ethoxy-3-pyridyl)-1-(2-methoxyphenyl)sulfonyl-2-oxo-indolin-3-yl]-2-(1-methyl-4-piperidyl)-2,6-diazaspiro[3.3]heptane-6-carboxamide;
N-[(3S)-5-Cyano-3-(2-ethoxy-3-pyridyl)-1-(2-methoxyphenyl)sulfonyl-2-oxo-indolin-3-yl]-2-(1-methyl-4-piperidyl)-2,6-diazaspiro[3.3]heptane-6-carboxamide;
N-[(3R)-5-Cyano-3-(2-ethoxy-3-pyridyl)-1-(2-methoxyphenyl)sulfonyl-2-oxo-indolin-3-yl]-2-(1-methyl-4-piperidyl)-2,6-diazaspiro[3.3]heptane-6-carboxamide;
N-[5-Cyano-3-(2-ethoxy-3-pyridyl)-1-(4-methoxyphenyl)sulfonyl-2-oxo-indolin-3-yl]-2-(1-methyl-4-piperidyl)-2,6-diazaspiro[3.3]heptane-6-carboxamide;
N-[(3S)-5-Cyano-3-(2-ethoxy-3-pyridyl)-1-(4-methoxyphenyl)sulfonyl-2-oxo-indolin-3-yl]-2-(1-methyl-4-piperidyl)-2,6-diazaspiro[3.3]heptane-6-carboxamide;
N-[(3R)-5-Cyano-3-(2-ethoxy-3-pyridyl)-1-(4-methoxyphenyl)sulfonyl-2-oxo-indolin-3-yl]-2-(1-methyl-4-piperidyl)-2,6-diazaspiro[3.3]heptane-6-carboxamide;
N-[1-(Benzenesulfonyl)-5-cyano-3-(2-ethoxy-3-pyridyl)-2-oxo-indolin-3-yl]-2-(1-methyl-4-piperidyl)-2,6-diazaspiro[3.3]heptane-6-carboxamide;
N-[(3S)-1-(Benzenesulfonyl)-5-cyano-3-(2-ethoxy-3-pyridyl)-2-oxo-indolin-3-yl]-2-(1-methyl-4-piperidyl)-2,6-diazaspiro[3.3]heptane-6-carboxamide;
N-[(3R)-1-(Benzenesulfonyl)-5-cyano-3-(2-ethoxy-3-pyridyl)-2-oxo-indolin-3-yl]-2-(1-methyl-4-piperidyl)-2,6-diazaspiro[3.3]heptane-6-carboxamide;
N-[5-Cyano-3-(2-ethoxyphenyl)-1-(4-methoxyphenyl)sulfonyl-2-oxo-indolin-3-yl]-2-[1-(oxetan-3-yl)-4-piperidyl]-2,6-diazaspiro[3.3]heptane-6-carboxamide;
N-[(3S)-5-Cyano-3-(2-ethoxyphenyl)-1-(4-methoxyphenyl)sulfonyl-2-oxo-indolin-3-yl]-2-[1-(oxetan-3-yl)-4-piperidyl]-2,6-diazaspiro[3.3]heptane-6-carboxamide;
N-[(3R)-5-Cyano-3-(2-ethoxyphenyl)-1-(4-methoxyphenyl)sulfonyl-2-oxo-indolin-3-yl]-2-[1-(oxetan-3-yl)-4-piperidyl]-2,6-diazaspiro[3.3]heptane-6-carboxamide;
N-[5-Cyano-1-(4-cyanophenyl)sulfonyl-3-(2-ethoxyphenyl)-2-oxo-indolin-3-yl]-2-[1-(oxetan-3-yl)-4-piperidyl]-2,6-diazaspiro[3.3]heptane-6-carboxamide;
N-[(3S)-5-Cyano-1-(4-cyanophenyl)sulfonyl-3-(2-ethoxyphenyl)-2-oxo-indolin-3-yl]-2-[1-(oxetan-3-yl)-4-piperidyl]-2,6-diazaspiro[3.3]heptane-6-carboxamide;
N-[(3R)-5-Cyano-1-(4-cyanophenyl)sulfonyl-3-(2-ethoxyphenyl)-2-oxo-indolin-3-yl]-2-[1-(oxetan-3-yl)-4-piperidyl]-2,6-diazaspiro[3.3]heptane-6-carboxamide;
N-[5-Cyano-3-(2-ethoxyphenyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[(3S)-5-Cyano-3-(2-ethoxyphenyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[(3R)-5-Cyano-3-(2-ethoxyphenyl)-1-(4-fluorophenyl)sulfonyl-2-oxo-indolin-3-yl]-2-[1-(oxetan-3-yl)-4-piperidyl]-2,6-diazaspiro[3.3]heptane-6-carboxamide;
N-[5-Cyano-3-(2-ethoxyphenyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[(3S)-5-Cyano-3-(2-ethoxyphenyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[(3R)-5-Cyano-3-(2-ethoxyphenyl)-2-oxo-1-(p-tolylsulfonyl)indolin-3-yl]-2-[1-(oxetan-3-yl)-4-piperidyl]-2,6-diazaspiro[3.3]heptane-6-carboxamide;
N-[5-Cyano-1-(2,4-dimethoxyphenyl)sulfonyl-3-(2-ethoxyphenyl)-2-oxo-indolin-3-yl]-2-(1-methyl-4-piperidyl)-2,6-diazaspiro[3.3]heptane-6-carboxamide;
N-[(3S)-5-Cyano-1-(2,4-dimethoxyphenyl)sulfonyl-3-(2-ethoxyphenyl)-2-oxo-indolin-3-yl]-2-(1-methyl-4-piperidyl)-2,6-diazaspiro[3.3]heptane-6-carboxamide;
N-[(3R)-5-Cyano-1-(2,4-dimethoxyphenyl)sulfonyl-3-(2-ethoxyphenyl)-2-oxo-indolin-3-yl]-2-(1-methyl-4-piperidyl)-2,6-diazaspiro[3.3]heptane-6-carboxamide;
N-[5-Cyano-3-(2-ethoxyphenyl)-1-(4-methoxyphenyl)sulfonyl-2-oxo-indolin-3-yl]-2-(1-isopropyl-4-piperidyl)-2,6-diazaspiro[3.3]heptane-6-carboxamide;
N-[(3S)-5-Cyano-3-(2-ethoxyphenyl)-1-(4-methoxyphenyl)sulfonyl-2-oxo-indolin-3-yl]-2-(1-isopropyl-4-piperidyl)-2,6-diazaspiro[3.3]heptane-6-carboxamide;
N-[(3R)-5-Cyano-3-(2-ethoxyphenyl)-1-(4-methoxyphenyl)sulfonyl-2-oxo-indolin-3-yl]-2-(1-isopropyl-4-piperidyl)-2,6-diazaspiro[3.3]heptane-6-carboxamide;
N-[5-Cyano-3-(2-ethoxyphenyl)-2-oxo-1-(p-tolylsulfonyl)indolin-3-yl]-2-(1-isopropyl-4-piperidyl)-2,6-diazaspiro[3.3]heptane-6-carboxamide;
N-[(3S)-5-Cyano-3-(2-ethoxyphenyl)-2-oxo-1-(p-tolylsulfonyl)indolin-3-yl]-2-(1-isopropyl-4-piperidyl)-2,6-diazaspiro[3.3]heptane-6-carboxamide;
N-[(3R)-5-Cyano-3-(2-ethoxyphenyl)-2-oxo-1-(p-tolylsulfonyl)indolin-3-yl]-2-(1-isopropyl-4-piperidyl)-2,6-diazaspiro[3.3]heptane-6-carboxamide;
N-[5-Cyano-1-(4-cyanophenyl)sulfonyl-3-(2-ethoxyphenyl)-2-oxo-indolin-3-yl]-2-(1-isopropyl-4-piperidyl)-2,6-diazaspiro[3.3]heptane-6-carboxamide;
N-[(3S)-5-Cyano-1-(4-cyanophenyl)sulfonyl-3-(2-ethoxyphenyl)-2-oxo-indolin-3-yl]-2-(1-isopropyl-4-piperidyl)-2,6-diazaspiro[3.3]heptane-6-carboxamide;
N-[(3R)-5-Cyano-1-(4-cyanophenyl)sulfonyl-3-(2-ethoxyphenyl)-2-oxo-indolin-3-yl]-2-(1-isopropyl-4-piperidyl)-2,6-diazaspiro[3.3]heptane-6-carboxamide;
N-[5-Cyano-3-(2-ethoxyphenyl)-1-(4-fluorophenyl)sulfonyl-2-oxo-indolin-3-yl]-2-(1-isopropyl-4-piperidyl)-2,6-diazaspiro[3.3]heptane-6-carboxamide;
N-[(3S)-5-Cyano-3-(2-ethoxyphenyl)-1-(4-fluorophenyl)sulfonyl-2-oxo-indolin-3-yl]-2-(1-isopropyl-4-piperidyl)-2,6-diazaspiro[3.3]heptane-6-carboxamide;
N-[(3R)-5-Cyano-3-(2-ethoxyphenyl)-1-(4-fluorophenyl)sulfonyl-2-oxo-indolin-3-yl]-2-(1-isopropyl-4-piperidyl)-2,6-diazaspiro[3.3]heptane-6-carboxamide;

N-[5-Cyano-3-(2-ethoxy-3-pyridyl)-1-(4-methoxyphenyl)sulfonyl-2-oxo-indolin-3-yl]-6-azaspiro[3.3]heptane-2-carboxamide;
N-[(3S)-5-Cyano-3-(2-ethoxy-3-pyridyl)-1-(4-methoxyphenyl)sulfonyl-2-oxo-indolin-3-yl]-6-azaspiro[3.3]heptane-2-carboxamide;
N-[(3R)-5-Cyano-3-(2-ethoxy-3-pyridyl)-1-(4-methoxyphenyl)sulfonyl-2-oxo-indolin-3-yl]-6-azaspiro[3.3]heptane-2-carboxamide;
N-[5-Cyano-3-(2-ethoxy-3-pyridyl)-1-(4-methoxyphenyl)sulfonyl-2-oxo-indolin-3-yl]-6-(1-isopropyl-4-piperidyl)-6-azaspiro[3.3]heptane-2-carboxamide;
N-[(3S)-5-Cyano-3-(2-ethoxy-3-pyridyl)-1-(4-methoxyphenyl)sulfonyl-2-oxo-indolin-3-yl]-6-(1-isopropyl-4-piperidyl)-6-azaspiro[3.3]heptane-2-carboxamide;
N-[(3R)-5-Cyano-3-(2-ethoxy-3-pyridyl)-1-(4-methoxyphenyl)sulfonyl-2-oxo-indolin-3-yl]-6-(1-isopropyl-4-piperidyl)-6-azaspiro[3.3]heptane-2-carboxamide;
N-[5-Cyano-3-(2-ethoxy-3-pyridyl)-1-(4-methoxyphenyl)sulfonyl-2-oxo-indolin-3-yl]-6-(1-methylazetidin-3-yl)-6-azaspiro[3.3]heptane-2-carboxamide;
N-[(3S)-5-Cyano-3-(2-ethoxy-3-pyridyl)-1-(4-methoxyphenyl)sulfonyl-2-oxo-indolin-3-yl]-6-(1-methylazetidin-3-yl)-6-azaspiro[3.3]heptane-2-carboxamide;
N-[(3R)-5-Cyano-3-(2-ethoxy-3-pyridyl)-1-(4-methoxyphenyl)sulfonyl-2-oxo-indolin-3-yl]-6-(1-methylazetidin-3-yl)-6-azaspiro[3.3]heptane-2-carboxamide;
N-(5-Cyano-1-(2,4-dimethoxyphenylsulfonyl)-3-(2-ethoxypyridin-3-yl)-2-oxoindolin-3-yl)-3-(piperidin-4-yl)-3-azaspiro[5.5]undecane-9-carboxamide;
N-[(3S)-5-Cyano-1-(2,4-dimethoxyphenylsulfonyl)-3-(2-ethoxypyridin-3-yl)-2-oxoindolin-3-yl]-3-(piperidin-4-yl)-3-azaspiro[5.5]undecane-9-carboxamide;
N-[(3R)-5-Cyano-1-(2,4-dimethoxyphenylsulfonyl)-3-(2-ethoxypyridin-3-yl)-2-oxoindolin-3-yl]-3-(piperidin-4-yl)-3-azaspiro[5.5]undecane-9-carboxamide;
N-(5-Cyano-1-(2,4-dimethoxyphenylsulfonyl)-3-(2-ethoxypyridin-3-yl)-2-oxoindolin-3-yl)-6-(2,6-diazaspiro[3.3]heptan-2-yl)spiro[3.3]heptane-2-carboxamide;
N-[(3S)-5-Cyano-1-(2,4-dimethoxyphenylsulfonyl)-3-(2-ethoxypyridin-3-yl)-2-oxoindolin-3-yl]-6-(2,6-diazaspiro[3.3]heptan-2-yl)spiro[3.3]heptane-2-carboxamide;
N-[(3R)-5-Cyano-1-(2,4-dimethoxyphenylsulfonyl)-3-(2-ethoxypyridin-3-yl)-2-oxoindolin-3-yl]-6-(2,6-diazaspiro[3.3]heptan-2-yl)spiro[3.3]heptane-2-carboxamide;
N-(5-cyano-1-(2,4-dimethoxyphenylsulfonyl)-3-(2-ethoxypyridin-3-yl)-2-oxoindolin-3-yl)-7-(piperidin-4-yl)-2,7-diazaspiro[3.5]nonane-2-carboxamide;
N-[(3S)-5-cyano-1-(2,4-dimethoxyphenylsulfonyl)-3-(2-ethoxypyridin-3-yl)-2-oxo-indolin-3-yl]-7-(piperidin-4-yl)-2,7-diazaspiro[3.5]nonane-2-carboxamide;
N-[(3R)-5-cyano-1-(2,4-dimethoxyphenylsulfonyl)-3-(2-ethoxypyridin-3-yl)-2-oxo-indolin-3-yl]-7-(piperidin-4-yl)-2,7-diazaspiro[3.5]nonane-2-carboxamide;
N-(5-Cyano-1-(2,4-dimethoxyphenylsulfonyl)-3-(2-ethoxypyridin-3-yl)-2-oxoindolin-3-yl)-2-(piperidin-4-yl)-2,7-diazaspiro[3.5]nonane-7-carboxamide;
N-[(3S)-5-Cyano-1-(2,4-dimethoxyphenylsulfonyl)-3-(2-ethoxypyridin-3-yl)-2-oxoindolin-3-yl]-2-(piperidin-4-yl)-2,7-diazaspiro[3.5]nonane-7-carboxamide;
N-[(3R)-5-Cyano-1-(2,4-dimethoxyphenylsulfonyl)-3-(2-ethoxypyridin-3-yl)-2-oxoindolin-3-yl]-2-(piperidin-4-yl)-2,7-diazaspiro[3.5]nonane-7-carboxamide;
N-(5-Cyano-1-(2,4-dimethoxyphenylsulfonyl)-3-(2-ethoxypyridin-3-yl)-2-oxoindolin-3-yl)-2,7-diazaspiro[3.5]nonane-7-carboxamide;
N-[(3S)-5-Cyano-1-(2,4-dimethoxyphenylsulfonyl)-3-(2-ethoxypyridin-3-yl)-2-oxoindolin-3-yl]-2,7-diazaspiro[3.5]nonane-7-carboxamide;
N-[(3R)-5-Cyano-1-(2,4-dimethoxyphenylsulfonyl)-3-(2-ethoxypyridin-3-yl)-2-oxoindolin-3-yl]-2,7-diazaspiro[3.5]nonane-7-carboxamide;
N-(5-Cyano-1-(2,4-dimethoxyphenylsulfonyl)-3-(2-ethoxypyridin-3-yl)-2-oxoindolin-3-yl)-3-azaspiro[5.5]undecane-9-carboxamide;
N-[(3S)-5-Cyano-1-(2,4-dimethoxyphenylsulfonyl)-3-(2-ethoxypyridin-3-yl)-2-oxoindolin-3-yl]-3-azaspiro[5.5]undecane-9-carboxamide;
N-[(3R)-5-Cyano-1-(2,4-dimethoxyphenylsulfonyl)-3-(2-ethoxypyridin-3-yl)-2-oxoindolin-3-yl]-3-azaspiro[5.5]undecane-9-carboxamide;
N-(5-Cyano-1-(2,4-dimethoxyphenylsulfonyl)-3-(2-ethoxypyridin-3-yl)-2-oxoindolin-3-yl)-9-methyl-3,9-diazaspiro[5.5]undecane-3-carboxamide;
N-[(3S)-5-Cyano-1-(2,4-dimethoxyphenylsulfonyl)-3-(2-ethoxypyridin-3-yl)-2-oxoindolin-3-yl]-9-methyl-3,9-diazaspiro[5.5]undecane-3-carboxamide;
N-[(3R)-5-Cyano-1-(2,4-dimethoxyphenylsulfonyl)-3-(2-ethoxypyridin-3-yl)-2-oxoindolin-3-yl]-9-methyl-3,9-diazaspiro[5.5]undecane-3-carboxamide;
N-(5-Cyano-1-(2,4-dimethoxyphenylsulfonyl)-3-(2-ethoxypyridin-3-yl)-2-oxoindolin-3-yl)-6-(4-ethylpiperazin-1-yl)spiro[3.3]heptane-2-carboxamide;
N-[(3S)-5-Cyano-1-(2,4-dimethoxyphenylsulfonyl)-3-(2-ethoxypyridin-3-yl)-2-oxoindolin-3-yl]-6-(4-ethylpiperazin-1-yl)spiro[3.3]heptane-2-carboxamide;
N-[(3R)-5-Cyano-1-(2,4-dimethoxyphenylsulfonyl)-3-(2-ethoxypyridin-3-yl)-2-oxoindolin-3-yl]-6-(4-ethylpiperazin-1-yl)spiro[3.3]heptane-2-carboxamide;
N-(5-Cyano-1-(2,4-dimethoxyphenylsulfonyl)-3-(2-ethoxypyridin-3-yl)-2-oxoindolin-3-yl)-7-methyl-2,7-diazaspiro[3.5]nonane-2-carboxamide;
N-[(3S)-5-Cyano-1-(2,4-dimethoxyphenylsulfonyl)-3-(2-ethoxypyridin-3-yl)-2-oxoindolin-3-yl]-7-methyl-2,7-diazaspiro[3.5]nonane-2-carboxamide;
N-[(3R)-5-Cyano-1-(2,4-dimethoxyphenylsulfonyl)-3-(2-ethoxypyridin-3-yl)-2-oxoindolin-3-yl]-7-methyl-2,7-diazaspiro[3.5]nonane-2-carboxamide;
N-(5-Cyano-1-(2,4-dimethoxyphenylsulfonyl)-3-(2-ethoxypyridin-3-yl)-2-oxoindolin-3-yl)-9-ethyl-3,9-diazaspiro[5.5]undecane-3-carboxamide;
N-[(3S)-5-Cyano-1-(2,4-dimethoxyphenylsulfonyl)-3-(2-ethoxypyridin-3-yl)-2-oxoindolin-3-yl]-9-ethyl-3,9-diazaspiro[5.5]undecane-3-carboxamide;
N-[(3R)-5-Cyano-1-(2,4-dimethoxyphenylsulfonyl)-3-(2-ethoxypyridin-3-yl)-2-oxoindolin-3-yl]-9-ethyl-3,9-diazaspiro[5.5]undecane-3-carboxamide;
N-(5-Cyano-1-(2,4-dimethoxyphenylsulfonyl)-3-(2-ethoxypyridin-3-yl)-2-oxoindolin-3-yl)-2-azaspiro[3.3]heptane-6-carboxamide;
N-[(3S)-5-Cyano-1-(2,4-dimethoxyphenylsulfonyl)-3-(2-ethoxypyridin-3-yl)-2-oxoindolin-3-yl]-2-azaspiro[3.3]heptane-6-carboxamide;
N-[(3R)-5-Cyano-1-(2,4-dimethoxyphenylsulfonyl)-3-(2-ethoxypyridin-3-yl)-2-oxoindolin-3-yl]-2-azaspiro[3.3]heptane-6-carboxamide;
N-(5-Cyano-1-(2,4-dimethoxyphenylsulfonyl)-3-(2-ethoxypyridin-3-yl)-2-oxoindolin-3-yl)-2,6-diazaspiro[3.3]heptane-2-carboxamide;

N-[(3S)-5-Cyano-1-(2,4-dimethoxyphenylsulfonyl)-3-(2-ethoxypyridin-3-yl)-2-oxoindolin-3-yl]-2,6-diazaspiro[3.3]heptane-2-carboxamide;

N-[(3R)-5-Cyano-1-(2,4-dimethoxyphenylsulfonyl)-3-(2-ethoxypyridin-3-yl)-2-oxoindolin-3-yl]-2,6-diazaspiro[3.3]heptane-2-carboxamide;

N-(5-Cyano-1-(2,4-dimethoxyphenylsulfonyl)-3-(2-ethoxypyridin-3-yl)-2-oxoindolin-3-yl)-6-(piperidin-4-yl)-2,6-diazaspiro[3.3]heptane-2-carboxamide;

N-[(3S)-5-Cyano-1-(2,4-dimethoxyphenylsulfonyl)-3-(2-ethoxypyridin-3-yl)-2-oxoindolin-3-yl]-6-(piperidin-4-yl)-2,6-diazaspiro[3.3]heptane-2-carboxamide;

N-[(3R)-5-Cyano-1-(2,4-dimethoxyphenylsulfonyl)-3-(2-ethoxypyridin-3-yl)-2-oxoindolin-3-yl]-6-(piperidin-4-yl)-2,6-diazaspiro[3.3]heptane-2-carboxamide;

N-(5-Cyano-1-(2,4-dimethoxyphenylsulfonyl)-3-(2-ethoxypyridin-3-yl)-2-oxoindolin-3-yl)-2,7-diazaspiro[3.5]nonane-2-carboxamide;

N-[(3S)-5-Cyano-1-(2,4-dimethoxyphenylsulfonyl)-3-(2-ethoxypyridin-3-yl)-2-oxoindolin-3-yl]-2,7-diazaspiro[3.5]nonane-2-carboxamide; and N-[(3R)-5-Cyano-1-(2,4-dimethoxyphenylsulfonyl)-3-(2-ethoxypyridin-3-yl)-2-oxoindolin-3-yl]-2,7-diazaspiro[3.5]nonane-2-carboxamide;

or an N-oxide, stereoisomer, and or pharmaceutically acceptable salt thereof, or wherein at least one of the atoms has been replaced by its stable, non-radioactive isotope.

33. A pharmaceutical composition comprising at least one compound of the formula I as defined in claim 1 and/or an N-oxide, a stereoisomer or at least one pharmaceutically acceptable salt thereof and at least one pharmaceutically acceptable carrier.

34. A method for the treatment of vasopressin-related diseases comprising administering a compound of claim 1, or an N-oxide, a steroisomer or pharmaceutically acceptable salt thereof, to a subject in need thereof.

35. The method as claimed in claim 34, wherein the vasopressin-related diseases are selected from the group consisting of diabetes; insulin resistance; nocturnal enuresis; incontinence and diseases in which impairments of blood clotting occur; hypertension; pulmonary hypertension; heart failure; myocardial infarction; coronary spasm; unstable angina; PTCA (percutaneous transluminal coronary angioplasty); ischemias of the heart; impairments of the renal system; edemas; renal vasospasm; necrosis of the renal cortex; hyponatremia; hypokalemia; Schwartz-Bartter syndrome; impairments of the gastrointestinal tract; gastritic vasospasm; hepatocirrhosis; gastric and intestinal ulcers; emesis; emesis occurring during chemotherapy; travel sickness; affective disorders; Alzheimer's disease; mild cognitive impairment and cognitive impairment associated with schizophrenia, aging, Alzheimer disease, Parkinson's disease and/or dementia; increased aggression in conditions selected from the group consisting of Alzheimer's disease, schizophrenia, bipolar disorder, frontal lobe injuries and substance use disorders; Cushing's syndrome and stress-dependent diseases; sleep disorders; vasomotor symptoms; thermoregulatory dysfunctions; substance-related and addictive disorders; schizophrenia and psychosis; pain; and micturition disorders.

36. The method as claimed in claim 35, where the affective disorders are selected from the group consisting of depressive disorders, anxiety disorders and stress-dependent anxiety disorders; where the substance-related and addictive disorders are selected from the group consisting of alcohol use disorder, alcohol intoxication, and alcohol withdrawal.

37. The method as claimed in claim 35, where the affective disorders are selected from the group consisting of depressive disorders, anxiety disorders, obsessive-compulsive disorders, trauma and stressor-related disorders; and bipolar disorders;

where substance-related and addictive disorders are selected from the group consisting of substance use disorder, substance-induced disorder, alcohol use disorder, alcohol intoxication, alcohol withdrawal, caffeine intoxication, caffeine withdrawal, cannabis use disorder, cannabis withdrawal, phencyclidine use disorder, other hallucinogen use disorders, phencyclidine intoxication, other hallucinogen disorders, hallucinogen persisting perception disorder, inhalant use disorder, inhalant intoxication, opioid use disorder, opioid withdrawal, sedative, hypnotic or anxiolytic use disorder, sedative, hypnotic or anxiolytic withdrawal, stimulant use disorder, stimulant intoxication, stimulant withdrawal, tobacco use disorder, tobacco withdrawal, and gambling disorder.

38. The method as claimed in claim 37, where the depressive disorders are selected from the group consisting of dysthymic disorders, major depression, seasonal depression, treatment-resistant depression disorders, disruptive mood dysregulation disorder, premenstrual dysphoric disorder, substance/medication-induced depressive disorder and childhood onset mood disorders; where the anxiety disorders are selected from the group consisting of phobias, specific phobias, general anxiety disorders, panic disorders, drug withdrawal-induced anxiety disorders, separation anxiety disorder, selective mutism, social anxiety disorder, agoraphobia, and substance/medication-induced anxiety disorder; the obsessive-compulsive are selected from the group consisting of obsessive-compulsive disorder, body dysmorphic disorder, hoarding disorder, trichotillomania, excoriation disorder, and substance/medication-induced obsessive-compulsive disorder;

the trauma and stressor-related disorders are selected from the group consisting of reactive attachment disorder, disinhibited social engagement disorder, post-traumatic stress disorder, acute stress disorder, ad adjustment disorder; and the bipolar disorders are selected from the group consisting of bipolar I disorder, bipolar II disorder, cyclothymic disorder, and substance/medication-induced bipolar disorder.

* * * * *